United States Patent
Guo et al.

(10) Patent No.: US 9,447,086 B2
(45) Date of Patent: Sep. 20, 2016

(54) 6-AMINO ACID HETEROARYLDIHYDROPYRIMIDINES FOR THE TREATMENT AND PROPHYLAXIS OF HEPATITIS B VIRUS INFECTION

(71) Applicant: HOFFMANN-LA ROCHE INC., Nutley, NJ (US)

(72) Inventors: Lei Guo, Shanghai (CN); Taishan Hu, Shanghai (CN); Yimin Hu, Shanghai (CN); Buelent Kocer, Steinen (DE); Xianfeng Lin, Shanghai (CN); Haixia Liu, Shanghai (CN); Alexander V Mayweg, Basel (CH); Zongxing Qiu, Shanghai (CN); Hong Shen, Shanghai (CN); Guozhi Tang, Shanghai (CN); Lisha Wang, Basel (CH); Guolong Wu, Shanghai (CN); Shixiang Yan, Shanghai (CN); Weixing Zhang, Shanghai (CN); Mingwei Zhou, Shanghai (CN); Wei Zhu, Shanghai (CN)

(73) Assignee: Hoffmann-LA Roche INC., Little Falls, NJ (US)

( * ) Notice: Subject to any disclaimer, the term of this patent is extended or adjusted under 35 U.S.C. 154(b) by 0 days.

(21) Appl. No.: 14/022,519

(22) Filed: Sep. 10, 2013

(65) Prior Publication Data

US 2015/0031687 A1 Jan. 29, 2015
US 2016/0237078 A9 Aug. 18, 2016

Related U.S. Application Data

(63) Continuation of application No. PCT/CN2012/081190, filed on Sep. 10, 2012, and a continuation of application No. PCT/CN2013/080301, filed on Jul. 29, 2013, and a continuation of application No. PCT/CN2013/081196, filed on Aug. 9, 2013, and a continuation of application No. PCT/CN2013/081287, filed on Aug. 12, 2013.

(51) Int. Cl.
| | |
|---|---|
| *C07D 401/14* | (2006.01) |
| *A61K 31/506* | (2006.01) |
| *C07D 417/14* | (2006.01) |
| *A61K 31/5377* | (2006.01) |
| *A61K 31/541* | (2006.01) |

(52) U.S. Cl.
CPC .......... *C07D 417/14* (2013.01); *A61K 31/506* (2013.01); *A61K 31/5377* (2013.01); *A61K 31/541* (2013.01); *C07D 401/14* (2013.01)

(58) Field of Classification Search
CPC .............. C07D 401/14; C07D 417/14; A61K 31/506; A61K 31/5377
USPC ...... 544/55, 60, 122, 333; 514/226.8, 227.8, 514/235.8, 256
See application file for complete search history.

(56) References Cited

U.S. PATENT DOCUMENTS

| | | |
|---|---|---|
| 4,822,798 A | 4/1989 | Stoltefuss et al. |
| 5,250,531 A | 10/1993 | Cooper |
| 6,218,538 B1 | 4/2001 | Downs et al. |
| 6,436,943 B1 | 8/2002 | Stoltefuss et al. |
| 6,503,913 B1 | 1/2003 | Goldmann et al. |
| 6,696,451 B1 | 2/2004 | Stoltefuss et al. |
| 7,074,784 B2 | 7/2006 | Goldmann et al. |
| 7,157,461 B2 | 1/2007 | Murugesan et al. |
| 8,106,196 B2 | 1/2012 | Li et al. |
| 8,168,642 B2 | 5/2012 | Li et al. |
| 8,236,797 B2 | 8/2012 | Goldmann et al. |
| 8,329,902 B2 | 12/2012 | Li et al. |
| 2005/0059687 A1 | 3/2005 | Makings et al. |
| 2007/0112015 A1 | 5/2007 | Hurt et al. |
| 2008/0125427 A1 | 5/2008 | Sehon et al. |
| 2010/0056569 A1 | 3/2010 | Nan et al. |

(Continued)

FOREIGN PATENT DOCUMENTS

| | | |
|---|---|---|
| CN | 101575314 A | 11/2009 |
| CN | 103570626 A | 8/2012 |

(Continued)

OTHER PUBLICATIONS

Gentile et al., Vertical transmission of hepatitis B virus: challenges and solutions, International Journal of Women's Health, 6 :605-611, 2014.*
Halegoua-De Marzio et al., Then and now: The progress in hepatitis B treatment over the past 20 years, World Journal of Gastroenterology, 20(2): 401-413, Jan. 2014.*
Bourne et al., "Small-molecule effectors of hepatitis B virus capsid assembly give insight into virus life cycle" J Virol. 82(20):10262-70 ( 2008).
Deres et al., "Inhibition of hepatitis B virus replication by drug-induced depletion of nucleocapsids" Science 299(5608):893-6 ( 2003).

(Continued)

*Primary Examiner* — Deepak Rao
(74) *Attorney, Agent, or Firm* — Jonathan Duffield

(57) ABSTRACT

The invention provides novel compounds having the general formula:

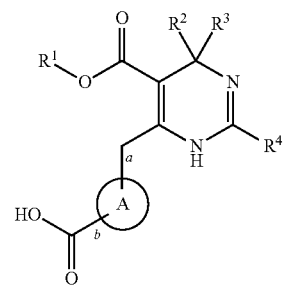

wherein $R^1$, $R^2$, $R^3$, $R^4$ and A are as described herein, compositions including the compounds and methods of using the compounds.

5 Claims, 1 Drawing Sheet

(56) References Cited

U.S. PATENT DOCUMENTS

| | | |
|---|---|---|
| 2011/0021771 A1 | 1/2011 | Mallais et al. |
| 2012/0149695 A1 | 6/2012 | Li et al. |
| 2012/0263646 A1 | 10/2012 | Catoen et al. |

FOREIGN PATENT DOCUMENTS

| | | |
|---|---|---|
| CN | 103664897 A | 8/2013 |
| CN | 103664899 A | 9/2013 |
| CN | 103664925 a | 9/2013 |
| WO | 99/35125 | 7/1999 |
| WO | 00/58302 | 10/2000 |
| WO | WO 00/58302 | 10/2000 |
| WO | 01/45712 A1 | 6/2001 |
| WO | WO 01/45712 | 6/2001 |
| WO | 01/68639 A1 | 9/2001 |
| WO | 01/68640 A1 | 9/2001 |
| WO | 01/68641 | 9/2001 |
| WO | 01/68642 A1 | 9/2001 |
| WO | 01/68647 A1 | 9/2001 |
| WO | WO 01/68639 | 9/2001 |
| WO | WO 01/68641 | 9/2001 |
| WO | WO 01/68642 | 9/2001 |
| WO | WO 01/68647 | 9/2001 |
| WO | 2006/033995 A2 | 3/2006 |
| WO | 2007/014023 A1 | 2/2007 |
| WO | 2008/154817 | 12/2008 |
| WO | 2008/154818 A1 | 12/2008 |
| WO | 2008/154819 A1 | 12/2008 |
| WO | 2008/154820 A1 | 12/2008 |
| WO | WO 2008/154818 | 12/2008 |
| WO | WO 2008/154819 | 12/2008 |
| WO | WO 2008/154820 | 12/2008 |
| WO | 2010/069147 A1 | 6/2010 |
| WO | WO 2010069147 | 6/2010 |
| WO | 2013/019967 A1 | 2/2013 |
| WO | 2013/102655 | 7/2013 |
| WO | 2013/144129 | 10/2013 |
| WO | WO 2013/144129 | * 10/2013 |
| WO | 2014/029193 | 2/2014 |
| WO | 2014/048355 | 4/2014 |
| WO | 2014/074906 | 5/2014 |
| WO | 2014/153459 | 9/2014 |
| WO | 2014/184328 | 11/2014 |

OTHER PUBLICATIONS

Li et al., "Phase diagrams map the properties of antiviral agents directed against hepatitis B virus core assembly" Antimicrob Agents Chemother. 57(3):1505-8 ( 2013).

Stray et al., "A heteroaryldihydropyrimidine activates and can misdirect hepatitis B virus capsid assembly" Proc Natl Acad Sci U S A. 102(23):8138-43 (Jun. 2005).

Stray et al., "BAY 41-4109 has multiple effects on Hepatitis B virus capsid assmebly" J Mol Recognit. 19(6):542-8 ( 2006).

Wang et al., "In vitro inhibition of HBV replication by a novel compound, GLS4, and its efficacy against adefovir-dipivoxil-resistant HBV mutations" Antivir Ther. 17(5):793-803 ( 2012).

Gentile et al., "Vertical transmission of hepatitis B virus: challenges and solutions" International Journal of Women's Health 6:605-611 (2014).

Halegoua-De Marzio et al., "Then and now: The progress in hepatitis B treatment over" World Journal of Gastroenterology 20(2):401-413 (Jan. 14, 2014).

* cited by examiner

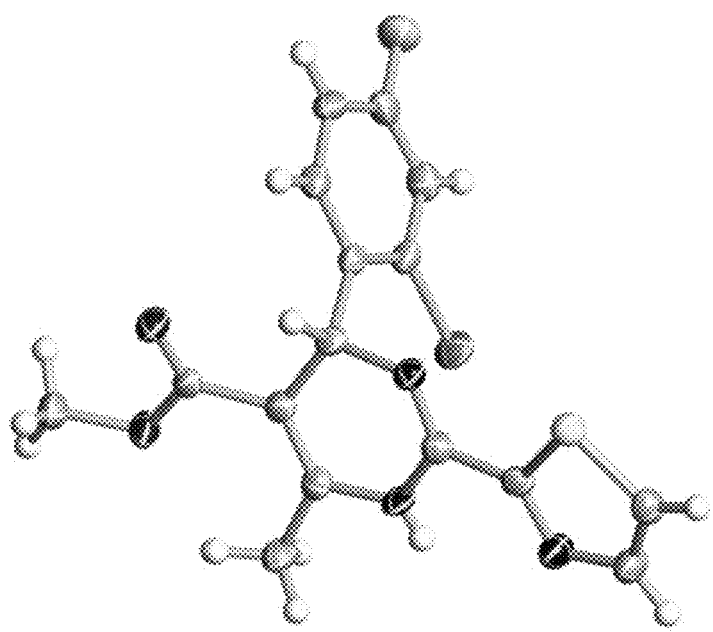
X-ray crystal structure of compound E

6-AMINO ACID HETEROARYLDIHYDROPYRIMIDINES FOR THE TREATMENT AND PROPHYLAXIS OF HEPATITIS B VIRUS INFECTION

This patent application claims the benefit under 35 U.S.C. §119(a) of International Application No. PCT/CN2012/081190 filed Sep. 10, 2012 and claims the benefit under 35 U.S.C. §119(a) of International Application No. PCT/CN2013/080301 filed Jul. 29, 2013 and claims the benefit under 35 U.S.C. §119(a) of International Application No. PCT/CN2013/081196 filed Aug. 9, 2013 and claims the benefit under 35 U.S.C. §119(a) of International Application No. PCT/CN2013/081287 filed Aug. 12, 2013. The entire contents of these applications are hereby incorporated herein by reference.

The present invention relates to organic compounds useful for therapy and/or prophylaxis in a human, and in particular to Hepatitis B virus (HBV) inhibitors by targeting on HBV capsid for the treatment of HBV infection.

FIELD OF THE INVENTION

HBV is a species of the hepadnaviridae family of viruses. HBV is a serious public health problem worldwide, with more than 400 million people especially in Asia-pacific regions chronically infected by this small enveloped DNA virus. Although most individuals seem to resolve the infection following acute symptoms, 15-40% of HBV patients will finally develop clinical diseases during their lifespan, most notably, hepatitis, liver cirrhosis, and hepatocellular carcinoma. Every year 500,000 to 1 million people die from the end stage of liver diseases caused by HBV infection.

HBV lifecycle begins with the binding of the "Dane" particle with an unidentified receptor on the surface of hepatocyte. Following entry, viral genome is delivered into nucleus where a covalently closed circular DNA (cccDNA) is formed through DNA repair of viral relaxed circular DNA. Unlike the mechanisms of most other DNA viruses, HBV cccDNA replicates through the retrotranscription of a 1.1-genome unit-length RNA copy (pregenomic RNA). Viral pregenomic RNA interacts with other two viral components, capsid protein and polymerase, as well as some host factors, to form capsid particles where viral DNA replication occurs. Most copies of the encapsidated genome then efficiently associate with the envelope proteins for virion assembly and secretion; a minority of these genomes is shunted to the nucleus, where they are converted to cccDNA.

Currently, there are two types of anti-HBV agents on the market, nucleoside (tide) analogs targeting viral polymerase (lamivudine, adefovir, tenofovir, telbivudine and entecavir) and interferon modulating host immune functions. Mutations in the primary sequence of the polymerase that confer resistance to lamivudine and adefovir have been identified clinically and underlie a rebound of serum virus titers that 70% of treated patients experience within 3 years of the start of lamivudine therapy. Although resistance to telbivudine, adefovir, and entecavir occurs more rarely, it has been recorded. Interferon alpha is the other major therapy available for hepatitis B, but it is limited by a poor long-term response and debilitating side effects. Some viral genotypes do not show good responses to interferon therapy. Now, the standard of clinic cure of HBV infection is the loss and/or seroconversion of HBsAg. The majority (around or more than 90%) of treated patients fail to achieve this goal. This drawback is mainly due to the presence of a stable pool of viral cccDNA in nucleus that doesn't replicate itself, therefore, shows no accessibility to nucleoside (tide) analogs.

Hence, there is certainly a medical need for treatments with improved characteristics and for a diversity of approaches in the development of therapies for HBV infection.

HBV capsid protein plays essential roles in HBV replication. HBV has an icosahedral core comprising of 240 copies of the capsid (or core) protein. The predominant biological function of capsid protein is to act as a structural protein to encapsidate pre-genomic RNA and form immature capsid particles in the cytoplasm. This step is prerequisite for viral DNA replication. The HBV capsid spontaneously self-assembles from many copies of core dimers present in the cytoplasm. It has been shown that the formation of a trimeric nucleus and the subsequent elongation reactions occur by adding one dimeric subunit at a time until it is complete. Besides this function, capsid protein regulates viral DNA synthesis through different phosphorylation status of its C-terminal phosphorylation sites. When a near full-length relaxed circular DNA is formed through reverse-transcription of viral pregenomic RNA, an immature capsid becomes a mature capsid. On one hand, capsid protein might facilitate the nuclear translocation of viral relaxed circular genome by means of the nuclear localization signals located in the Arginine-rich domain of the C-terminal region of capsid protein. In nucleus, as a component of viral cccDNA minichromosome, capsid protein could play a structural and regulatory role in the functionality of cccDNA minichromosomes. Capsid protein also interacts with viral large envelope protein in endoplasmic reticulum and triggers the release of intact viral particles from hepatocytes.

There has been a couple of capsid related anti-HBV inhibitors reported. For example, phenylpropenamide derivatives, including compounds named AT-61 and AT-130 (Feld J. et al. *Antiviral Research* 2007, 168-177), and a class of thiazolidin-4-ones from Valeant R&D (WO2006/033995), have been shown to inhibit pgRNA packaging. A recent study suggested that phenylpropenamides are, in fact, accelerators of HBV capsid assembly, and their actions result in the formation of empty capsids. These very interesting results illustrate the importance of the kinetic pathway in successful virus assembly.

Heteroaryldihydropyrimidines or HAP, including compounds named Bay 41-4109, Bay 38-7690 and Bay 39-5493, were discovered in a tissue culture-based screening (Deres K. et al. *Science* 2003, 893). These HAP analogs act as synthetic allosteric activators and are able to induce aberrant capsid formation that leads to degradation of the core protein. HAP analogs also reorganized core protein from preassembled capsids into noncapsid polymers, presumably by interaction of HAP with dimers freed during capsid 'breathing', the transitory breaking of individual intersubunit bonds. Bay 41-4109 was administered to HBV infected transgenic mouse or humanized mouse models and demonstrated in vivo efficacy with HBV DNA reduction (Deres K. et al. *Science* 2003, 893; Brezillon N. et al. *PLoS ONE* 2011, e25096). It was also shown that bis-ANS, a small molecule that acts as a molecular 'wedge' and interferes with normal capsid-protein geometry and capsid formation (Zlotnick A. et al. *J. Virol.* 2002, 4848-4854).

SUMMARY OF THE INVENTION

Objects of the present invention are novel compounds of formula I, their manufacture, medicaments based on a compound in accordance with the invention and their production as well as the use of compounds of formula I as HBV inhibitors and for the treatment or prophylaxis of HBV infection. The compounds of formula I show superior anti-HBV activity. In addition, the compounds of formula I also show high selectivity index, better solubility and mouse SDPK profiles.

BRIEF DESCRIPTION OF THE DRAWINGS

FIG. 1. X-ray crystal structure of compound E.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "—$C_xH_{2x}$—" alone or in combination signifies a saturated, linear or branched chain alkyl group containing from 1 to 6 carbon atoms, particularly from 1 to 4 carbon atoms.

The term "cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "cycloalkyl" groups are cyclopropyl, cyclopentyl and cyclohexyl.

The term "carboxy" alone or in combination refers to the group —COOH.

The term "cyano" alone or in combination refers to the group —CN.

The term "halogen" means fluorine, chlorine, bromine or iodine. Halogen is particularly fluorine, chlorine or bromine.

The term "sulfanyl" alone or in combination refers to the group —S—.

The term "enantiomer" denotes two stereoisomers of a compound which are non-superimposable mirror images of one another.

The term "diastereomer" denotes a stereoisomer with two or more centers of chirality and whose molecules are not mirror images of one another.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitors of HBV

The present invention provides (i) novel compounds having the general formula I:

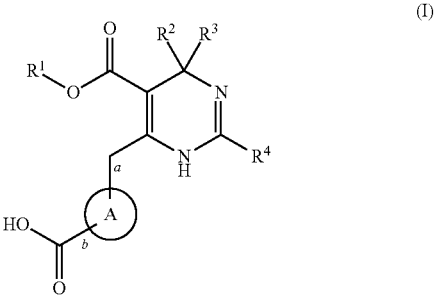

(I)

wherein
$R^1$ is $C_{1-6}$alkyl or trifluoromethyl-$C_xH_{2x}$—, wherein x is 1-6;

One of $R^2$ and $R^3$ is phenyl, which is once or twice or three times substituted by $C_{1-6}$alkyl, cyano or halogen; and the other one is hydrogen or deuterium;

$R^4$ is phenyl, thiazolyl, oxazolyl, imidazolyl, thienyl or pyridinyl, which is unsubstituted or substituted by $C_{1-6}$alkyl, $C_{1-6}$alkylsulfanyl, halogen or cycloalkyl, where said $C_{1-6}$alkyl can be further optionally substituted with halogen;

A is

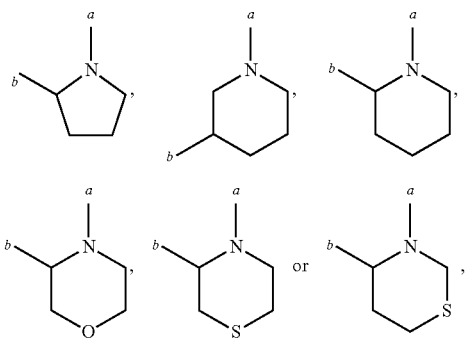

which is unsubstituted or substituted by groups selected from $C_{1-6}$alkyl, deuterium and halogen;

or pharmaceutically acceptable salts, or enantiomers, or diastereomers thereof.

Further embodiment of present invention is (ii) a compound of formula I, wherein
$R^1$ is methyl, ethyl, propyl, isopropyl, tert-butyl or trifluoromethylmethyl;

One of $R^2$ and $R^3$ is phenyl, which is once or twice or three times substituted by fluoro, chloro, bromo, iodo, methyl, or cyano; and the other one is hydrogen or deuterium;

$R^4$ is phenyl, thiazolyl, oxazolyl, imidazolyl, thienyl or pyridinyl, which is unsubstituted or substituted by methyl, isopropyl, tert-butyl, bifluoromethyl, trifluoromethyl, cyclopropyl, methylsulfanyl, fluoro or chloro;

A is

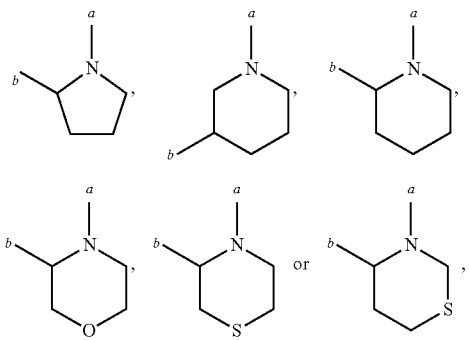

which is unsubstituted or substituted by groups selected from methyl, isopropyl, deuterium and fluoro;

or pharmaceutically acceptable salts, or enantiomers, or diastereomers thereof.

Another embodiment of present invention is (iii) a compound of formula I, wherein $R^1$ is $C_{1-6}$alkyl or trifluoromethyl-$C_xH_{2x}$—, wherein x is 1-6;

One of $R^2$ and $R^3$ is phenyl, which is once or twice or three times substituted by $C_{1-6}$alkyl, cyano or halogen; and the other one is hydrogen or deuterium;

$R^4$ is phenyl, thiazolyl, oxazolyl, imidazolyl, thienyl or pyridinyl, which is unsubstituted or substituted by $C_{1-6}$alkyl, $C_{1-6}$alkylsulfanyl, halogen or cycloalkyl, where said $C_{1-6}$alkyl can be further optionally substituted with halogen;

A is

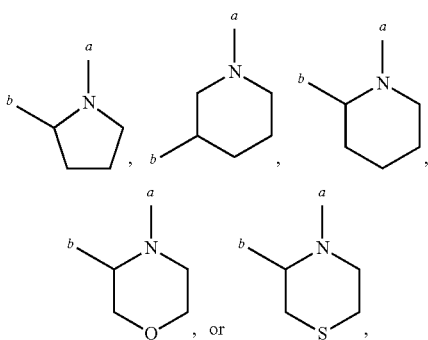

which is unsubstituted or substituted by groups selected from $C_{1-6}$alkyl, deuterium and halogen; or pharmaceutically acceptable salts, or enantiomers, or diastereomers thereof.

Further embodiment of present invention is (iv) a compound of formula I, wherein $R^1$ is methyl, ethyl, propyl, isopropyl or trifluoromethyl-methyl;

One of $R^2$ and $R^3$ is phenyl, which is once or twice or three times substituted by fluoro, chloro, bromo, iodo, methyl or cyano; and the other one is hydrogen or deuterium;

$R^4$ is phenyl, thiazolyl, oxazolyl, imidazolyl, thienyl or pyridinyl, which is unsubstituted or substituted by methyl, isopropyl, trifluoromethyl, cyclopropyl, methylsulfanyl, fluoro or chloro;

A is

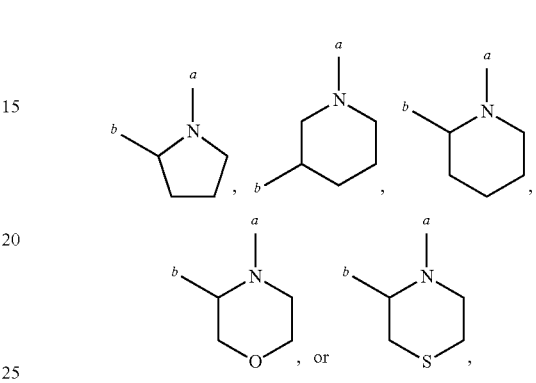

which is unsubstituted or substituted by groups selected from methyl, isopropyl, deuterium and fluoro; or pharmaceutically acceptable salts, or enantiomers, or diastereomers thereof.

Another embodiment of present invention is (v) a compound of formula I, wherein $R^1$ is $C_{1-6}$alkyl;

One of $R^2$ and $R^3$ is phenyl, which is once or twice or three times substituted by $C_{1-6}$alkyl or halogen; and the other one is hydrogen or deuterium;

$R^4$ is thiazolyl, oxazolyl, imidazolyl, thienyl or pyridinyl, which is unsubstituted or substituted by $C_{1-6}$alkyl, halogen or cycloalkyl, where said $C_{1-6}$alkyl can be further optionally substituted with halogen;

A is

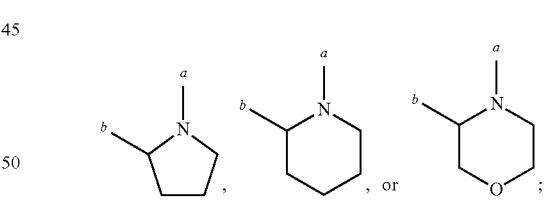

which is unsubstituted or substituted by groups selected from $C_{1-6}$alkyl, deuterium and halogen;

or pharmaceutically acceptable salts, or enantiomers, or diastereomers thereof.

Further embodiment of present invention is (vi) a compound of formula I, wherein $R^1$ is methyl or ethyl;

One of $R^2$ and $R^3$ is phenyl, which is once or twice or three times substituted by fluoro, chloro, bromo, iodo or methyl; and the other one is hydrogen or deuterium;

$R^4$ is thiazolyl, oxazolyl, imidazolyl, thienyl or pyridinyl, which is unsubstituted or substituted by methyl, isopropyl, trifluoromethyl, cyclopropyl or fluoro;

A is

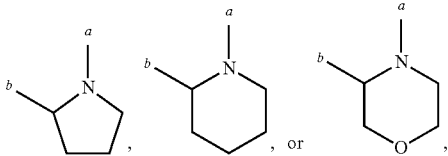

which is unsubstituted or substituted by groups selected from methyl, isopropyl, deuterium and fluoro;

or pharmaceutically acceptable salts, or enantiomers, or diastereomers thereof.

Another embodiment of present invention is (vii) a compound of formula I or pharmaceutically acceptable salts, or enantiomers, or diastereomers thereof, wherein $R^1$ is $C_{1-6}$alkyl;

One of $R^2$ and $R^3$ is phenyl, which is once or twice or three times substituted by halogen; and the other one is hydrogen;

$R^4$ is

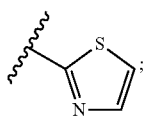

A is

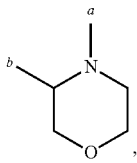

which is unsubstituted or substituted by $C_{1-6}$alkyl.

A further embodiment of present invention is (viii) a compound of formula I or pharmaceutically acceptable salts, or enantiomers, or diastereomers thereof, wherein $R^1$ is methyl or ethyl;

One of $R^2$ and $R^3$ is phenyl, which is once or twice or three times substituted by fluoro, chloro or bromo; and the other one is hydrogen;

$R^4$ is

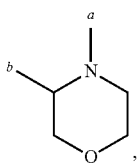

A is

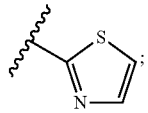 [SMILES: *c1nccs1]

which is unsubstituted or substituted by methyl.

A further embodiment of present invention is (ix) a compound of formula I or pharmaceutically acceptable salts, or enantiomers, or diastereomers thereof, wherein $R^1$ is methyl or ethyl;

One of $R^2$ and $R^3$ is

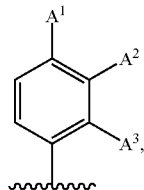

and the other one is hydrogen, wherein $A^1$ is hydrogen or fluoro;

$A^2$ is hydrogen or fluoro;

$A^3$ is fluoro, chloro or bromo; provided that at least one of $A^1$ and $A^2$ is hydrogen;

$R^4$ is

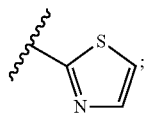 [SMILES: *c1nccs1]

A is

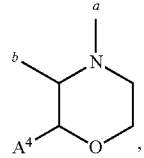

wherein $A^4$ is hydrogen or methyl.

Another embodiment of present invention is (x) a compound of formula I, wherein $R^1$ is $C_{1-6}$alkyl or trifluoromethyl-$C_xH_{2x}$—, wherein x is 1-6;

One of $R^2$ and $R^3$ is phenyl, which is once or twice or three times substituted by $C_{1-6}$alkyl, cyano or halogen; and the other one is hydrogen or deuterium;

$R^4$ is thiazolyl, oxazolyl, imidazolyl, thienyl or pyridinyl, which is unsubstituted or substituted by $C_{1-6}$alkyl, $C_{1-6}$alkyl-sulfanyl, halogen or cycloalkyl, where said $C_{1-6}$alkyl can be further optionally substituted with halogen;

A is

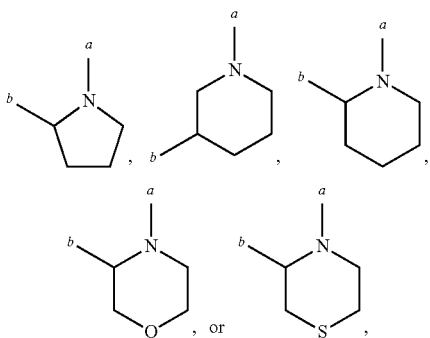

which is unsubstituted or substituted by groups selected from $C_{1-6}$alkyl, deuterium and halogen; or pharmaceutically acceptable salts, or enantiomers, or diastereomers thereof.

Further embodiment of present invention is (xi) a compound of formula I, wherein $R^1$ is methyl, ethyl, propyl, isopropyl or trifluoromethylmethyl;

One of $R^2$ and $R^3$ is phenyl, which is once or twice or three times substituted by fluoro, chloro, bromo, methyl, or cyano; and the other one is hydrogen or deuterium;

$R^4$ is thiazolyl, oxazolyl, imidazolyl, thienyl or pyridinyl, which is unsubstituted or substituted by methyl, isopropyl, trifluoromethyl, cyclopropyl, methylsulfanyl, fluoro or chloro;

A is

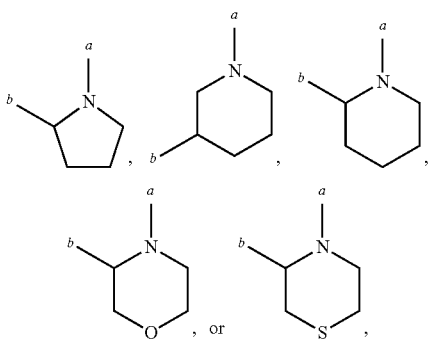

which is unsubstituted or substituted by groups selected from methyl, deuterium and fluoro; or pharmaceutically acceptable salts, or enantiomers, or diastereomers thereof.

Another embodiment of present invention is (xii) a compound of formula I, wherein $R^1$ is $C_{1-6}$alkyl or trifluoromethyl-$C_xH_{2x}$—, wherein x is 1-6;

One of $R^2$ and $R^3$ is phenyl, which is once or twice or three times substituted by $C_{1-6}$alkyl or halogen; and the other one is hydrogen or deuterium;

$R^4$ is thiazolyl, oxazolyl, imidazolyl, thienyl or pyridinyl, which is unsubstituted or substituted by $C_{1-6}$alkyl, $C_{1-6}$alkyl-sulfanyl, halogen or cycloalkyl, where said $C_{1-6}$alkyl can be further optionally substituted with halogen;

A is

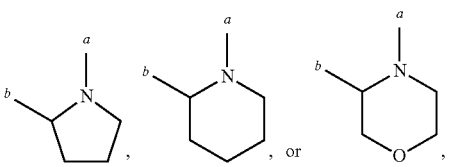

which is unsubstituted or substituted by groups selected from $C_{1-6}$alkyl, deuterium and halogen;

or pharmaceutically acceptable salts, or enantiomers, or diastereomers thereof.

Further embodiment of present invention is (xiii) a compound of formula I, wherein $R^1$ is methyl, ethyl, isopropyl or trifluoromethylmethyl;

One of $R^2$ and $R^3$ is phenyl, which is once or twice or three times substituted by fluoro, chloro, bromo, iodo or methyl; and the other one is hydrogen or deuterium;

$R^4$ is thiazolyl, oxazolyl, imidazolyl, thienyl or pyridinyl, which is unsubstituted or substituted by methyl, isopropyl, trifluoromethyl, cyclopropyl, methylsulfanyl or fluoro;

A is

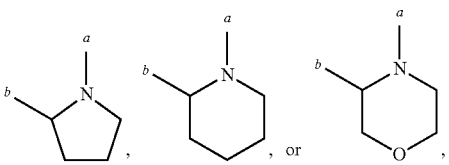

which is unsubstituted or substituted by groups selected from methyl, isopropyl, deuterium and fluoro;

or pharmaceutically acceptable salts, or enantiomers, or diastereomers thereof.

Another embodiment of present invention is (xiv) a compound of formula I or pharmaceutically acceptable salts, or enantiomers, or diastereomers thereof, wherein $R^1$ is $C_{1-6}$alkyl or trifluoromethyl-$C_xH_{2x}$—, wherein x is 1-6;

One of $R^2$ and $R^3$ is phenyl, which is once or twice or three times substituted by halogen; and the other one is hydrogen or deuterium;

$R^4$ is

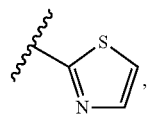 [SMILES: *c1nccs1]

which is unsubstituted or substituted by $C_{1-6}$alkyl, $C_{1-6}$alkyl-sulfanyl or cycloalkyl, where said $C_{1-6}$alkyl can be further optionally substituted with halogen;

A is

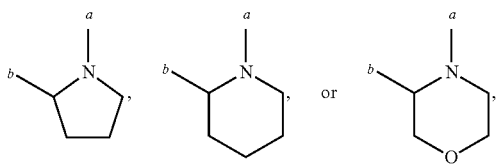

which is unsubstituted or substituted by groups selected from $C_{1-6}$alkyl, deuterium and halogen.

Further embodiment of present invention is (xv) a compound of formula I or pharmaceutically acceptable salts, or enantiomers, or diastereomers thereof, wherein $R^1$ is methyl, ethyl, propyl, isopropyl or trifluoromethylmethyl;

One of $R^2$ and $R^3$ is phenyl, which is once or twice or three times substituted by fluoro, chloro, bromo or iodo; and the other one is hydrogen or deuterium;

$R^4$ is

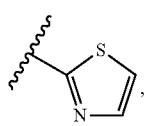

which is unsubstituted or substituted by methyl, isopropyl, trifluoromethyl, cyclopropyl or methylsulfanyl;

A is

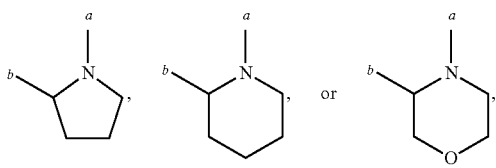

which is unsubstituted or substituted by groups selected from methyl, isopropyl, deuterium and fluoro.

Another embodiment of present invention is (xvi) a compound of formula I or pharmaceutically acceptable salts, or enantiomers, or diastereomers thereof, wherein $R^1$ is $C_{1-6}$alkyl;

One of $R^2$ and $R^3$ is

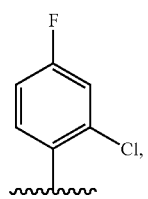 [SMILES: *c1ccc(F)cc1Cl]

and the other one is hydrogen;

$R^4$ is

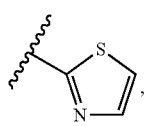

which is unsubstituted or substituted by $C_{1-6}$alkyl;

A is

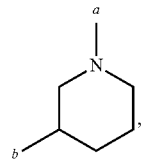

which is substituted by halogen.

Another embodiment of present invention is (xvii) a compound of formula I or pharmaceutically acceptable salts, or enantiomers, or diastereomers thereof, wherein $R^1$ is $C_{1-6}$alkyl;

One of $R^2$ and $R^3$ is phenyl, which is substituted by halogen; and the other one is hydrogen;

$R^4$ is

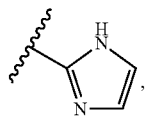

which is substituted by $C_{1-6}$alkyl;

A is

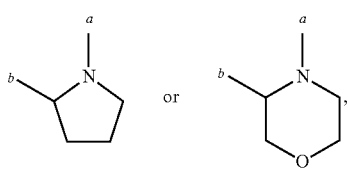

which is unsubstituted or substituted by halogen.

Further embodiment of present invention is (xviii) a compound of formula I or pharmaceutically acceptable salts, or enantiomers, or diastereomers thereof, wherein $R^1$ is methyl or ethyl;

One of $R^2$ and $R^3$ is phenyl, which is substituted by fluoro or chloro; and the other one is hydrogen;

$R^4$ is

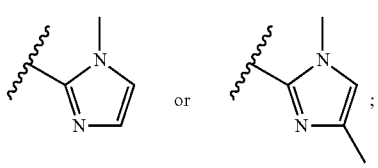

A is

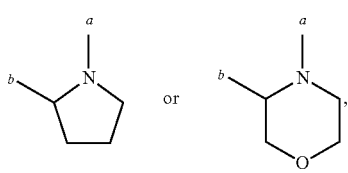

which is unsubstituted or substituted by fluoro.

Another embodiment of present invention is (xix) a compound of formula I or pharmaceutically acceptable salts, or enantiomers, or diastereomers thereof, wherein $R^1$ is $C_{1-6}$alkyl;

One of $R^2$ and $R^3$ is phenyl, which is substituted by halogen; and the other one is hydrogen;

$R^4$ is

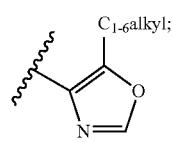

A is

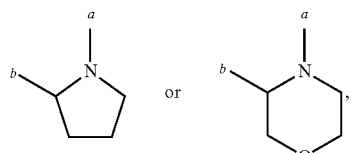

which is unsubstituted or substituted by halogen.

Further embodiment of present invention is (xx) a compound of formula I or pharmaceutically acceptable salts, or enantiomers, or diastereomers thereof, wherein $R^1$ is methyl or ethyl;

One of $R^2$ and $R^3$ is phenyl, which is substituted by fluoro, chloro or bromo; and the other one is hydrogen;

$R^4$ is

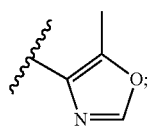

A is

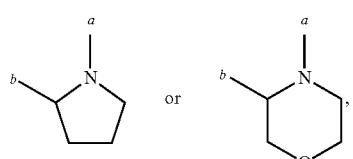

which is unsubstituted or substituted by fluoro.

Another embodiment of present invention is (xxi) a compound of formula Ib or pharmaceutically acceptable salts, or enantiomers, or diastereomers thereof,

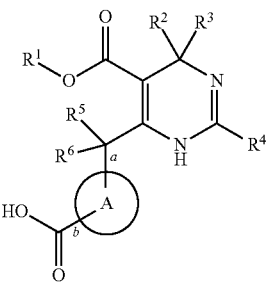

wherein $R^1$ is $C_{1-6}$alkyl;

One of $R^2$ and $R^3$ is phenyl, which is twice or thrice substituted by cyano or halogen; and the other one is hydrogen or deuterium;

$R^4$ is phenyl, thiazolyl, oxazolyl, imidazolyl, thienyl or pyridinyl; which is unsubstituted or once or twice substituted by $C_{1-6}$alkyl, halogen, cycloalkyl or trifluoromethyl;

$R^5$ is hydrogen;

$R^6$ is hydrogen;

A is

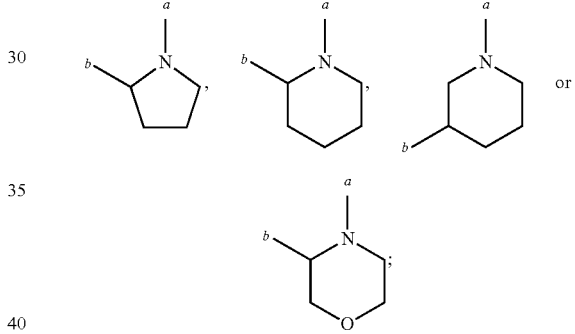

which is unsubstituted or twice or four times substituted by deuterium or halogen.

Further embodiment of present invention is (xxii) a compound of formula Ib or pharmaceutically acceptable salts, or enantiomers, or diastereomers thereof, wherein $R^1$ is methyl or ethyl;

One of $R^2$ and $R^3$ is phenyl, which is twice or thrice substituted by cyano, fluoro, chloro or bromo; and the other one is hydrogen or deuterium;

$R^4$ is phenyl, thiazolyl, oxazolyl, imidazolyl, thienyl or pyridinyl; which is unsubstituted or once or twice substituted by methyl, isopropyl, tert-butyl, fluoro, chloro, cyclopropyl or trifluoromethyl;

$R^5$ is hydrogen;

$R^6$ is hydrogen;

A is

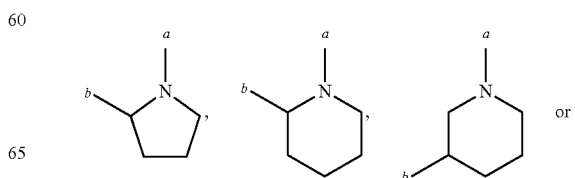

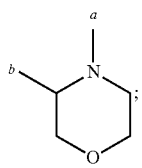

which is unsubstituted or twice or four times substituted by deuterium or fluoro.

Another embodiment of present invention is (xxiii) a compound of formula Ib or pharmaceutically acceptable salts, or enantiomers, or diastereomers thereof, wherein $R^1$ is $C_{1-6}$alkyl;

One of $R^2$ and $R^3$ is phenyl, which is twice or thrice substituted by cyano or halogen; and the other one is hydrogen or deuterium;

$R^4$ is thiazolyl or imidazolyl; which is unsubstituted or once or twice substituted by $C_{1-6}$alkyl, halogen, cycloalkyl or trifluoromethyl;

$R^5$ is hydrogen;

$R^6$ is hydrogen;

A is

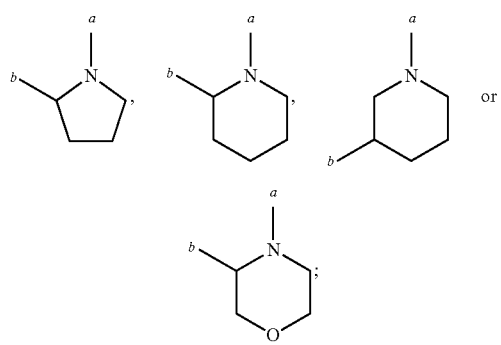

which is unsubstituted or twice or four times substituted by deuterium or halogen.

Further embodiment of present invention is (xxiv) a compound of formula Ib or pharmaceutically acceptable salts, or enantiomers, or diastereomers thereof, wherein $R^1$ is methyl or ethyl;

One of $R^2$ and $R^3$ is phenyl, which is twice or thrice substituted by cyano, fluoro, chloro or bromo; and the other one is hydrogen or deuterium;

$R^4$ is thiazolyl or imidazolyl; which is unsubstituted or once or twice substituted by methyl, isopropyl, tert-butyl, cyclopropyl or trifluoromethyl;

$R^5$ is hydrogen;

$R^6$ is hydrogen;

A is

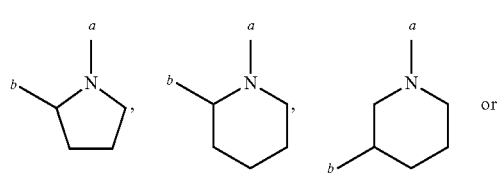

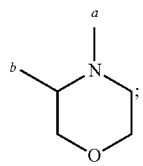

which is unsubstituted or twice or four times substituted by deuterium or fluoro.

Another embodiment of present invention is (xxv) a compound of formula Ib or pharmaceutically acceptable salts, or enantiomers, or diastereomers thereof, wherein $R^1$ is $C_{1-6}$alkyl;

One of $R^2$ and $R^3$ is phenyl, which is twice substituted by halogen; and the other one is hydrogen;

$R^4$ is phenyl, oxazolyl, thienyl or pyridinyl; which is unsubstituted or once or twice substituted by $C_{1-6}$alkyl, halogen, cycloalkyl or trifluoromethyl;

$R^5$ is hydrogen;

$R^6$ is hydrogen;

A is

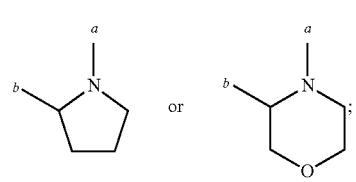

which is unsubstituted or twice substituted by halogen.

Further embodiment of present invention is (xxvi) a compound of formula Ib or pharmaceutically acceptable salts, or enantiomers, or diastereomers thereof, wherein $R^1$ is methyl;

One of $R^2$ and $R^3$ is phenyl, which is twice substituted by fluoro or chloro; and the other one is hydrogen;

$R^4$ is phenyl, oxazolyl, thienyl or pyridinyl; which is once or twice substituted by methyl, fluoro or chloro;

$R^5$ is hydrogen;

$R^6$ is hydrogen;

A is

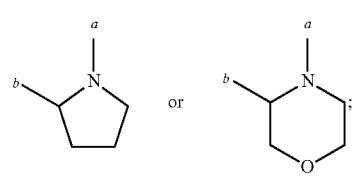

which is unsubstituted or twice substituted by fluoro.

Particular compounds of formula I, including NMR data and MS data are summarized in the following Table 1 and 2.

TABLE 1

Structure and name of particular compounds

| Example No. | Structure | Name |
|---|---|---|
| 1 | 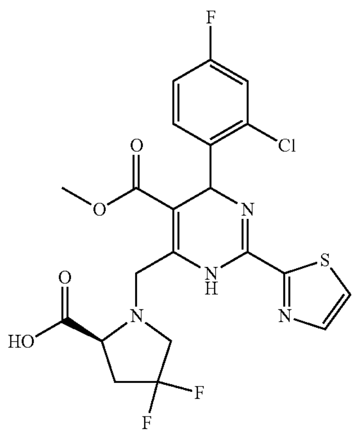 [SMILES: COC(=O)C1=C(CN2CC(F)(F)C[C@H]2C(=O)O)NC(c2nccs2)=NC1c1ccc(F)cc1Cl] | 6-((S)-2-Carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester |
| 2 | 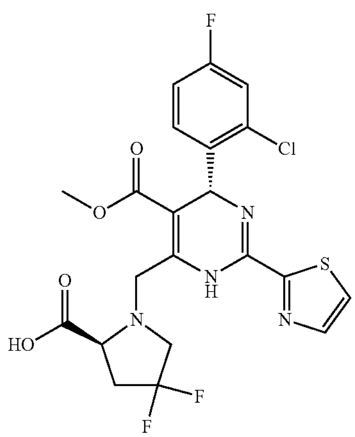 [SMILES: COC(=O)C1=C(CN2CC(F)(F)C[C@H]2C(=O)O)NC(c2nccs2)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester |
| 3 | 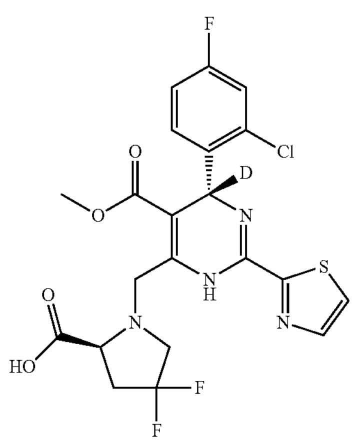 [SMILES: [2H][C@@]1(c2ccc(F)cc2Cl)N=C(c2nccs2)NC(CN2CC(F)(F)C[C@H]2C(=O)O)=C1C(=O)OC] | (S)-6-((S)-2-Carboxy-4,4-difluoro-pyrrolidin-1-ylmethyl)-4-(2-chloro-4-fluoro-phenyl)-[4-$^2$H]-2-thiazol-2-yl-1,4-dihydro-pyrimidine-5-carboxylic acid methyl ester |

TABLE 1-continued

Structure and name of particular compounds

| Example No. | Structure | Name |
|---|---|---|
| 4 | 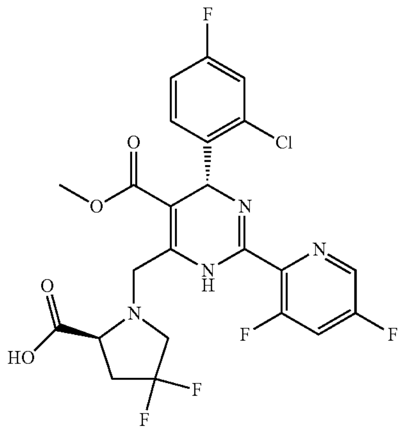 [SMILES: COC(=O)C1=C(CN2CC(F)(F)C[C@H]2C(=O)O)NC(c2ncc(F)cc2F)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-(3,5-difluoro-pyridin-2-yl)-1,4-dihydro-pyrimidine-5-carboxylic acid methyl ester |
| 5 | 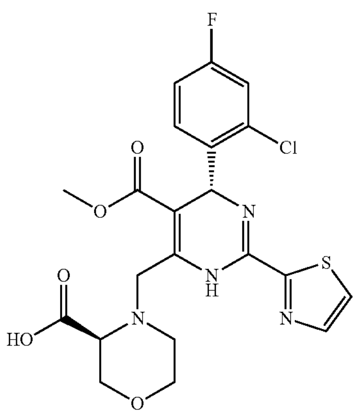 [SMILES: COC(=O)C1=C(CN2CCOC[C@H]2C(=O)O)NC(c2nccs2)=N[C@H]1c1ccc(F)cc1Cl] | (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid |
| 6 | 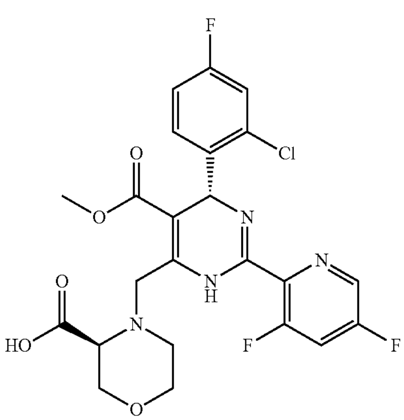 [SMILES: COC(=O)C1=C(CN2CCOC[C@H]2C(=O)O)NC(c2ncc(F)cc2F)=N[C@H]1c1ccc(F)cc1Cl] | (S)-4-[(R)-6-(2-Chloro-4-fluoro-phenyl)-2-(3,5-difluoro-pyridin-2-yl)-5-methoxycarbonyl-3,6-dihydro-pyrimidin-4-ylmethyl]-morpholine-3-carboxylic acid |

TABLE 1-continued

Structure and name of particular compounds

| Example No. | Structure | Name |
|---|---|---|
| 7 | 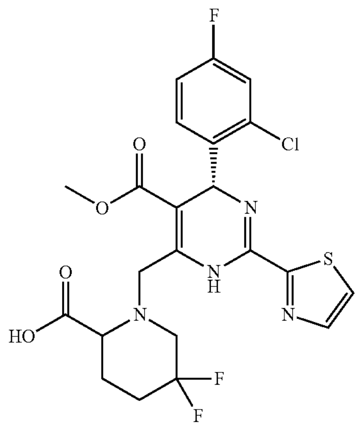 [SMILES: COC(=O)C1=C(CN2CC(F)(F)CCC2C(=O)O)NC(c2nccs2)=N[C@H]1c1ccc(F)cc1Cl] | (R)-6-(2-Carboxy-5,5-difluoro-piperidin-1-ylmethyl)-4-(2-chloro-4-fluoro-phenyl)-2-thiazol-2-yl-1,4-dihydro-pyrimidine-5-carboxylic acid methyl ester |
| 8 | 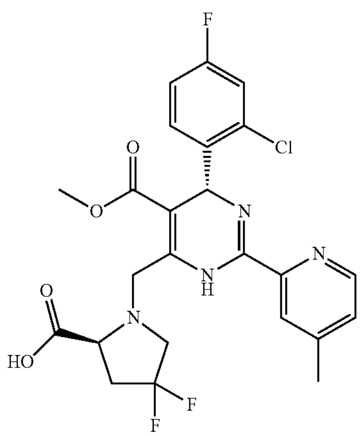 [SMILES: COC(=O)C1=C(CN2CC(F)(F)C[C@H]2C(=O)O)NC(c2cc(C)ccn2)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-(4-methyl-pyridin-2-yl)-1,4-dihydro-pyrimidine-5-carboxylic acid methyl ester |
| 9 | 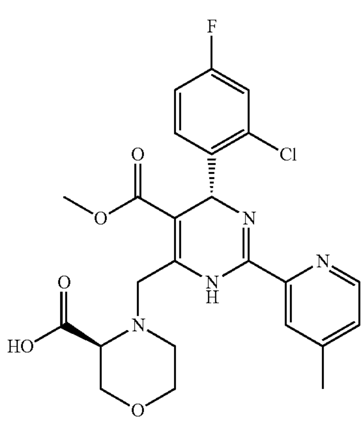 [SMILES: COC(=O)C1=C(CN2CCOC[C@H]2C(=O)O)NC(c2cc(C)ccn2)=N[C@H]1c1ccc(F)cc1Cl] | (S)-4-[(R)-6-(2-Chloro-4-fluoro-phenyl)-5-methoxycarbonyl-2-(4-methyl-pyridin-2-yl)-3,6-dihydro-pyrimidin-4-ylmethyl]-morpholine-3-carboxylic acid |

TABLE 1-continued

Structure and name of particular compounds

| Example No. | Structure | Name |
|---|---|---|
| 10 | 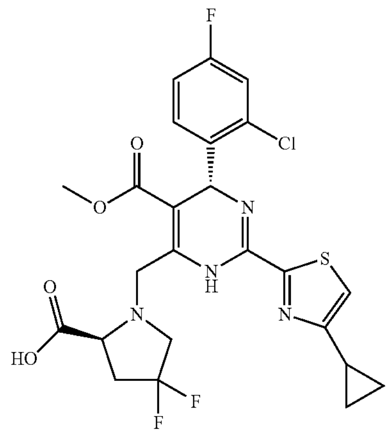 [SMILES: COC(=O)C1=C(CN2CC(F)(F)C[C@H]2C(=O)O)NC(c2nc(C3CC3)cs2)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-(4-cyclopropyl-thiazol-2-yl)-1,4-dihydro-pyrimidine-5-carboxylic acid methyl ester |
| 11 | 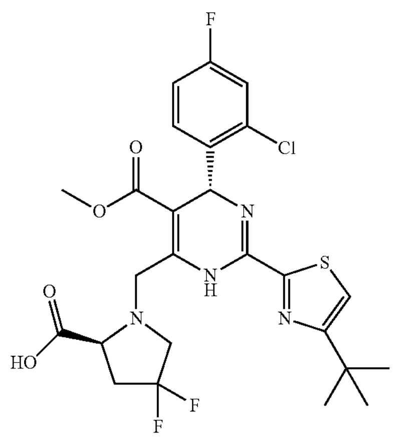 [SMILES: COC(=O)C1=C(CN2CC(F)(F)C[C@H]2C(=O)O)NC(c2nc(C(C)(C)C)cs2)=N[C@H]1c1ccc(F)cc1Cl] | (R)-2-(4-tert-Butyl-thiazol-2-yl)-6((S)-2-carboxy-4,4-difluoro-pyrrolidin-1-ylmethyl)-4-(2-chloro-4-fluoro-phenyl)-1,4-dihydro-pyrimidine-5-carboxylic acid methyl ester |
| 12 | 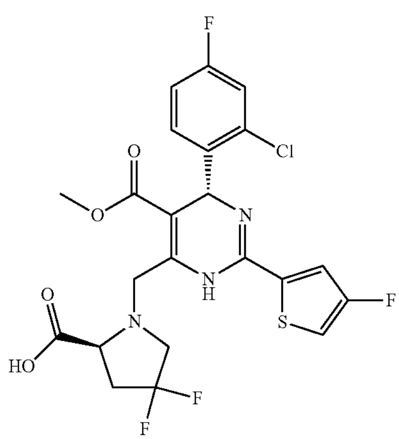 [SMILES: COC(=O)C1=C(CN2CC(F)(F)C[C@H]2C(=O)O)NC(c2cc(F)cs2)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-(4-fluoro-thiophen-2-yl)-1,4-dihydro-pyrimidine-5-carboxylic acid methyl ester |

TABLE 1-continued

Structure and name of particular compounds

| Example No. | Structure | Name |
|---|---|---|
| 13 | 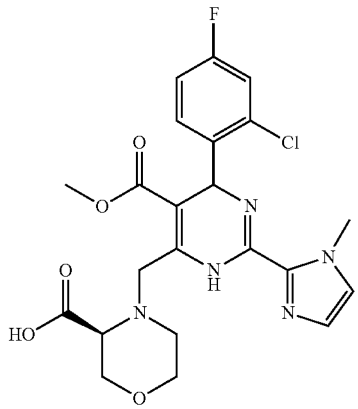 [SMILES: COC(=O)C1=C(CN2CCOC[C@H]2C(=O)O)NC(c2nccn2C)=NC1c1ccc(F)cc1Cl] | (S)-4-[6-(2-Chloro-4-fluoro-phenyl)-5-methoxycarbonyl-2-(1-methyl-1H-imidazol-2-yl)-3,6-dihydro-pyrimidin-4-ylmethyl]-morpholine-3-carboxylic acid |
| 14 | 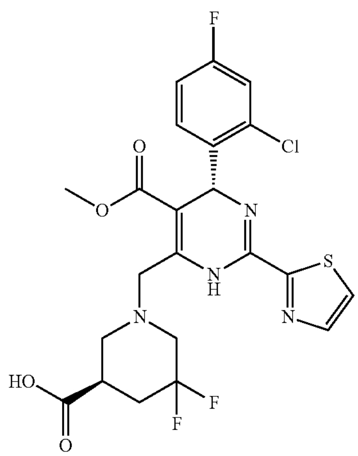 [SMILES: COC(=O)C1=C(CN2C[C@H](C(=O)O)CC(F)(F)C2)NC(c2nccs2)=N[C@H]1c1ccc(F)cc1Cl] | (R)-6-((R)-5-Carboxy-3,3-difluoro-piperidin-1-ylmethyl)-4-(2-chloro-4-fluoro-phenyl)-2-thiazol-2-yl-1,4-dihydro-pyrimidine-5-carboxylic acid methyl ester |
| 15 | 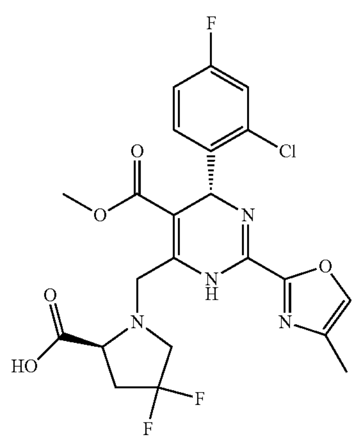 | (R)-6-((S)-2-Carboxy-4,4-difluoro-pyrrolidin-1-ylmethyl)-4-(2-chloro-4-fluoro-phenyl)-2-(4-methyl-oxazol-2-yl)-1,4-dihydro-pyrimidine-5-carboxylic acid methyl ester |

TABLE 1-continued

Structure and name of particular compounds

| Example No. | Structure | Name |
|---|---|---|
| 16 | 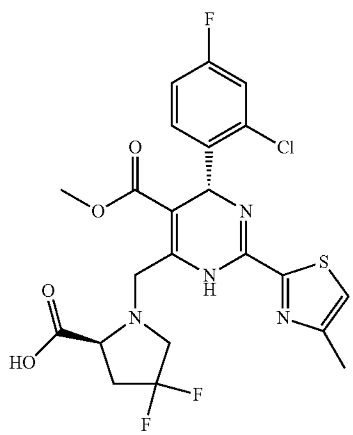 [SMILES: COC(=O)C1=C(CN2CC(F)(F)C[C@H]2C(=O)O)NC(c2nc(C)cs2)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-(4-methyl-thiazol-2-yl)-1,4-dihydro-pyrimidine-5-carboxylic acid methyl ester |
| 17 | 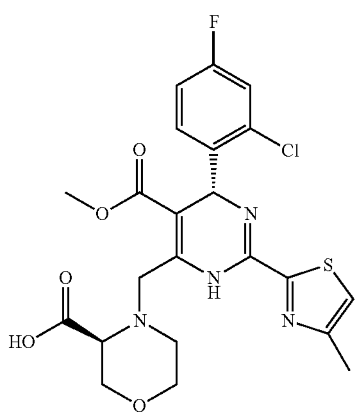 [SMILES: COC(=O)C1=C(CN2CCOC[C@H]2C(=O)O)NC(c2nc(C)cs2)=N[C@H]1c1ccc(F)cc1Cl] | (S)-4-[(R)-6-(2-Chloro-4-fluoro-phenyl)-5-methoxycarbonyl-2-(4-methyl-thiazol-2-yl)-3,6-dihydro-pyrimidin-4-ylmethyl]-morpholine-3-carboxylic acid |
| 18 | 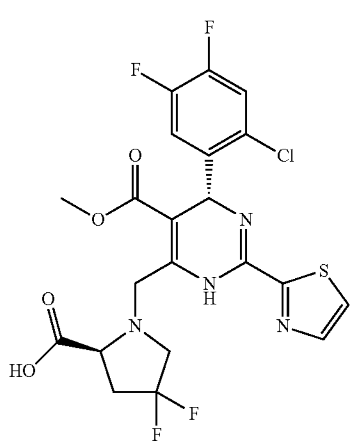 [SMILES: COC(=O)C1=C(CN2CC(F)(F)C[C@H]2C(=O)O)NC(c2nccs2)=N[C@H]1c1cc(F)c(F)cc1Cl] | (R)-6-((S)-2-Carboxy-4,4-difluoro-pyrrolidin-1-ylmethyl)-4-(2-chloro-4,5-difluoro-phenyl)-2-thiazol-2-yl-1,4-dihydro-pyrimidine-5-carboxylic acid methyl ester |

TABLE 1-continued

Structure and name of particular compounds

| Example No. | Structure | Name |
|---|---|---|
| 19 | 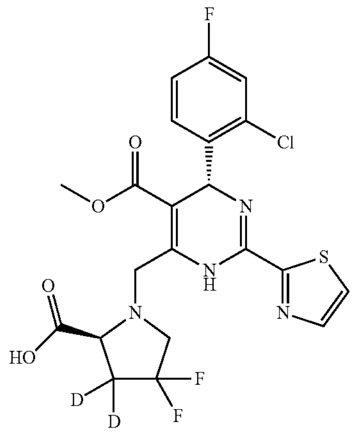 [SMILES: [2H]C1([2H])[C@@H](C(=O)O)N(CC2=C(C(=O)OC)[C@H](c3ccc(F)cc3Cl)N=C(c3nccs3)N2)CC1(F)F] | (R)-6-((S)-2-Carboxy-[3,3-²H2]-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester |
| 20 | 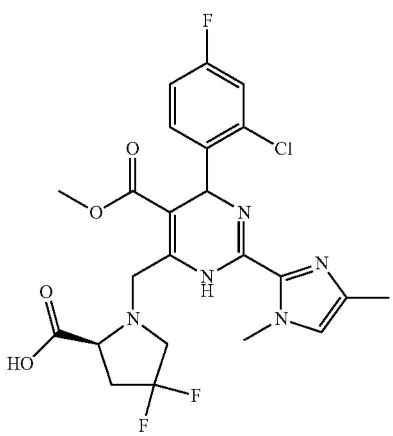 [SMILES: COC(=O)C1=C(CN2CC(F)(F)C[C@H]2C(=O)O)NC(c2nc(C)cn2C)=NC1c1ccc(F)cc1Cl] | 6-((S)-2-Carboxy-4,4-difluoro-pyrrolidin-1-ylmethyl)-4-(2-chloro-4-fluoro-phenyl)-2-(1,4-dimethyl-1H-imidazol-2-yl)-1,4-dihydro-pyrimidine-5-carboxylic acid methyl ester |
| 21 | 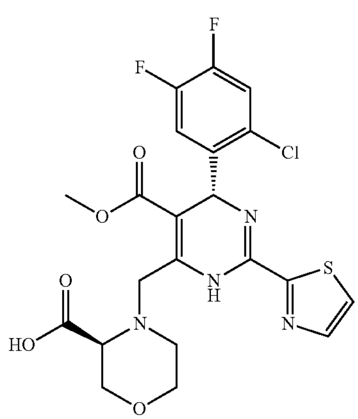 [SMILES: COC(=O)C1=C(CN2CCOC[C@H]2C(=O)O)NC(c2nccs2)=N[C@H]1c1cc(F)c(F)cc1Cl] | (S)-4-[(R)-6-(2-Chloro-4,5-difluoro-phenyl)-5-methoxycarbonyl-2-thiazol-2-yl-3,6-dihydro-pyrimidin-4-ylmethyl]-morpholine-3-carboxylic acid |

TABLE 1-continued

Structure and name of particular compounds

| Example No. | Structure | Name |
|---|---|---|
| 22 | 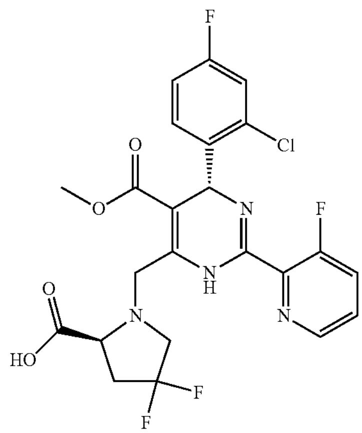 [SMILES: COC(=O)C1=C(CN2CC(F)(F)C[C@H]2C(=O)O)NC(c2ncccc2F)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-(3-fluoro-pyridin-2-yl)-1,4-dihydro-pyrimidine-5-carboxylic acid methyl ester |
| 23 | 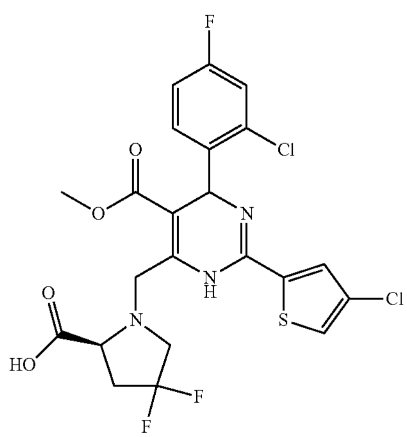 [SMILES: COC(=O)C1=C(CN2CC(F)(F)C[C@H]2C(=O)O)NC(c2cc(Cl)cs2)=NC1c1ccc(F)cc1Cl] | (R)-6-((S)-2-Carboxy-4,4-difluoro-pyrrolidin-1-ylmethyl)-4-(2-chloro-4-fluoro-phenyl)-2-(4-chloro-thiophen-2-yl)-1,4-dihydro-pyrimidine-5-carboxylic acid methyl ester |
| 24 | 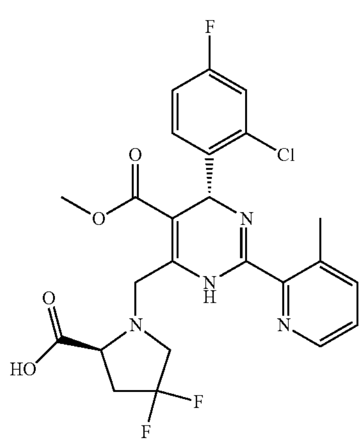 [SMILES: COC(=O)C1=C(CN2CC(F)(F)C[C@H]2C(=O)O)NC(c2ncccc2C)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-(3-methyl-pyridin-2-yl)-1,4-dihydro-pyrimidine-5-carboxylic acid methyl ester |

TABLE 1-continued

Structure and name of particular compounds

| Example No. | Structure | Name |
|---|---|---|
| 25 | 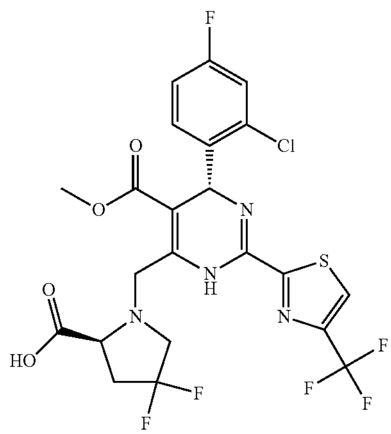 [SMILES: COC(=O)C1=C(CN2CC(F)(F)C[C@H]2C(=O)O)NC(c2nc(C(F)(F)F)cs2)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-(4-trifluoromethyl-thiazol-2-yl)-1,4-dihydro-pyrimidine-5-carboxylic acid methyl ester |
| 26 | 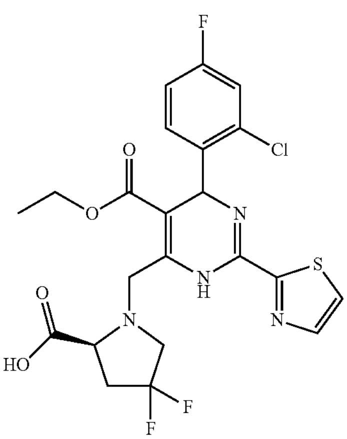 [SMILES: CCOC(=O)C1=C(CN2CC(F)(F)C[C@H]2C(=O)O)NC(c2nccs2)=NC1c1ccc(F)cc1Cl] | 6-((S)-2-Carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid ethyl ester |
| 27 | 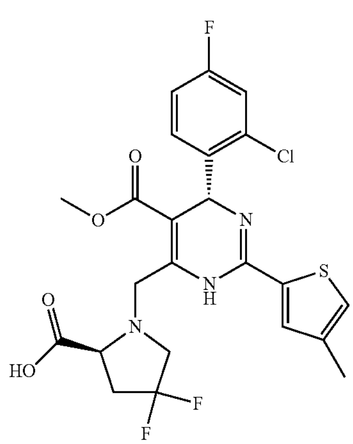 [SMILES: COC(=O)C1=C(CN2CC(F)(F)C[C@H]2C(=O)O)NC(c2cc(C)cs2)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-(4-methyl-thiophen-2-yl)-1,4-dihydro-pyrimidine-5-carboxylic acid methyl ester |

TABLE 1-continued

Structure and name of particular compounds

| Example No. | Structure | Name |
|---|---|---|
| 28 | 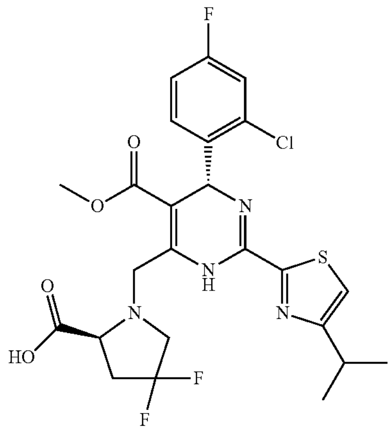 [SMILES: COC(=O)C1=C(CN2CC(F)(F)C[C@H]2C(=O)O)NC(c2nc(C(C)C)cs2)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-(4-isopropyl-thiazol-2-yl)-1,4-dihydro-pyrimidine-5-carboxylic acid methyl ester |
| 29 | 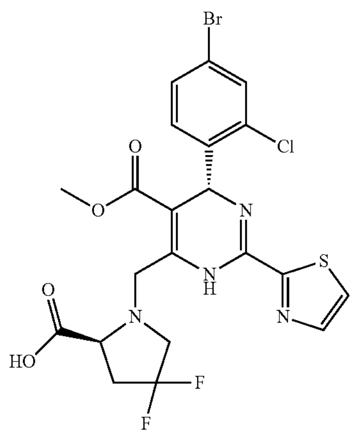 [SMILES: COC(=O)C1=C(CN2CC(F)(F)C[C@H]2C(=O)O)NC(c2nccs2)=N[C@H]1c1ccc(Br)cc1Cl] | (R)-4-(4-Bromo-2-chloro-phenyl)-6-((S)-2-carboxy-4,4-difluoro-pyrrolidin-1-ylmethyl)-2-thiazol-2-yl-1,4-dihydro-pyrimidine-5-carboxylic acid methyl ester |
| 30 | 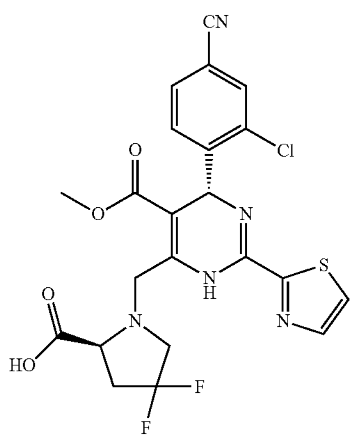 [SMILES: COC(=O)C1=C(CN2CC(F)(F)C[C@H]2C(=O)O)NC(c2nccs2)=N[C@H]1c1ccc(C#N)cc1Cl] | (R)-6-((S)-2-Carboxy-4,4-difluoro-pyrrolidin-1-ylmethyl)-4-(2-chloro-4-cyano-phenyl)-2-thiazol-2-yl-1,4-dihydro-pyrimidine-5-carboxylic acid methyl ester |

TABLE 1-continued

Structure and name of particular compounds

| Example No. | Structure | Name |
|---|---|---|
| 31 | 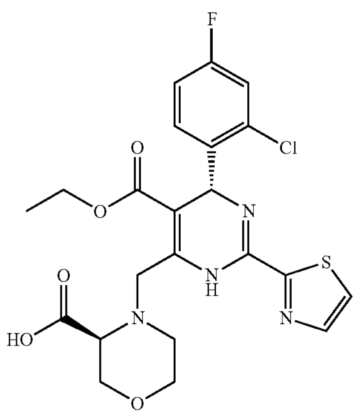 [SMILES: CCOC(=O)C1=C(CN2CCOC[C@H]2C(=O)O)NC(c2nccs2)=N[C@H]1c1ccc(F)cc1Cl] | (S)-4-[(R)-6-(2-Chloro-4-fluoro-phenyl)-5-ethoxycarbonyl-2-thiazol-2-yl-3,6-dihydro-pyrimidin-4-ylmethyl]-morpholine-3-carboxylic acid |
| 32 | 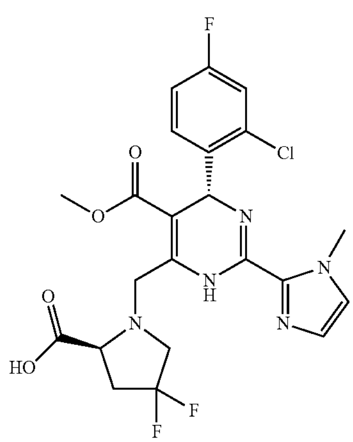 [SMILES: COC(=O)C1=C(CN2CC(F)(F)C[C@H]2C(=O)O)NC(c2nccn2C)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-(1-methyl-1H-imidazol-2-yl)-1,4-dihydro-pyrimidine-5-carboxylic acid methyl ester |
| 33 | 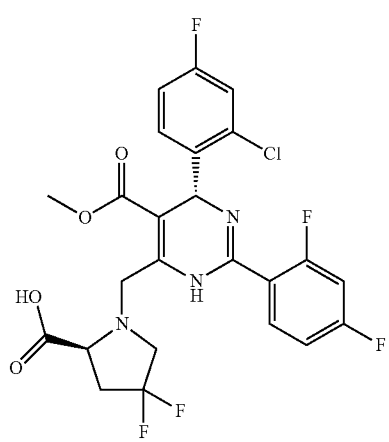 [SMILES: COC(=O)C1=C(CN2CC(F)(F)C[C@H]2C(=O)O)NC(c2ccc(F)cc2F)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-(2,4-difluoro-phenyl)-1,4-dihydro-pyrimidine-5-carboxylic acid methyl ester |

TABLE 1-continued

Structure and name of particular compounds

| Example No. | Structure | Name |
|---|---|---|
| 34 | 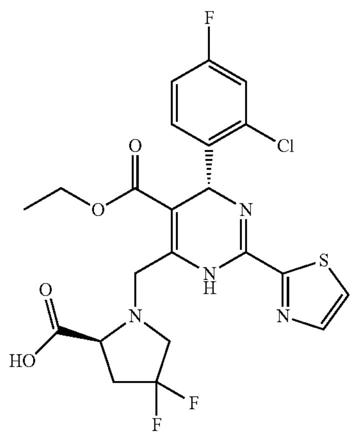 [SMILES: CCOC(=O)C1=C(CN2CC(F)(F)C[C@H]2C(=O)O)NC(c2nccs2)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid ethyl ester |
| 35 | 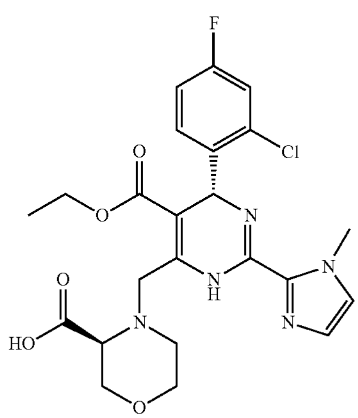 [SMILES: CCOC(=O)C1=C(CN2CCOC[C@H]2C(=O)O)NC(c2nccn2C)=N[C@H]1c1ccc(F)cc1Cl] | (S)-4-[(R)-6-(2-Chloro-4-fluoro-phenyl)-5-ethoxycarbonyl-2-(1-methyl-1H-imidazol-2-yl)-3,6-dihydro-pyrimidin-4-ylmethyl]-morpholine-3-carboxylic acid |
| 36 | 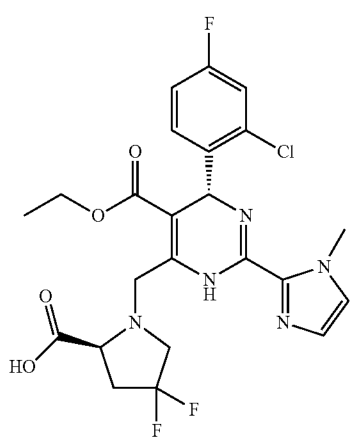 [SMILES: CCOC(=O)C1=C(CN2CC(F)(F)C[C@H]2C(=O)O)NC(c2nccn2C)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-(1-methyl-1H-imidazol-2-yl)-1,4-dihydro-pyrimidine-5-carboxylic acid ethyl ester |

TABLE 1-continued

Structure and name of particular compounds

| Example No. | Structure | Name |
|---|---|---|
| 37 | 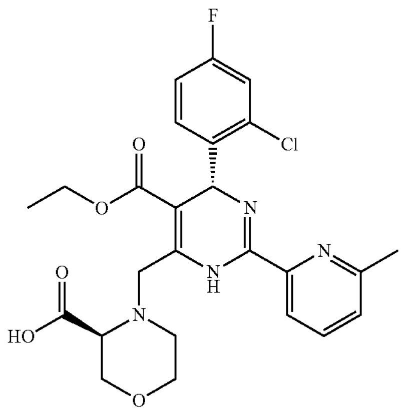 [SMILES: CCOC(=O)C1=C(CN2CCOC[C@H]2C(=O)O)NC(c2cccc(C)n2)=N[C@H]1c1ccc(F)cc1Cl] | (S)-4-[(R)-6-(2-Chloro-4-fluoro-phenyl)-5-ethoxycarbonyl-2-(6-methyl-pyridin-2-yl)-3,6-dihydro-pyrimidin-4-ylmethyl]-morpholine-3-carboxylic acid |
| 38 | 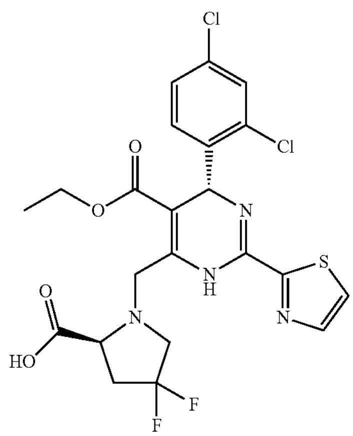 [SMILES: CCOC(=O)C1=C(CN2CC(F)(F)C[C@H]2C(=O)O)NC(c2nccs2)=N[C@H]1c1ccc(Cl)cc1Cl] | (R)-6-((S)-2-Carboxy-4,4-difluoro-pyrrolidin-1-ylmethyl)-4-(2,4-dichloro-phenyl)-2-thiazol-2-yl-1,4-dihydro-pyrimidine-5-carboxylic acid ethyl ester |
| 39 | 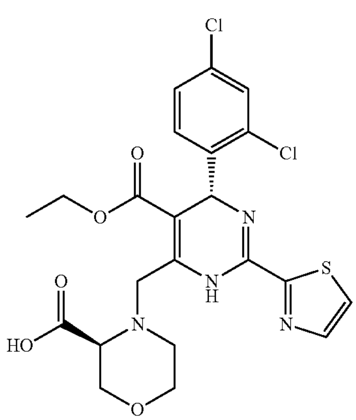 [SMILES: CCOC(=O)C1=C(CN2CCOC[C@H]2C(=O)O)NC(c2nccs2)=N[C@H]1c1ccc(Cl)cc1Cl] | (S)-4-[(R)-6-(2,4-Dichloro-phenyl)-5-ethoxycarbonyl-2-thiazol-2-yl-3,6-dihydro-pyrimidin-4-ylmethyl]-morpholine-3-carboxylic acid |

TABLE 1-continued

Structure and name of particular compounds

| Example No. | Structure | Name |
|---|---|---|
| 40 | 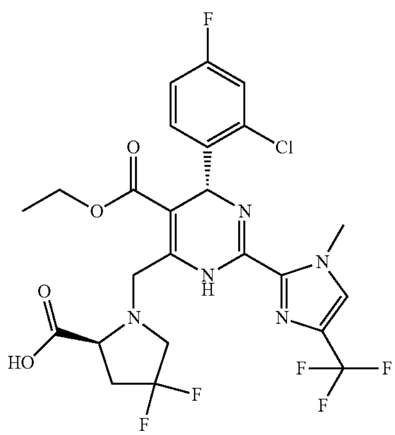 [SMILES: CCOC(=O)C1=C(CN2CC(F)(F)C[C@H]2C(=O)O)NC(c2nc(C(F)(F)F)cn2C)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-(1-methyl-4-trifluoromethyl-1H-imidazol-2-yl)-1,4-dihydro-pyrimidine-5-carboxylic acid ethyl ester |
| 41 | 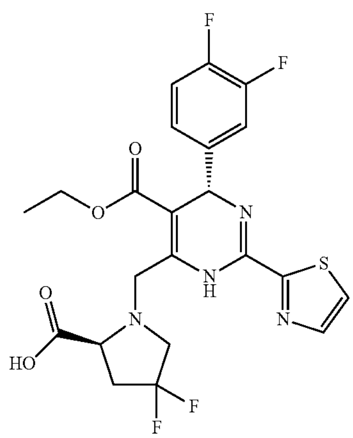 [SMILES: CCOC(=O)C1=C(CN2CC(F)(F)C[C@H]2C(=O)O)NC(c2nccs2)=N[C@H]1c1ccc(F)c(F)c1] | (S)-6-((S)-2-Carboxy-4,4-difluoro-pyrrolidin-1-ylmethyl)-4-(3,4-difluoro-phenyl)-2-thiazol-2-yl-1,4-dihydro-pyrimidine-5-carboxylic acid ethyl ester |
| 42 | 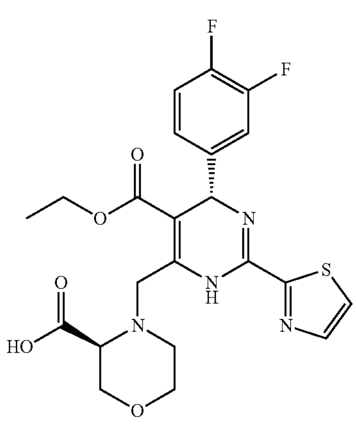 [SMILES: CCOC(=O)C1=C(CN2CCOC[C@H]2C(=O)O)NC(c2nccs2)=N[C@H]1c1ccc(F)c(F)c1] | (S)-4-[(S)-6-(3,4-Difluoro-phenyl)-5-ethoxycarbonyl-2-thiazol-2-yl-3,6-dihydro-pyrimidin-4-ylmethyl]-morpholine-3-carboxylic acid |

TABLE 1-continued

Structure and name of particular compounds

| Example No. | Structure | Name |
|---|---|---|
| 43 | 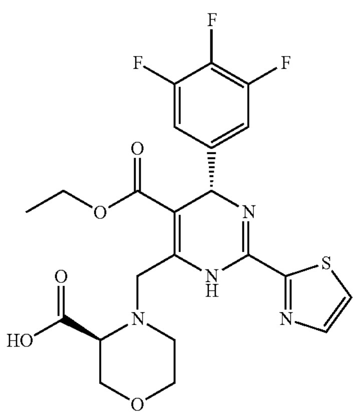 [SMILES: CCOC(=O)C1=C(CN2CCOC[C@H]2C(=O)O)NC(c2nccs2)=N[C@H]1c1cc(F)c(F)c(F)c1] | (S)-4-[(S)-5-Ethoxycarbonyl-2-thiazol-2-yl-6-(3,4,5-trifluoro-phenyl)-3,6-dihydro-pyrimidin-4-ylmethyl]-morpholine-3-carboxylic acid |
| 44 | 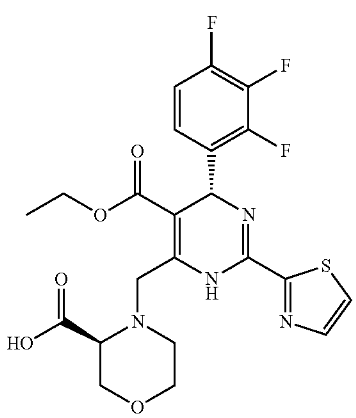 [SMILES: CCOC(=O)C1=C(CN2CCOC[C@H]2C(=O)O)NC(c2nccs2)=N[C@H]1c1ccc(F)c(F)c1F] | (S)-4-[(R)-5-Ethoxycarbonyl-2-thiazol-2-yl-6-(2,3,4-trifluoro-phenyl)-3,6-dihydro-pyrimidin-4-ylmethyl]-morpholine-3-carboxylic acid |
| 45 | 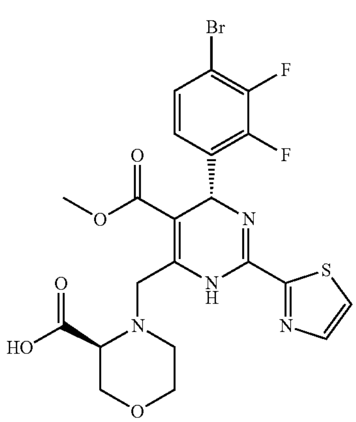 [SMILES: COC(=O)C1=C(CN2CCOC[C@H]2C(=O)O)NC(c2nccs2)=N[C@H]1c1ccc(Br)c(F)c1F] | (S)-4-[(R)-6-(4-Bromo-2,3-difluoro-phenyl)-5-methoxycarbonyl-2-thiazol-2-yl-3,6-dihydro-pyrimidin-4-ylmethyl]-morpholine-3-carboxylic acid |

TABLE 1-continued

Structure and name of particular compounds

| Example No. | Structure | Name |
|---|---|---|
| 46 | 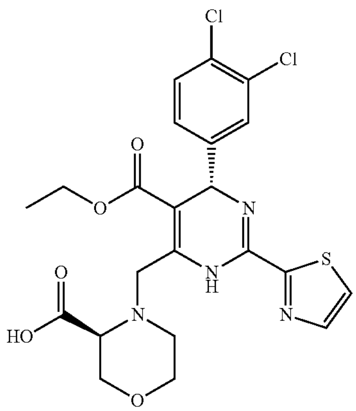 | (S)-4-[(S)-6-(3,4-Dichloro-phenyl)-5-ethoxycarbonyl-2-thiazol-2-yl-3,6-dihydro-pyrimidin-4-ylmethyl]-morpholine-3-carboxylic acid |
| 47 | 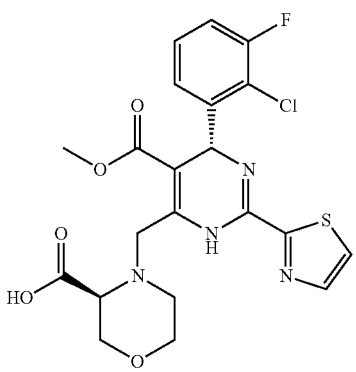 [SMILES: COC(=O)C1=C(CN2CCOC[C@H]2C(=O)O)NC(c2nccs2)=N[C@H]1c1cccc(F)c1Cl] | (S)-4-[(R)-6-(2-Chloro-3-fluoro-phenyl)-5-methoxycarbonyl-2-thiazol-2-yl-3,6-dihydro-pyrimidin-4-ylmethyl]-morpholine-3-carboxylic acid |
| 48 | 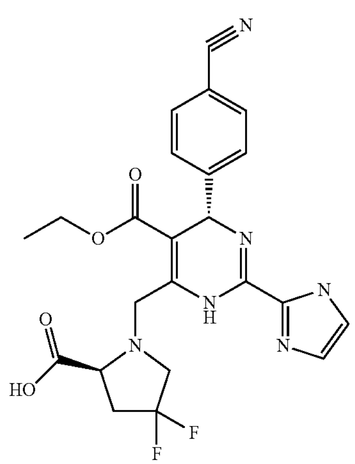 [SMILES: CCOC(=O)C1=C(CN2CC(F)(F)C[C@H]2C(=O)O)NC(c2ncc[nH]2)=N[C@H]1c1ccc(C#N)cc1] | (S)-6-((S)-2-Carboxy-4,4-difluoro-pyrrolidin-1-ylmethyl)-4-(4-cyano-phenyl)-2-thiazol-2-yl-1,4-dihydro-pyrimidine-5-carboxylic acid ethyl ester |

TABLE 1-continued

Structure and name of particular compounds

| Example No. | Structure | Name |
|---|---|---|
| 49 | 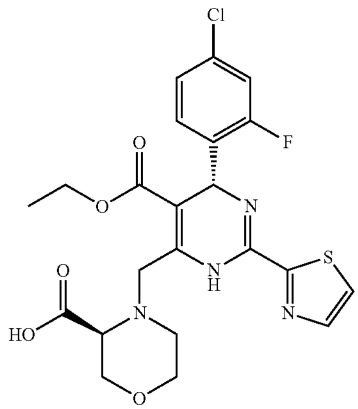 | (S)-4-[(R)-6-(4-Chloro-2-fluoro-phenyl)-5-ethoxycarbonyl-2-thiazol-2-yl-3,6-dihydro-pyrimidin-4-ylmethyl]-morpholine-3-carboxylic acid |
| 50 | 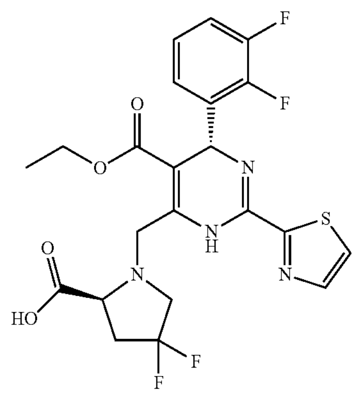 [SMILES: CCOC(=O)C1=C(CN2CC(F)(F)C[C@H]2C(=O)O)NC(c2nccs2)=N[C@H]1c1cccc(F)c1F] | (R)-6-((S)-2-Carboxy-4,4-difluoro-pyrrolidin-1-ylmethyl)-4-(2,3-difluoro-phenyl)-2-thiazol-2-yl-1,4-dihydro-pyrimidine-5-carboxylic acid ethyl ester |
| 51 | 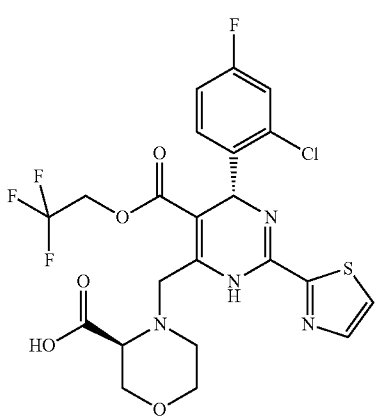 [SMILES: O=C(OCC(F)(F)F)C1=C(CN2CCOC[C@H]2C(=O)O)NC(c2nccs2)=N[C@H]1c1ccc(F)cc1Cl] | (S)-4-[(R)-6-(2-Chloro-4-fluoro-phenyl)-2-thiazol-2-yl-5-(2,2,2-trifluoro-ethoxycarbonyl)-3,6-dihydro-pyrimidin-4-ylmethyl]-morpholine-3-carboxylic acid |

TABLE 1-continued

Structure and name of particular compounds

| Example No. | Structure | Name |
|---|---|---|
| 52 | 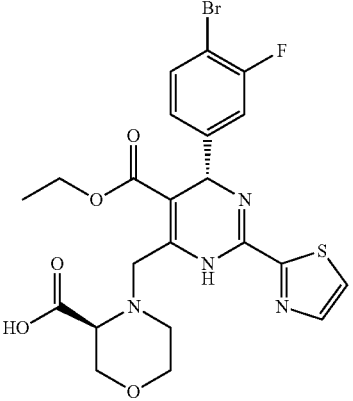 [SMILES: CCOC(=O)C1=C(CN2CCOC[C@H]2C(=O)O)NC(c2nccs2)=N[C@H]1c1ccc(Br)c(F)c1] | (S)-4-[(S)-6-(4-Bromo-3-fluoro-phenyl)-5-ethoxycarbonyl-2-thiazol-2-yl-3,6-dihydro-pyrimidin-4-ylmethyl]-morpholine-3-carboxylic acid |
| 53 | 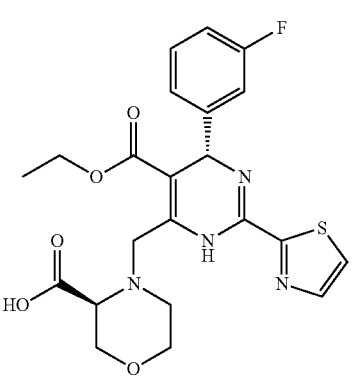 [SMILES: CCOC(=O)C1=C(CN2CCOC[C@H]2C(=O)O)NC(c2nccs2)=N[C@H]1c1cccc(F)c1] | (S)-4-[(S)-5-Ethoxycarbonyl-6-(3-fluoro-phenyl)-2-thiazol-2-yl-3,6-dihydro-pyrimidin-4-ylmethyl]-morpholine-3-carboxylic acid |
| 54 | 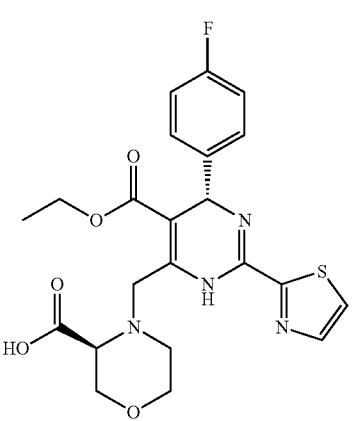 [SMILES: CCOC(=O)C1=C(CN2CCOC[C@H]2C(=O)O)NC(c2nccs2)=N[C@H]1c1ccc(F)cc1] | (S)-4-[(S)-5-Ethoxycarbonyl-6-(4-fluoro-phenyl)-2-thiazol-2-yl-3,6-dihydro-pyrimidin-4-ylmethyl]-morpholine-3-carboxylic acid |

TABLE 1-continued

Structure and name of particular compounds

| Example No. | Structure | Name |
|---|---|---|
| 55 | 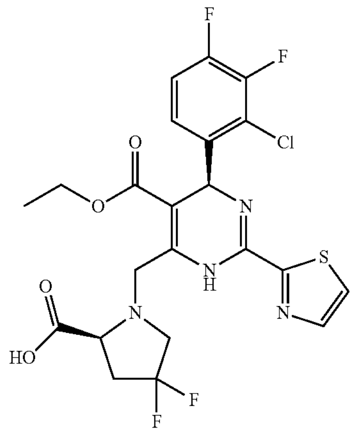 [SMILES: CCOC(=O)C1=C(CN2CC(F)(F)C[C@H]2C(=O)O)NC(c2nccs2)=N[C@@H]1c1ccc(F)c(F)c1Cl] | (R)-6-((S)-2-Carboxy-4,4-difluoro-pyrrolidin-1-ylmethyl)-4-(2-chloro-3,4-difluoro-phenyl)-2-thiazol-2-yl-1,4-dihydro-pyrimidine-5-carboxylic acid ethyl ester |
| 56 | 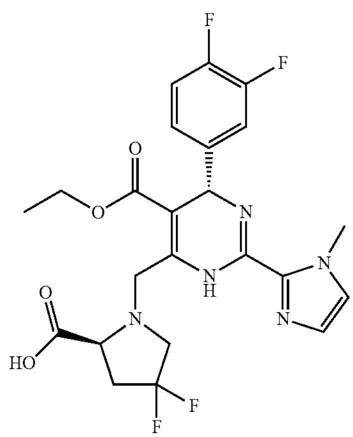 [SMILES: CCOC(=O)C1=C(CN2CC(F)(F)C[C@H]2C(=O)O)NC(c2nccn2C)=N[C@H]1c1ccc(F)c(F)c1] | (S)-6-((S)-2-Carboxy-4,4-difluoro-pyrrolidin-1-ylmethyl)-4-(3,4-difluoro-phenyl)-2-(1-methyl-1H-imidazol-2-yl)-1,4-dihydro-pyrimidine-5-carboxylic acid ethyl ester |
| 57 | 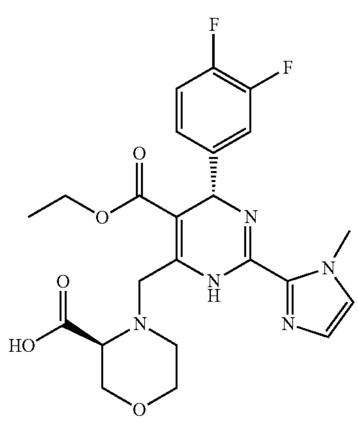 [SMILES: CCOC(=O)C1=C(CN2CCOC[C@H]2C(=O)O)NC(c2nccn2C)=N[C@H]1c1ccc(F)c(F)c1] | (S)-4-[(S)-6-(3,4-Difluoro-phenyl)-5-ethoxycarbonyl-2-(1-methyl-1H-imidazol-2-yl)-3,6-dihydro-pyrimidin-4-ylmethyl]-morpholine-3-carboxylic acid |

TABLE 1-continued

Structure and name of particular compounds

| Example No. | Structure | Name |
|---|---|---|
| 58 | 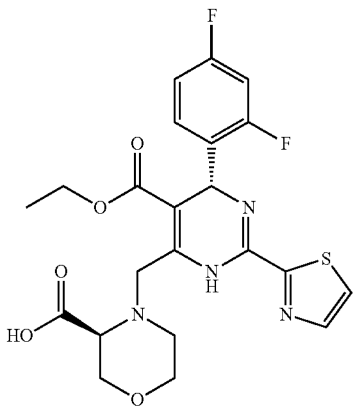 [SMILES: CCOC(=O)C1=C(CN2CCOC[C@H]2C(=O)O)NC(c2nccs2)=N[C@H]1c1ccc(F)cc1F] | (S)-4-[(R)-6-(2,4-Difluoro-phenyl)-5-ethoxycarbonyl-2-thiazol-2-yl-3,6-dihydro-pyrimidin-4-ylmethyl]-morpholine-3-carboxylic acid |
| 59 | 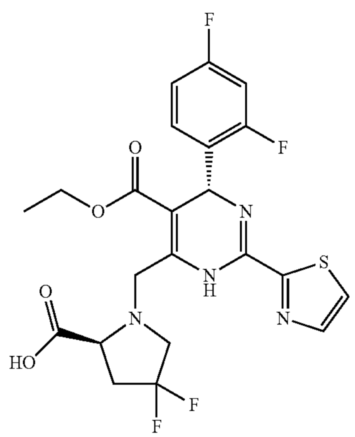 [SMILES: CCOC(=O)C1=C(CN2CC(F)(F)C[C@H]2C(=O)O)NC(c2nccs2)=N[C@H]1c1ccc(F)cc1F] | (R)-6-((S)-2-Carboxy-4,4-difluoro-pyrrolidin-1-ylmethyl)-4-(2,4-difluoro-phenyl)-2-thiazol-2-yl-1,4-dihydro-pyrimidine-5-carboxylic acid ethyl ester |
| 60 | 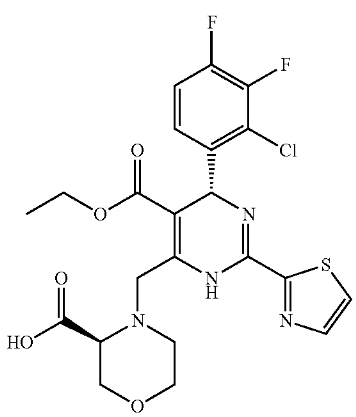 [SMILES: CCOC(=O)C1=C(CN2CCOC[C@H]2C(=O)O)NC(c2nccs2)=N[C@H]1c1ccc(F)c(F)c1Cl] | (S)-4-[(R)-6-(2-Chloro-3,4-difluoro-phenyl)-5-ethoxycarbonyl-2-thiazol-2-yl-3,6-dihydro-pyrimidin-4-ylmethyl]-morpholine-3-carboxylic acid |

TABLE 1-continued

Structure and name of particular compounds

| Example No. | Structure | Name |
|---|---|---|
| 61 | 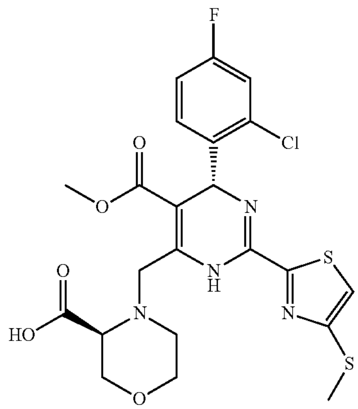 [SMILES: COC(=O)C1=C(CN2CCOC[C@H]2C(=O)O)NC(c2nc(SC)cs2)=N[C@H]1c1ccc(F)cc1Cl] | (3S)-4-[[(4R)-4-(2-Chloro-4-fluorophenyl)-5-methoxycarbonyl-2-(4-methylsulfanyl-1,3-thiazol-2-yl)-1,4-dihydropyrimidin-6-yl]methyl]morpholine-3-carboxylic acid |
| 62 | 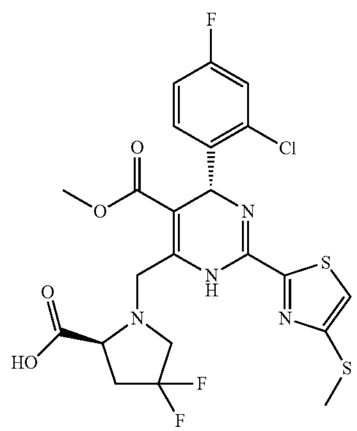 [SMILES: COC(=O)C1=C(CN2CC(F)(F)C[C@H]2C(=O)O)NC(c2nc(SC)cs2)=N[C@H]1c1ccc(F)cc1Cl] | (2S)-1-[[(4R)-4-(2-Chloro-4-fluorophenyl)-5-methoxycarbonyl-2-(4-methylsulfanyl-1,3-thiazol-2-yl)-1,4-dihydropyrimidin-6-yl]methyl]-4,4-difluoropyrrolidine-2-carboxylic acid |
| 63 | 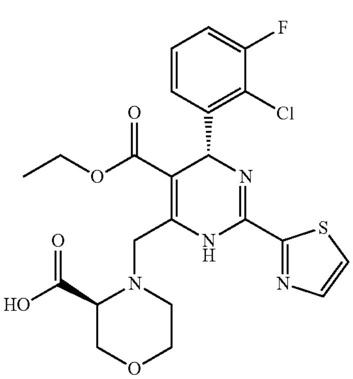 [SMILES: CCOC(=O)C1=C(CN2CCOC[C@H]2C(=O)O)NC(c2nccs2)=N[C@H]1c1cccc(F)c1Cl] | (S)-4-[(R)-6-(2-Chloro-3-fluoro-phenyl)-5-ethoxycarbonyl-2-thiazol-2-yl-3,6-dihydro-pyrimidin-4-ylmethyl]-morpholine-3-carboxylic acid |

TABLE 1-continued

Structure and name of particular compounds

| Example No. | Structure | Name |
|---|---|---|
| 64 | 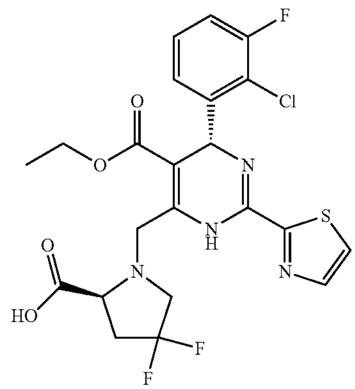 [SMILES: CCOC(=O)C1=C(CN2CC(F)(F)C[C@H]2C(=O)O)NC(c2nccs2)=N[C@H]1c1cccc(F)c1Cl] | (R)-6-((S)-2-Carboxy-4,4-difluoro-pyrrolidin-1-ylmethyl)-4-(2-chloro-3-fluoro-phenyl)-2-thiazol-2-yl-1,4-dihydro-pyrimidine-5-carboxylic acid ethyl ester |
| 65 | 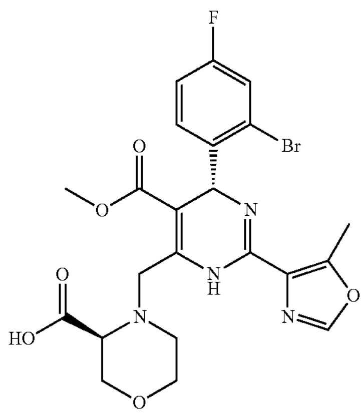 [SMILES: COC(=O)C1=C(CN2CCOC[C@H]2C(=O)O)NC(c2ncoc2C)=N[C@H]1c1ccc(F)cc1Br] | (S)-4-[(R)-6-(2-Bromo-4-fluoro-phenyl)-5-methoxycarbonyl-2-(5-methyl-oxazol-4-yl)-3,6-dihydro-pyrimidin-4-ylmethyl]-morpholine-3-carboxylic acid |
| 66 | 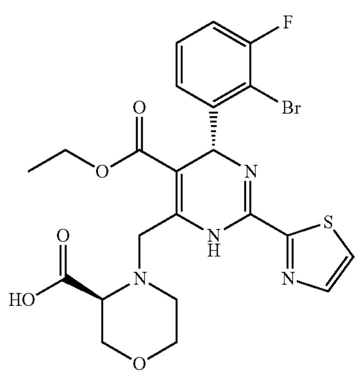 [SMILES: CCOC(=O)C1=C(CN2CCOC[C@H]2C(=O)O)NC(c2nccs2)=N[C@H]1c1cccc(F)c1Br] | (S)-4-[(R)-6-(2-Bromo-3-fluoro-phenyl)-5-ethoxycarbonyl-2-thiazol-2-yl-3,6-dihydro-pyrimidin-4-ylmethyl]-morpholine-3-carboxylic acid |
| 67 | 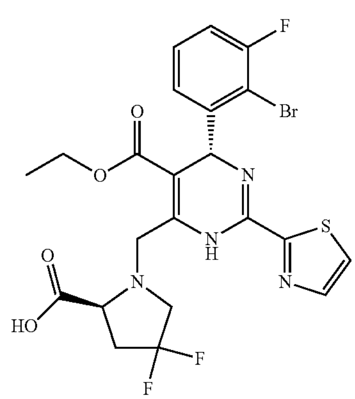 [SMILES: CCOC(=O)C1=C(CN2CC(F)(F)C[C@H]2C(=O)O)NC(c2nccs2)=N[C@H]1c1cccc(F)c1Br] | (R)-4-(2-Bromo-3-fluoro-phenyl)-6-((S)-2-carboxy-4,4-difluoro-pyrrolidin-1-ylmethyl)-2-thiazol-2-yl-1,4-dihydro-pyrimidine-5-carboxylic acid ethyl ester |

TABLE 1-continued

Structure and name of particular compounds

| Example No. | Structure | Name |
|---|---|---|
| 68 | 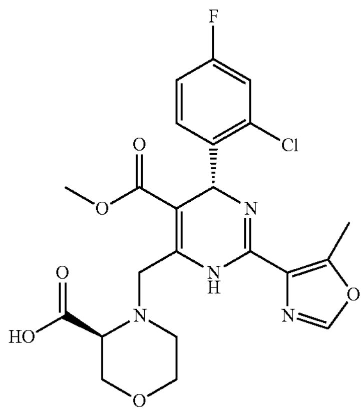 [SMILES: COC(=O)C1=C(CN2CCOC[C@H]2C(=O)O)NC(c2ncoc2C)=N[C@H]1c1ccc(F)cc1Cl] | (S)-4-[(R)-6-(2-Chloro-4-fluoro-phenyl)-5-methoxycarbonyl-2-(5-methyl-oxazol-4-yl)-3,6-dihydro-pyrimidin-4-ylmethyl]-morpholine-3-carboxylic acid |
| 69 | 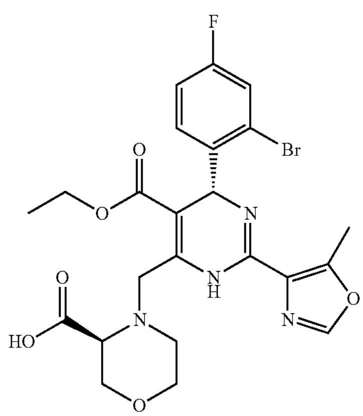 [SMILES: CCOC(=O)C1=C(CN2CCOC[C@H]2C(=O)O)NC(c2ncoc2C)=N[C@H]1c1ccc(F)cc1Br] | (S)-4-[(R)-6-(2-Bromo-4-fluoro-phenyl)-5-ethoxycarbonyl-2-(5-methyl-oxazol-4-yl)-3,6-dihydro-pyrimidin-4-ylmethyl]-morpholine-3-carboxylic acid |
| 70 | 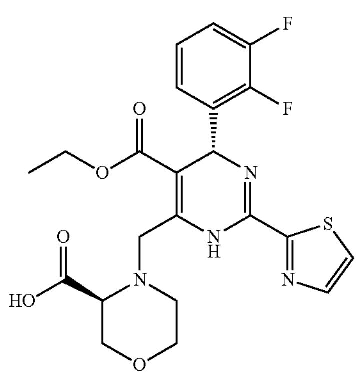 [SMILES: CCOC(=O)C1=C(CN2CCOC[C@H]2C(=O)O)NC(c2nccs2)=N[C@H]1c1cccc(F)c1F] | (S)-4-[(R)-6-(2,3-Difluoro-phenyl)-5-ethoxycarbonyl-2-thiazol-2-yl-3,6-dihydro-pyrimidin-4-ylmethyl]-morpholine-3-carboxylic acid |

TABLE 1-continued

Structure and name of particular compounds

| Example No. | Structure | Name |
|---|---|---|
| 71 | 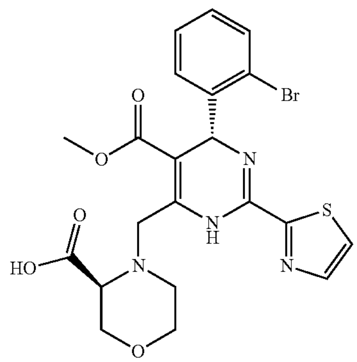 [SMILES: COC(=O)C1=C(CN2CCOC[C@H]2C(=O)O)NC(c2nccs2)=N[C@H]1c1ccccc1Br] | (S)-4-[(R)-6-(2-Bromo-phenyl)-5-methoxycarbonyl-2-thiazol-2-yl-3,6-dihydro-pyrimidin-4-ylmethyl]-morpholine-3-carboxylic acid |
| 72 | 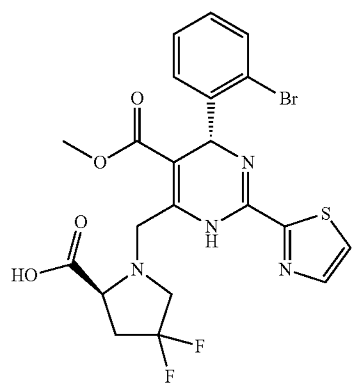 [SMILES: COC(=O)C1=C(CN2CC(F)(F)C[C@H]2C(=O)O)NC(c2nccs2)=N[C@H]1c1ccccc1Br] | (R)-4-(2-Bromo-phenyl)-6-((S)-2-carboxy-4,4-difluoro-pyrrolidin-1-ylmethyl)-2-thiazol-2-yl-1,4-dihydro-pyrimidine-5-carboxylic acid methyl ester |
| 73 | 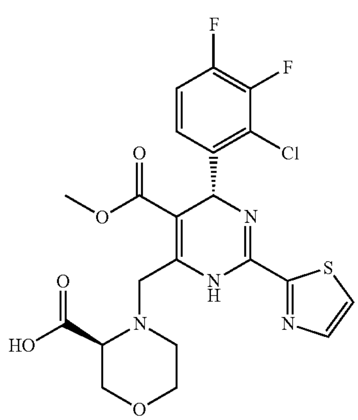 [SMILES: COC(=O)C1=C(CN2CCOC[C@H]2C(=O)O)NC(c2nccs2)=N[C@H]1c1ccc(F)c(F)c1Cl] | (S)-4-[(R)-6-(2-Chloro-3,4-difluoro-phenyl)-5-methoxycarbonyl-2-thiazol-2-yl-3,6-dihydro-pyrimidin-4-ylmethyl]-morpholine-3-carboxylic acid |

TABLE 1-continued

Structure and name of particular compounds

| Example No. | Structure | Name |
|---|---|---|
| 74 | 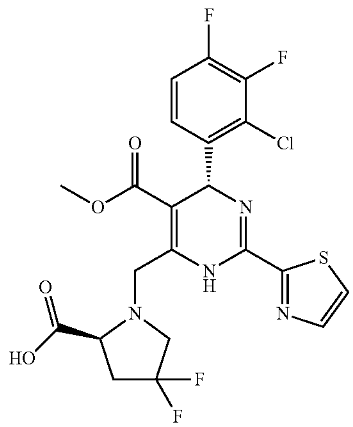 [SMILES: COC(=O)C1=C(CN2CC(F)(F)C[C@H]2C(=O)O)NC(c2nccs2)=N[C@H]1c1ccc(F)c(F)c1Cl] | (R)-6-((S)-2-Carboxy-4,4-difluoro-pyrrolidin-1-ylmethyl)-4-(2-chloro-3,4-difluoro-phenyl)-2-thiazol-2-yl-1,4-dihydro-pyrimidine-5-carboxylic acid methyl ester |
| 75 | 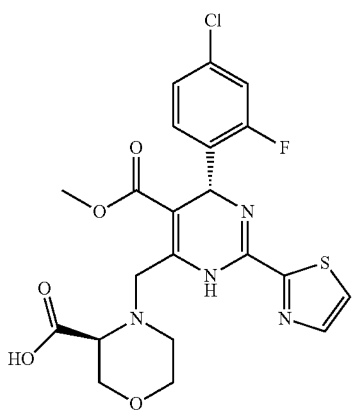 [SMILES: COC(=O)C1=C(CN2CCOC[C@H]2C(=O)O)NC(c2nccs2)=N[C@H]1c1ccc(Cl)cc1F] | (S)-4-[(R)-6-(4-Chloro-2-fluoro-phenyl)-5-methoxycarbonyl-2-thiazol-2-yl-3,6-dihydro-pyrimidin-4-ylmethyl]-morpholine-3-carboxylic acid |
| 76 | 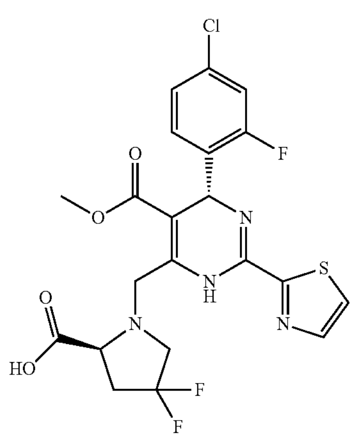 [SMILES: COC(=O)C1=C(CN2CC(F)(F)C[C@H]2C(=O)O)NC(c2nccs2)=N[C@H]1c1ccc(Cl)cc1F] | (R)-6-((S)-2-Carboxy-4,4-difluoro-pyrrolidin-1-ylmethyl)-4-(4-chloro-2-fluoro-phenyl)-2-thiazol-2-yl-1,4-dihydro-pyrimidine-5-carboxylic acid methyl ester |

TABLE 1-continued

Structure and name of particular compounds

| Example No. | Structure | Name |
|---|---|---|
| 77 | 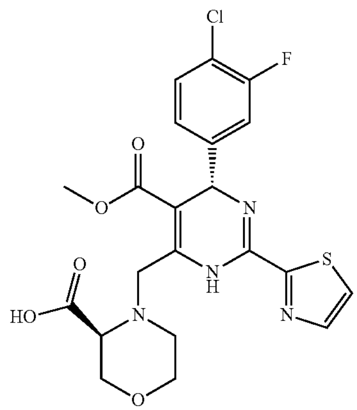 [SMILES: COC(=O)C1=C(CN2CCOC[C@H]2C(=O)O)NC(c2nccs2)=N[C@H]1c1ccc(Cl)c(F)c1] | (S)-4-[(S)-6-(4-Chloro-3-fluoro-phenyl)-5-methoxycarbonyl-2-thiazol-2-yl-3,6-dihydro-pyrimidin-4-ylmethyl]-morpholine-3-carboxylic acid |
| 78 | 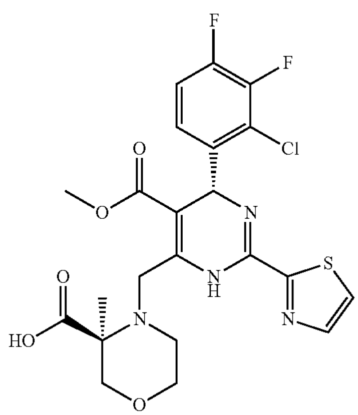 [SMILES: COC(=O)C1=C(CN2CCOC[C@@]2(C)C(=O)O)NC(c2nccs2)=N[C@H]1c1ccc(F)c(F)c1Cl] | (S)-4-[(R)-6-(2-Chloro-3,4-difluoro-phenyl)-5-methoxycarbonyl-2-thiazol-2-yl-3,6-dihydro-pyrimidin-4-ylmethyl]-3-methyl-morpholine-3-carboxylic acid |
| 79 | 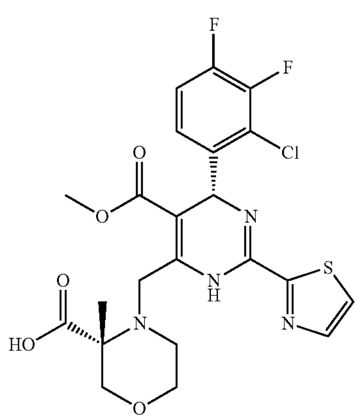 [SMILES: COC(=O)C1=C(CN2CCOC[C@]2(C)C(=O)O)NC(c2nccs2)=N[C@H]1c1ccc(F)c(F)c1Cl] | (R)-4-[(R)-6-(2-Chloro-3,4-difluoro-phenyl)-5-methoxycarbonyl-2-thiazol-2-yl-3,6-dihydro-pyrimidin-4-ylmethyl]-3-methyl-morpholine-3-carboxylic acid |

TABLE 1-continued

Structure and name of particular compounds

| Example No. | Structure | Name |
|---|---|---|
| 80 | 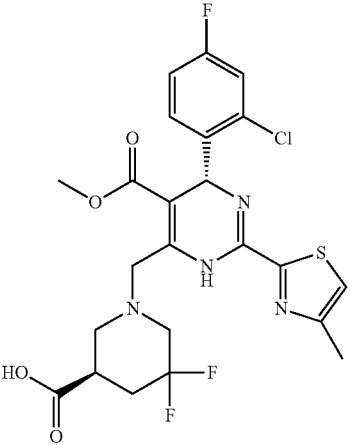 [SMILES: COC(=O)C1=C(CN2C[C@H](C(=O)O)CC(F)(F)C2)NC(c2nc(C)cs2)=N[C@H]1c1ccc(F)cc1Cl] | (R)-6-((R)-5-Carboxy-3,3-difluoro-piperidin-1-ylmethyl)-4-(2-chloro-4-fluoro-phenyl)-2-(4-methyl-thiazol-2-yl)-1,4-dihydro-pyrimidine-5-carboxylic acid methyl ester |
| 81 | 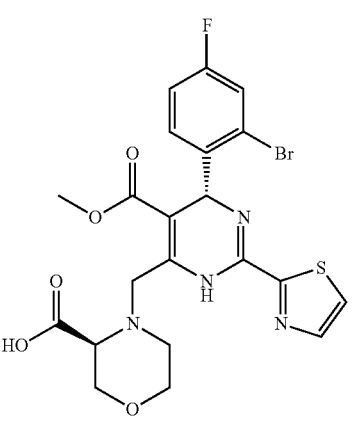 [SMILES: COC(=O)C1=C(CN2CCOC[C@H]2C(=O)O)NC(c2nccs2)=N[C@H]1c1ccc(F)cc1Br] | (S)-4-[(R)-6-(2-Bromo-4-fluoro-phenyl)-5-methoxycarbonyl-2-thiazol-2-yl-3,6-dihydro-pyrimidin-4-ylmethyl]-morpholine-3-carboxylic acid |
| 82 | 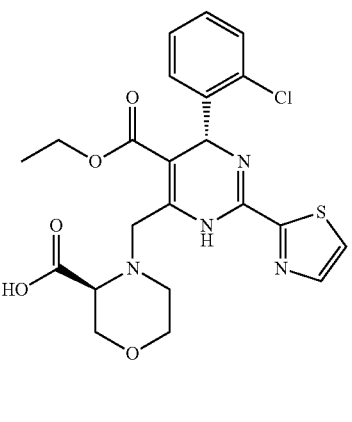 [SMILES: CCOC(=O)C1=C(CN2CCOC[C@H]2C(=O)O)NC(c2nccs2)=N[C@H]1c1ccccc1Cl] | (S)-4-[(R)-6-(2-Chloro-phenyl)-5-ethoxycarbonyl-2-thiazol-2-yl-3,6-dihydro-pyrimidin-4-ylmethyl]-morpholine-3-carboxylic acid |

TABLE 1-continued

Structure and name of particular compounds

| Example No. | Structure | Name |
|---|---|---|
| 83 | 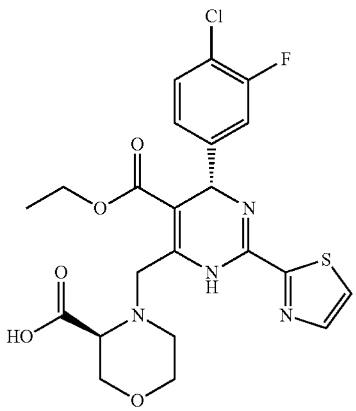 [SMILES: CCOC(=O)C1=C(CN2CCOC[C@H]2C(=O)O)NC(c2nccs2)=N[C@H]1c1ccc(Cl)c(F)c1] | (S)-4-[(S)-6-(4-Chloro-3-fluoro-phenyl)-5-ethoxycarbonyl-2-thiazol-2-yl-3,6-dihydro-pyrimidin-4-ylmethyl]-morpholine-3-carboxylic acid |
| 84 | 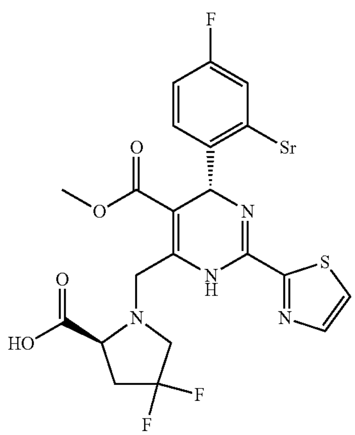 | (R)-4-(2-Bromo-4-fluoro-phenyl)-6-((S)-2-carboxy-4,4-difluoro-pyrrolidin-1-ylmethyl)-2-thiazol-2-yl-1,4-dihydro-pyrimidine-5-carboxylic acid methyl ester |
| 85 | 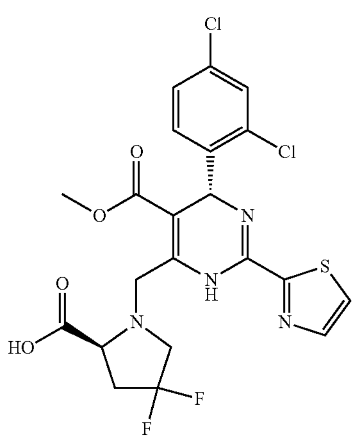 [SMILES: COC(=O)C1=C(CN2CC(F)(F)C[C@H]2C(=O)O)NC(c2nccs2)=N[C@H]1c1ccc(Cl)cc1Cl] | (R)-6-((S)-2-Carboxy-4,4-difluoro-pyrrolidin-1-ylmethyl)-4-(2,4-dichloro-phenyl)-2-thiazol-2-yl-1,4-dihydro-pyrimidine-5-carboxylic acid methyl ester |

TABLE 1-continued

Structure and name of particular compounds

| Example No. | Structure | Name |
|---|---|---|
| 86 | 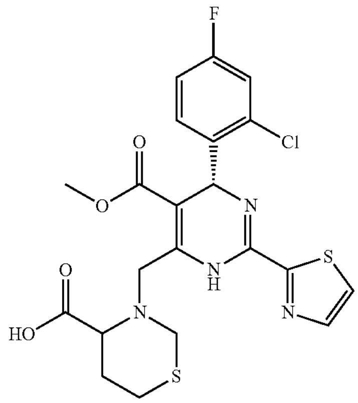 [SMILES: COC(=O)C1=C(CN2CSCCC2C(=O)O)NC(c2nccs2)=N[C@H]1c1ccc(F)cc1Cl] | 3-[[(4R)-4-(2-Chloro-4-fluoro-phenyl)-5-methoxycarbonyl-2-thiazol-2-yl-1,4-dihydropyrimidin-6-yl]methyl]-1,3-thiazinane-4-carboxylic acid |
| 87 | 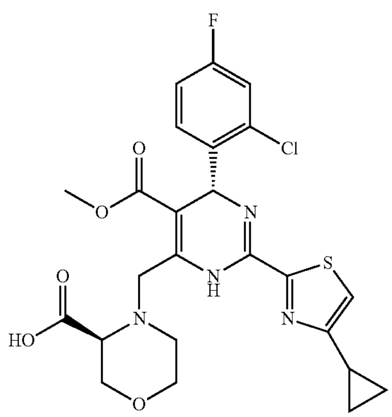 [SMILES: COC(=O)C1=C(CN2CCOC[C@H]2C(=O)O)NC(c2nc(C3CC3)cs2)=N[C@H]1c1ccc(F)cc1Cl] | (3S)-4-[[(4R)-4-(2-Chloro-4-fluoro-phenyl)-2-(4-cyclopropylthiazol-2-yl)-5-methoxycarbonyl-1,4-dihydropyrimidin-6-yl]methyl]morpholine-3-carboxylic acid |
| 88 | 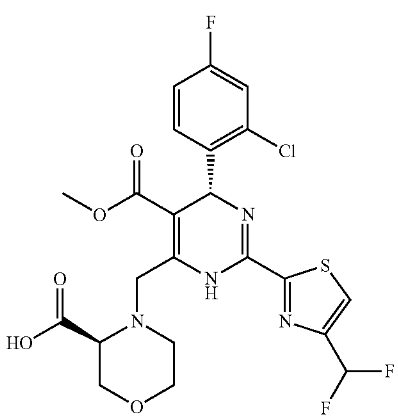 [SMILES: COC(=O)C1=C(CN2CCOC[C@H]2C(=O)O)NC(c2nc(C(F)F)cs2)=N[C@H]1c1ccc(F)cc1Cl] | (3S)-4-[[(4R)-4-(2-Chloro-4-fluoro-phenyl)-2-[4-(difluoromethyl)thiazol-2-yl]-5-methoxycarbonyl-1,4-dihydropyrimidin-6-yl]methyl]morpholine-3-carboxylic acid |

TABLE 1-continued

Structure and name of particular compounds

| Example No. | Structure | Name |
|---|---|---|
| 89 | 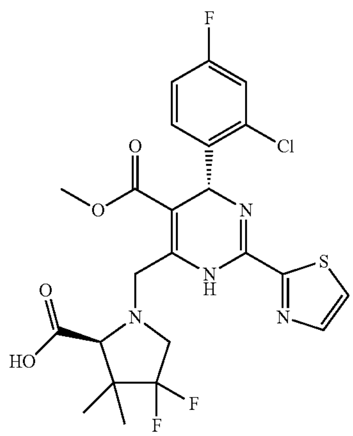 [SMILES: COC(=O)C1=C(CN2CC(F)(F)C(C)(C)[C@H]2C(=O)O)NC(c2nccs2)=N[C@H]1c1ccc(F)cc1Cl] | (R)-6-((S)-2-Carboxy-4,4-difluoro-3,3-dimethyl-pyrrolidin-1-ylmethyl)-4-(2-chloro-4-fluoro-phenyl)-2-thiazol-2-yl-1,4-dihydro-pyrimidine-5-carboxylic acid methyl ester |
| 90 | 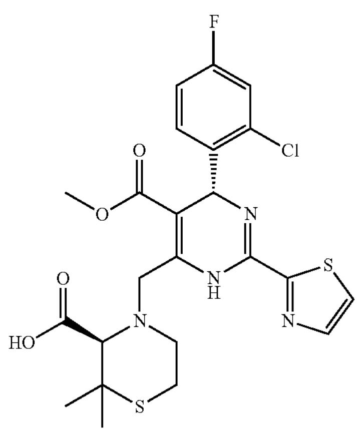 [SMILES: COC(=O)C1=C(CN2CCSC(C)(C)[C@H]2C(=O)O)NC(c2nccs2)=N[C@H]1c1ccc(F)cc1Cl] | (3R)-4-[[(4R)-4-(2-Chloro-4-fluoro-phenyl)-5-methoxycarbonyl-2-thiazol-2-yl-1,4-dihydropyrimidin-6-yl]methyl]-2,2-dimethyl-thiomorpholine-3-carboxylic acid |
| 91 | 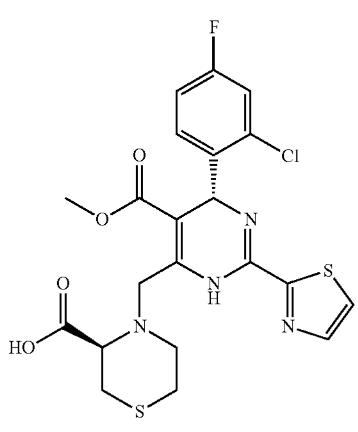 [SMILES: COC(=O)C1=C(CN2CCSC[C@H]2C(=O)O)NC(c2nccs2)=N[C@H]1c1ccc(F)cc1Cl] | (3S)-4-[[(4R)-4-(2-Chloro-4-fluoro-phenyl)-5-methoxycarbonyl-2-thiazol-2-yl-1,4-dihydropyrimidin-6-yl]methyl]thiomorpholine-3-carboxylic acid |

TABLE 1-continued

Structure and name of particular compounds

| Example No. | Structure | Name |
|---|---|---|
| 92 | 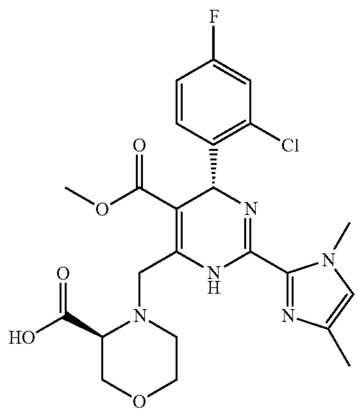 [SMILES: COC(=O)C1=C(CN2CCOC[C@H]2C(=O)O)NC(c2nc(C)cn2C)=N[C@H]1c1ccc(F)cc1Cl] | (S)-4-[(S)-6-(2-Chloro-4-fluoro-phenyl)-2-(1,4-dimethyl-1H-imidazol-2-yl)-5-methoxycarbonyl-3,6-dihydro-pyrimidin-4-ylmethyl]-morpholine-3-carboxylic acid |
| 93 | 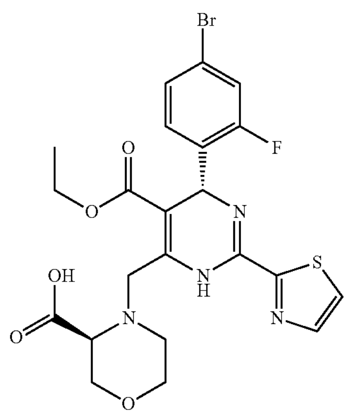 [SMILES: CCOC(=O)C1=C(CN2CCOC[C@H]2C(=O)O)NC(c2nccs2)=N[C@H]1c1ccc(Br)cc1F] | (S)-4-[(R)-6-(4-Bromo-2-fluoro-phenyl)-5-ethoxycarbonyl-2-thiazol-2-yl-3,6-dihydro-pyrimidin-4-ylmethyl]-morpholine-3-carboxylic acid |
| 94 | 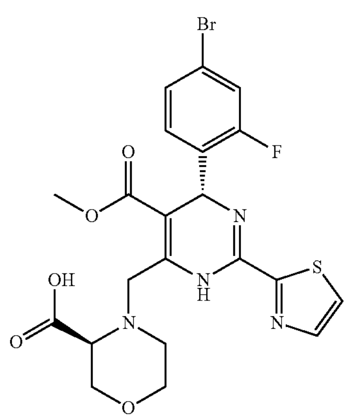 [SMILES: COC(=O)C1=C(CN2CCOC[C@H]2C(=O)O)NC(c2nccs2)=N[C@H]1c1ccc(Br)cc1F] | (S)-4-[(R)-6-(4-Bromo-2-fluoro-phenyl)-5-methoxycarbonyl-2-thiazol-2-yl-3,6-dihydro-pyrimidin-4-ylmethyl]-morpholine-3-carboxylic acid |

TABLE 1-continued

Structure and name of particular compounds

| Example No. | Structure | Name |
|---|---|---|
| 95 | 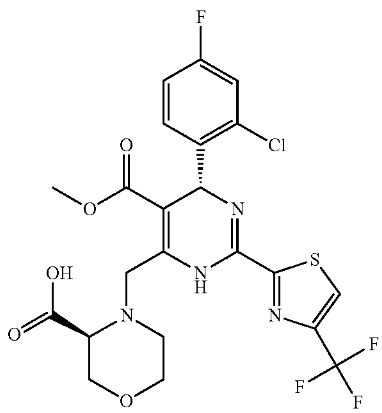 [SMILES: COC(=O)C1=C(CN2CCOC[C@H]2C(=O)O)NC(c2nc(C(F)(F)F)cs2)=N[C@H]1c1ccc(F)cc1Cl] | (S)-4-[(R)-6-(2-Chloro-4-fluoro-phenyl)-5-methoxycarbonyl-2-(4-trifluoromethyl-thiazol-2-yl)-3,6-dihydro-pyrimidin-4-ylmethyl]-morpholine-3-carboxylic acid |
| 96 | 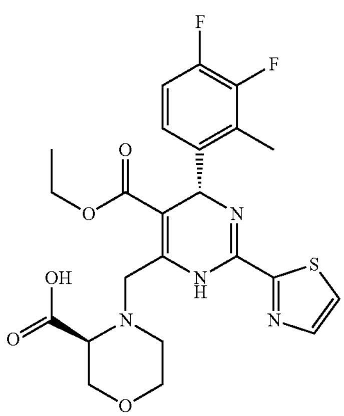 [SMILES: CCOC(=O)C1=C(CN2CCOC[C@H]2C(=O)O)NC(c2nccs2)=N[C@H]1c1ccc(F)c(F)c1C] | (S)-4-[(S)-6-(3,4-Difluoro-2-methyl-phenyl)-5-ethoxycarbonyl-2-thiazol-2-yl-3,6-dihydro-pyrimidin-4-ylmethyl]-morpholine-3-carboxylic acid |
| 97 | 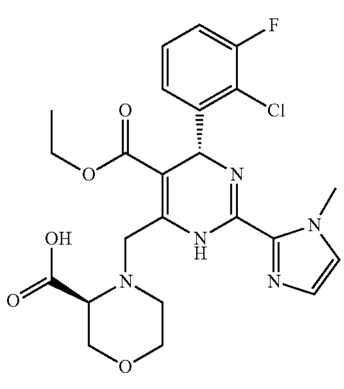 [SMILES: CCOC(=O)C1=C(CN2CCOC[C@H]2C(=O)O)NC(c2nccn2C)=N[C@H]1c1cccc(F)c1Cl] | (S)-4-[(R)-6-(2-Chloro-3-fluoro-phenyl)-5-ethoxycarbonyl-2-(1-methyl-1H-imidazol-2-yl)-3,6-dihydro-pyrimidin-4-ylmethyl]-morpholine-3-carboxylic acid |

TABLE 1-continued

Structure and name of particular compounds

| Example No. | Structure | Name |
|---|---|---|
| 98 | 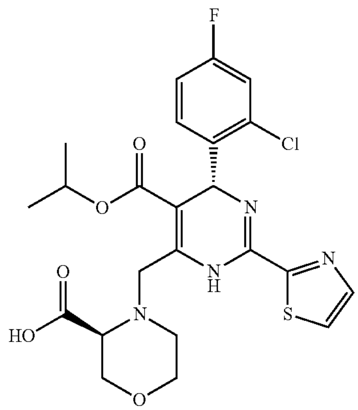 [SMILES: CC(C)OC(=O)C1=C(CN2CCOC[C@H]2C(=O)O)NC(c2nccs2)=N[C@H]1c1ccc(F)cc1Cl] | (S)-4-[(R)-6-(2-Chloro-4-fluoro-phenyl)-5-isopropoxycarbonyl-2-thiazol-2-yl-3,6-dihydro-pyrimidin-4-ylmethyl]-morpholine-3-carboxylic acid |
| 99 | 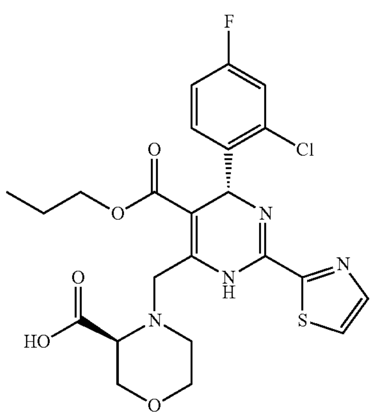 [SMILES: CCCOC(=O)C1=C(CN2CCOC[C@H]2C(=O)O)NC(c2nccs2)=N[C@H]1c1ccc(F)cc1Cl] | (S)-4-[6-(2-Chloro-4-fluoro-phenyl)-5-propoxycarbonyl-2-thiazol-2-yl-3,6-dihydro-pyrimidin-4-ylmethyl]-morpholine-3-carboxylic acid |
| 100 | 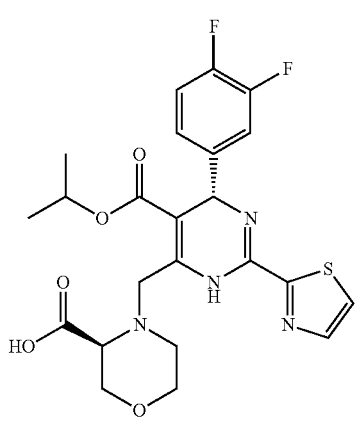 [SMILES: CC(C)OC(=O)C1=C(CN2CCOC[C@H]2C(=O)O)NC(c2nccs2)=N[C@H]1c1ccc(F)c(F)c1] | (S)-4-[(S)-6-(3,4-Difluoro-phenyl)-5-isopropoxycarbonyl-2-thiazol-2-yl-3,6-dihydro-pyrimidin-4-ylmethyl]-morpholine-3-carboxylic acid |

TABLE 1-continued

Structure and name of particular compounds

| Example No. | Structure | Name |
|---|---|---|
| 101 | 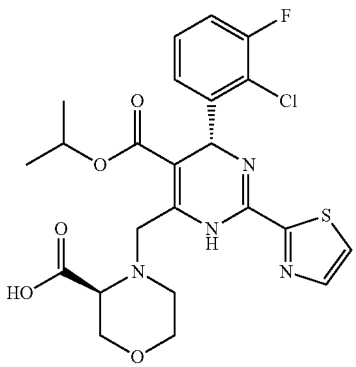 [SMILES: CC(C)OC(=O)C1=C(CN2CCOC[C@H]2C(=O)O)NC(c2nccs2)=N[C@H]1c1cccc(F)c1Cl] | (S)-4-[(R)-6-(2-Chloro-3-fluoro-phenyl)-5-isopropoxycarbonyl-2-thiazol-2-yl-3,6-dihydro-pyrimidin-4-ylmethyl]-morpholine-3-carboxylic acid |
| 102 | 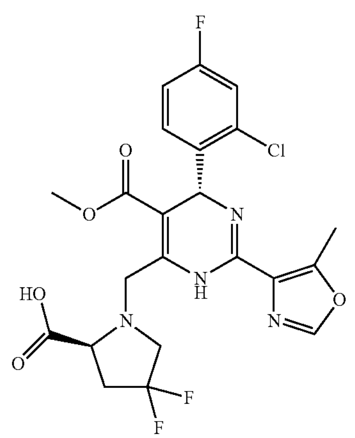 [SMILES: COC(=O)C1=C(CN2CC(F)(F)C[C@H]2C(=O)O)NC(c2ncoc2C)=N[C@H]1c1ccc(F)cc1Cl] | (R)-6-((S)-2-Carboxy-4,4-difluoro-pyrrolidin-1-ylmethyl)-4-(2-chloro-4-fluoro-phenyl)-2-(5-methyl-oxazol-4-yl)-1,4-dihydro-pyrimidine-5-carboxylic acid methyl ester |
| 103 | 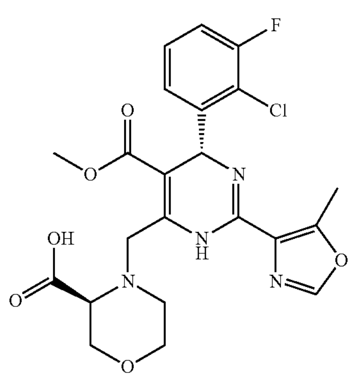 [SMILES: COC(=O)C1=C(CN2CCOC[C@H]2C(=O)O)NC(c2ncoc2C)=N[C@H]1c1cccc(F)c1Cl] | (S)-4-[(R)-6-(2-Chloro-3-fluoro-phenyl)-5-methoxycarbonyl-2-(5-methyl-oxazol-4-yl)-3,6-dihydro-pyrimidin-4-ylmethyl]-morpholine-3-carboxylic acid |

TABLE 1-continued

Structure and name of particular compounds

| Example No. | Structure | Name |
|---|---|---|
| 104 | 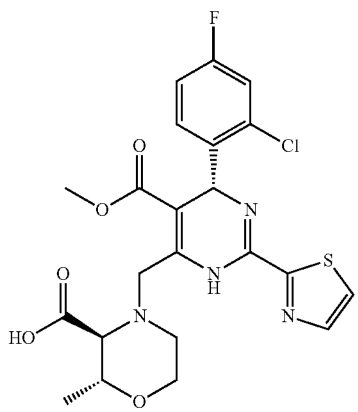 [SMILES: COC(=O)C1=C(CN2CCO[C@H](C)[C@H]2C(=O)O)NC(c2nccs2)=N[C@H]1c1ccc(F)cc1Cl] | (2R,3S)-4-[(R)-6-(2-Chloro-4-fluoro-phenyl)-5-methoxycarbonyl-2-thiazol-2-yl-3,6-dihydro-pyrimidin-4-ylmethyl]-2-methyl-morpholine-3-carboxylic acid |
| 105 | 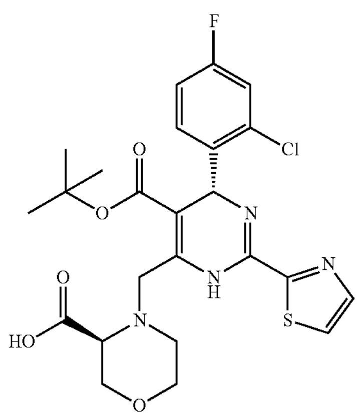 [SMILES: CC(C)(C)OC(=O)C1=C(CN2CCOC[C@H]2C(=O)O)NC(c2nccs2)=N[C@H]1c1ccc(F)cc1Cl] | (S)-4-[5-tert-Butoxycarbonyl-6-(2-chloro-4-fluoro-phenyl)-2-thiazol-2-yl-3,6-dihydro-pyrimidin-4-ylmethyl]-morpholine-3-carboxylic acid |
| 106 | 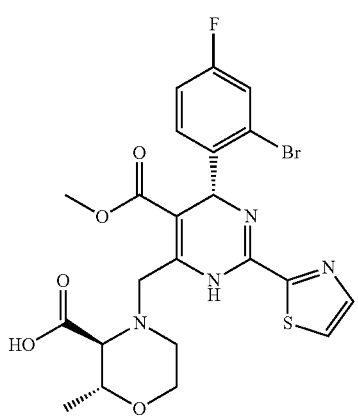 [SMILES: COC(=O)C1=C(CN2CCO[C@H](C)[C@H]2C(=O)O)NC(c2nccs2)=N[C@H]1c1ccc(F)cc1Br] | (2R,3S)-4-[(R)-6-(2-Bromo-4-fluoro-phenyl)-5-methoxycarbonyl-2-thiazol-2-yl-3,6-dihydro-pyrimidin-4-ylmethyl]-2-methyl-morpholine-3-carboxylic acid |

TABLE 1-continued

Structure and name of particular compounds

| Example No. | Structure | Name |
|---|---|---|
| 107 | 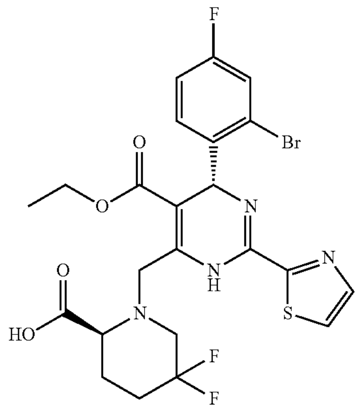 [SMILES: CCOC(=O)C1=C(CN2CC(F)(F)CC[C@H]2C(=O)O)NC(c2nccs2)=N[C@H]1c1ccc(F)cc1Br] | (R)-4-(2-Bromo-4-fluoro-phenyl)-6-((S)-2-carboxy-5,5-difluoro-piperidin-1-ylmethyl)-2-thiazol-2-yl-1,4-dihydro-pyrimidine-5-carboxylic acid ethyl ester |
| 108 | 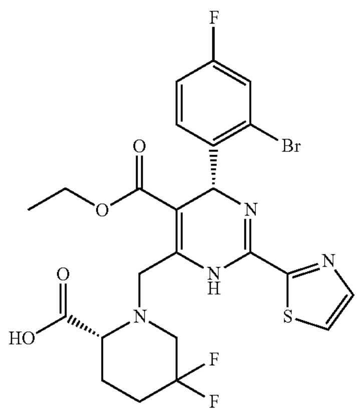 [SMILES: CCOC(=O)C1=C(CN2CC(F)(F)CC[C@@H]2C(=O)O)NC(c2nccs2)=N[C@H]1c1ccc(F)cc1Br] | (R)-4-(2-Bromo-4-fluoro-phenyl)-6-((R)-2-carboxy-5,5-difluoro-piperidin-1-ylmethyl)-2-thiazol-2-yl-1,4-dihydro-pyrimidine-5-carboxylic acid ethyl ester |
| 109 | 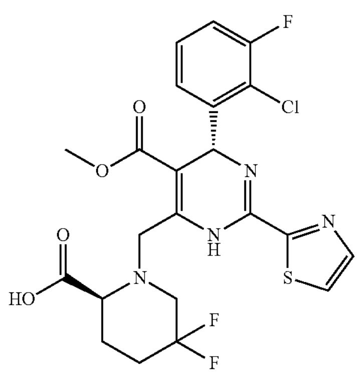 [SMILES: COC(=O)C1=C(CN2CC(F)(F)CC[C@H]2C(=O)O)NC(c2nccs2)=N[C@H]1c1cccc(F)c1Cl] | (R)-6-((S)-2-Carboxy-5,5-difluoro-piperidin-1-ylmethyl)-4-(2-chloro-3-fluoro-phenyl)-2-thiazol-2-yl-1,4-dihydro-pyrimidine-5-carboxylic acid methyl ester |
| 110 | 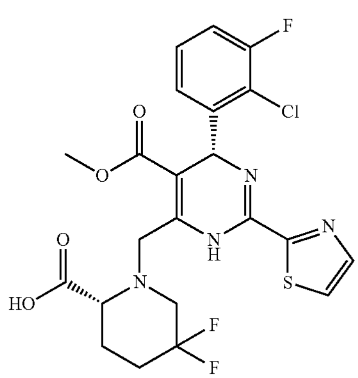 [SMILES: COC(=O)C1=C(CN2CC(F)(F)CC[C@@H]2C(=O)O)NC(c2nccs2)=N[C@H]1c1cccc(F)c1Cl] | (R)-6-((R)-2-Carboxy-5,5-difluoro-piperidin-1-ylmethyl)-4-(2-chloro-3-fluoro-phenyl)-2-thiazol-2-yl-1,4-dihydro-pyrimidine-5-carboxylic acid methyl ester |

TABLE 1-continued

Structure and name of particular compounds

| Example No. | Structure | Name |
|---|---|---|
| 111 | 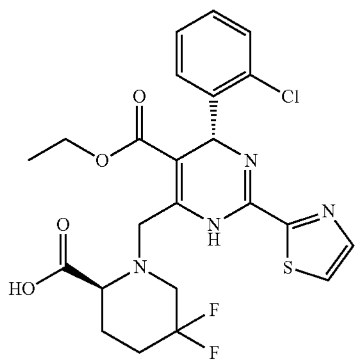 [SMILES: CCOC(=O)C1=C(CN2CC(F)(F)CC[C@H]2C(=O)O)NC(c2nccs2)=N[C@H]1c1ccccc1Cl] | (R)-6-((S)-2-Carboxy-5,5-difluoro-piperidin-1-ylmethyl)-4-(2-chloro-phenyl)-2-thiazol-2-yl-1,4-dihydro-pyrimidine-5-carboxylic acid ethyl ester |
| 112 | 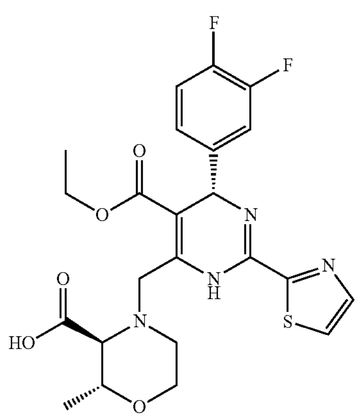 [SMILES: CCOC(=O)C1=C(CN2CCO[C@H](C)[C@H]2C(=O)O)NC(c2nccs2)=N[C@H]1c1ccc(F)c(F)c1] | (2R,3S)-4-[(S)-6-(3,4-Difluoro-phenyl)-5-ethoxycarbonyl-2-thiazol-2-yl-3,6-dihydro-pyrimidin-4-ylmethyl]-2-methyl-morpholine-3-carboxylic acid |
| 113 | 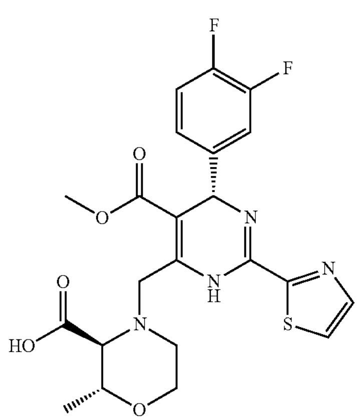 [SMILES: COC(=O)C1=C(CN2CCO[C@H](C)[C@H]2C(=O)O)NC(c2nccs2)=N[C@H]1c1ccc(F)c(F)c1] | (2R,3S)-4-[(S)-6-(3,4-Difluoro-phenyl)-5-methoxycarbonyl-2-thiazol-2-yl-3,6-dihydro-pyrimidin-4-ylmethyl]-2-methyl-morpholine-3-carboxylic acid |

TABLE 1-continued

Structure and name of particular compounds

| Example No. | Structure | Name |
|---|---|---|
| 114 | 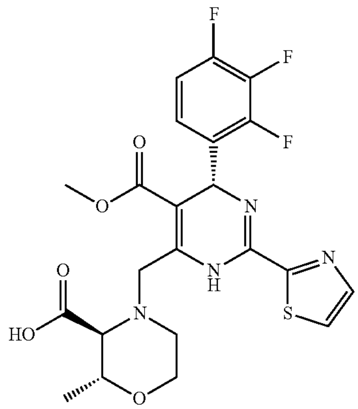 [SMILES: COC(=O)C1=C(CN2CCO[C@H](C)[C@H]2C(=O)O)NC(c2nccs2)=N[C@H]1c1ccc(F)c(F)c1F] | (2R,3S)-4-[(R)-5-Methoxycarbonyl-2-thiazol-2-yl-6-(2,3,4-trifluoro-phenyl)-3,6-dihydro-pyrimidin-4-ylmethyl]-2-methyl-morpholine-3-carboxylic acid |
| 115 | 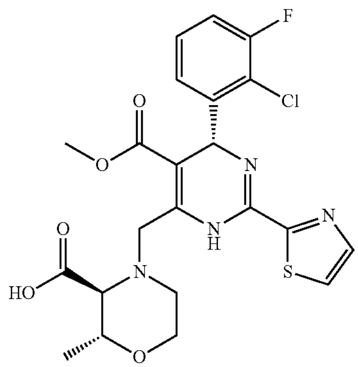 [SMILES: COC(=O)C1=C(CN2CCO[C@H](C)[C@H]2C(=O)O)NC(c2nccs2)=N[C@H]1c1cccc(F)c1Cl] | (2R,3S)-4-[(R)-6-(2-Chloro-3-fluoro-phenyl)-5-methoxycarbonyl-2-thiazol-2-yl-3,6-dihydro-pyrimidin-4-ylmethyl]-2-methyl-morpholine-3-carboxylic acid |
| 116 | 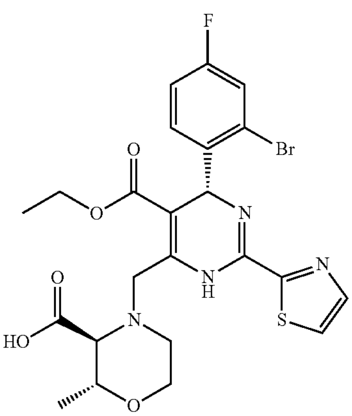 [SMILES: CCOC(=O)C1=C(CN2CCO[C@H](C)[C@H]2C(=O)O)NC(c2nccs2)=N[C@H]1c1ccc(F)cc1Br] | (2R,3S)-4-[(R)-6-(2-Bromo-4-fluoro-phenyl)-5-ethoxycarbonyl-2-thiazol-2-yl-3,6-dihydro-pyrimidin-4-ylmethyl]-2-methyl-morpholine-3-carboxylic acid |
| 117 | 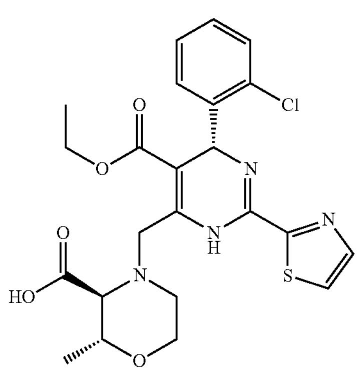 [SMILES: CCOC(=O)C1=C(CN2CCO[C@H](C)[C@H]2C(=O)O)NC(c2nccs2)=N[C@H]1c1ccccc1Cl] | (2R,3S)-4-[(R)-6-(2-Chloro-phenyl)-5-ethoxycarbonyl-2-thiazol-2-yl-3,6-dihydro-pyrimidin-4-ylmethyl]-2-methyl-morpholine-3-carboxylic acid |

TABLE 1-continued

Structure and name of particular compounds

| Example No. | Structure | Name |
|---|---|---|
| 118 | 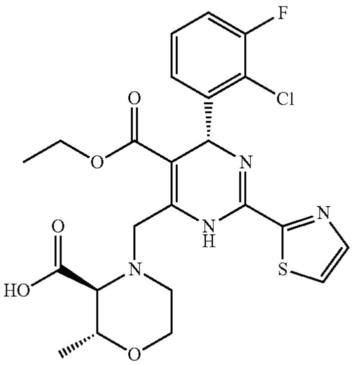 [SMILES: CCOC(=O)C1=C(CN2CCO[C@H](C)[C@H]2C(=O)O)NC(c2nccs2)=N[C@H]1c1cccc(F)c1Cl] | (2R,3S)-4-[(R)-6-(2-Chloro-3-fluoro-phenyl)-5-ethoxycarbonyl-2-thiazol-2-yl-3,6-dihydro-pyrimidin-4-ylmethyl]-2-methyl-morpholine-3-carboxylic acid |
| 119 | 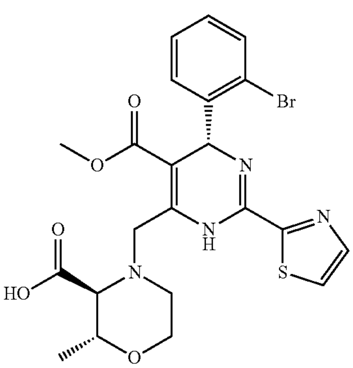 [SMILES: COC(=O)C1=C(CN2CCO[C@H](C)[C@H]2C(=O)O)NC(c2nccs2)=N[C@H]1c1ccccc1Br] | (2R,3S)-4-[(R)-6-(2-Bromo-phenyl)-5-methoxycarbonyl-2-thiazol-2-yl-3,6-dihydro-pyrimidin-4-ylmethyl]-2-methyl-morpholine-3-carboxylic acid |
| 120 | 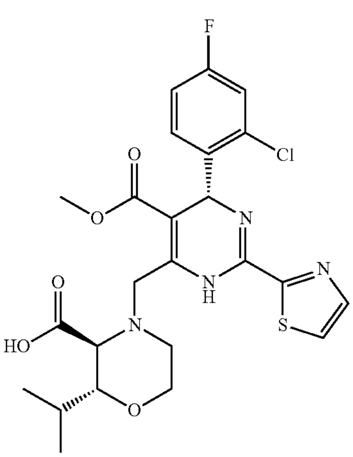 [SMILES: COC(=O)C1=C(CN2CCO[C@H](C(C)C)[C@H]2C(=O)O)NC(c2nccs2)=N[C@H]1c1ccc(F)cc1Cl] | (2R,3S)-4-[(R)-6-(2-Chloro-4-fluoro-phenyl)-5-methoxycarbonyl-2-thiazol-2-yl-3,6-dihydro-pyrimidin-4-ylmethyl]-2-isopropyl-morpholine-3-carboxylic acid |

TABLE 1-continued

Structure and name of particular compounds

| Example No. | Structure | Name |
|---|---|---|
| 121 | 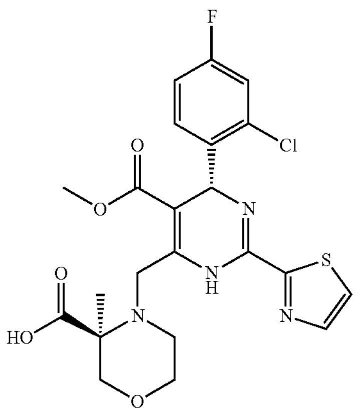 [SMILES: COC(=O)C1=C(CN2CCOC[C@@]2(C)C(=O)O)NC(c2nccs2)=N[C@H]1c1ccc(F)cc1Cl] | (S)-4-(((R)-6-(2-Chloro-4-fluorophenyl)-5-(methoxycarbonyl)-2-(thiazol-2-yl)-3,6-dihydropyrimidin-4-yl)methyl)-3-methylmorpholine-3-carboxylic acid |
| 122 | 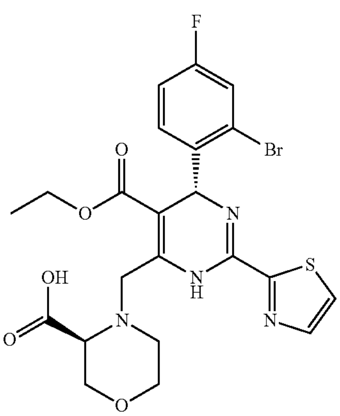 [SMILES: CCOC(=O)C1=C(CN2CCOC[C@H]2C(=O)O)NC(c2nccs2)=N[C@H]1c1ccc(F)cc1Br] | (S)-4-(((R)-6-(2-Bromo-4-fluorophenyl)-5-(ethoxycarbonyl)-2-(thiazol-2-yl)-3,6-dihydropyrimidin-4-yl)methyl)morpholine-3-carboxylic acid |
| 123 | 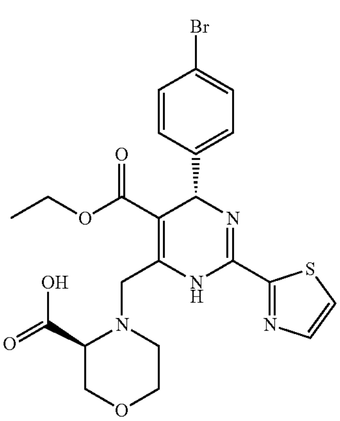 [SMILES: CCOC(=O)C1=C(CN2CCOC[C@H]2C(=O)O)NC(c2nccs2)=N[C@H]1c1ccc(Br)cc1] | (3S)-4-[[(4S)-4-(4-Bromophenyl)-5-ethoxycarbonyl-2-(1,3-thiazol-2-yl)-1,4-dihydropyrimidin-6-yl]methyl]morpholine-3-carboxylic acid |

TABLE 1-continued

Structure and name of particular compounds

| Example No. | Structure | Name |
|---|---|---|
| 124 | 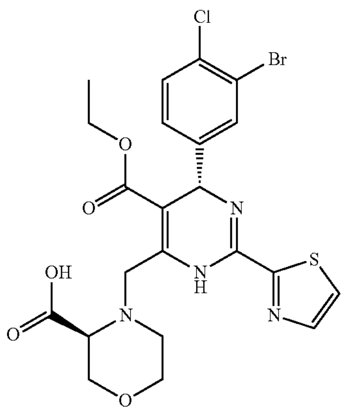 [SMILES: CCOC(=O)C1=C(CN2CCOC[C@H]2C(=O)O)NC(c2nccs2)=N[C@H]1c1ccc(Cl)c(Br)c1] | (3S)-4-[[(4S)-4-(3-Bromo-4-chlorophenyl)-5-ethoxycarbonyl-2-(1,3-thiazol-2-yl)-1,4-dihydropyrimidin-6-yl]methyl]morpholine-3-carboxylic acid |
| 125 | 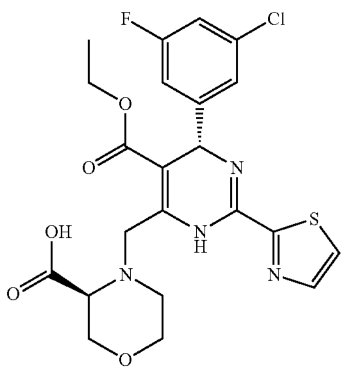 [SMILES: CCOC(=O)C1=C(CN2CCOC[C@H]2C(=O)O)NC(c2nccs2)=N[C@H]1c1cc(F)cc(Cl)c1] | (3S)-4-[[(4S)-4-(3-Chloro-5-fluorophenyl)-5 ethoxycarbonyl-2-(1,3-thiazol-2-yl)-1,4-dihydropyrimidin-6-yl]methyl]morpholine-3 carboxylic acid |
| 126 | 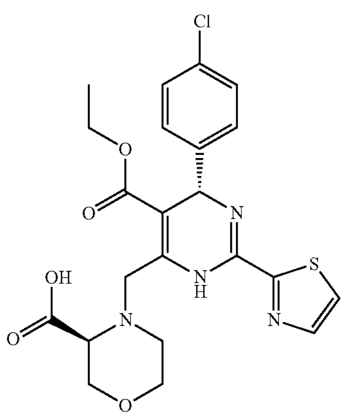 [SMILES: CCOC(=O)C1=C(CN2CCOC[C@H]2C(=O)O)NC(c2nccs2)=N[C@H]1c1ccc(Cl)cc1] | (3S)-4-[[(4S)-4-(4-Chlorophenyl)-5-ethoxycarbonyl-2-(1,3-thiazol-2-yl)-1,4-dihydropyrimidin-6-yl]methyl]morpholine-3 carboxylic acid |
| 127 | 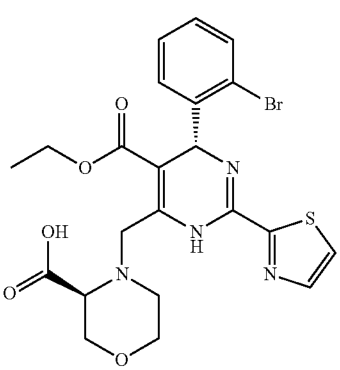 [SMILES: CCOC(=O)C1=C(CN2CCOC[C@H]2C(=O)O)NC(c2nccs2)=N[C@H]1c1ccccc1Br] | (S)-4-(((R)-6-(2-Bromophenyl)-5-(ethoxycarbonyl)-2-(thiazol-2-yl)-3,6-dihydropyrimidin-4-yl)methyl)morpholine-3 carboxylic acid |

TABLE 1-continued

Structure and name of particular compounds

| Example No. | Structure | Name |
|---|---|---|
| 128 | 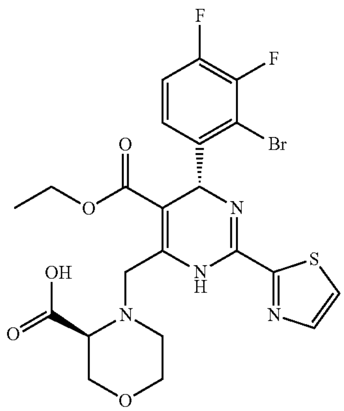 [SMILES: CCOC(=O)C1=C(CN2CCOC[C@H]2C(=O)O)NC(c2nccs2)=N[C@H]1c1ccc(F)c(F)c1Br] | (3S)-4-[[(4R)-4-(2-Bromo-3,4-difluorophenyl)-5-ethoxycarbonyl-2-(1,3-thiazol-2-yl)-1,4-dihydropyrimidin-6-yl]methyl]morpholine-3-carboxylic acid |
| 129 | 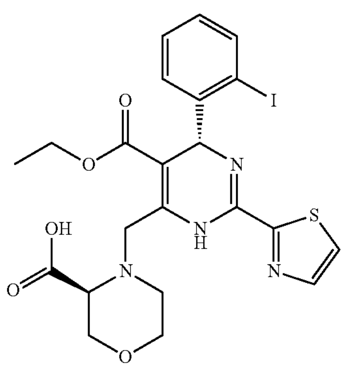 [SMILES: CCOC(=O)C1=C(CN2CCOC[C@H]2C(=O)O)NC(c2nccs2)=N[C@H]1c1ccccc1I] | (3S)-4-[[(4R)-5-Ethoxycarbonyl-4-(2-iodophenyl)-2-(1,3-thiazol-2-yl)-1,4-dihydropyrimidin-6-yl]methyl]morpholine-3-carboxylic acid |
| 130 | 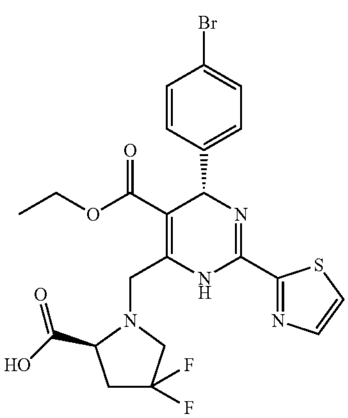 [SMILES: CCOC(=O)C1=C(CN2CC(F)(F)C[C@H]2C(=O)O)NC(c2nccs2)=N[C@H]1c1ccc(Br)cc1] | (2S)-1-[[(4S)-4-(4-Bromophenyl)-5-ethoxycarbonyl-2-(1,3-thiazol-2-yl)-1,4-dihydropyrimidin-6-yl]methyl]-4,4-difluoropyrrolidine-2-carboxylic acid |

TABLE 2

NMR and MS data of particular compounds

| Example No. | $^1$H NMR data | MW data |
|---|---|---|
| 1 | $^1$H NMR (MeOD-d$_4$, 400 MHz): δ ppm 7.94-7.93 (m, 1H), 7.75-7.73 (m, 1H), 7.50-7.44 (m, 1H), 7.25-7.21 (m, 1H), 7.10-7.05 (m, 1H), 6.17 (s, 0.5H), 6.15 (s, 0.5H), 4.49-4.39 (m, 1H), 4.17-4.13 (m, 1H), 3.90-3.83 (m, 1H), 3.65-3.55 (m, 4H), 3.25-3.08 (m, 1H), 2.86-2.73 (m, 1H), 2.62-2.51 (m, 1H) | MS: calc'd (MH$^+$) 515, measured (MH$^+$) 515 |
| 2 | $^1$H NMR (MeOD-d$_4$, 400 MHz): δ ppm 8.21 (s, 2H), 7.63-7.60 (m, 1H), 7.38-7.35 (m, 1H), 7.22-7.18 (m, 1H), 6.29 (s, 1H), | MS: calc'd (MH$^+$) 515, measured |

TABLE 2-continued

NMR and MS data of particular compounds

| Example No. | ¹H NMR data | MW data |
|---|---|---|
| | 4.57 (d, 1H, J = 16 Hz), 4.13-4.08 (m, 2H), 3.70-3.67 (m, 4H), 3.33-3.28 (m, 1H), 2.92-2.82 (m, 1H), 2.63-2.56 (m, 1H) | (MH⁺) 515 |
| 3 | ¹H NMR (CDCl₃-d, 400 MHz): δ ppm 7.85 (br. s., 1H), 7.50-7.55 (m, 1H), 7.29-7.35 (m, 1H), 7.16 (ddd, J = 8.34, 5.96, 2.51 Hz, 1H), 6.93-7.02 (m, 1H), 4.56-4.69 (m, 1H), 3.91 (dd, J = 11.80, 2.76 Hz, 1H), 3.78 (d, J = 14.81 Hz, 1H), 3.63 (s, 3H), 3.46-3.59 (m, 1H), 3.06-3.29 (m, 1H), 2.72-2.86 (m, 1H), 2.49-2.64 (m, 1H) | MS: calc'd 514 (MH⁻), measured 514 (MH⁻) |
| 4 | ¹H NMR (MeOD-d₄, 400 MHz): δ ppm 8.71 (d, J = 2.01 Hz, 1H), 7.98 (d, J = 2.01 Hz, 1H), 7.65-7.80 (m, 1H), 7.41-7.56 (m, 1H), 7.33 (br. s., 1H), 6.47 (s, 1H), 4.65 (br. s., 1H), 4.37 (br. s., 1H), 4.12 (br. s., 1H), 3.74-3.90 (m, 4H), 3.31-3.50 (m, 1H), 2.92-3.09 (m, 1H), 2.64-2.86 (m, 1H) | MS: calc'd (MH⁺) 545, measured (MH⁺) 545 |
| 5 | ¹H NMR (DMSO-d₆, 400 MHz): δ ppm 12.88 (br. s, 1H), 9.87 (s, 1H), 8.04 (d, 1H, J = 4 Hz), 7.95 (d, 1H, J = 4 Hz), 7.44-7.39 (m, 2H), 7.19-7.14 (m, 1H), 6.04 (s, 1H), 4.25 (d, 1H, J = 20 Hz), 4.07-3.97 (m, 2H), 3.86-3.61 (m, 4H), 3.51 (s, 3H), 3.12-3.07 (m, 1H), 2.45-2.39 (m, 1H) | MS: calc'd (MH⁺) 495, measured (MH⁺) 495 |
| 6 | ¹H NMR (MeOD-d₄, 400 MHz): δ ppm 8.51 (s, 1H), 8.47 (s, 2H), 7.73-7.72 (m, 1H), 7.50-7.46 (m, 1H), 7.25-7.22 (m, 1H), 7.08-7.04 (m, 1H), 6.22 (s, 1H), 4.24 (d, 1H, J = 16 Hz), 4.12 (d, 1H, J = 16 Hz), 4.07-4.04 (m, 1H), 3.89-3.79 (m, 3H), 3.62 (s, 3H), 3.47-3.44 (m, 1H), 3.25-3.19 (m, 1H), 2.67-2.65 (m, 1H) | MS: calc'd (MH⁺) 525, measured (MH⁺) 525 |
| 7 | ¹H NMR (MeOD-d₄, 400 MHz): δ ppm 7.93 (d, J = 3.01 Hz, 1H), 7.73 (d, J = 3.01 Hz, 1H), 7.45 (dd, J = 8.66, 6.15 Hz, 1H), 7.23 (dd, J = 8.78, 2.51 Hz, 1H), 7.06 (td, J = 8.41, 2.51 Hz, 1H), 6.16 (s, 1H), 4.13-4.39 (m, 2H), 3.66 (d, J = 8.78 Hz, 2H), 3.60 (s, 3H), 2.88 (d, J = 10.04 Hz, 1H), 2.23 (d, J = 5.02 Hz, 2H), 1.89-2.16 (m, 2H) | MS: calc'd (MH⁺) 529, measured (MH⁺) 529 |
| 8 | ¹H NMR (MeOD-d₄, 400 MHz): δ ppm 8.70 (s, 1H), 8.30 (d, J = 8.28 Hz, 1H), 7.95 (d, J = 7.03 Hz, 1H), 7.62 (dd, J = 8.66, 5.90 Hz, 1H), 7.38 (dd, J = 8.66, 2.64 Hz, 1H), 7.21 (td, J = 8.34, 2.64 Hz, 1H), 6.32 (s, 1H), 4.59 (d, J = 16.06 Hz, 1H), 4.01 (t, J = 8.41 Hz, 1H), 3.94 (d, J = 16.31 Hz, 1H), 3.69 (s, 3H), 3.49-3.65 (m, 1H), 3.21 (td, J = 14.62, 11.17 Hz, 1H), 2.76-2.93 (m, 1H), 2.43-2.61 (m, 4H) | MS: calc'd (MH⁺) 523, measured (MH⁺) 523 |
| 9 | ¹H NMR (MeOD-d₄, 400 MHz): δ ppm 8.74 (s, 1H), 8.20 (d, J = 8.28 Hz, 1H), 7.96 (d, J = 7.28 Hz, 1H), 7.62 (dd, J = 8.66, 5.90 Hz, 1H), 7.37 (dd, J = 8.53, 2.51 Hz, 1H), 7.19 (td, J = 8.28, 2.51 Hz, 1H), 6.35 (s, 1H), 4.23-4.34 (m, 1H), 4.05-4.22 (m, 2H), 3.99 (d, J = 6.27 Hz, 1H), 3.85-3.93 (m, 1H), 3.74-3.83 (m, 1H), 3.64-3.73 (s, 3H), 3.11-3.27 (m, 2H), 2.64-2.76 (m, 1H), 2.52 (s, 3H) | MS: calc'd (MH⁺) 503, measured (MH⁺) 503 |
| 10 | ¹H NMR (MeOD-d₄, 400 MHz): δ ppm 7.69 (s, 1H), 7.53-7.62 (m, 1H), 7.30-7.38 (m, 1H), 7.08-7.23 (m, 1H), 6.23-6.27 (m, 1H), 4.43-4.55 (m, 1H), 3.96-4.12 (m, 1H), 3.65 (s, 4H), 3.14-3.30 (m, 1H), 2.74-2.97 (m, 1H), 2.45-2.64 (m, 1H), 2.09-2.25 (m, 1H), 0.94-1.10 (m, 4H) | MS: calc'd (MH⁺) 555, measured (MH⁺) 555 |
| 11 | ¹H NMR (MeOD-d₄, 400 MHz): δ ppm 7.67-7.73 (m, 1H), 7.53-7.63 (m, 1H), 7.28-7.37 (m, 1H), 7.11-7.22 (m, 1H), 6.22-6.28 (m, 1H), 4.44-4.52 (m, 1H), 4.08-4.18 (m, 1H), 3.99-4.07 (m, 1H), 3.65 (s, 4H), 3.16-3.30 (m, 1H), 2.77-2.95 (m, 1H), 2.46-2.64 (m, 1H), 1.41 (s, 9H) | MS: calc'd (MH⁺) 571, measured (MH⁺) 571 |
| 12 | ¹H NMR (MeOD-d₄, 400 MHz): δ ppm 7.67 (d, J = 1.3 Hz, 1H), 7.42 (dd, J = 8.7, 6.1 Hz, 1H), 7.21 (dd, J = 8.8, 2.5 Hz, 1H), 6.98-7.11 (m, 2H), 6.07 (s, 1H), 4.61 (d, J = 15.8 Hz, 2H), 3.79 (d, J = 15.8 Hz, 1H), 3.60-3.69 (m, 4H), 2.93-3.19 (m, 1H), 2.63-2.77 (m, 1H), 2.35-2.54 (m, 1H) | MS: calc'd (MH⁺) 532, measured (MH⁺) 532 |
| 13 | ¹H NMR (MeOD-d₄, 400 MHz): δ ppm 7.39 (ddd, J = 14.18, 8.41, 6.02 Hz, 1H), 7.24 (dd, J = 8.66, 2.13 Hz, 1H), 7.19 (d, J = 2.51 Hz, 1H), 6.99-7.11 (m, 2H), 6.17 (d, J = 1.76 Hz, 1H), 4.18-4.35 (m, 2H), 3.97-4.14 (m, 2H), 3.94 (s, 1.5H), 3.77-3.91 (m, 3.5H), 3.62 (d, J = 2.01 Hz, 3H), 3.44-3.53 (m, 0.5H), 3.39 (dd, J = 7.65, 3.39 Hz, 0.5H), 3.21-3.30 (m, 0.5H), 3.07 (d, J = 12.30 Hz, 0.5H), 2.52-2.65 (m, 1H) | MS: calc'd (MH⁺) 492, measured (MH⁺) 492 |
| 14 | ¹H NMR (MeOD-d₄, 400 MHz): δ ppm 7.94 (d, 1H, J = 4 Hz), 7.74 (d, 1H, J = 4 Hz), 7.46-7.43 (m, 1H), 7.25-7.22 (m, 1H), 7.09-7.06 (m, 1H), 6.18 (s, 1H), 4.11 (dd, 2H, J₁ = 56 Hz, J₂ = 16 Hz), 3.62 (s, 3H), 3.21-3.01 (m, 3H), 2.79-2.43 (m, 3H), 2.11-1.98 (m, 1H) | MS: calc'd (MH⁺) 529, measured (MH⁺) 529 |
| 15 | ¹H NMR (MeOD-d₄, 400 MHz): δ ppm 7.93 (s, 1H), 7.56-7.52(m, 1H), 7.33-7.30 (m, 1H), 7.18-7.15 (m, 1H), 6.24 (s, 1H), 4.47(d, 1H, J = 16 Hz), 4.05 (d, 1H, J = 16 Hz), 3.99 (t, 1H, J = | MS: calc'd (MH⁺) 513, measured (MH⁺) 513 |

TABLE 2-continued

NMR and MS data of particular compounds

| Example No. | $^1$H NMR data | MW data |
|---|---|---|
|  | 8 Hz), 3.64-3.58 (m, 4H), 3.27-3.15 (m, 1H), 2.85-2.79 (m, 1H), 2.68-2.51 (m, 1H), 2.26 (s, 3H) |  |
| 16 | $^1$H NMR (MeOD-d$_4$, 400 MHz): δ ppm 7.69 (d, J = 0.75 Hz, 1H), 7.54-7.63 (m, 1H), 7.28-7.38 (m, 1H), 7.10-7.20 (m, 1H), 6.27 (s, 1H), 4.52-4.61 (m, 1H), 4.12-4.21 (m, 1H), 4.03-4.12 (m, 1H), 3.66 (s, 4H), 3.17-3.29 (m, 1H), 2.78-2.98 (m, 1H), 2.53 (d, J = 0.75 Hz, 4H) | MS: calc'd (MH$^+$) 529, measured (MH$^+$) 529 |
| 17 | $^1$H NMR (MeOD-d$_4$, 400 MHz): δ ppm 7.51-7.59 (m, 2H), 7.28-7.34 (m, 1H), 7.09-7.18 (m, 1H), 6.19-6.26 (m, 1H), 4.71-4.79 (m, 1H), 4.44-4.53 (m, 1H), 4.08-4.23 (m, 3H), 3.90-4.04 (m, 2H), 3.66 (s, 4H), 3.07-3.18 (m, 1H), 2.51 (s, 3H) | MS: calc'd (MH$^+$) 509, measured (MH$^+$) 509 |
| 18 | $^1$H NMR (MeOD-d$_4$, 400 MHz): δ ppm 8.10-8.19 (m, 2H), 7.47-7.60 (m, 2H), 6.22-6.26 (m, 1H), 4.53-4.60 (m, 1H), 4.09-4.23 (m, 2H), 3.68 (s, 4H), 3.27-3.38 (m, 1H), 2.80-2.98 (m, 1H), 2.52-2.66 (m, 1H) | MS: calc'd (MH$^+$) 533, measured (MH$^+$) 533 |
| 19 | $^1$H NMR (CDCl$_3$-d, 400 MHz): δ ppm 10.62 (s, 1H), 8.02 (s, 1H), 7.81 (br. s., 1H), 7.36 (dd, J = 8.53, 5.77 Hz, 1H), 7.21 (dd, J = 8.16, 2.38 Hz, 1H), 7.05 (td, J = 8.09, 2.38 Hz, 1H), 6.25 (s, 1H), 4.62 (d, J = 15.56 Hz, 1H), 3.93-4.00 (m, 1H), 3.88 (d, J = 15.56 Hz, 1H), 3.68 (s, 3H), 3.57-3.65 (m, 1H), 3.16-3.29 (m, 1H), 2.49-2.63 (m, 1H) | MS: calc'd 516 (MH$^+$), measured 516 (MH$^+$) |
| 20 | $^1$H NMR (MeOD-d$_4$, 400 MHz): δ ppm 7.36-7.48 (m, 1H), 7.17-7.29 (m, 1H), 7.02-7.13 (m, 1H), 6.91 (s, 1H), 6.16 (s, 1H), 4.30-4.53 (m, 1H), 4.02-4.25 (m, 1H), 3.73-3.86 (m, 5H), 3.62 (d, J = 3.01 Hz, 3H), 2.95-3.24 (m, 1H), 2.71 (s, 1H), 2.45-2.62 (m, 1H), 2.08-2.28 (m, 3H) | MS: calc'd (MH$^+$) 526, measured (MH$^+$) 526 |
| 21 | $^1$H NMR (MeOD-d$_4$, 400 MHz): δ ppm 8.02-8.07 (m, 1H), 7.91-7.97 (m, 1H), 7.39-7.54 (m, 2H), 6.16-6.23 (m, 1H), 4.81-4.85(m, 1H), 4.48-4.58 (m, 1H), 4.13-4.29 (m, 3H), 3.91-4.07 (m, 2H), 3.70-3.81 (m, 1H), 3.67 (s, 3H), 3.12-3.25 (m, 1H) | MS: calc'd (MH$^+$) 513, measured (MH$^+$) 513 |
| 22 | $^1$H NMR (MeOD-d$_4$, 400 MHz): δ ppm 8.56 (d, J = 4.5 Hz, 1H), 7.80-7.91 (m, 1H), 7.73 (dt, J = 8.5, 4.2 Hz, 1H), 7.57 (dd, J = 8.8, 6.0 Hz, 1H), 7.30 (dd, J = 8.8, 2.5 Hz, 1H), 7.12 (td, J = 8.4, 2.5 Hz, 1H), 6.25-6.35 (m, 1H), 4.52 (d, J = 17.3 Hz, 1H), 4.14 (d, J = 17.3 Hz, 1H), 3.92 (t, J = 8.3 Hz, 1H), 3.54-3.73 (m, 4H), 3.13 (td, J = 14.7, 11.2 Hz, 1H), 2.80 (t, J = 9.7 Hz, 1H), 2.42-2.63 (m, 1H) | MS: calc'd (MH$^+$) 527, measured (MH$^+$) 527 |
| 23 | $^1$H NMR (MeOD-d$_4$, 400 MHz): δ ppm 7.71 (d, J = 11.3 Hz, 2H), 7.50 (dd, J = 8.5, 6.0 Hz, 1H), 7.29 (dd, J = 8.5, 2.5 Hz, 1H), 7.11 (td, J = 8.4, 2.5 Hz, 1H), 6.16 (s, 1H), 4.69 (d, J = 16.3 Hz, 1H), 3.89-4.08 (m, 2H), 3.52-3.70 (m, 4H), 3.13-3.28 (m, 1H), 2.87 (dd, J = 14.4, 9.4 Hz, 1H), 2.43-2.64 (m, 1H) | MS: calc'd (MH$^+$) 548, measured (MH$^+$) 548 |
| 24 | $^1$H NMR (MeOD-d$_4$, 400 MHz): δ ppm 8.59 (d, J = 4.5 Hz, 1H), 7.91 (d, J = 8.0 Hz, 1H), 7.58-7.74 (m, 2H), 7.43 (dd, J = 8.5, 2.3 Hz, 1H), 7.28 (td, J = 8.3, 2.3 Hz, 1H), 6.39 (s, 1H), 4.44 (d, J = 16.1 Hz, 1H), 4.12 (d, J = 15.8 Hz, 1H), 3.89-4.01 (m, 1H), 3.66-3.77 (m, 3H), 3.51-3.63 (m, 1H), 3.16-3.28 (m, 1H), 2.70-2.88 (m, 1H), 2.42-2.57 (m, 4H) | MS: calc'd (MH$^+$) 523, measured (MH$^+$) 523 |
| 25 | $^1$H NMR (MeOD-d$_4$, 400 MHz): δ ppm 8.36 (s, 1H), 7.41-7.54 (m, 1H), 7.23-7.29 (m, 1H), 7.01-7.14 (m, 1H), 6.19 (s, 1H), 4.40 (s, 1H), 4.28 (s, 1H), 3.97-4.09 (m, 1H), 3.65-3.74 (m, 1H), 3.62 (s, 3H), 3.37 (s, 2H), 2.73-2.91 (m, 1H) | MS: calc'd (MH$^+$) 583, measured (MH$^+$) 583 |
| 26 | $^1$H NMR (MeOD-d$_4$, 400 MHz): δ ppm 7.93 (br. s, 1H), 7.74 (br. s, 1H), 7.48 (dt, J = 8.53, 6.02 Hz, 1H), 7.23 (dt, J = 8.66, 2.82 Hz, 1H), 7.07 (qd, J = 8.53, 2.26 Hz, 1H), 6.17 (d, J = 8.28 Hz, 1H), 4.39-4.56 (m, 1H), 4.17 (d, J = 17.07 Hz, 1H), 4.06 (q, J = 7.03 Hz, 2H), 3.93 (q, J = 7.95 Hz, 1H), 3.52-3.72 (m, 1H), 3.08-3.29 (m, 1H), 2.71-2.89 (m, 1H), 2.48-2.68 (m, 1H), 1.15 (t, J = 7.15 Hz, 3H) | MS: calc'd (MH$^+$) 529, measured (MH$^+$) 529 |
| 27 | $^1$H NMR (MeOD-d$_4$, 400 MHz): δ ppm 7.89 (s, 1H), 7.78 (s, 1H), 7.59 (dd, J = 5.90, 8.66 Hz, 1H), 7.39 (dd, J = 2.51, 8.53 Hz, 1H), 7.19 (dt, J = 2.51, 8.28 Hz, 1H), 6.26 (s, 1H), 4.71 (d, J = 17.32 Hz, 1H), 3.88-4.13 (m, 2H), 3.69 (s, 3H), 3.45-3.63 (m, 2H), 3.08-3.26 (m, 1H), 2.90 (dd, J = 9.66, 15.18 Hz, 1H), 2.45-2.63 (m, 1H), 2.36 (s, 3H) | MS: calc'd (MH$^+$) 528, measured (MH$^+$) 528 |
| 28 | $^1$H NMR (MeOD-d$_4$, 400 MHz): δ ppm 7.69 (s, 1H), 7.58 (dd, J = 8.78, 6.02 Hz, 1H), 7.34 (dd, J = 8.78, 2.26 Hz, 1H), 7.17 (td, J = 8.34, 2.13 Hz, 1H), 6.25 (s, 1H), 4.50 (d, J = 16.81 Hz, 1H), 4.13 (d, J = 16.81 Hz, 1H), 4.04 (t, J = 8.16 Hz, 1H), 3.59-3.69 (m, 4H), 3.13-3.29 (m, 2H), 2.76-2.94 (m, 1H), 2.46-2.65 (m, 1H), 1.36 (d, J = 6.78 Hz, 6H) | MS: calc'd (MH$^+$) 557, measured (MH$^+$) 557 |
| 29 | $^1$H NMR (MeOD-d$_4$, 400 MHz): δ ppm 8.10 (d, J = 3.01 Hz, 1H), 8.04 (d, J = 3.01 Hz, 1H), 7.70 (s, 1H), 7.55 (d, J = 8.28 Hz, 1H), 7.45 (d, J = 8.53 Hz, 1H), 6.23 (s, 1H), 4.52 (d, J = 16.31 Hz, 1H), 4.15 (d, J = 16.06 Hz, 1H), 4.07 (t, J = 8.16 Hz, | MS: calc'd (MH$^+$) 557, measured (MH$^+$) 557 |

TABLE 2-continued

NMR and MS data of particular compounds

| Example No. | $^1$H NMR data | MW data |
|---|---|---|
| | 1H), 3.61-3.73 (m, 4H), 3.21-3.31 (m, 1 H) 2.78-2.94 (m, 1H), 2.48-2.66 (m, 1H) | |
| 30 | $^1$H NMR (MeOD-d$_4$, 400 MHz): δ ppm 8.04 (d, J = 3.01 Hz, 1H), 7.88-7.94 (m, 2H), 7.70 (s, 2H), 6.30 (s, 1H), 4.56 (d, J = 17.07 Hz, 1H), 4.20 (d, J = 16.81 Hz, 1H), 4.04 (t, J = 8.28 Hz, 1H), 3.57-3.68 (m, 4H), 3.14-3.28 (m, 1H) 2.77-2.93 (m, 1H), 2.50-2.66 (m, 1H) | MS: calc'd (MH$^+$) 522, measured (MH$^+$) 522 |
| 31 | $^1$H NMR (MeOD-d$_4$, 400 MHz): δ ppm 8.08 (d, J = 3.01 Hz, 1H), 8.01 (d, J = 3.01 Hz, 1H), 7.60 (dd, J = 8.53, 6.02 Hz, 1H), 7.31 (dd, J = 8.66, 2.38 Hz, 1H), 7.15 (td, J = 8.34, 2.38 Hz, 1H), 6.26 (s, 1H), 4.88 (d, J = 16.31 Hz, 1H), 4.59 (d, J = 16.56 Hz, 1H), 4.26-4.33 (m, 1H), 4.22 (d, J = 4.02 Hz, 2H), 4.11 (q, J = 6.94 Hz, 2H), 3.93-4.05 (m, 2H), 3.78 (ddd, J = 12.42, 8.28, 3.64 Hz, 1H), 3.27 (d, J = 13.05 Hz, 1H), 1.16 (t, J = 7.15 Hz, 3H) | MS: calc'd (MH$^+$) 509, measured (MH$^+$) 509 |
| 32 | $^1$H NMR (MeOD-d$_4$, 400 MHz): δ ppm 7.51-7.66 (m, 2H), 7.38 (t, J = 5.27 Hz, 2H), 7.15-7.25 (m, 1H), 6.29 (s, 1H), 4.42 (d, J = 15.81 Hz, 1H), 4.24 (d, J = 15.81 Hz, 1H), 3.95-4.11 (m, 4H), 3.59-3.78 (m, 4H), 2.76-2.95 (m, 1H), 2.53 (td, J = 17.63, 7.40 Hz, 1H) | MS: calc'd (MH$^+$) 512, measured (MH$^+$) 512 |
| 33 | $^1$H NMR (MeOD-d$_4$, 400 MHz): δ ppm 7.95 (m, 1H), 7.62 (dd, J = 5.9, 8.7 Hz, 1H), 7.42 (m, 1H), 7.29 (m, 3H), 6.29 (s, 1H), 4.49 (d, J = 16.0 Hz, 1H), 4.00 (d, J = 16.0 Hz, 1H), 3.69 (s, 3H), 3.57 (m, 1H), 3.20 (m, 1H), 2.79 (m, 1H), 2.45 (m, 1H) | MS: calc'd (MH$^+$) 544, measured (MH$^+$) 544 |
| 34 | $^1$H NMR (MeOD-d$_4$, 400 MHz): δ ppm 8.09 (d, J = 3.01 Hz, 1H), 8.02 (d, J = 3.01 Hz, 1H), 7.57 (dd, J = 8.78, 6.02 Hz, 1H), 7.32 (dd, J = 8.78, 2.51 Hz, 1H), 7.16 (td, J = 8.41, 2.51 Hz, 1H), 6.25 (s, 1H), 4.53 (d, J = 16.06 Hz, 1H), 4.00-4.18 (m, 4H), 3.68 (q, J = 11.13 Hz, 1H), 3.20-3.30 (m, 1H), 2.77-2.94 (m, 1H), 2.49-2.65 (m, 1H), 1.17 (t, J = 7.15 Hz, 3 H) | MS: calc'd 529 (MH$^+$), exp 529 (MH$^+$). |
| 35 | $^1$H NMR (MeOD-d$_4$, 400 MHz): δ ppm 8.09 (s, 1H), 7.44 (dd, J = 6.0, 8.5 Hz, 1H), 7.32-7.23 (m, 2H), 7.17-7.03 (m, 2H), 6.21 (s, 1H), 4.57-4.45 (m, 1H), 4.38-4.27 (m, 1H), 4.19-4.05 (m, 3H), 4.00 (s, 3H), 3.97-3.80 (m, 2H), 3.75 (t, J = 4.1 Hz, 1H), 3.49-3.36 (m, 1H), 2.84-2.72 (m, 1H), 1.16 (t, J = 7.2 Hz, 3H). | MS: calc'd 506 (MH$^+$), exp 506 (MH$^+$). |
| 36 | $^1$H NMR (MeOD-d$_4$, 400 MHz): δ ppm 7.63 (dd, J = 8.78, 5.77 Hz, 1 H), 7.57 (s, 1 H), 7.39 (dd, J = 8.53, 2.51 Hz, 1 H), 7.33 (d, J = 1.00 Hz, 1 H), 7.20 (td, J = 8.41, 2.51 Hz, 1 H), 6.32 (s, 1 H), 4.63 (d, J = 17.32 Hz, 1 H), 4.14 (qd, J = 6.86, 3.01 Hz, 3 H), 4.01-4.07 (m, 1 H), 4.00 (s, 3 H), 3.67 (td, J = 11.54, 7.78 Hz, 1 H), 3.13-3.28 (m, 1 H), 2.88 (dd, J = 14.43, 9.41 Hz, 1 H), 2.45-2.61 (m, 1 H), 1.17 (t, J = 7.03 Hz, 3 H). | MS: calc'd 526 (MH$^+$), exp 526 (MH$^+$). |
| 37 | $^1$H NMR (MeOD-d$_4$, 400 MHz): δ ppm 8.09-8.28 (m, 1 H), 7.85 (t, J = 7.78 Hz, 1 H), 7.38-7.57 (m, 2 H), 7.27 (dd, J = 8.53, 2.51 Hz, 1 H), 7.09 (d, J = 2.51 Hz, 1 H), 6.24 (s, 1 H), 4.36 (d, J = 4.52 Hz, 2 H), 3.99-4.20 (m, 4 H), 3.92 (br. s., 1 H), 3.86 (d, J = 2.76 Hz, 1 H), 3.63 (t, J = 4.39 Hz, 1 H), 3.35 (br. s., 1 H), 2.69-2.82 (m, 1 H), 2.63 (s, 3 H), 1.17 (t, J = 7.15 Hz, 3 H). | MS: calc'd 517 (MH$^+$), exp 517 (MH$^+$). |
| 38 | $^1$H NMR (MeOD-d$_4$, 400 MHz): δ ppm 7.93-8.06 (m, 1 H), 7.82-7.90 (m, 1 H), 7.43-7.57 (m, 2 H), 7.37 (dd, J = 8.53, 2.01 Hz, 1 H), 6.20 (s, 1 H), 4.48 (d, J = 16.31 Hz, 1 H), 4.18 (d, J = 16.31 Hz, 1 H), 4.08 (q, J = 7.11 Hz, 2 H), 4.01 (t, J = 8.16 Hz, 1 H), 3.65 (s, 1 H), 3.18-3.29 (m, 2 H), 2.75-2.91 (m, 1 H), 2.50-2.67 (m, 1 H), 1.16 (t, J = 7.15 Hz, 3 H). | MS: calc'd 545 (MH$^+$), exp 545 (MH$^+$). |
| 39 | $^1$H NMR (MeOD-d$_4$, 400 MHz): δ ppm 7.97 (d, J = 3.01 Hz, 1 H), 7.78 (d, J = 3.01 Hz, 1 H), 7.49 (d, J = 2.01 Hz, 1 H), 7.44 (d, J = 8.28 Hz, 1 H), 7.32 (dd, J = 8.28, 2.01 Hz, 1 H), 6.18 (s, 1 H), 4.33-4.49 (m, 1 H), 4.17-4.30 (m, 1 H), 4.07 (d, J = 7.03 Hz, 5 H), 3.78-3.96 (m, 2 H), 3.61 (br. s., 1 H), 2.62-2.79 (m, 1H), 1.16 (t, J = 7.15 Hz, 3 H). | MS: calc'd 525 (MH$^+$), exp 525 (MH$^+$). |
| 40 | $^1$H NMR (MeOD-d$_4$, 400 MHz): δ ppm 7.66 (s, 1 H), 7.42 (dd, J = 8.66, 6.15 Hz, 1 H), 7.25 (dd, J = 8.78, 2.51 Hz, 1 H), 7.07 (td, J = 8.41, 2.51 Hz, 1 H), 6.20 (s, 1 H), 4.41 (d, J = 16.31 Hz, 1 H), 4.20-4.28 (m, 1 H), 4.06 (q, J = 7.11 Hz, 2 H), 3.97 (m, 4 H), 3.53-3.69 (m, 1 H), 3.16-3.32 (m, 1 H), 2.68-2.88 (m, 1 H), 2.47-2.65 (m, 1 H), 1.15 (t, J = 7.03 Hz, 3 H). | MS: calc'd 594 (MH$^+$), exp 594 (MH$^+$). |
| 41 | $^1$H NMR (MeOD-d$_4$, 400 MHz): δ ppm 8.15 (d, J = 3.01 Hz, 1 H), 8.10 (d, J = 3.01 Hz, 1 H), 7.24-7.46 (m, 3 H), 5.80 (s, 1 H), 4.52 (d, J = 16.06 Hz, 1 H), 4.13-4.25 (m, 3 H), 4.04-4.11 (m, 1 H), 3.67 (d, J = 11.04 Hz, 1 H), 3.22-3.31 (m, 1 H), 2.74-2.96 (m, 1 H), 2.45-2.69 (m, 1 H), 1.23 (t, J = 7.15 Hz, 3 H). | MS: calc'd 513 (MH$^+$), exp 513 (MH$^+$). |
| 42 | $^1$H NMR (MeOD-d$_4$, 400 MHz): δ ppm 8.00 (d, J = 3.26 Hz, 1 H), 7.83 (d, J = 3.01 Hz, 1 H), 7.14-7.31 (m, 3 H), 5.71 (s, 1 | MS: calc'd 493 (MH$^+$), exp 493 |

TABLE 2-continued

NMR and MS data of particular compounds

| Example No. | $^1$H NMR data | MW data |
|---|---|---|
|  | H), 4.54 (d, J = 17.07 Hz, 1 H), 4.02-4.30 (m, 5 H), 3.78-3.98 (m, 2 H), 3.67 (t, J = 3.89 Hz, 1 H), 3.41 (br. s., 1 H), 2.70-2.86 (m, 1 H), 1.24 (t, J = 7.15 Hz, 3 H). | (MH$^+$). |
| 43 | $^1$H NMR (MeOD-d$_4$, 400 MHz): δ ppm 8.01 (d, J = 3.26 Hz, 1 H), 7.83 (d, J = 3.26 Hz, 1 H), 7.13 (dd, J = 8.66, 6.65 Hz, 2 H), 5.72 (s, 1 H), 4.55 (d, J = 17.32 Hz, 1 H), 4.01-4.26 (m, 5 H), 3.78-3.96 (m, 2 H), 3.67 (t, J = 3.76 Hz, 1 H), 3.35-3.47 (m, 1 H), 2.61-2.79 (m, 1 H), 1.25 (t, J = 7.03 Hz, 3 H). | MS: calc'd 511 (MH$^+$), exp 511 (MH$^+$). |
| 44 | $^1$H NMR (MeOD-d$_4$, 400 MHz): δ ppm 7.93-8.08 (m, 1 H), 7.76-7.90 (m, 1 H), 7.19-7.31 (m, 1 H), 7.04-7.16 (m, 1 H), 6.02 (br. s., 1 H), 4.35-4.54 (m, 1 H), 4.10 (d, J = 4.77 Hz, 4 H), 3.79-3.97 (m, 2 H), 3.56-3.70 (m, 1 H), 2.61-2.81 (m, 1 H), 1.09-1.30 (m, 3H). | MS: calc'd 511 (MH$^+$), exp 511 (MH$^+$). |
| 45 | $^1$H NMR (MeOD-d$_4$, 400 MHz): δ ppm 7.99 (d, J = 3.26 Hz, 1 H), 7.80 (d, J = 2.76 Hz, 1 H), 7.35-7.45 (m, 1 H), 7.14 (t, J = 6.90 Hz, 1 H), 6.03 (s, 1 H), 4.39 (br. s., 1 H), 4.14-4.27 (m, 1 H), 4.08 (br. s., 3 H), 3.87 (d, J = 12.80 Hz, 3 H), 3.65 (s, 3 H), 2.68 (br. s., 1 H). | MS: calc'd 557 (MH$^+$), exp 557 (MH$^+$). |
| 46 | $^1$H NMR (MeOD-d$_4$, 400 MHz): δ ppm 8.01 (d, J = 3.26 Hz, 1 H), 7.83 (d, J = 3.01 Hz, 1 H), 7.43-7.57 (m, 2 H), 7.32 (dd, J = 8.41, 2.13 Hz, 1H), 5.71 (s, 1 H), 4.44 (d, J = 14.81 Hz, 1 H), 4.02-4.31 (m, 5 H), 3.78-3.98 (m, 3 H), 3.60 (br. s., 1 H), 2.68 (br. s., 1 H), 1.25 (t, J = 7.15 Hz, 3 H). | MS: calc'd 525 (MH$^+$), exp 525 (MH$^+$). |
| 47 | $^1$H NMR (MeOD-d$_4$, 400 MHz): δ ppm 7.97 (d, J = 2.76 Hz, 1 H), 7.78 (br. s., 1 H), 7.24-7.38 (m, 2 H), 7.10-7.21 (m, 1 H), 6.23 (s, 1 H), 4.40 (m, 1H), 4.25 (m, 1 H), 4.07 (m, 2 H), 3.87 (m, 2 H), 3.62 (m, 4 H), 2.70 (m, 2 H). | MS: calc'd 495 (MH$^+$), exp 495 (MH$^+$). |
| 48 | $^1$H NMR (MeOD-d$_4$, 400 MHz): δ ppm 7.97 (d, J = 3.3 Hz, 1H), 7.78 (d, J = 3.0 Hz, 1H), 7.75-7.68 (m, 2H), 7.59 (d, J = 8.3 Hz, 2H), 5.78 (s, 1H), 4.35 (d, J = 16.3 Hz, 1H), 4.14 (q, J = 7.0 Hz, 3H), 3.81 (t, J = 7.8 Hz, 1H), 3.60-3.49 (m, 1H), 3.16-3.05 (m, 1H), 2.74 (dd, J = 7.9, 13.2 Hz, 1H), 2.53 (dd, J = 7.9, 14.9 Hz, 1H), 1.22 (t, J = 7.0 Hz, 3H) | MS: calc'd 502 (MH$^+$), exp 502 (MH$^+$). |
| 49 | $^1$H NMR (MeOD-d$_4$, 400 MHz): δ ppm 7.99 (d, J = 3.3 Hz, 1H), 7.81 (d, J = 3.3 Hz, 1H), 7.40 (t, J = 8.3 Hz, 1H), 7.26-7.15 (m, 2H), 5.99 (s, 1H), 4.43 (d, J = 17.1 Hz, 1H), 4.26 (d, J = 14.3 Hz, 1H), 4.10 (dq, J = 2.3, 7.1 Hz, 4H), 3.96-3.78 (m, 2H), 3.65 (br. s., 1H), 3.36 (d, J = 8.3 Hz, 1H), 2.75 (br. s., 1H), 1.19 (t, J = 7.2 Hz, 3H) | MS: calc'd 509 (MH$^+$), exp 509 (MH$^+$). |
| 50 | $^1$H NMR (MeOD-d$_4$, 400 MHz): δ ppm 7.95 (d, J = 3.3 Hz, 1H), 7.77 (d, J = 3.0 Hz, 1H), 7.29-7.06 (m, 3H), 6.04 (s, 1H), 4.43 (d, J = 16.3 Hz, 1H), 4.17 (d, J = 16.3 Hz, 1H), 4.12-4.03 (m, 2H), 4.00-3.85 (m, 2H), 3.62 (q, J = 11.3 Hz, 1H), 3.28-3.13 (m, 2H), 2.87-2.73 (m, 1H), 2.65-2.50 (m, 1H), 1.17 (t, J = 7.2 Hz, 3H) | MS: calc'd 513 (MH$^+$), exp 513 (MH$^+$). |
| 51 | $^1$H NMR (MeOD-d$_4$, 400 MHz): δ ppm 7.98 (d, J = 3.3 Hz, 1H), 7.77 (d, J = 3.0 Hz, 1H), 7.45 (dd, J = 6.0, 8.5 Hz, 1H), 7.24 (dd, J = 2.6, 8.7 Hz, 1H), 7.06 (dt, J = 2.8, 8.4 Hz, 1H), 6.20 (s, 1H), 4.62-4.46 (m, 2H), 4.35 (br. s., 1H), 4.20 (br. s., 1H), 4.06 (d, J = 4.3 Hz, 2H), 3.98-3.79 (m, 3H), 3.60 (d, J = 11.0 Hz, 1H), 2.66 (d, J = 17.8 Hz, 1H) | MS: calc'd 563 (MH$^+$), exp 563 (MH$^+$). |
| 52 | $^1$H NMR (MeOD-d$_4$, 400 MHz): δ ppm 8.01 (d, J = 3.3 Hz, 1H), 7.83 (d, J = 3.0 Hz, 1H), 7.59 (dd, J = 7.3, 8.3 Hz, 1H), 7.22 (dd, J = 2.0, 9.8 Hz, 1H), 7.15 (dd, J = 2.0, 8.3 Hz, 1H), 5.73 (s, 1H), 4.53 (d, J = 16.8 Hz, 1H), 4.27-4.01 (m, 5H), 3.98-3.80 (m, 2H), 3.67 (br. s., 1H), 3.36 (d, J = 6.0 Hz, 1H), 2.73 (br. s., 1H), 1.24 (t, J = 7.2 Hz, 3H) | MS: calc'd 553 (MH$^+$), exp 553 (MH$^+$). |
| 53 | $^1$H NMR (MeOD-d$_4$, 400 MHz): δ ppm 8.01 (d, J = 3.0 Hz, 1H), 7.83 (d, J = 3.3 Hz, 1H), 7.35 (dt, J = 6.0, 7.9 Hz, 1H), 7.22 (d, J = 7.5 Hz, 1H), 7.10 (td, J = 2.0, 9.9 Hz, 1H), 7.01 (dt, J = 2.0, 8.4 Hz, 1H), 5.74 (s, 1H), 4.53 (d, J = 14.1 Hz, 1H), 4.34-4.02 (m, 5H), 3.98-3.80 (m, 2H), 3.66 (br. s., 1H), 3.47-3.36 (m, 1H), 2.77 (br. s., 1H), 1.24 (t, J = 7.2 Hz, 3H) | MS: calc'd 475 (MH$^+$), exp 475 (MH$^+$). |
| 54 | $^1$H NMR (MeOD-d$_4$, 400 MHz): δ ppm 8.00 (d, J = 3.0 Hz, 1H), 7.84 (d, J = 3.0 Hz, 1H), 7.41 (dd, J = 5.4, 8.7 Hz, 2H), 7.07 (t, J = 8.8 Hz, 2H), 5.71 (s, 1H), 4.58 (d, J = 16.1 Hz, 1H), 4.31 (br. s., 1H), 4.21-4.03 (m, 4H), 3.98-3.81 (m, 2H), 3.71 (br. s., 1H), 3.50 (dd, J = 1.6, 3.4 Hz, 1H), 2.85 (br. s., 1H), 1.23 (t, J = 7.2 Hz, 3H) | MS: calc'd 475 (MH$^+$), exp 475 (MH$^+$). |
| 55 | $^1$H NMR (MeOD-d$_4$, 400 MHz): δ ppm 7.93 (d, J = 3.0 Hz, 1H), 7.74 (d, J = 3.3 Hz, 1H), 7.34-7.20 (m, 2H), 6.16 (s, 1H), 4.43 (d, J = 16.6 Hz, 1H), 4.17 (d, J = 16.6 Hz, 1H), 4.06 (q, J = 7.0 Hz, 2H), 3.91 (t, J = 8.0 Hz, 1H), 3.70-3.57 (m, 1H), 3.23-3.14 (m, 1H), 2.85-2.73 (m, 1H), 2.65-2.50 (m, 1H), 1.15 (t, J = 7.2 Hz, 3H) | MS: calc'd 547 (MH$^+$), exp 547 (MH$^+$). |

TABLE 2-continued

NMR and MS data of particular compounds

| Example No. | $^1$H NMR data | MW data |
|---|---|---|
| 56 | $^1$H NMR (MeOD-d$_4$, 400 MHz): δ ppm 7.36-7.13 (m, 4H), 7.04 (d, J = 0.8 Hz, 1H), 5.73 (s, 1H), 4.29 (d, J = 15.8 Hz, 1H), 4.14 (q, J = 7.2 Hz, 2H), 3.96 (d, J = 15.8 Hz, 1H), 3.89 (s, 3H), 3.55-3.46 (m, 2H), 3.01-2.82 (m, 1H), 2.68-2.52 (m, 1H), 2.50-2.33 (m, 1H), 1.23 (t, J = 7.2 Hz, 3H) | MS: calc'd 510 (MH$^+$), exp 510 (MH$^+$). |
| 57 | $^1$H NMR (MeOD-d$_4$, 400 MHz): δ ppm 8.57 (s, 1H), 7.33-7.15 (m, 4H), 7.06 (d, J = 1.0 Hz, 1H), 5.74 (s, 1H), 4.19-4.09 (m, 2H), 4.08-4.02 (m, 1H), 4.01-3.95 (m, 1H), 3.93 (s, 3H), 3.87-3.71 (m, 2H), 3.19 (dd, J = 3.5, 8.0 Hz, 1H), 3.05-2.97 (m, 1H), 2.43 (ddd, J = 3.8, 8.3, 11.7 Hz, 1H), 1.24 (t, J = 7.2 Hz, 3H) | MS: calc'd 490 (MH$^+$), exp 490 (MH$^+$). |
| 58 | $^1$H NMR (MeOD-d$_4$, 400 MHz): δ ppm 7.98 (d, J = 2.8 Hz, 1H), 7.79 (d, J = 2.8 Hz, 1H), 7.50-7.36 (m, 1H), 7.04-6.87 (m, 2H), 6.02-5.93 (m, 1H), 4.38-4.19 (m, 2H), 4.17-4.00 (m, 4H), 3.97-3.78 (m, 3H), 3.58 (br. s., 1H), 2.71 (br. s., 1H), 1.19 (t, J = 7.0 Hz, 3H) | MS: calc'd 493 (MH$^+$), exp 493 (MH$^+$). |
| 59 | $^1$H NMR (MeOD-d$_4$, 400 MHz): δ ppm 7.95 (d, J = 3.0 Hz, 1H), 7.73 (d, J = 3.0 Hz, 1H), 7.47-7.38 (m, 1H), 6.95 (t, J = 8.7 Hz, 2H), 5.96 (s, 1H), 4.36 (d, J = 15.8 Hz, 1H), 4.13 - 3.99 (m, 3H), 3.68 (t, J = 8.4 Hz, 1H), 3.59 (q, J = 11.1 Hz, 1H), 3.03 (dt, J = 11.0, 15.2 Hz, 1H), 2.76-2.62 (m, 1H), 2.56-2.41 (m, 1H), 1.18 (t, J = 7.2 Hz, 3H) | MS: calc'd 513 (MH$^+$), exp 513 (MH$^+$). |
| 60 | $^1$H NMR (MeOD-d$_4$, 400 MHz): δ ppm 7.97 (d, J = 3.3 Hz, 1H), 7.78 (d, J = 3.0 Hz, 1H), 7.35-7.19 (m, 2H), 6.18 (s, 1H), 4.48 (d, J = 17.3 Hz, 1H), 4.31-4.19 (m, 1H), 4.16-4.01 (m, 4H), 3.97-3.82 (m, 2H), 3.67 (br. s., 1H), 3.36 (d, J = 6.0 Hz, 1H), 2.80-2.63 (m, 1H), 1.16 (t, J = 7.0 Hz, 3H) | MS: calc'd 527 (MH$^+$), exp 527 (MH$^+$). |
| 61 | $^1$H NMR (MeOD-d$_4$, 400 MHz): δ ppm 7.44 (dd, J = 6.0, 8.5 Hz, 1H), 7.35 (s, 1H), 7.24 (dd, J = 2.5, 8.8 Hz, 1H), 7.06 (d, J = 2.5 Hz, 1H), 6.15 (s, 1H), 4.51-4.35 (m, 1H), 4.27-4.15 (m, 1H), 4.14-4.02 (m, 2H), 3.96-3.79 (m, 2H), 3.76-3.65 (m, 1H), 3.61 (s, 3H), 2.78-2.66 (m, 1H), 2.62 (s, 3H) | MS: calc'd (MH$^+$) 541, measured (MH$^+$) 541 |
| 62 | $^1$H NMR (MeOD-d$_4$, 400 MHz): δ ppm 7.58-7.52 (m, 2H), 7.30 (dd, J = 2.6, 8.7 Hz, 1H), 7.16-7.07 (m, 1H), 6.24 (s, 1H), 4.58 (d, J = 17.1 Hz, 1H), 4.21-3.94 (m, 2H), 3.64 (s, 4H), 3.23 (s, 1H), 2.87 (dd, J = 8.9, 12.7 Hz, 1H), 2.63 (s, 3H), 2.57-2.44 (m, 1H) | MS: calc'd (MH$^+$) 561, measured (MH$^+$) 561 |
| 63 | $^1$H NMR (MeOD-d$_4$, 400 MHz): δ ppm 8.05 (d, J = 3.01 Hz, 1H), 7.95 (d, J = 3.26 Hz, 1H), 7.33-7.42 (m, 2H), 7.22-7.29 (m, 1H), 6.29 (s, 1H), 4.83 (d, J = 16.56 Hz, 1H), 4.52 (d, J = 16.56 Hz, 1H), 4.15-4.27 (m, 3H), 4.10 (q, J = 6.94 Hz, 2H), 3.92-4.06 (m, 2H), 3.72 (ddd, J = 12.55, 8.28, 4.02 Hz, 1H), 3.11-3.21 (m, 1H), 1.15 (t, J = 7.15 Hz, 3 H) | MS: calc'd (MH$^+$) 509, measured (MH$^+$) 509 |
| 64 | $^1$H NMR (MeOD-d$_4$, 400 MHz): δ ppm 8.10-8.15 (m, 1H), 8.03-8.08 (m, 1H), 7.35-7.45 (m, 2H), 7.24-7.32 (m, 1H), 6.32 (s, 1H), 4.55 (d, J = 16.06 Hz, 1H), 4.04-4.19 (m, 4H), 3.63-3.73 (m, 1H), 3.23-3.31 (m, 1H), 2.79-2.94 (m, 1H), 2.51-2.65 (m, 1H), 1.15 (t, J = 7.15 Hz, 3 H) | MS: calc'd (MH$^+$) 529, measured (MH$^+$) 529 |
| 65 | $^1$H NMR (MeOD-d$_4$, 400 MHz): δ ppm 8.07 (s, 1H), 7.35-7.48 (m, 2H), 7.12 (td, J = 8.34, 2.64 Hz, 1H), 6.12 (s, 1H), 4.35-4.50 (m, 2H), 4.02-4.15 (m, 2H), 3.92-3.99 (m, 1H), 3.83 (ddd, J = 12.05, 6.15, 3.14 Hz, 1H), 3.70 (br. s., 1H), 3.63-3.64 (s, 3H), 3.44 (br. s., 1H), 2.84 (d, J = 11.80 Hz, 1H), 2.66 (s, 3 H) | MS: calc'd (MH$^+$) 538, measured (MH$^+$) 537&539 |
| 66 | $^1$H NMR (MeOD-d$_4$, 400 MHz): δ ppm 7.93-8.00 (m, 1H), 7.78 (d, J = 3.26 Hz, 1H), 7.32-7.40 (m, 1H), 7.25-7.30 (m, 1H), 7.14 (td, J = 8.22, 1.38 Hz, 1H), 6.25 (s, 1H), 4.50 (d, J = 17.32 Hz, 1H), 4.26 (d, J = 11.54 Hz, 1H), 4.00-4.16 (m, 4H), 3.81-3.96 (m, 2H), 3.68 (br. s., 1H), 3.39 (br. s., 1H), 2.75 (br. s., 1H), 1.14 (t, J = 7.03 Hz, 3 H) | MS: calc'd (MH$^+$) 554, measured (MH$^+$) 553&555 |
| 67 | $^1$H NMR (MeOD-d$_4$, 400 MHz): δ ppm 7.95 (d, J = 3.26 Hz, 1H), 7.77 (d, J = 3.26 Hz, 1H), 7.33-7.41 (m, 1H), 7.26-7.32 (m, 1H), 7.14 (td, J = 8.28, 1.51 Hz, 1H), 6.21-6.27 (m, 1H), 4.46 (d, J = 16.56 Hz, 1H), 4.20 (d, J = 16.31 Hz, 1H), 4.02-4.08 (m, 2H), 3.97 (t, J = 8.03 Hz, 1H), 3.65 (q, J = 11.29 Hz, 1H), 3.19-3.30 (m, 1H), 2.75-2.89 (m, 1H), 2.51-2.66 (m, 1H), 1.13 (t, J = 7.15 Hz, 3 H) | MS: calc'd (MH$^+$) 574, measured (MH$^+$) 573&575 |
| 68 | $^1$H NMR (MeOD-d$_4$, 400 MHz): δ ppm 8.32 (s, 1H), 7.57 (dd, J = 8.66, 5.90 Hz, 1H), 7.39 (dd, J = 8.53, 2.51 Hz, 1H), 7.20 (td, J = 8.34, 2.64 Hz, 1H), 6.27 (s, 1H), 4.18-4.29 (m, 2H), 4.07 (dd, J = 11.42, 3.64 Hz, 1H), 3.85-3.94 (m, 2H), 3.73-3.81 (m, 1H), 3.63-3.71 (m, 4H), 3.21 (ddd, J = 11.98, 5.84, 3.01 Hz, 1H), 2.67-2.79 (m, 4 H) | MS: calc'd (MH$^+$) 493, measured (MH$^+$) 493 |
| 69 | $^1$H NMR (MeOD-d$_4$, 400 MHz): δ ppm 8.07 (s, 1H), 7.40-7.48 (m, 2H), 7.13 (td, J = 8.38, 2.57 Hz, 1H), 6.14 (s, 1H), 4.34- | MS: calc'd (MH$^+$) 552, measured |

TABLE 2-continued

NMR and MS data of particular compounds

| Example No. | $^1$H NMR data | MW data |
|---|---|---|
| | 4.50 (m, 2H), 4.03-4.13 (m, 4H), 3.91-4.00 (m, 1H), 3.83 (ddd, J = 12.11, 6.15, 3.07 Hz, 1H), 3.70 (t, J = 4.45 Hz, 1H), 3.40-3.52 (m, 1H), 2.86 (br. s., 1H), 2.66 (s, 3H), 1.15 (t, J = 7.09 Hz, 3 H) | (MH$^+$) 551&553 |
| 70 | $^1$H NMR (MeOD-d$_4$, 400 MHz): δ ppm 8.34-7.89 (m, 1H), 7.82-7.60 (m, 1H), 7.30-7.01 (m, 3H), 6.08 (s, 1H), 4.29 (d, J = 16.8 Hz, 1H), 4.13-3.97 (m, 4H), 3.90-3.75 (m, 3H), 3.42-3.40 (m, 1H), 3.02 (d, J = 11.9 Hz, 1H), 2.57 (ddd, J = 4.0, 8.0, 11.9 Hz, 1H), 1.21 (t, 3H) | MS: calc'd (MH$^+$) 493, measured (MH$^+$) 493 |
| 71 | $^1$H NMR (MeOD-d$_4$, 400 MHz): δ ppm 7.99-8.28 (m, 1H), 7.92-8.00 (m, 1H), 7.74-7.81 (m, 1H), 7.61 (m, 1H), 7.44 (m, 1H), 7.33 (m, 1H), 7.17 (m, 1H), 6.19 (s, 1H), 4.53 (d, 1H), 4.31 (d, 1H), 4.04-4.17 (m, 2H), 3.82-3.98 (m, 2H), 3.67-3.74 (m, 1H), 3.71 (br. s., 1H), 3.61 (s, 3H), 3.44 (d, 1H), 2.81 (br. s., 1H) | MS: calc'd (MH$^+$) 521 measured (MH$^+$) 521 |
| 72 | $^1$H NMR (MeOD-d$_4$, 400 MHz): δ ppm 7.90-7.97 (m, 1H), 7.72-7.78 (m, 1H), 7.57-7.66 (m, 1H), 7.45 (m, 1H), 7.35 (m, 1H), 7.17 (m, 1H), 6.18 (s, 1H), 4.45 (d, 1H), 4.20 (d, 1H), 3.98 (m, 1H), 3.63-3.72 (m, 1H), 3.61 (m, 3H), 3.20-3.30 (m, 1H), 2.82 (tm, 1H), 2.49-2.65 (m, 1H) | MS: calc'd (MH$^+$) 541 measured (MH$^+$) 541 |
| 73 | $^1$H NMR (MeOD-d$_4$, 400 MHz): δ ppm 7.99-8.08 (m, 1H), 7.93 (d, 1H), 7.20-7.41 (m, 2H), 6.13-6.30 (m, 1H), 6.22 (s, 1H), 4.84 (d, 2H), 4.77 (br. s., 2H), 4.51 (d, 1H), 4.11-4.27 (m, 3H), 3.89-4.07 (m, 2H), 3.72 (m, 1H), 3.65 (s, 3H), 3.10-3.23 (m, 1H) | MS: calc'd (MH$^+$) 513 measured (MH$^+$) 513 |
| 74 | $^1$H NMR (MeOD-d$_4$, 400 MHz): δ ppm 8.09-8.16 (m, 1H), 7.99-8.09 (m, 1H), 7.25-7.43 (m, 2H), 6.19-6.30 (m, 1H), 4.54 (d, 1H), 4.18 (d, 1H), 4.10 (m, 1H), 3.67-3.76 (m, 1H), 3.66 (s, 3H), 3.22-3.31 (m, 1H), 2.88 (tm, 1H), 2.48-2.66 (m, 1H) | MS: calc'd (MH$^+$) 533 measured (MH$^+$) 533 |
| 75 | $^1$H NMR (MeOD-d$_4$, 400 MHz): δ ppm 8.04-8.12 (m, 1H), 7.95-8.03 (m, 1H), 7.47 (m, 1H), 7.21-7.31 (m, 2H), 6.03 (s, 1H), 4.81 (d, 1H), 4.58 (d, 1H), 4.23-4.29 (m, 1H), 4.15-4.23 (m, 2H), 3.92-4.06 (m, 2H), 3.75 (m, 1H), 3.69 (s, 3H), 3.19-3.29 (m, 1H) | MS: calc'd (MH$^+$) 495 measured (MH$^+$) 495 |
| 76 | $^1$H NMR (MeOD-d$_4$, 400 MHz): δ ppm 8.14-8.17 (m, 1H), 8.12 (d, 1H), 7.49 (m, 1H), 7.26-7.35 (m, 2H), 6.04 (s, 1H), 4.54 (d, 1H), 4.04-4.16 (m, 2H), 3.69 (s, 3H), 3.58-3.67 (m, 1H), 3.19-3.30 (m, 1H), 2.80-2.94 (m, 1H), 2.50-2.65 (m, 1H) | MS: calc'd (MH$^+$) 515 measured (MH$^+$) 515 |
| 77 | $^1$H NMR (MeOD-d$_4$, 400 MHz): δ ppm 7.99-8.10 (m, 1H), 7.95 (d, 1H), 7.48 (m, 1H), 7.15-7.34 (m, 2H), 5.75 (s, 1H), 4.75-4.82 (m, 1H), 4.48 (d, 1H), 4.08-4.26 (m, 3H), 3.90-4.03 (m, 2H), 3.72 (s, 3H), 3.68 (d, 1H), 3.14 (d, 1H) | MS: calc'd (MH$^+$) 495 measured (MH$^+$) 495 |
| 78 | $^1$H NMR (MeOD-d$_4$, 400 MHz): δ ppm 8.10 (d, 1H), 7.93-8.02 (m, 1H), 7.22-7.41 (m, 2H), 6.17-6.29 (m, 1H), 4.60 (d, 1H), 4.37 (d, 1H), 4.13 (d, 1H), 3.89-4.02 (m, 2H), 3.84 (d, 1H), 3.65 (s, 3H), 3.41 (m, 1H), 3.15 (m, 1H), 1.60 (s, 3H) | MS: calc'd (MH$^+$) 527 measured (MH$^+$) 527 |
| 79 | $^1$H NMR (MeOD-d$_4$, 400 MHz): δ ppm 8.03-8.13 (m, 1H), 7.96 (d, 1H), 7.20-7.36 (m, 2H), 6.14-6.28 (m, 1H), 4.35-4.56 (m, 2H), 4.11-4.22 (m, 1H), 3.85-4.03 (m, 2H), 3.78 (d, 1H), 3.65 (s, 3H), 3.39-3.46 (m, 1H), 3.00 (d, 1H), 1.57 (s, 3H) | MS: calc'd (MH$^+$) 527 measured (MH$^+$) 527 |
| 80 | $^1$H NMR (MeOD-d$_4$, 400 MHz): δ ppm 7.56-7.52 (m, 2H), 7.31-7.29 (m, 1H), 7.14-7.10 (m, 1H), 6.23 (s, 1H), 4.31 (dd, 2H, J1 = 32 Hz, J2 = 16 Hz), 3.65 (s, 3H), 3.51-2.92 (m, 5H), 2.52-2.22(m, 5H). | MS: calc'd (MH$^+$) 543exp (MH$^+$) 543 |
| 81 | $^1$H NMR (MeOD-d$_4$, 400 MHz): δ ppm 7.97 (d, J = 3.01 Hz, 1H), 7.78 (d, J = 3.01 Hz, 1H), 7.47-7.40 (m, 2H), 7.14-7.09 (m, 1H), 6.14 (s, 1H), 4.52 (d, J = 16.31 Hz, 1H), 4.15 (d, J = 16.06 Hz, 1H), 4.07 (t, J = 8.16 Hz, 1H), 3.61-3.73 (m, 4H), 3.21-3.31 (m, 1 H)2.78-2.94 (m, 1H), 2.48-2.66 (m, 1H) | MS: calc'd (MH$^+$) 539 exp (MH$^+$) 539. |
| 82 | $^1$H NMR (MeOD-d$_4$, 400 MHz): δ ppm 10.00(br, 1H), 8.02 (d, J = 3.3 Hz, 1H), 7.93 (d, J = 3.0 Hz, 1H), 7.55-7.35 (m, 2H), 7.28 (dt, J = 2.0, 7.4 Hz, 2H), 6.09 (s, 1H), 4.32-3.77 (m, 6H), 3.77-3.45 (m, 3H), 3.14-2.97 (m, 1H), 2.41 (d, J = 12.3 Hz, 1H), 1.05 (t, J = 7.2 Hz, 3H) | MS: calc'd (MH$^+$) 491, measured (MH$^+$) 491 |
| 83 | $^1$H NMR (MeOD-d$_4$, 400 MHz): δ ppm 8.06-8.04 (m, 1H), 7.97-7.95 (m, 1H), 7.46-7.42 (m, 1H), 7.25-7.20 (m, 2H), 5.73 (s, 1H), 4.25-4.09 (m, 5H), 3.95-3.81 (m, 3H), 3.75-3.61 (m, 3H), 1.25 (t, J = 7.2 Hz, 3H). | MS: calc'd (MH$^+$) 509, measured (MH$^+$) 509 |
| 84 | $^1$H NMR (MeOD-d$_4$, 400 MHz): δ ppm 7.93 (d, J = 3.01 Hz, 1 H)7.72 (d, J = 3.01 Hz, 1H), 7.47-7.39 (m, 2H), 7.15-7.10 (m, 1H), 6.13 (s, 1H), 4.42 (d, J = 16.31 Hz, 1H), 4.15 (d, J = 16.06 Hz, 1H), 4.07 (t, J = 8.16 Hz, 1H), 3.61-3.73 (m, 4H), 3.21-3.31 (m, 1 H)2.78-2.94 (m, 1H), 2.48-2.66 (m, 1H) | MS: calc'd (MH$^+$) 559exp (MH$^+$) 559 |
| 85 | $^1$H NMR (MeOD-d$_4$, 400 MHz): δ ppm 8.05 (d, J = 3.01 Hz, 1 H)7.93(d, J = 3.01 Hz, 1H), 7.54-7.36 (m, 3H),) 6.20 (s, 1H), 4.48(d, J = 16.31 Hz, 1H), 4.16 (d, J = 16.06 Hz, 1H), 4.07 (t, | MS: calc'd (MH$^+$) 531exp (MH$^+$) 531 |

TABLE 2-continued

NMR and MS data of particular compounds

| Example No. | $^1$H NMR data | MW data |
|---|---|---|
|  | J = 8.16 Hz, 1H), 3.61-3.73 (m, 4H), 3.21-3.31 (m, 1 H)2.78-2.94 (m, 1H), 2.48-2.66 (m, 1H) |  |
| 86 | $^1$H NMR (MeOD-d$_4$, 400 MHz): δ ppm 8.01-8.18 (m, 2 H), 7.51-7.68 (m, 1 H), 7.26-7.40 (m, 1 H), 7.08-7.19 (m, 1 H), 6.28 (s, 1 H), 5.02-5.15 (m, 1 H), 4.92-4.99 (m, 1 H), 4.25-4.53 (m, 2 H), 4.05-4.25 (m, 1 H), 3.68 (s, 3 H), 2.81-3.09 (m, 2 H), 2.30-2.47 (m, 1 H), 2.08-2.28 (m, 1 H) | MS: calc'd (MH$^+$) 511 exp (MH$^+$) 511. |
| 87 | $^1$H NMR (MeOD-d$_4$, 400 MHz): δ ppm 7.61-7.64 (m, 1 H), 7.53-7.61 (m, 1 H), 7.29-7.34 (m, 1 H), 7.10-7.19 (m, 1 H), 6.24 (s, 1 H), 4.57-4.70 (m, 1 H), 4.39-4.52 (m, 1 H), 4.04-4.24 (m, 3 H), 3.83-4.04 (m, 2 H), 3.66 (s, 3 H), 3.51-3.63 (m, 1 H), 3.01-3.15(m, 1 H), 2.12-2.27 (m, 1 H), 0.90-1.11 (m, 4 H) | MS: calc'd (MH$^+$) 535 exp (MH$^+$)535. |
| 88 | $^1$H NMR (MeOD-d$_4$, 400 MHz): δ ppm 8.17-8.25 (m, 1 H), 7.47-7.61 (m, 1 H), 7.23-7.33 (m, 1 H), 7.02-7.16 (m, 1 H), 6.73-6.94 (m, 1 H), 6.21 (s, 1 H), 4.54-4.72 (m, 1 H), 4.42-4.54 (m, 1 H), 4.16 (s, 3 H), 3.88-4.07 (m, 2 H), 3.67-3.81 (m, 1 H), 3.65 (d, J = 1.51 Hz, 3 H), 3.10-3.24 (m, 1 H) | MS: calc'd (MH$^+$) 545 exp (MH$^+$)545. |
| 89 | $^1$H NMR (MeOD-d$_4$, 400 MHz): δ ppm 8.03-8.18 (m, 2 H), 7.57 (dd, J = 8.66, 5.90 Hz, 1 H), 7.34 (dd, J = 8.53, 2.51 Hz, 1 H), 7.18 (td, J = 8.41, 2.51 Hz, 1 H), 6.20-6.31 (m, 1 H), 4.58 (d, J = 16.31 Hz, 1 H), 3.69-3.93 (m, 3 H), 3.66 (s, 3 H), 3.20-3.31 (m, 1 H), 1.34 (d, J = 2.26 Hz, 3 H), 1.22 (d, J = 2.26 Hz, 3H) | MS: calc'd (MH$^+$) 543 exp (MH$^+$) 543. |
| 90 | $^1$H NMR (MeOD-d$_4$, 400 MHz): δ ppm 8.09 (d, J = 3.01 Hz, 1 H), 8.01 (d, J = 3.26 Hz, 1 H), 7.54 (s, 1 H), 7.31 (dd, J = 8.78, 2.51 Hz, 1 H), 7.03-7.20 (m, 1 H), 6.24 (s, 1 H), 4.17-4.31 (m, 2H), 3.92 (s, 1H), 3.70 (ddd, J = 11.54, 6.15, 2.89 Hz, 1 H), 3.64 (s, 3 H), 2.85-3.12 (m, 3 H), 1.53-1.69 (m, 6 H) | MS: calc'd (MH$^+$) 539 exp (MH$^+$) 539. |
| 91 | $^1$H NMR (MeOD-d$_4$, 400 MHz): δ ppm 8.02-8.09 (m, 1 H), 7.86-8.00 (m, 1 H), 7.46-7.60 (m, 1 H), 7.24-7.36 (m, 1 H), 6.99-7.19 (m, 1 H), 6.12-6.31 (m, 1 H), 4.80-4.87 (m, 1 H), 4.38-4.52 (m, 2 H), 3.80-3.99 (m, 1 H), 3.66 (s, 3 H), 3.36-3.51 (m, 2 H), 3.10-3.29 (m, 2 H), 2.76-2.89 (m, 1 H) | MS: calc'd (MH$^+$) 511 exp (MH$^+$) 511. |
| 92 | $^1$H NMR (MeOD-d$_4$, 400 MHz): δ ppm 8.16 (br. s., 1H), 7.38 (dd, J = 8.7, 6.1 Hz, 1H), 7.26 (dd, J = 8.8, 2.5 Hz, 1H), 7.06 (td, J = 8.3, 2.6 Hz, 1H), 6.95 (s, 1H), 6.16 (s, 1H), 4.28-4.55 (m, 2H), 4.01-4.21 (m, 2H), 3.80-3.99 (m, 4H), 3.56-3.74 (m, 3H), 3.38-3.51 (m, 1H), 2.77 (br. s., 1H), 2.19 ppm (s, 3H) | MS: calc'd 507(MH$^+$), measured 507(MH$^+$) |
| 93 | $^1$H NMR (MeOD-d$_4$, 400 MHz): δ ppm 7.99 (d, J = 3.0 Hz, 1H), 7.81 (d, J = 3.3 Hz, 1H), 7.27-7.40 (m, 3H), 5.99 (s, 1H), 4.46 (d, J = 16.3 Hz, 1H), 4.27 (br. s., 1H), 4.03-4.16 (m, 4H), 3.79-3.99 (m, 2H), 3.67 (br. s., 1H), 3.35-3.51 (m, 1H), 2.64-2.84 (m, 1H), 1.19 ppm (t, J = 7.2 Hz, 3H) | MS: calc'd 554(MH$^+$), measured 554(MH$^+$) |
| 94 | $^1$H NMR (MeOD-d$_4$, 400 MHz): δ ppm 8.00 (d, J = 3.0 Hz, 1H), 7.84 (d, J = 2.8 Hz, 1H), 7.27-7.42 (m, 3H), 5.99 (s, 1H), 4.53 (d, J = 17.6 Hz, 1H), 4.30 (d, J = 15.3 Hz, 1H), 4.05-4.18 (m, 2H), 3.74-3.99 (m, 3H), 3.66 (s, 3H), 3.39-3.55 (m, 1H), 2.83 ppm (br. s., 1H) | MS: calc'd 540(MH$^+$), measured 540(MH$^+$) |
| 95 | $^1$H NMR (MeOD-d$_4$, 400 MHz): δ ppm 8.46 (s, 1H), 7.53 (dd, J = 8.5, 6.0 Hz, 1H), 7.28 (dd, J = 8.7, 2.6 Hz, 1H), 7.10 (td, J = 8.4, 2.8 Hz, 1H), 6.21 (s, 1H), 4.48 (d, J = 16.6 Hz, 1H), 4.11-4.30 (m, 3H), 3.90-4.05 (m, 2H), 3.73 (ddd, J = 12.7, 8.4, 3.8 Hz, 2H), 3.65 (s, 3H), 3.07-3.23 ppm (m, 1H) | MS: calc'd 563(MH$^+$), measured 563(MH$^+$) |
| 96 | $^1$H NMR (MeOD-d$_4$, 400 MHz): δ ppm 7.97 (d, J = 3.3 Hz, 1H), 7.79 (br. s., 1H), 6.97-7.24 (m, 2H), 5.93 (s, 1H), 4.21-4.60 (m, 3H), 4.09 (q, J = 7.1 Hz, 3H), 3.87 (br. s., 2H), 3.66 (br. s., 1H), 2.79 (br. s., 2H), 2.56 (d, J = 2.5 Hz, 3H), 1.16 ppm (t, J = 7.0 Hz, 3H) | MS: calc'd 507(MH$^+$), measured 507(MH$^+$) |
| 97 | $^1$H NMR (MeOD-d$_4$, 400 MHz): δ ppm 7.09-7.35 (m, 4H), 7.06 (d, J = 1.3 Hz, 1H), 6.24 (s, 1H), 4.20-4.49 (m, 2H), 3.98-4.14 (m, 3H), 3.81-3.94 (m, 5H), 3.55 (br. s., 1H), 3.17-3.29 (m, 2H), 2.69 (br. s., 1H), 1.15 ppm (t, J = 7.2 Hz, 3H) | MS: calc'd 506(MH$^+$), measured 506(MH$^+$) |
| 98 | $^1$H NMR (MeOD-d$_4$, 400 MHz): δ ppm 7.97 (d, J = 3.0 Hz, 1H), 7.80 (d, J = 2.8 Hz, 1H), 7.49 (dd, J = 6.1, 8.7 Hz, 1H), 7.26 (dd, J = 2.6, 8.7 Hz, 1H), 7.08 (dt, J = 2.6, 8.3 Hz, 1H), 6.17 (s, 1H), 4.96-4.90 (m, 1H), 4.51 (br. s., 1H), 4.39-4.19 (m, 1H), 4.19-4.04 (m, 2H), 3.88 (br. s., 2H), 3.70 (br. s., 1H), 3.36-3.34 (m, 1H), 2.72 (br. s., 1H), 1.24 (d, J = 6.3 Hz, 3H), 0.99 (d, J = 6.3 Hz, 3H) | MS: calc'd (MH$^+$) 523, measured (MH$^+$) 523 |
| 99 | $^1$H NMR (MeOD-d$_4$, 400 MHz): δ ppm 7.97 (dd, J = 1.6, 3.1 Hz, 1H), 7.79 (d, J = 3.0 Hz, 1H), 7.54-7.43 (m, 1H), 7.25 (td, J = 2.5, 8.8 Hz, 1H), 7.12-7.03 (m, 1H), 6.19 (s, 1H), 4.43 (d, J = 17.6 Hz, 1H), 4.29 (br. s., 1H), 4.16-3.80 (m, 6H), 3.65 (d, | MS: calc'd (MH$^+$) 523, measured (MH$^+$) 523 |

TABLE 2-continued

NMR and MS data of particular compounds

| Example No. | ¹H NMR data | MW data |
|---|---|---|
|  | J = 19.3 Hz, 1H), 3.35 (br. s., 1H), 2.78 (br. s., 1H), 1.62-1.51 (m, 2H), 0.84-0.76 (m, 3H) |  |
| 100 | ¹H NMR (MeOD-$d_4$, 400 MHz): δ ppm 8.06 (d, J = 3.0 Hz, 1H), 7.95 (d, J = 3.0 Hz, 1H), 7.40-7.21 (m, 3H), 5.72 (s, 1H), 5.02 (quin, J = 6.2 Hz, 1H), 4.84 (d, J = 16.8 Hz, 1H), 4.48 (d, J = 16.8 Hz, 1H), 4.27-4.08 (m, 3H), 4.05-3.92 (m, 2H), 3.76-3.65 (m, 1H), 3.19-3.09 (m, 1H), 1.28 (d, J = 6.3 Hz, 3H), 1.11 (d, J = 6.3 Hz, 3H) | MS: calc'd (MH⁺) 507, measured (MH⁺) 507 |
| 101 | ¹H NMR (MeOD-$d_4$, 400 MHz): δ ppm 7.97 (d, J = 3.0 Hz, 1H), 7.78 (d, J = 2.8 Hz, 1H), 7.39-7.27 (m, 2H), 7.22-7.12 (m, 1H), 6.23 (s, 1H), 4.92 (d, J = 6.3 Hz, 1H), 4.46 (d, J = 17.1 Hz, 1H), 4.26 (d, J = 16.1 Hz, 1H), 4.10 (d, J = 7.5 Hz, 2H), 3.95-3.81 (m, 2H), 3.64 (d, J = 6.8 Hz, 1H), 3.39 (br. s., 1H), 2.74 (br. s., 1H), 1.23 (d, J = 6.0 Hz, 3H), 0.96 (d, J = 6.3 Hz, 3H) | MS: calc'd (MH⁺) 523, measured (MH⁺) 523 |
| 102 | ¹H NMR (MeOD-$d_4$, 400 MHz): δ ppm 8.08 (s, 1H), 7.45 (dd, J = 8.8, 6.0 Hz, 1H), 7.28 (dd, J = 8.8, 2.5 Hz, 1H), 7.11 (td, J = 8.4, 2.5 Hz, 1H), 6.14 (s, 1H), 4.51 (d, J = 16.1 Hz, 1H), 4.05 (d, J = 16.1 Hz, 1H), 3.84 (t, J = 8.2 Hz, 1H), 3.65 (m, 1H), 3.63 (s, 3H), 3.09-3.30 (m, 1H), 2.68-2.90 (m, 1H), 2.60 (s, 3H), 2.40-2.56 (m, 1H) | MS: calc'd (MH⁺) 513, measured (MH⁺) 513 |
| 103 | ¹H NMR (MeOD-$d_4$, 400 MHz): δ ppm 8.30 (s, 1H), 7.22-7.59 (m, 3H), 6.31 (s, 1H), 4.27 (m, 2H), 4.08 (dd, J = 11.5, 3.5 Hz, 1H), 3.92 (m, 2H), 3.79 (m, 1H), 3.71 (m, 1H), 3.69 (s, 3H), 3.23 (m, 1H), 2.73-2.80 (m, 1H), 2.72 (s, 3H) | MS: calc'd (MH⁺) 493, measured (MH⁺) 493 |
| 104 | ¹H NMR (MeOD-$d_4$, 400 MHz): δ ppm 8.03 (d, J = 3.01 Hz, 1H), 7.87-7.92 (m, 1H), 7.51 (dd, J = 8.78, 6.02 Hz, 1H), 7.28(dd, J = 8.78, 2.51 Hz, 1H), 7.11(td, J = 8.41 Hz, 2.76 Hz, 1H) 6.19 (s, 1H), 4.42-4.20 (m, 2H), 4.00-4.13 (m, 1H), 3.71-3.97 (m, 2H), 3.63 (s, 3H), 3.51 (d, J = 8.78 Hz, 1H) 3.06 (td, J = 11.73, 3.64 Hz, 2H), 1.30-1.44 (d, J = 8.0 Hz, 3 H) | MS: calc'd (MH⁺) 509, measured (MH⁺) 509 |
| 105 | ¹H NMR (MeOD-$d_4$, 400 MHz): δ ppm 7.96 (s, 1H), 7.79(s, 1H), 7.47 (m, 1H) 7.27 (m, 1H), 7.09 (m, 1H), 6.12 (s, 1H), 4.37-4.58 (m, 2 Hz), 3.99-4.23 (m, 2H), 3.80-3.97 (m, 2H), 3.68 (m, 1H), 3.45(m, 1H) 2.82 (m, 1H), 1.35 (s, 9H) | MS: calc'd (MH⁺) 537, measured (MH⁺) 537 |
| 106 | ¹H NMR (MeOD-$d_4$, 400 MHz): δ ppm 7.97 (s, 1H), 7.78 (s, 1H), 7.36-7.52 (m, 2H), 7.12 (m, 1H), 6.13 (s, 1H), 4.33 (m, 1H), 3.95-4.23 (m, 2H), 3.68-3.95 (m, 3H), 3.61 (s, 3H), 3.29-3.36 (m, 2H), 2.87 (m, 1H), 1.27-1.45(m, 3H) | MS: calc'd (MH⁺) 554, measured (MH⁺) 554 |
| 107 | ¹H NMR (MeOD-$d_4$, 400 MHz): δ ppm 7.92 (s, 1H), 7.73 (s, 1H), 7.31-7.50 (m, 2H), 7.11 (m, 1H), 6.16 (s, 1H), 4.30 (m, 2H), 4.05 (m, 2H), 3.70 (m, 2H), 2.89 (m, 2H), 2.24 (m, 1H), 2.08 (m, 2H), 1.16(t, J = 7.15 Hz, 3H) | MS: calc'd (MH⁺) 588, measured (MH⁺) 588 |
| 108 | ¹H NMR (MeOD-$d_4$, 400 MHz): δ ppm 7.93 (s, 1H), 7.74 (s, 1H), 7.39-7.59 (m, 2H), 7.12 (m, 1H), 6.16 (s, 1H), 4.30 (m, 2H), 4.05 (m, 2H), 3.63 (m, 2H), 2.95(m, 2H), 2.08-2.24(m, 3H), 1.16(t, J = 7.03 Hz, 3H) | MS: calc'd (MH⁺) 588, measured (MH⁺) 588 |
| 109 | ¹H NMR (MeOD-$d_4$, 400 MHz): δ ppm 7.92 (s, 2H), 7.73 (s, 1H), 7.25-7.31 (m, 2H), 7.13-7.17 (m, 1H), 6.22 (s, 1H), 4.19-4.34 (m, 2H), 3.70 (m, 1H), 3.60 (s, 3H), 3.36-3.48 (m, 1H), 2.92-2.88 (m, 1H), 2.00-2.23 (m, 4H) | MS: calc'd (MH⁺) 529, measured (MH⁺) 529 |
| 110 | ¹H NMR (MeOD-$d_4$, 400 MHz): δ ppm 7.94 (s, 2H), 7.74 (s, 1H), 7.24-7.45 (m, 2H), 7.06-7.21 (m, 1H), 6.22 (s, 1H), 4.21-4.38 (m, 2H), 3.63 (m, 1H), 3.60 (s, 3H), 3.38-3.46 (m, 1H), 2.92-2.98 (m, 1H), 2.00-2.33 (m, 4H) | MS: calc'd (MH⁺) 529, measured (MH⁺) 529 |
| 111 | ¹H NMR (MeOD-$d_4$, 400 MHz): δ ppm 8.14 (d, J = 4.0 Hz, 1H), 8.08 (d, J = 4.0 Hz, 1H), 7.57-7.49 (m, 2H), 7.38-7.36 (m, 2H), 6.31 (s, 1H), 4.27-4.26 (m, 2H), 4.10-4.06 (m, 2H), 3.75 (m, 1H), 3.40-3.37 (m, 1H), 2.98-2.96 (m, 1H), 2.27-2.06 (m, 4H), 1.15 (t, J = 8.0 Hz, 3H) | MS: calc'd (MH⁺) 525 measured (MH⁺) 525 |
| 112 | ¹H NMR (MeOD-$d_4$, 400 MHz): δ ppm 8.06 (d, J = 3.26 Hz, 1H), 7.94 (d, J = 3.26 Hz, 1H), 7.11-7.36 (m, 3H), 5.72 (s, 1H), 4.42 (d, J = 16.5 Hz, 1H), 4.27 (d, J = 16.8 Hz, 1H), 4.17 (m, 3H), 4.06 (d, J = 12.5 Hz, 1H), 3.73-3.98 (m, 2H), 3.58 (d, J = 9.3 Hz, 1H), 3.01-3.20 (m, 2H), 1.36(d, J = 6.3 Hz, 3H), 1.22 (t, J = 7.1 Hz, 3H) | MS: calc'd (MH⁺) 506, measured (MH⁺) 507 |
| 113 | ¹H NMR (MeOD-$d_4$, 400 MHz): δ ppm 8.02 (d, J = 3.01 Hz, 1H), 7.86 (brs, 1H), 7.15-7.30 (m, 3H), 5.69 (s, 1H), 4.34 (d, J = 15.6 Hz, 1H), 4.12(brs, 1H), 4.03 (d, J = 12.5 Hz, 1H), 4.77-3.95 (m, 2H), 3.70(s, 3H), 3.43-3.60 (m, 1H), 3.22 (brs, 1H), 3.08-3.19 (m, 1H), 1.35(d, J = 6.3 Hz, 3H) | MS: calc'd (MH⁺) 492, measured (MH⁺) 493 |
| 114 | ¹H NMR (MeOD-$d_4$, 400 MHz): δ ppm 8.04 (d, J = 3.01 Hz, 1H), 7.90 (d, J = 3.01 Hz, 1H), 7.24 (d, J = 7.78 Hz, 1H), 7.06-7.19 (m, 1H), 6.01 (s, 1H), 4.37-4.42 (d, J = 16.3 Hz, 1H), 3.89-3.90 (d, J = 11.0 Hz, 1H), 3.87-3.89 (m, 2H), 3.67 (s, 3H), 3.52- | MS: calc'd (MH⁺) 511, measured (MH⁺) 511 |

TABLE 2-continued

NMR and MS data of particular compounds

| Example No. | $^1$H NMR data | MW data |
|---|---|---|
|  | 3.54 (d, J = 9.0 Hz, 1H), 3.02-3.08 (m, 1H), 1.36 (d, J = 6.0 Hz, 3H) |  |
| 115 | $^1$H NMR (MeOD-d$_4$, 400 MHz): δ ppm 8.05 (d, J = 3.26 Hz, 1H), 7.94 (d, J = 3.01 Hz, 1H), 7.35-7.37 (m, 1H), 7.23-7.34 (m, 1H), 6.26 (s, 1H), 4.43-4.47 (d, J = 16.0 Hz, 1H), 4.30-4.34 (d, J = 16.0 Hz, 1H), 4.08 (d, J = 12.4 Hz, 1H), 3.78-3.98 (m, 2H), 3.61-3.69 (m, 4H), 3.42-3.45 (d, J = 12.3 Hz, 1H), 3.15-3.19 (m, 1H), 1.36 (d, J = 6.0 Hz, 3H) | MS: calc'd (MH$^+$) 508, measured (MH$^+$) 509 |
| 116 | $^1$H NMR (MeOD-d$_4$, 400 MHz): δ ppm 7.99-8.00 (d, J = 3.01 Hz, 1H), 7.83-7.84 (d, J = 3.01 Hz, 1H), 7.43-7.50 (m, 2H), 7.13-7.15 (m, 1H), 6.17 (s, 1H), 4.36-4.41 (d, J = 17.3 Hz, 1H), 4.04-4.13 (m, 5H), 3.84-3.89 (m, 2H), 2.97-3.15 (m, 2H), 1.34-1.36 (d, J = 6.0 Hz, 3H), 1.15(t, J = 7.15 Hz, 3H) | MS: calc'd (MH$^+$) 567, measured (MH$^+$) 568 |
| 117 | $^1$H NMR (MeOD-d$_4$, 400 MHz): δ ppm 8.06-8.07 (d, J = 3.01 Hz, 1H), 7.96-7.97(d, J = 3.01 Hz, 1H), 7.40-7.46 (m, 2H), 7.25-7.29 (m, 2H), 6.18 (s, 1H), 4.26-4.49 (m, 2H), 4.06 (d, J = 12.5 Hz, 1H), 3.78-3.97 (m, 4H), 3.72 (s, 3H), 3.65 (d, J = 8.8 Hz, 1H), 3.37-3.44 (m, 2H), 1.36 (d, J = 6.3 Hz, 3H), 1.11-1.14 (t, J = 6.0 Hz, 3H) | MS: calc'd (MH$^+$) 505, measured (MH$^+$) 505 |
| 118 | $^1$H NMR (MeOD-d$_4$, 400 MHz): δ ppm 7.98 (d, J = 4.0 Hz, 1H), 7.79 (d, J = 4.0 Hz, 1H), 7.35-7.27 (m, 2H), 7.20-7.16 (m, 1H), 6.22 (s, 1H), 4.36-4.34 (m, 1H), 4.08-4.03 (m, 3H), 3.90-3.83 (m, 2H), 3.30-2.78 (m, 4H), 1.35 (d, J = 8.0 Hz, 3H), 1.15 (t, J = 8.0 Hz, 3H) | MS: calc'd (MH$^+$) 523 measured (MH$^+$) 523 |
| 119 | $^1$H NMR (MeOD-d$_4$, 400 MHz): δ ppm 8.0 (d, J = 4.0 Hz, 1H), 7.81 (d, J = 4.0 Hz, 1H), 7.63-7.61 (m, 1H), 7.45-7.33(m, 2H), 7.17 (m, 1H), 6.17 (s, 1H), 4.41-4.38 (m, 2H), 4.06-4.03 (m, 2H), 3.92-3.84 (m, 3H), 3.61 (s, 3H), 3.01-2.89 (m, 1h), 1.36 (d, J = 8.0 Hz, 3H), 1.15 (t, J = 8.0 Hz, 3H) | MS: calc'd (MH$^+$) 536 measured (MH$^+$) 536 |
| 120 | $^1$H NMR (MeOD-d$_4$, 400 MHz): δ ppm 8.01-8.02 (d, J = 3.01 Hz, 1H), 7.48-7.52 (dd, J = 8.7Hz, 6.0 Hz 1H), 7.26-7.30 (dd, J = 8.7 Hz, 2.7 Hz, 1H), 7.10 (m, 1H), 6.18 (s, 1H), 4.20-4.35 (m, 1H), 4.11 (d, J = 12.3 Hz, 1H), 3.81-3.84 (m, 3H), 3.01 (m, 2H), 2.01-2.10 (m, 1H), 1.06-1.09 (m, 6H) | MS: calc'd (MH$^+$) 537, measured (MH$^+$) 537 |
| 121 | $^1$H NMR (MeOD-d$_4$, 400 MHz): δ ppm 8.06 (d, J = 3.01 Hz, 1H), 7.85 (d, J = 2.76 Hz, 1H), 7.36 (dd, J = 8.66, 5.90 Hz, 1H), 7.20 (dd, J = 8.28, 2.51 Hz, 1H), 7.03 (td, J = 8.16, 2.51 Hz, 1H), 6.30 (s, 1H), 4.46 (d, J = 17.07 Hz, 1H), 4.21 (d, J = 17.32 Hz, 1H), 3.95-4.09 (m, 2H), 3.80-3.89 (m, 2H), 3.66 (s, 3H), 3.21-3.30 (m, 1H), 2.98-3.08 (m, 1H), 1.58 (s, 3 H) | MS: calc'd (MH$^+$) 509 measured (MH$^+$) 511 |
| 122 | $^1$H NMR (MeOD-d$_4$, 400 MHz): δ ppm 7.89 (d, J = 3.0 Hz, 1H), 7.55 (d, J = 3.0 Hz, 1H), 7.33-7.42 (m, 2H), 6.97-7.09 (m, 1H), 6.21 (s, 1H), 4.36 (d, J = 16.1 Hz, 1H), 3.97-4.18 (m, 5H), 3.92 (d, J = 6.0 Hz, 1H), 3.78-3.86 (m, 1H), 3.70 (br. s., 1H), 3.26 (br. s., 1H), 2.76 (br. s., 1H), 1.16 (t, J = 7.0 Hz, 3H) | MS: calc'd (MH$^+$) 554, measured (MH$^+$) 555 |
| 123 | $^1$H NMR (MeOD-d$_4$, 400 MHz): δ ppm 7.95 (s, 1H), 7.64 (br. s., 1H), 7.46 (d, J = 8.3 Hz, 2H), 7.32 (d, J = 8.3 Hz, 2H), 5.87 (s, 1H), 4.37 (d, J = 16.8 Hz, 1H), 4.14 (d, J = 7.3 Hz, 2H), 4.01 (d, J = 18.3 Hz, 2H), 3.84 (d, J = 19.3 Hz, 2H), 3.62 (br. s., 1H), 3.11 (br. s., 1H), 2.66 (br. s., 1H), 1.21 (t, J = 7.2 Hz, 3H) | MS: calc'd (MH$^+$) 536, measured (MH$^+$) 537 |
| 124 | $^1$H NMR (MeOD-d$_4$, 400 MHz): δ ppm 7.98 (br. s., 1H), 7.62-7.69 (m, 2H), 7.35-7.45 (m, 3H), 5.88 (br. s., 1H), 4.23-4.38 (m, 1H), 4.15 (br. s., 4H), 3.87 (br. s., 2H), 3.62 (br. s., 1H), 3.11 (br. s., 1H), 2.66 (br. s., 1H), 1.20-1.26 (m, 3H) | MS: calc'd (MH$^-$) 568, measured (MH$^-$) 567 |
| 125 | $^1$H NMR (MeOD-d$_4$, 400 MHz): δ ppm 7.93 (s, 1H), 7.57 (br. s., 1H), 7.18 (s, 1H), 6.95-7.06 (m, 2H), 5.84 (s, 1H), 4.04-4.28 (m, 5H), 3.84 (br. s., 2H), 3.60 (br. s., 1H), 3.17 (br. s., 1H), 2.56 (br. s., 1H), 1.26 (t, J = 7.2 Hz, 3H) | MS: calc'd (MH$^+$) 509, measured (MH$^+$) 509 |
| 126 | $^1$H NMR (MeOD-d$_4$, 400 MHz): δ ppm 8.10 (s, 1H), 7.83-7.94 (m, 1H), 7.47 (d, J = 4.0 Hz, 2H), 7.38 (d, J = 7.5 Hz, 2H), 6.16 (br. s, 1H), 3.73-4.53 (m, 11H), 1.22 (t, J = 7.2 Hz, 3H) | MS: calc'd (MH$^+$) 491, measured (MH$^+$) 491 |
| 127 | $^1$H NMR (MeOD-d$_4$, 400 MHz): δ ppm 7.84-7.91 (m, 1H), 7.58-7.65 (m, 1H), 7.54 (d, J = 2.5 Hz, 1H), 7.34-7.40 (m, 1H), 7.32 (d, J = 6.8 Hz, 1H), 7.17 (t, J = 7.5 Hz, 1H), 6.20-6.26 (m, 1H), 4.44 (d, J = 14.6 Hz, 1H), 4.03-4.18 (m, 3H), 3.83-3.97 (m, 2H), 3.72-3.82 (m, 2H), 3.61 (d, J = 3.8 Hz, 1H), 3.22 (d, J = 11.5 Hz, 1H), 2.03 (d, J = 5.5 Hz, 1H), 1.98-2.08 (m, 1H), 1.13 (q, J = 7.0 Hz, 3H) | MS: calc'd (MH$^+$) 536, measured (MH$^+$) 537 |
| 128 | $^1$H NMR (MeOD-d$_4$, 400 MHz): δ ppm 10.01 (br. s., 1H), 8.03 (d, J = 3.0 Hz, 1H), 7.94 (d, J = 3.3 Hz, 1H), 7.40-7.49 (m, 1H), 7.25 (ddd, J = 8.8, 5.3, 1.9 Hz, 1H), 6.05 (s, 1H), 4.17-4.26 (m, 1H), 4.05 (d, J = 17.3 Hz, 1H), 3.95 (q, J = 7.0 Hz, 3H), 3.79-3.86 (m, 1H), 3.68 (td, J = 7.8, 3.4 Hz, 2H), 3.56 (br. s., 1H), 3.02-3.12 (m, 1H), 2.36-2.45 (m, 1H), 1.05 (t, J = 7.0 Hz, 3H) | MS: calc'd (MH$^+$) 571 measured (MH$^+$) 571 |

TABLE 2-continued

NMR and MS data of particular compounds

| Example No. | ¹H NMR data | MW data |
|---|---|---|
| 129 | ¹H NMR (MeOD-$d_4$, 400 MHz): δ ppm 7.83-7.93 (m, 2H), 7.53 (d, J = 3.0 Hz, 1H), 7.34 (d, J = 3.8 Hz, 2H), 6.93-7.04 (m, 1H), 6.07 (d, J = 7.5 Hz, 1H), 4.41 (d, J = 15.6 Hz, 1H), 4.14 (dd, J = 11.4, 3.9 Hz, 1H), 4.02-4.11 (m, 2H), 3.86-3.97 (m, 2H), 3.75-3.84 (m, 1H), 3.62 (d, J = 4.3 Hz, 1H), 3.07-3.31 (m, 2H), 2.73 (br. s., 1H), 1.13 (q, J = 7.0 Hz, 3H) | MS: calc'd (MH$^+$) 583 measured (MH$^+$) 583 |
| 130 | ¹H NMR (MeOD-$d_4$, 400 MHz): δ ppm 7.98 (d, J = 3.0 Hz, 1H), 7.75 (d, J = 3.0 Hz, 1H), 7.48-7.57 (m, 2H), 7.26 (d, J = 8.5 Hz, 2H), 5.85 (s, 1H), 4.59 (d, J = 15.6 Hz, 1H), 4.16 (q, J = 7.0 Hz, 2H), 3.78-3.94 (m, 2H), 3.54 (q, J = 10.8 Hz, 1H), 3.10-3.24 (m, 1H), 2.73-2.89 (m, 1H), 2.55 (qd, J = 14.7, 9.0 Hz, 1H), 1.22 (t, J = 7.2 Hz, 3H) | MS: calc'd (MH$^+$) 555 measured (MH$^+$) 555 |

More particular compounds of formula I include the following:

(R)-6-((S)-2-carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester;

(S)-6-((S)-2-carboxy-4,4-difluoro-pyrrolidin-1-ylmethyl)-4-(2-chloro-4-fluoro-phenyl)-[4-2H]-2-thiazol-2-yl-1,4-dihydro-pyrimidine-5-carboxylic acid methyl ester;

(R)-6-((S)-2-carboxy-4,4-difluoro-pyrrolidin-1-ylmethyl)-4-(2-chloro-4-fluoro-phenyl)-2-(3,5-difluoro-pyridin-2-yl)-1,4-dihydro-pyrimidine-5-carboxylic acid methyl ester;

(S)-4-[(R)-6-(2-chloro-4-fluoro-phenyl)-5-methoxycarbonyl-2-thiazol-2-yl-3,6-dihydro-pyrimidin-4-ylmethyl]-morpholine-3-carboxylic acid;

(S)-4-[(R)-6-(2-chloro-4-fluoro-phenyl)-2-(3,5-difluoro-pyridin-2-yl)-5-methoxycarbonyl-3,6-dihydro-pyrimidin-4-ylmethyl]-morpholine-3-carboxylic acid;

(R)-6-((S)-2-carboxy-4,4-difluoro-pyrrolidin-1-ylmethyl)-4-(2-chloro-4-fluoro-phenyl)-2-(4-cyclopropyl-thiazol-2-yl)-1,4-dihydro-pyrimidine-5-carboxylic acid methyl ester;

(R)-6-((S)-2-Carboxy-4,4-difluoro-pyrrolidin-1-ylmethyl)-4-(2-chloro-4-fluoro-phenyl)-2-(4-fluoro-thiophen-2-yl)-1,4-dihydro-pyrimidine-5-carboxylic acid methyl ester;

(R)-6-((S)-2-carboxy-4,4-difluoro-pyrrolidin-1-ylmethyl)-4-(2-chloro-4-fluoro-phenyl)-2-(4-methyl-thiazol-2-yl)-1,4-dihydro-pyrimidine-5-carboxylic acid methyl ester;

(S)-4-[(R)-6-(2-chloro-4-fluoro-phenyl)-5-methoxycarbonyl-2-(4-methyl-thiazol-2-yl)-3,6-dihydro-pyrimidin-4-ylmethyl]-morpholine-3-carboxylic acid;

(R)-6-(S)-2-carboxy-[3,3-2H2]-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester;

(R)-6-((S)-2-Carboxy-4,4-difluoro-pyrrolidin-1-ylmethyl)-4-(2-chloro-4-fluoro-phenyl)-2-(4-trifluoromethyl-thiazol-2-yl)-1,4-dihydro-pyrimidine-5-carboxylic acid methyl ester;

(R)-6-((S)-2-carboxy-4,4-difluoro-pyrrolidin-1-ylmethyl)-4-(2-chloro-4-fluoro-phenyl)-2-(4-isopropyl-thiazol-2-yl)-1,4-dihydro-pyrimidine-5-carboxylic acid methyl ester;

(S)-4-[(R)-6-(2-chloro-4-fluoro-phenyl)-5-ethoxycarbonyl-2-thiazol-2-yl-3,6-dihydro-pyrimidin-4-ylmethyl]-morpholine-3-carboxylic acid;

(R)-6-((S)-2-Carboxy-4,4-difluoro-pyrrolidin-1-ylmethyl)-4-(2-chloro-4-fluoro-phenyl)-2-(1-methyl-1H-imidazol-2-yl)-1,4-dihydro-pyrimidine-5-carboxylic acid methyl ester;

(R)-6-((S)-2-Carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid ethyl ester;

(S)-4-[(R)-6-(2-Chloro-4-fluoro-phenyl)-5-ethoxycarbonyl-2-(1-methyl-1H-imidazol-2-yl)-3,6-dihydro-pyrimidin-4-ylmethyl]-morpholine-3-carboxylic acid;

(R)-6-((S)-2-Carboxy-4,4-difluoro-pyrrolidin-1-ylmethyl)-4-(2-chloro-4-fluoro-phenyl)-2-(1-methyl-1H-imidazol-2-yl)-1,4-dihydro-pyrimidine-5-carboxylic acid ethyl ester;

(R)-6-((S)-2-Carboxy-4,4-difluoro-pyrrolidin-1-ylmethyl)-4-(2,4-dichloro-phenyl)-2-thiazol-2-yl-1,4-dihydro-pyrimidine-5-carboxylic acid ethyl ester;

(S)-4-[(R)-6-(2,4-Dichloro-phenyl)-5-ethoxycarbonyl-2-thiazol-2-yl-3,6-dihydro-pyrimidin-4-ylmethyl]-morpholine-3-carboxylic acid;

(S)-6-((S)-2-Carboxy-4,4-difluoro-pyrrolidin-1-ylmethyl)-4-(3,4-difluoro-phenyl)-2-thiazol-2-yl-1,4-dihydro-pyrimidine-5-carboxylic acid ethyl ester;

(S)-4-[(S)-6-(3,4-Difluoro-phenyl)-5-ethoxycarbonyl-2-thiazol-2-yl-3,6-dihydro-pyrimidin-4-ylmethyl]-morpholine-3-carboxylic acid;

(S)-4-[(S)-5-Ethoxycarbonyl-2-thiazol-2-yl-6-(3,4,5-trifluoro-phenyl)-3,6-dihydro-pyrimidin-4-ylmethyl]-morpholine-3-carboxylic acid;

(S)-4-[(R)-5-Ethoxycarbonyl-2-thiazol-2-yl-6-(2,3,4-trifluoro-phenyl)-3,6-dihydro-pyrimidin-4-ylmethyl]-morpholine-3-carboxylic acid;

(S)-4-[(S)-6-(3,4-Dichloro-phenyl)-5-ethoxycarbonyl-2-thiazol-2-yl-3,6-dihydro-pyrimidin-4-ylmethyl]-morpholine-3-carboxylic acid;

(S)-4-[(R)-6-(2-Chloro-3-fluoro-phenyl)-5-methoxycarbonyl-2-thiazol-2-yl-3,6-dihydro-pyrimidin-4-ylmethyl]-morpholine-3-carboxylic acid;

(S)-4-[(R)-6-(4-Chloro-2-fluoro-phenyl)-5-ethoxycarbonyl-2-thiazol-2-yl-3,6-dihydro-pyrimidin-4-ylmethyl]-morpholine-3-carboxylic acid;

(R)-6-((S)-2-Carboxy-4,4-difluoro-pyrrolidin-1-ylmethyl)-4-(2,3-difluoro-phenyl)-2-thiazol-2-yl-1,4-dihydro-pyrimidine-5-carboxylic acid ethyl ester;

(S)-4-[(R)-6-(2-Chloro-4-fluoro-phenyl)-2-thiazol-2-yl-5-(2,2,2-trifluoro-ethoxycarbonyl)-3,6-dihydro-pyrimidin-4-ylmethyl]-morpholine-3-carboxylic acid;

(S)-4-[(S)-6-(4-Bromo-3-fluoro-phenyl)-5-ethoxycarbonyl-2-thiazol-2-yl-3,6-dihydro-pyrimidin-4-ylmethyl]-morpholine-3-carboxylic acid;

(S)-4-[(S)-5-Ethoxycarbonyl-6-(3-fluoro-phenyl)-2-thiazol-2-yl-3,6-dihydro-pyrimidin-4-ylmethyl]-morpholine-3-carboxylic acid;

(S)-4-[(S)-5-Ethoxycarbonyl-6-(4-fluoro-phenyl)-2-thiazol-2-yl-3,6-dihydro-pyrimidin-4-ylmethyl]-morpholine-3-carboxylic acid;

(R)-6-((S)-2-Carboxy-4,4-difluoro-pyrrolidin-1-ylmethyl)-4-(2-chloro-3,4-difluoro-phenyl)-2-thiazol-2-yl-1,4-dihydro-pyrimidine-5-carboxylic acid ethyl ester;

(S)-6-((S)-2-Carboxy-4,4-difluoro-pyrrolidin-1-ylmethyl)-4-(3,4-difluoro-phenyl)-2-(1-methyl-1H-imidazol-2-yl)-1,4-dihydro-pyrimidine-5-carboxylic acid ethyl ester;

(S)-4-[(S)-6-(3,4-Difluoro-phenyl)-5-ethoxycarbonyl-2-(1-methyl-1H-imidazol-2-yl)-3,6-dihydro-pyrimidin-4-ylmethyl]-morpholine-3-carboxylic acid;

(S)-4-[(R)-6-(2,4-Difluoro-phenyl)-5-ethoxycarbonyl-2-thiazol-2-yl-3,6-dihydro-pyrimidin-4-ylmethyl]-morpholine-3-carboxylic acid;

(R)-6-((S)-2-Carboxy-4,4-difluoro-pyrrolidin-1-ylmethyl)-4-(2,4-difluoro-phenyl)-2-thiazol-2-yl-1,4-dihydro-pyrimidine-5-carboxylic acid ethyl ester;

(S)-4-[(R)-6-(2-Chloro-3,4-difluoro-phenyl)-5-ethoxycarbonyl-2-thiazol-2-yl-3,6-dihydro-pyrimidin-4-ylmethyl]-morpholine-3-carboxylic acid;

(3S)-4-[[(4R)-4-(2-Chloro-4-fluorophenyl)-5-methoxycarbonyl-2-(4-methylsulfanyl-1,3-thiazol-2-yl)-1,4-dihydro-pyrimidin-6-yl]methyl]morpholine-3-carboxylic acid;

(2S)-1-[[(4R)-4-(2-Chloro-4-fluorophenyl)-5-methoxycarbonyl-2-(4-methylsulfanyl-1,3-thiazol-2-yl)-1,4-dihydro-pyrimidin-6-yl]methyl]-4,4-difluoropyrrolidine-2-carboxylic acid;

(S)-4-[(R)-6-(2-Chloro-3-fluoro-phenyl)-5-ethoxycarbonyl-2-thiazol-2-yl-3,6-dihydro-pyrimidin-4-ylmethyl]-morpholine-3-carboxylic acid;

(R)-6-(S)-2-Carboxy-4,4-difluoro-pyrrolidin-1-ylmethyl)-4-(2-chloro-3-fluoro-phenyl)-2-thiazol-2-yl-1,4-dihydro-pyrimidine-5-carboxylic acid ethyl ester;

(S)-4-[(R)-6-(2-Bromo-4-fluoro-phenyl)-5-methoxycarbonyl-2-(5-methyl-oxazol-4-yl)-3,6-dihydro-pyrimidin-4-ylmethyl]-morpholine-3-carboxylic acid;

(S)-4-[(R)-6-(2-Bromo-3-fluoro-phenyl)-5-ethoxycarbonyl-2-thiazol-2-yl-3,6-dihydro-pyrimidin-4-ylmethyl]-morpholine-3-carboxylic acid;

(S)-4-[(R)-6-(2-Chloro-4-fluoro-phenyl)-5-methoxycarbonyl-2-(5-methyl-oxazol-4-yl)-3,6-dihydro-pyrimidin-4-ylmethyl]-morpholine-3-carboxylic acid;

(S)-4-[(R)-6-(2-Bromo-4-fluoro-phenyl)-5-ethoxycarbonyl-2-(5-methyl-oxazol-4-yl)-3,6-dihydro-pyrimidin-4-ylmethyl]-morpholine-3-carboxylic acid;

(S)-4-[(R)-6-(2,3-Difluoro-phenyl)-5-ethoxycarbonyl-2-thiazol-2-yl-3,6-dihydro-pyrimidin-4-ylmethyl]-morpholine-3-carboxylic acid;

(S)-4-[(R)-6-(2-Bromo-phenyl)-5-methoxycarbonyl-2-thiazol-2-yl-3,6-dihydro-pyrimidin-4-ylmethyl]-morpholine-3-carboxylic acid (S)-4-[(R)-6-(2-Chloro-3,4-difluoro-phenyl)-5-methoxycarbonyl-2-thiazol-2-yl-3,6-dihydro-pyrimidin-4-ylmethyl]-morpholine-3-carboxylic acid;

(R)-6-(S)-2-Carboxy-4,4-difluoro-pyrrolidin-1-ylmethyl)-4-(2-chloro-3,4-difluoro-phenyl)-2-thiazol-2-yl-1,4-dihydro-pyrimidine-5-carboxylic acid methyl ester;

(S)-4-[(R)-6-(4-Chloro-2-fluoro-phenyl)-5-methoxycarbonyl-2-thiazol-2-yl-3,6-dihydro-pyrimidin-4-ylmethyl]-morpholine-3-carboxylic acid;

(S)-4-[(S)-6-(4-Chloro-3-fluoro-phenyl)-5-methoxycarbonyl-2-thiazol-2-yl-3,6-dihydro-pyrimidin-4-ylmethyl]-morpholine-3-carboxylic acid;

(R)-4-[(R)-6-(2-Chloro-3,4-difluoro-phenyl)-5-methoxycarbonyl-2-thiazol-2-yl-3,6-dihydro-pyrimidin-4-ylmethyl]-3-methyl-morpholine-3-carboxylic acid;

(S)-4-[(R)-6-(2-Bromo-4-fluoro-phenyl)-5-methoxycarbonyl-2-thiazol-2-yl-3,6-dihydro-pyrimidin-4-ylmethyl]-morpholine-3-carboxylic acid;

(S)-4-[(R)-6-(2-Chloro-phenyl)-5-ethoxycarbonyl-2-thiazol-2-yl-3,6-dihydro-pyrimidin-4-ylmethyl]-morpholine-3-carboxylic acid;

(S)-4-[(S)-6-(4-Chloro-3-fluoro-phenyl)-5-ethoxycarbonyl-2-thiazol-2-yl-3,6-dihydro-pyrimidin-4-ylmethyl]-morpholine-3-carboxylic acid;

(R)-4-(2-Bromo-4-fluoro-phenyl)-6-(S)-2-carboxy-4,4-difluoro-pyrrolidin-1-ylmethyl)-2-thiazol-2-yl-1,4-dihydro-pyrimidine-5-carboxylic acid methyl ester;

(R)-6-(S)-2-Carboxy-4,4-difluoro-pyrrolidin-1-ylmethyl)-4-(2,4-dichloro-phenyl)-2-thiazol-2-yl-1,4-dihydro-pyrimidine-5-carboxylic acid methyl ester;

(S)-4-[(S)-6-(2-Chloro-4-fluoro-phenyl)-2-(1,4-dimethyl-1H-imidazol-2-yl)-5-methoxycarbonyl-3,6-dihydro-pyrimidin-4-ylmethyl]-morpholine-3-carboxylic acid;

(S)-4-[(R)-6-(4-Bromo-2-fluoro-phenyl)-5-ethoxycarbonyl-2-thiazol-2-yl-3,6-dihydro-pyrimidin-4-ylmethyl]-morpholine-3-carboxylic acid;

(S)-4-[(R)-6-(2-Chloro-4-fluoro-phenyl)-5-methoxycarbonyl-2-(4-trifluoromethyl-thiazol-2-yl)-3,6-dihydro-pyrimidin-4-ylmethyl]-morpholine-3-carboxylic acid;

(S)-4-[(S)-6-(3,4-Difluoro-2-methyl-phenyl)-5-ethoxycarbonyl-2-thiazol-2-yl-3,6-dihydro-pyrimidin-4-ylmethyl]-morpholine-3-carboxylic acid;

(S)-4-[(R)-6-(2-Chloro-3-fluoro-phenyl)-5-ethoxycarbonyl-2-(1-methyl-1H-imidazol-2-yl)-3,6-dihydro-pyrimidin-4-ylmethyl]-morpholine-3-carboxylic acid;

(S)-4-[(R)-6-(2-Chloro-4-fluoro-phenyl)-5-isopropoxycarbonyl-2-thiazol-2-yl-3,6-dihydro-pyrimidin-4-ylmethyl]-morpholine-3-carboxylic acid;

(S)-4-[(R)-6-(2-Chloro-3-fluoro-phenyl)-5-isopropoxycarbonyl-2-thiazol-2-yl-3,6-dihydro-pyrimidin-4-ylmethyl]-morpholine-3-carboxylic acid;

(R)-6-(S)-2-Carboxy-4,4-difluoro-pyrrolidin-1-ylmethyl)-4-(2-chloro-4-fluoro-phenyl)-2-(5-methyl-oxazol-4-yl)-1,4-dihydro-pyrimidine-5-carboxylic acid methyl ester;

(S)-4-[(R)-6-(2-Chloro-3-fluoro-phenyl)-5-methoxycarbonyl-2-(5-methyl-oxazol-4-yl)-3,6-dihydro-pyrimidin-4-ylmethyl]-morpholine-3-carboxylic acid;

(2R,3S)-4-[(R)-6-(2-Chloro-4-fluoro-phenyl)-5-methoxycarbonyl-2-thiazol-2-yl-3,6-dihydro-pyrimidin-4-ylmethyl]-2-methyl-morpholine-3-carboxylic acid;

(2R,3S)-4-[(R)-6-(2-Bromo-4-fluoro-phenyl)-5-methoxycarbonyl-2-thiazol-2-yl-3,6-dihydro-pyrimidin-4-ylmethyl]-2-methyl-morpholine-3-carboxylic acid;

(R)-4-(2-Bromo-4-fluoro-phenyl)-6-(S)-2-carboxy-5,5-difluoro-piperidin-1-ylmethyl)-2-thiazol-2-yl-1,4-dihydro-pyrimidine-5-carboxylic acid ethyl ester;

(R)-4-(2-Bromo-4-fluoro-phenyl)-6-(R)-2-carboxy-5,5-difluoro-piperidin-1-ylmethyl)-2-thiazol-2-yl-1,4-dihydro-pyrimidine-5-carboxylic acid ethyl ester;

(R)-6-((S)-2-Carboxy-5,5-difluoro-piperidin-1-ylmethyl)-4-(2-chloro-3-fluoro-phenyl)-2-thiazol-2-yl-1,4-dihydro-pyrimidine-5-carboxylic acid methyl ester;

(R)-6-((S)-2-Carboxy-5,5-difluoro-piperidin-1-ylmethyl)-4-(2-chloro-phenyl)-2-thiazol-2-yl-1,4-dihydro-pyrimidine-5-carboxylic acid ethyl ester;

(2R,3S)-4-[(S)-6-(3,4-Difluoro-phenyl)-5-ethoxycarbonyl-2-thiazol-2-yl-3,6-dihydro-pyrimidin-4-ylmethyl]-2-methyl-morpholine-3-carboxylic acid;

(2R,3S)-4-[(S)-6-(3,4-Difluoro-phenyl)-5-methoxycarbonyl-2-thiazol-2-yl-3,6-dihydro-pyrimidin-4-ylmethyl]-2-methyl-morpholine-3-carboxylic acid;

(2R,3S)-4-[(R)-5-Methoxycarbonyl-2-thiazol-2-yl-6-(2,3,4-trifluoro-phenyl)-3,6-dihydro-pyrimidin-4-ylmethyl]-2-methyl-morpholine-3-carboxylic acid;
(2R,3S)-4-[(R)-6-(2-Chloro-3-fluoro-phenyl)-5-methoxycarbonyl-2-thiazol-2-yl-3,6-dihydro-pyrimidin-4-ylmethyl]-2-methyl-morpholine-3-carboxylic acid;
(2R,3S)-4-[(R)-6-(2-Bromo-4-fluoro-phenyl)-5-ethoxycarbonyl-2-thiazol-2-yl-3,6-dihydro-pyrimidin-4-ylmethyl]-2-methyl-morpholine-3-carboxylic acid;
(2R,3S)-4-[(R)-6-(2-Chloro-phenyl)-5-ethoxycarbonyl-2-thiazol-2-yl-3,6-dihydro-pyrimidin-4-ylmethyl]-2-methyl-morpholine-3-carboxylic acid;
(2R,3S)-4-[(R)-6-(2-Chloro-3-fluoro-phenyl)-5-ethoxycarbonyl-2-thiazol-2-yl-3,6-dihydro-pyrimidin-4-ylmethyl]-2-methyl-morpholine-3-carboxylic acid;
(2R,3S)-4-[(R)-6-(2-Bromo-phenyl)-5-methoxycarbonyl-2-thiazol-2-yl-3,6-dihydro-pyrimidin-4-ylmethyl]-2-methyl-morpholine-3-carboxylic acid;
(2R,3S)-4-[(R)-6-(2-Chloro-4-fluoro-phenyl)-5-methoxycarbonyl-2-thiazol-2-yl-3,6-dihydro-pyrimidin-4-ylmethyl]-2-isopropyl-morpholine-3-carboxylic acid;
(S)-4-(R)-6-(2-Chloro-4-fluorophenyl)-5-(methoxycarbonyl)-2-(thiazol-2-yl)-3,6-dihydropyrimidin-4-yl)methyl)-3-methylmorpholine-3-carboxylic acid;
(S)-4-(R)-6-(2-Bromo-4-fluorophenyl)-5-(ethoxycarbonyl)-2-(thiazol-2-yl)-3,6-dihydropyrimidin-4-yl)methyl)morpholine-3-carboxylic acid;
(3S)-4-[[(4S)-4-(4-Bromophenyl)-5-ethoxycarbonyl-2-(1,3-thiazol-2-yl)-1,4-dihydropyrimidin-6-yl]methyl]morpholine-3-carboxylic acid;
(S)-4-(R)-6-(2-Bromophenyl)-5-(ethoxycarbonyl)-2-(thiazol-2-yl)-3,6-dihydropyrimidin-4-yl)methyl)morpholine-3-carboxylic acid;
(3S)-4-[[(4R)-4-(2-Bromo-3,4-difluorophenyl)-5-ethoxycarbonyl-2-(1,3-thiazol-2-yl)-1,4-dihydropyrimidin-6-yl]methyl]morpholine-3-carboxylic acid;
(3S)-4-[[(4R)-5-Ethoxycarbonyl-4-(2-iodophenyl)-2-(1,3-thiazol-2-yl)-1,4-dihydropyrimidin-6-yl]methyl]morpholine-3-carboxylic acid; and
(2S)-1-[[(4S)-4-(4-Bromophenyl)-5-ethoxycarbonyl-2-(1,3-thiazol-2-yl)-1,4-dihydropyrimidin-6-yl]methyl]-4,4-difluoropyrrolidine-2-carboxylic acid.

The compounds of the present invention have good anti-HBV activity, high selectivity index, superior solubility and mouse SDPK profiles compared to the previously reported capsid assembly effectors such as Bay 41-4109. As a reference, the in-house data of the Bayer compound which is Bay 41-4109, are also shown in Table 3, 4, 5 and 6.

TABLE 3

Anti-HBV activity data of particular compounds in HepG2.2.15 cells

| Example No. | EC$_{50}$ (µM) | Example No. | EC$_{50}$ (µM) |
|---|---|---|---|
| Bay 41-4109 | 0.087 (0.050)* | | |
| 2 | 0.0027 | 3 | 0.0011 |
| 4 | 0.0015 | 5 | 0.0031 |
| 6 | 0.0075 | 10 | 0.0073 |
| 12 | 0.0093 | 14 | 0.041 |
| 16 | 0.0020 | 17 | 0.0070 |
| 19 | 0.0057 | 23 | 0.025 |
| 24 | 0.026 | 25 | 0.0050 |
| 28 | 0.0044 | 29 | 0.028 |
| 31 | 0.002 | 32 | 0.013 |
| 33 | 0.023 | 34 | 0.010 |
| 35 | 0.0077 | 36 | 0.018 |

TABLE 3-continued

Anti-HBV activity data of particular compounds in HepG2.2.15 cells

| Example No. | EC$_{50}$ (µM) | Example No. | EC$_{50}$ (µM) |
|---|---|---|---|
| 38 | 0.0033 | 39 | 0.0011 |
| 41 | 0.017 | 42 | 0.0100 |
| 43 | 0.018 | 44 | 0.0046 |
| 45 | 0.028 | 46 | 0.016 |
| 47 | 0.0044 | 48 | 0.028 |
| 49 | 0.0047 | 50 | 0.014 |
| 51 | 0.013 | 52 | 0.0030 |
| 53 | 0.014 | 54 | 0.014 |
| 55 | 0.0010 | 56 | 0.015 |
| 57 | 0.015 | 58 | 0.014 |
| 59 | 0.013 | 60 | 0.0006 |
| 61 | 0.018 | 62 | 0.014 |
| 63 | 0.0008 | 64 | 0.0030 |
| 65 | 0.0076 | 66 | 0.0007 |
| 68 | 0.014 | 69 | 0.0060 |
| 70 | 0.0089 | 71 | 0.0048 |
| 73 | 0.0012 | 74 | 0.0021 |
| 75 | 0.0180 | 77 | 0.0070 |
| 78 | 0.026 | 79 | 0.0045 |
| 80 | 0.027 | 81 | 0.0060 |
| 82 | 0.014 | 83 | 0.0015 |
| 84 | 0.0024 | 85 | 0.0062 |
| 87 | 0.022 | 91 | 0.038 |
| 92 | 0.014 | 93 | 0.0043 |
| 94 | 0.020 | 95 | 0.0025 |
| 96 | 0.0006 | 97 | 0.0050 |
| 98 | 0.017 | 99 | 0.012 |
| 100 | 0.035 | 101 | 0.014 |
| 102 | 0.0090 | 103 | 0.015 |
| 104 | 0.0070 | 106 | 0.0021 |
| 107 | 0.0015 | 108 | 0.018 |
| 109 | 0.0044 | 110 | 0.042 |
| 111 | 0.0058 | 112 | 0.0052 |
| 113 | 0.016 | 114 | 0.0093 |
| 115 | 0.0023 | 116 | 0.0018 |
| 117 | 0.0015 | 118 | 0.0005 |
| 119 | 0.0030 | 120 | 0.0048 |
| 121 | 0.020 | 122 | 0.0013 |
| 123 | 0.0028 | 124 | 0.029 |
| 125 | 0.030 | 127 | 0.0067 |
| 128 | 0.0006 | 129 | 0.0076 |
| 130 | 0.0060 | | |

*Literature data, see: Deres K. et al. *Science* 2003, 893-896

Compound with favorable pharmacokinetics is more likely to be efficacious and safe. It is very important for a drug to have a moderate or low clearance and a reasonable half-life, as this often leads to a good oral bioavailability and high systemic exposure. Reducing the clearance of a compound or drug could reduce the daily dose required for efficacy and therefore give a better efficacy and safety profile. It is also very important for HBV infection treatment compound to show good liver exposure since this is the targeted organ. As shown in Table 4, compounds of the present invention exhibit good mouse SDPK profiles: low to moderate clearance, good exposure at low dose in both plasma and liver, and good bioavailability. As shown in Table 5, compounds of the present invention also exhibit low clearance in in vitro human hepatic microsome stability assay.

The single dose PK parameters of Bay 41-4109, Example 2, Example 5 and Example 16 in mouse plasma and liver are shown in Table 4.

TABLE 4

Pharmacokinetics of particular compounds in male ICR mice

| | | Example | | | |
|---|---|---|---|---|---|
| | | Bay 41-4109 | Example 2 | Example 5 | Example 16 |
| Dose (mg/kg) | | 5 (IV) 30 (PO) | 1 (IV) 3 (PO) | 1 (IV) 3 (PO) | 1 (IV) 3 (PO) |
| Plasma | Cl (IV) (mL/min/kg) | 60 (67[1]) | 17 | 19 | 57 |
| | $AUC_{(0-\infty)}$ (IV, μg/L * hr) | 1380 | 995 | 878 | 290 |
| | Normalized $AUC_{(0-\infty)}$ (IV, μg/L * hr) | 276 | 995 | 878 | 290 |
| | $AUC_{(0-\infty)}$ (PO, μg/L * hr) | 1740 | 2790 | 962 | 598 |
| | Normalized $AUC_{(0-\infty)}$ (PO, μg/L * hr) | 58 | 930 | 321 | 199 |
| | F (%) | 21 (31[1]) | 94 | 37 | 69 |
| Liver | $AUC_{(0-\infty)}$ (PO, μg/L * hr) | ND[2] | 18000 | 11800 | 35200 |

[1]Literature data, please see Deres K. et al. *Science* 2003, 893-896
[2]Not detectable in liver.
Cl: clearance;
$AUC_{(0-\infty)}$: area under the curve from the time of dosing to infinity
Normalized $AUC_{(0-\infty)} = AUC_{(0-\infty)}$/Dose
F: bioavailability.

TABLE 5

Metabolic stability in human microsome

| Example number | Human Hepatic Clearance (mL/min/kg) | Example number | Human Hepatic Clearance (mL/min/kg) | Example number | Human Hepatic Clearance (mL/min/kg) |
|---|---|---|---|---|---|
| 1 | 7.51 | 2 | 3.65 | 3 | 9.21 |
| 4 | 5.11 | 5 | 2.7 | 6 | 6.28 |
| 7 | 6.12 | 8 | 6.33 | 9 | 10.07 |
| 10 | 8.76 | 12 | 5.55 | 13 | 2.33 |
| 14 | 1.41 | 15 | 3.53 | 16 | 6.35 |
| 17 | 0.74 | 18 | 3.38 | 19 | 3.65 |
| 20 | 10.74 | 21 | 3.08 | 22 | 4.82 |
| 23 | 8.8 | 24 | 3.19 | 25 | 9.34 |
| 26 | 10.02 | 27 | 8.79 | 29 | 7.65 |
| 30 | 6.56 | 31 | 4.68 | 32 | 5.04 |
| 33 | 4.15 | 34 | 7.46 | 35 | 8.86 |
| 36 | 6.22 | 37 | 7 | 38 | 9.3 |
| 39 | 7.18 | 40 | 8.45 | 41 | 6.83 |
| 42 | 5.56 | 43 | 1.2 | 44 | 4.46 |
| 45 | 4.69 | 46 | 0 | 47 | 1.46 |
| 48 | 3.12 | 49 | 0 | 50 | 0 |
| 51 | 0 | 52 | 4.03 | 53 | 0 |
| 54 | 0 | 56 | 2.44 | 57 | 0 |
| 58 | 1.26 | 59 | 3.5 | 60 | 4.8 |
| 62 | 9.06 | 63 | 1.71 | 64 | 0 |
| 65 | 1.67 | 66 | 1.64 | 67 | 6.42 |
| 68 | 0.23 | 69 | 0 | 70 | 2.22 |
| 71 | 2.81 | 72 | 5.16 | 73 | 0 |
| 74 | 0.51 | 75 | 0 | 76 | 1.72 |
| 77 | 1.43 | 78 | 3.22 | 79 | 2.18 |
| 80 | 4.27 | 81 | 5.33 | 82 | 0 |
| 83 | 1.77 | 84 | 9.3 | 85 | 6.91 |
| 86 | 6.8 | 87 | 6.86 | 88 | 6.46 |
| 89 | 6.13 | 90 | 5.52 | 91 | 1.62 |
| 92 | 1.26 | 93 | 1.24 | 94 | 0.61 |
| 95 | 3.04 | 96 | 4.8 | 97 | 1.63 |
| 98 | 0 | 99 | 2.13 | 100 | 0.1 |
| 101 | 4.18 | 102 | 0.97 | 103 | 2.81 |
| 104 | 5.42 | 105 | 8.13 | 106 | 6.32 |
| 107 | 1.89 | 108 | 4.88 | 109 | 1.25 |
| 110 | 2.41 | 111 | 5.31 | 112 | 1.95 |
| 113 | 0 | 114 | 0 | 115 | 1.55 |
| 116 | 0 | 117 | 0 | 118 | 0.1 |
| 119 | 0.85 | 120 | 2.58 | 121 | 1.42 |
| 122 | 1.58 | 123 | 3.14 | 124 | 2.17 |
| 125 | 1.32 | 126 | 0 | 127 | 2.44 |
| 128 | 0.26 | 129 | 4.25 | 130 | 3.92 |

The aqueous solubility is an important physico-chemical property that plays a significant role in various physical and biological processes. It is desirable to have good solubility which enables good permeability and gastric and intestinal absorption, linear dose proportionality, less PK variability, and easy formulation for PD/PK studies. At different stages of the drug discovery/development process solubility has to be determined and especially in the early phases (lead generation to lead optimization) high throughput methods are needed. Lyophilisation solubility assay (Lysa) is a well adopted high throughput assay to measure compound solubility in industry.

Results of Lysa are given in Table 6.

TABLE 6

Solubility data of particular compounds

| Example No. | Lysa (μg/mL) | Example No. | Lysa (μg/mL) | Example No. | Lysa (μg/mL) |
|---|---|---|---|---|---|
| Bay 41-4109 | 38.0 | | | | |
| 2 | >698 | 3 | >644 | 4 | >700 |
| 5 | >660 | 6 | >100 | 7 | 398 |
| 8 | >620 | 9 | >645 | 10 | 246 |
| 12 | 488 | 13 | 594 | 14 | >644 |
| 15 | >627 | 16 | >622 | 17 | >673 |
| 18 | >659 | 19 | >654 | 20 | 683 |
| 21 | 828 | 22 | 630 | 23 | 172 |
| 24 | 656 | 25 | 546 | 26 | 668 |
| 28 | 247 | 29 | 420 | 30 | 667 |
| 31 | 630 | 32 | 632 | 34 | 531 |
| 35 | >599 | 36 | >637 | 37 | >593 |
| 38 | 291 | 39 | >654 | 40 | 409 |
| 41 | >630 | 42 | >613.0 | 43 | >606 |
| 44 | >626 | 45 | >695 | 46 | >655 |
| 47 | >660 | 48 | >635 | 49 | >679 |
| 50 | >580 | 51 | >695 | 52 | >665 |
| 53 | >621 | 54 | >606 | 55 | >670 |
| 56 | >645 | 57 | >613 | 58 | >638 |
| 59 | >630 | 60 | >703 | 61 | 495 |
| 63 | >679 | 64 | >620 | 65 | >678 |
| 66 | >669 | 67 | 590 | 68 | >627 |
| 69 | >658 | 70 | >611 | 71 | >642 |
| 72 | >670 | 73 | >656 | 74 | >655 |
| 75 | >632 | 76 | >630 | 77 | >631 |
| 78 | >653 | 79 | >660 | 80 | 518 |
| 81 | >691 | 82 | >618 | 83 | >652 |
| 84 | >668 | 85 | >599 | 86 | >596 |
| 87 | >600 | 88 | >665 | 89 | >525 |
| 90 | >610 | 91 | 584 | 92 | >602 |
| 93 | >690 | 94 | >677 | 95 | >705 |
| 96 | >628 | 97 | >640 | 98 | >650 |
| 99 | >677 | 100 | >656 | 101 | >571 |

TABLE 6-continued

Solubility data of particular compounds

| Example No. | Lysa (μg/mL) | Example No. | Lysa (μg/mL) | Example No. | Lysa (μg/mL) |
|---|---|---|---|---|---|
| 102 | >635 | 103 | >643 | 104 | >667 |
| 106 | >730 | 107 | 510 | 108 | 410 |
| 109 | >657 | 110 | >661 | 111 | >620 |
| 113 | >615 | 114 | >617 | 115 | >642 |
| 116 | >735 | 117 | >628 | 118 | >630 |
| 121 | 600 | 122 | >722 | 123 | >666 |
| 124 | >655 | 125 | >636 | 127 | >672 |
| 128 | >710 | 130 | >625 | | |

Based on FDA guidance, in order to support clinical testing in humans, the assessment of acceptable risk-benefit has to be achieved by providing clear evidence of in vitro antiviral activity ($EC_{50}$) and cytotoxicity ($CC_{50}$). It is important to establish that an investigational product has antiviral activity at concentrations that can be achieved in vivo without inducing toxic effects to cells. Furthermore, in a cell culture model, apparent antiviral activity of an investigational product can be the result of host cell death after exposure to the product. The relative effectiveness of the compound in inhibiting viral replication compared to inducing cell death is defined as the selectivity index ($CC_{50}$ value/$EC_{50}$ value). It is desirable to have a high selectivity index giving maximum antiviral activity with minimal cell toxicity.

Results of $CC_{50}$ and the corresponding selectivity index are given in Table 7.

TABLE 7

$CC_{50}$ and selectivity index of particular compounds

| Example No. | $CC_{50}$ (μM) | Selectivity index ($CC_{50}$/$EC_{50}$) | Example No. | $CC_{50}$ (μM) | Selectivity index ($CC_{50}$/$EC_{50}$) |
|---|---|---|---|---|---|
| Bay 41-4109 | 13 | 149 | | | |
| 2 | 85 | 31481 | 3 | 97 | 88182 |
| 5 | >100 | >32258 | 6 | 27 | 3600 |
| 10 | 39 | 5342 | 12 | >100 | >10753 |
| 16 | 30 | 15000 | 17 | >100 | >14286 |
| 19 | 89 | 15614 | 25 | >100 | >20000 |
| 28 | 31 | 7045 | 31 | >100 | >50000 |
| 32 | 40 | 3125 | 34 | >100 | >10000 |
| 35 | >100 | 12987 | 36 | 23 | 1251 |
| 38 | 21 | 6315 | 39 | 44 | 40227 |
| 41 | 40 | 2372 | 42 | >100 | >10000 |
| 43 | >100 | >5556 | 44 | 49 | 10748 |
| 46 | 36 | 2212 | 47 | >100 | >2273 |
| 49 | 42 | 8936 | 50 | 26 | 1905 |
| 51 | 27 | 2117 | 52 | 14 | 4693 |
| 53 | 69 | 4769 | 54 | 62 | 4293 |
| 57 | 35 | 2384 | 58 | >100 | >7353 |
| 59 | 52 | 3935 | 60 | 29 | 47783 |
| 61 | 56 | 3133 | 63 | >100 | >125000 |
| 64 | 47 | 15667 | 65 | >100 | >13157 |
| 66 | 95 | 135714 | 68 | >100 | >7407 |
| 69 | 57 | 9500 | 70 | >100 | >11236 |
| 71 | >100 | >20833 | 73 | >100 | >83333 |
| 74 | 72 | 34286 | 75 | >100 | 5556 |
| 77 | >100 | 14286 | 79 | 76 | 16889 |
| 81 | >100 | >16667 | 82 | >100 | >7194 |
| 83 | 25 | 16440 | 84 | >100 | >41667 |
| 85 | 66 | 10694 | 87 | 100 | >4545 |
| 93 | 30 | 6977 | 94 | 92 | 4600 |
| 95 | >100 | 40000 | 96 | 97 | 161667 |
| 97 | 44 | 8800 | 98 | 72 | 4224 |
| 101 | 91 | 6741 | 102 | 23 | 2599 |
| 103 | >100 | >6803 | 104 | >100 | >14286 |

TABLE 7-continued $CC_{50}$ and selectivity index of particular compounds

| Example No. | $CC_{50}$ (μM) | Selectivity index ($CC_{50}$/$EC_{50}$) | Example No. | $CC_{50}$ (μM) | Selectivity index ($CC_{50}$/$EC_{50}$) |
|---|---|---|---|---|---|
| 106 | >100 | >47619 | 107 | 24 | 16000 |
| 108 | 33 | 1784 | 109 | 55 | 12500 |
| 111 | >100 | 17241 | 112 | 73 | 14123 |
| 113 | >100 | >6061 | 114 | >100 | >10753 |
| 115 | >100 | >43478 | 116 | 77 | 42739 |
| 117 | >100 | 66667 | 118 | >100 | >200000 |
| 119 | >100 | >33333 | 120 | 81 | 16875 |
| 121 | >100 | >5000 | 122 | 73 | 55769 |
| 123 | 56 | 19900 | 127 | >100 | >14925 |
| 128 | 51 | 85000 | 129 | >100 | >13158 |
| 130 | 17 | 2833 | | | |

Synthesis

The compounds of the present invention can be prepared by any conventional means. Suitable processes for synthesizing these compounds as well as their starting materials are provided in the schemes below and in the examples. All substituents, in particular, $R^1$ to $R^4$, and A are as defined above unless otherwise indicated. Furthermore, and unless explicitly otherwise stated, all reactions, reaction conditions, abbreviations and symbols have the meanings well known to a person of ordinary skill in organic chemistry.

A. General Synthetic Route for Compound Ia, Iaa, and Iab (Scheme 1)

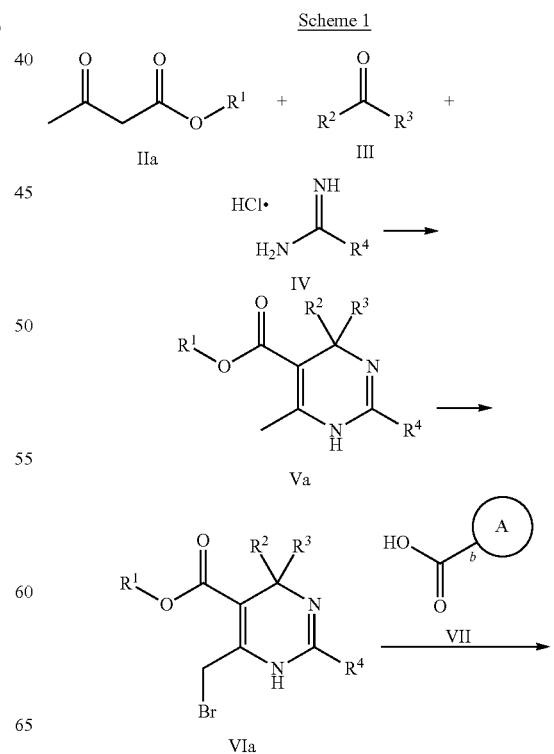

Scheme 1

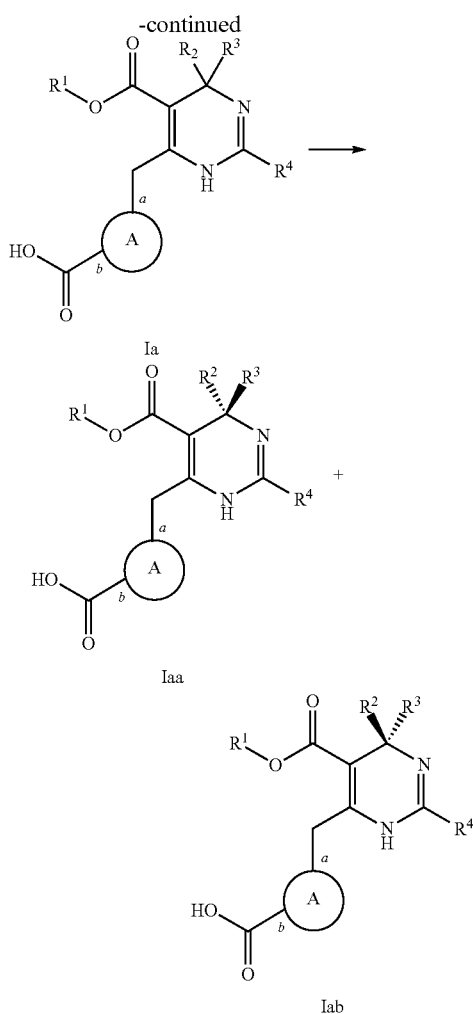

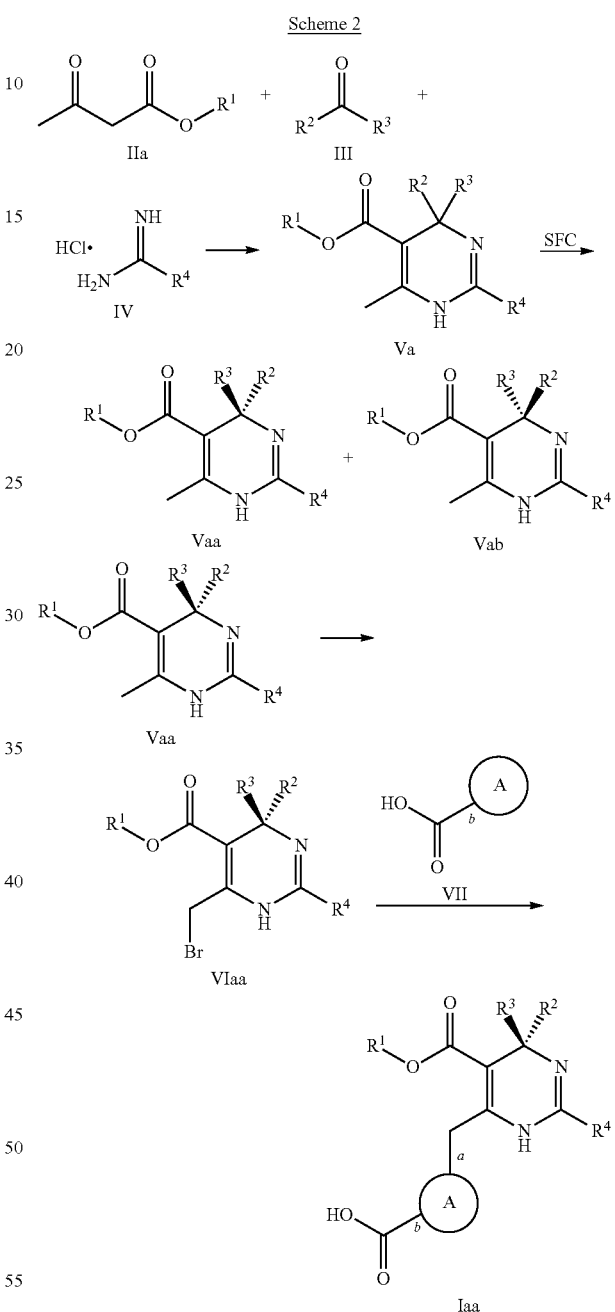

R³ is hydrogen or deuterium.

Compounds of interest Ia, Iaa and Iab can be prepared according to Scheme 1. Starting with acetyl acetate IIa, aldehyde III and amidine IV, dihydropyrimidine Va can be synthesized through a one-pot condensation reaction. Bromination of Compound Va provides bromide VIa. Coupling bromide VIa with cyclic amino acid VII generates compound of interest Ia. Further chiral separation of Ia affords two enantiomerically pure compounds of interest Iaa and Iab.

Dihydropyrimidine Va can be prepared from condensation and cyclization sequence of acetyl acetate II, aldehyde III and amidine IV. The reaction can be carried out in a suitable alcoholic solvent such as trifluoroethanol in the presence of a base like potassium acetate under a heating condition over several hours.

Bromide VIa can be prepared by reaction of Va with a bromination reagent, such as N-bromosuccinimide, in a suitable inert solvent such as carbon tetrachloride at 80-100 degrees Celsius for about 1 hour.

Compound of interest Ia can be obtained by coupling bromide VIa with cyclic amino acid VII. The reaction is typically performed in a suitable solvent like 1,2-dichloroethane at room temperature over several hours in the presence of an organic base such as N,N-diisopropylethylamine.

Compounds of further interest Iaa and Iab are obtained by preparative HPLC separation of diastereomeric mixture Ia.

The stereochemistry of Iaa is determined by comparing its ¹H NMR data and SFC retention time with the same compound made by synthetic route B.

B. An Alternative General Synthetic Route for Compound Iaa (Scheme 2)

Alternatively, compound of interest Iaa can be prepared according to Scheme 2. A one-pot reaction between acetyl acetate II, aldehyde III and amidine IV gives dihydropyrimidine Va. (−)-Enantiomer Vaa is then obtained by SFC chiral separation of Va and its stereochemistry is determined by comparing its SFC retention time with one of its particular Compound E which stereochemistry is determined by X-ray diffraction study (FIG. 1).

Bromination of Vaa then affords VIaa. Coupling VIaa with a suitable cyclic amino acid VII gives the compound of interest Iaa.

The synthetic procedure from Vaa to Iaa is identical to what is described in Scheme 1 except that chiral intermediate Vaa is used instead of racemic Va.

C. General Synthetic Route for Compound IV (Scheme 3)

Scheme 3

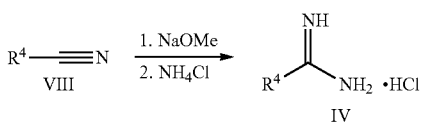

Any commercial unavailable amidine building block IV can be prepared from the corresponding nitrile VIII by first reacting with sodium methoxide followed by treatment with ammonium chloride as described in Scheme 3.

This invention also relates to a process for the preparation of a compound of formula I comprising the reaction of
(a) a compound of formula (XZ)

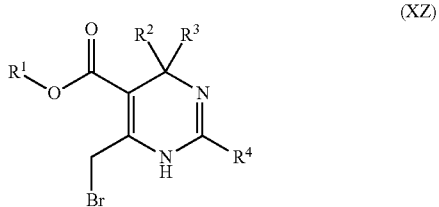

with

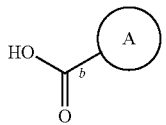

in the presence of a base;
(b) a compound of formula (YZ)

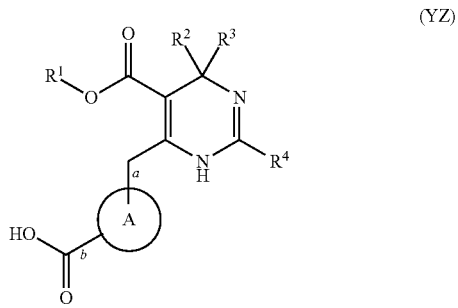

under chiral separation condition;
wherein $R^1$ to $R^4$ and A are defined above unless otherwise indicated.

In step (a), the base can be for example N,N-diisopropylethylamine.

A compound of formula I when manufactured according to the above process is also an object of the invention.

Pharmaceutical Compositions and Administration

The invention also relates to a compound of formula I for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular human being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to the suppression of serum HBV DNA levels, or HBeAg seroconversion to HBeAb, or HBsAg loss, or normalization of alanine aminotransferase levels and improvement in liver histology. For example, such amount may be below the amount that is toxic to normal cells, or the human as a whole.

In one example, the pharmaceutically effective amount of the compound of the invention administered parenterally per dose will be in the range of about 0.01 to 100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Deliv-* ery Systems. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 mg to 1000 mg of the compound of the invention compounded with about 90 mg to 30 mg anhydrous lactose, about 5 mg to 40 mg sodium croscarmellose, about 5 mg to 30 mg polyvinylpyrrolidone (PVP) K30, and about 1 mg to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 mg to 400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

Indications and Methods of Treatment

The compounds of the invention can inhibit HBV's de novo DNA synthesis and reduce HBV DNA levels. Accordingly, the compounds of the invention are useful for the treatment or prophylaxis of HBV infection.

The compounds of inventions are useful as inhibitors of HBV.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method of treating or prophylaxising HBV infection in a human in need of such treatment, wherein the method comprises administering to said human a therapeutically effective amount of a compound of Formula I, a stereoisomer, tautomer, prodrug or pharmaceutically acceptable salt thereof.

Combination Therapy

The compounds of the invention can be used together with interferon, pegylated interferons, Lamivudine, Adefovir dipivoxil, Entecavir, Telbivudine, and Tenofovir disoproxil for the treatment or prophylaxis of HBV.

EXAMPLES

The invention will be more fully understood by reference to the following examples. They should not, however, be construed as limiting the scope of the invention.
Abbreviations used herein are as follows:
$[\alpha]_D^{20}$: optical rotation at 20 degrees Celsius
calc'd: calculated
$CC_{50}$: concentration results in the death of 50 percent of the cells
CCK-8: cell counting kit-8
$CCl_4$: carbon tetrachloride
$CDCl_3$-d: deuterated chloroform
CLh: hepatic clearance
CMV: cytomegalovirus
CuOAc copper acetate
d: day
DIG: digoxigenin
DIPEA: N,N-diisopropylethylamine
DCM: dichloromethylene
DMAc: dimethylacetamide
$D_2O$: deuterium water
FDA: Food and Drug Administration
PE: petroleum ether
DMSO: dimethylsulfoxide
DMSO-$d_6$: deuterated dimethylsulfoxide
DNA: deoxyribonucleic acid
EDTA: ethylenediaminetetraacetic acid
EtOH: ethanol
EtOAc or EA: ethyl acetate
g: gram
$EC_{50}$: concentration required for 50% induction of acetylated tubulin
h or hr: hour
hrs: hours
HAP: heteroaryldihydropyrimidine
HBeAb: hepatitis B e antibody
HBeAg: hepatitis B e antigen
HBsAg: hepatitis B surface antigen
HCl: hydrogen chloride
HPLC: high performance liquid chromatography
HPLC-UV: high performance liquid chromatography with ultraviolet detector
Hz: hertz
IPA: isopropanol
KCN: potassium cyanide
MeOD-$d_4$: deuterated methanol
MeOH: methanol
mg: milligram
MHz: megahertz
min: minute
mins: minutes
mL: milliliter
mm: millimeter
mM: milliliter
mmol: millimole
MS: mass spectrometry
MW: molecular weight
NaCl: sodium chloride
$Na_2SO_4$: sodium sulfate
NaOH: sodium hydroxide
NBS: N-bromosuccinimide
NMR: nuclear magnetic resonance
PBS: phosphate buffered saline
PD: pharmacodynamic
PK: pharmacokinetic prep-HPLC: preparative high performance liquid chromatography
Prep-TLC: preparative thin layer chromatography
rpm: round per minute
rt: room temperature
sat. saturated
SDPK: single dose pharmacokinetics
SFC: supercritical fluid chromatography
SSC: saline-sodium citrate buffer
TEA: triethylamine
Tet: tetracycline
TFA: trifluoroacetic acid
THF: tetrahydrofuran
Tris: tris(hydroxymethyl)aminomethane
μg: microgram
μL: microliter
μM: micromole
UV: ultraviolet detector
ETV: entecavir
mpk: mg/kg
OD: optical density
pgRNA: pre-genom RNA
qPCR: quantitative polymerase chain reaction General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C18 (5 μm, OBDTM 30×100 mm) column or SunFire™ Prep-C18 (5 μm, OBDTM 30×100 mm) column. Waters AutoP purification System (Column: XBridge™ Prep-C18, 30×100 mm, Sample Manager 2767, Pump 2525, Detector: Micromass ZQ and UV 2487, solvent system: acetonitrile and 0.1% ammonium hydroxide in water). For SFC chiral separation, intermediates were separated by chiral column (Daicel chiralpak IC, 5 μm, 30×250 mm) column using Mettler Toledo SFC-Multigram III system, solvent system: 95% $CO_2$ and 5% IPA (0.5% TEA in IPA), back pressure 100 bar, detection UV@ 254 nm.

LC/MS spectra of compounds were obtained using a LC/MS (Waters™ Alliance 2795-Micromass ZQ), LC/MS conditions were as follows (running time 6 min):

Acidic condition: A: 0.1% formic acid in $H_2O$; B: 0.1% formic acid in acetonitrile;

Basic condition: A: 0.01% $NH_3 \cdot H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(MH)^+$.

NMR Spectra were obtained using Bruker Avance 400 MHz.

The microwave assisted reactions were carried out in a Biotage Initiator Sixty microwave synthesizer.

All reactions involving air-sensitive reagents were performed under an argon atmosphere. Reagents were used as received from commercial suppliers without further purification unless otherwise noted.

The following examples were prepared by the general methods outlined in the schemes above. They are intended to illustrate the meaning of the present invention but should by no means represent a limitation within the meaning of the present invention:

Preparative Examples

Example 1 and 2

6-((S)-2-Carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester (Example 1) and (R)-6-((S)-2-carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester (Example 2)

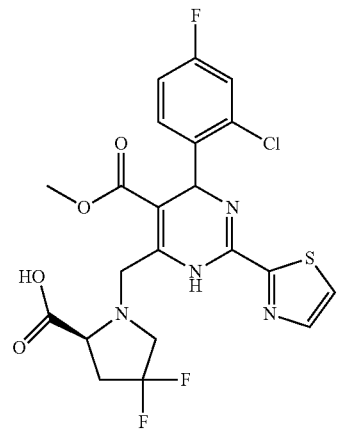

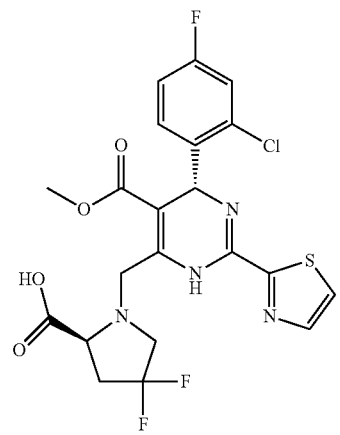

Procedure A

The title compounds were prepared according to the general synthetic routes shown in Scheme 1 and Scheme 3. A detailed synthetic route is provided in Scheme 4.

Scheme 4
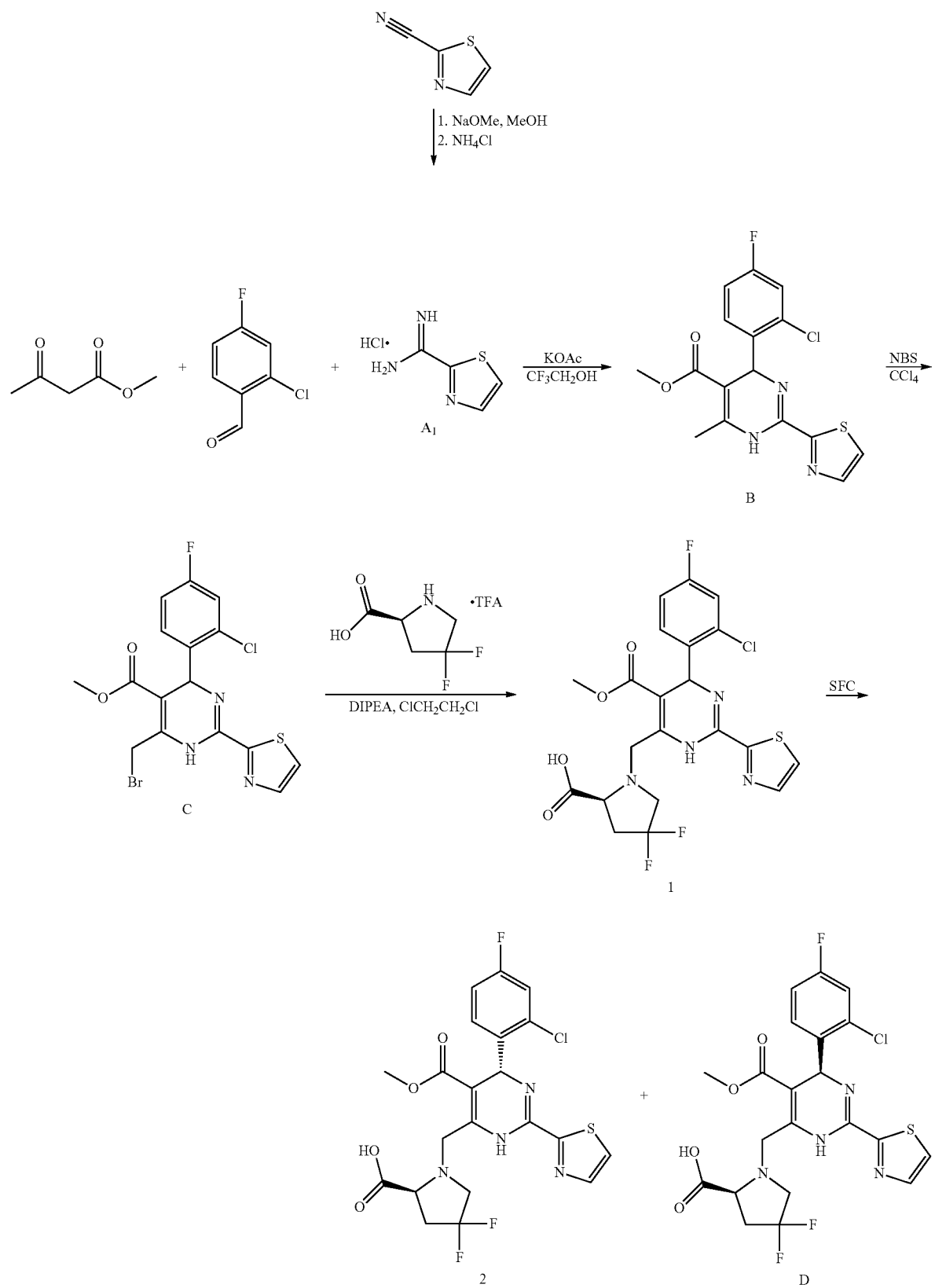

Preparation of Compound A₁

To a stirred solution of thiazole-2-carbonitrile (1.5 g, 14 mmol) in 5 mL of dry MeOH was added dropwise a solution of sodium methoxide (0.74 g, 14 mmol) in 10 mL of dry methanol. The reaction mixture was stirred at room temperature until the disappearance of starting material which was checked by LC/MS. After that, ammonium chloride (1.5 g, 28 mmol) was added in one portion and the reaction mixture was stirred overnight. The undissolved material was removed by filtration and the filtrate was concentrated to afford thiazole-2-carboxamidine hydrochloride (Compound A₁) as a grey solid which was used directly in the next step without further purification. MS: calc'd 128 (MH⁺), measured 128 (MH⁺).

Preparation of Compound B

To a stirred solution of thiazole-2-carboxamidine hydrochloride (0.13 g, 1.0 mmol), methyl acetoacetate (0.12 g, 1.0 mmol) and 2-chloro-5-fluorobenzaldehyde (0.16 g, 1.0 mmol) in CF₃CH₂OH (8 mL) was added potassium acetate (0.20 g, 2.0 mmol). The reaction mixture was either refluxed for 16 hrs or heated at 150° C. in microwave oven for 2 hours. After it was cooled to room temperature, the reaction mixture was concentrated and the residue was dissolved in ethyl acetate and washed with brine. The organic layer was dried over sodium sulfate and concentrated, and the residue was purified by column chromatography (ethyl acetate/petroleum ether is from ¼ to ½) to afford 4-(2-chloro-4-fluoro-phenyl)-6-methyl-2-thiazol-2-yl-1,4-dihydro-pyrimidine-5-carboxylic acid methyl ester (Compound B) as a yellow solid. MS: calc'd (MH⁺) 366, measured (MH⁺) 366. ¹H NMR (DMSO-d₆, 400 MHz): δ ppm 9.98 (s, 1H), 7.97 (d, J=4.0 Hz, 1H), 7.90 (d, J=4.0 Hz, 1H), 7.41 (dd, J=8.0, 4.0 Hz, 1H), 7.35 (dd, J=8.0, 8.0 Hz, 1H), 7.18 (td, J=8.0, 4.0 Hz, 1H), 5.98 (s, 1H), 3.53 (s, 3H), 2.47 (s, 3H).

Preparation of Compound C

To a stirred solution of 4-(2-chloro-4-fluoro-phenyl)-6-methyl-2-thiazol-2-yl-1,4-dihydro-pyrimidine-5-carboxylic acid methyl ester (0.37 g, 1.0 mmol) in CCl₄ (5 mL) was added NBS (0.20 g, 1.1 mmol) in portions. After the reaction mixture was stirred at room temperature for 1 hour, the solvent was removed in vacuo and the residue was purified by column chromatography to give 6-bromomethyl-4-(2-chloro-4-fluoro-phenyl)-2-thiazol-2-yl-1,4-dihydro-pyrimidine-5-carboxylic acid methyl ester (Compound C) as a yellow solid. MS: calc'd 429 (MH⁺), measured 429 (MH⁺).

Preparation of Example 1

To a stirred solution of 6-bromomethyl-4-(2-chloro-4-fluoro-phenyl)-2-thiazol-2-yl-1,4-dihydro-pyrimidine-5-carboxylic acid methyl ester (0.049 g, 0.11 mmol) and (S)-4,4-difluoro-pyrrolidine-2-carboxylic acid (0.044 g, 0.17 mmol) in 1,2-dichloroethane (5 mL) was added dropwise DIPEA (0.078 mL, 0.45 mmol). The reaction mixture was stirred at room temperature until the disappearance of starting material which was checked by LC/MS. The mixture was diluted with EtOAc (50 mL) and washed successively with saturated aqueous NH₄Cl solution and brine. The organic layer was separated and dried over Na₂SO₄. The solvent was concentrated in vacuo and the crude product was purified by prep-HPLC to give 6-((S)-2-carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester (Example 1).

Preparation of Example 2

The enantiopure (R)-6-((S)-2-carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester (Example 2) was obtained through the separation of diastereomeric mixture of 6-((S)-2-carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester (Example 1) by reverse preparative HPLC (Waters, SunFire™ Prep-C18) eluting with a mixed solvent of 15%-35% acetonitrile in water plus 0.1% TFA at 40 mL/min eluting rate. (+)-Compound D was separated as a diastereomer of Example 2.

Procedure B

Preparation of Example 2

In an alternative synthetic route, Example 2 was synthesized by using chiral intermediate E, which was obtained through SFC chiral separation of the stereomixture of dihydropyrimidine B. A detailed synthetic route is provided in Scheme 5.

Scheme 5

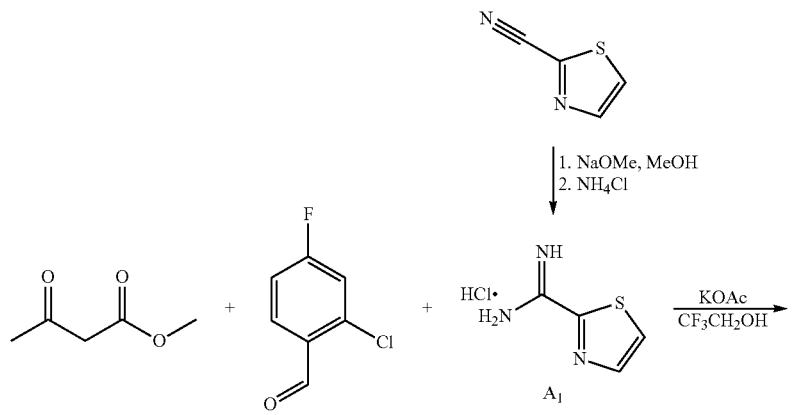

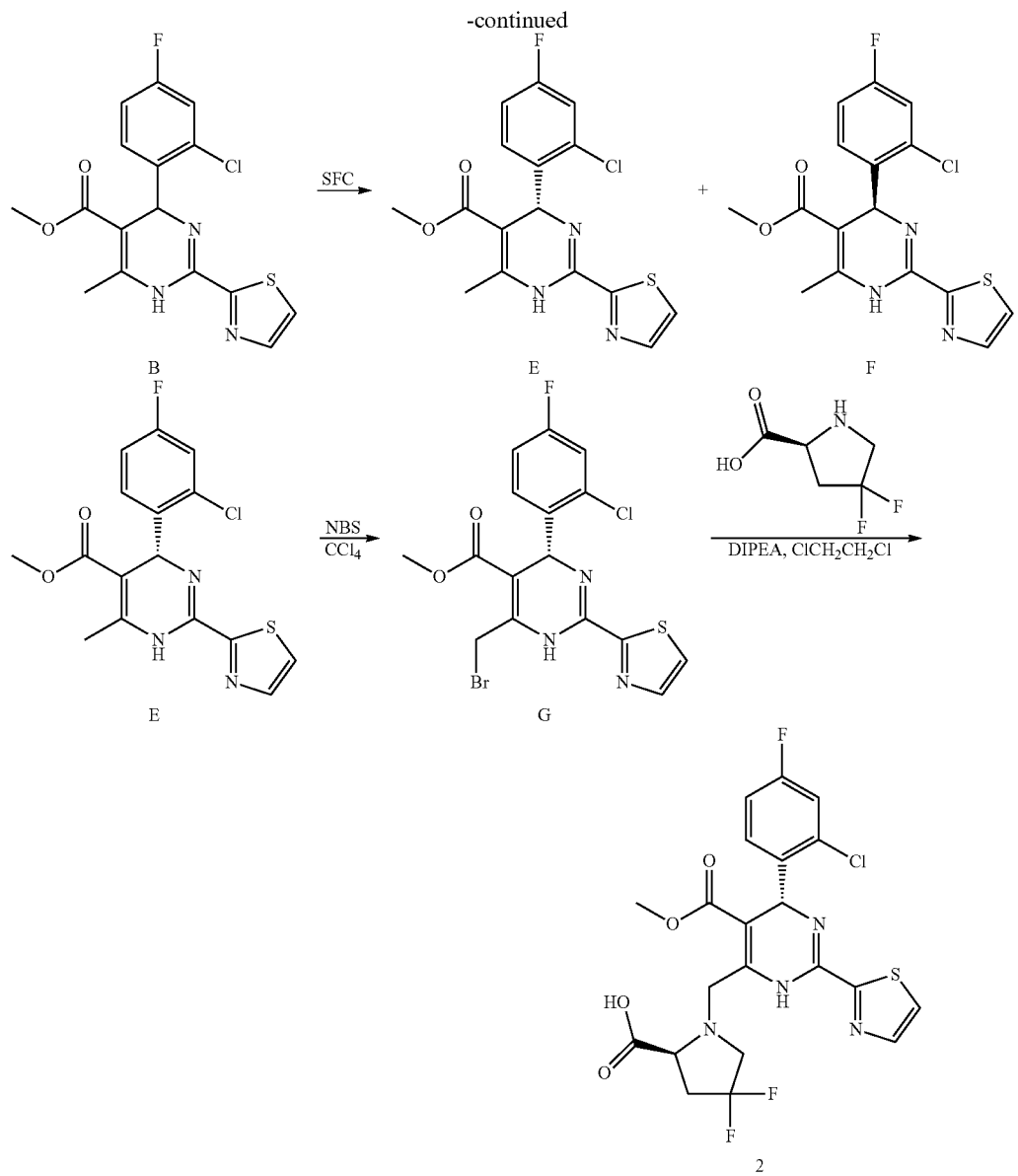

Preparation of Compound E

The enantiopure (R)-4-(2-chloro-4-fluoro-phenyl)-6-methyl-2-thiazol-2-yl-1,4-dihydro-pyrimidine-5-carboxylic acid methyl ester (Compound E) was obtained through SFC(SFC-Multigram; IC: 5×250 mm, 50 chiral separation of the stereomixture of 4-(2-chloro-4-fluoro-phenyl)-6-methyl-2-oxazol-2-yl-1,4-dihydro-pyrimidine-5-carboxylic acid methyl ester (Compound B) eluting with a mixed solvent of 85% supercritical $CO_2$/15% EtOH at 100 mL/min rate. The desired (−)-enantiomer E has a relatively short retention time. The absolute stereochemistry of (−)-enantiomer E was determined by X-ray diffraction study (FIG. 1).

Compound E: $[\alpha]_D^{20}$ −55.0 (c 0.845, MeOH).
Compound F: $[\alpha]_D^{20}$ +44.6 (c 0.175, MeOH).

Preparation of Compound G

To a stirred solution of (R)-4-(2-chloro-4-fluoro-phenyl)-6-methyl-2-thiazol-2-yl-1,4-dihydro-pyrimidine-5-carboxylic acid methyl ester (0.37 g, 1.0 mmol) in $CCl_4$ (5 mL) was added NBS (0.20 g, 1.1 mmol) in portions. After the reaction mixture was stirred at room temperature for 1 hour, the solvent was removed in vacuo and the residue was purified by column chromatography to give (R)-6-bromomethyl-4-(2-chloro-4-fluoro-phenyl)-2-thiazol-2-yl-1,4-dihydro-pyrimidine-5-carboxylic acid methyl ester (Compound G) as a yellow solid. MS: calc'd 445 ($MH^+$), measured 445 ($MH^+$).

Preparation of Example 2

To a stirred solution of (R)-6-bromomethyl-4-(2-chloro-4-fluoro-phenyl)-2-thiazol-2-yl-1,4-dihydro-pyrimidine-5-carboxylic acid methyl ester (0.049 g, 0.11 mmol) and (S)-4,4-difluoro-pyrrolidine-2-carboxylic acid (0.044 g, 0.17 mmol) in 1,2-dichloroethane (5 mL) was added dropwise DIPEA (0.078 mL, 0.45 mmol). The reaction mixture was stirred at room temperature until the disappearance of starting material which was checked by LC/MS. The mixture was diluted with EtOAc (50 mL) and washed successively with saturated aqueous NH₄Cl solution and brine. The organic layer was separated and dried over Na₂SO₄. The solvent was concentrated in vacuo and the crude product was purified by prep-HPLC to give (R)-6-((S)-2-carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester (Example 2) as a light yellow solid.

Example 3

(S)-6-((S)-2-Carboxy-4,4-difluoro-pyrrolidin-1-ylmethyl)-4-(2-chloro-4-fluoro-phenyl)-[4-2H]-2-thiazol-2-yl-1,4-dihydro-pyrimidine-5-carboxylic acid methyl ester The title compound was prepared in analogy to Example 2 with Procedure A shown in Scheme 4 by using 2-chloro-4-fluoro-[$^2$H1]-benzaldehyde instead of 2-chloro-4-fluorobenzaldehyde. The stereochemistry of Example 3 was determined by comparing its $^1$H NMR data and HPLC retention time with Example 2.

Preparation of 2-chloro-4-fluoro-[$^2$H1]-benzaldehyde (Compound H)

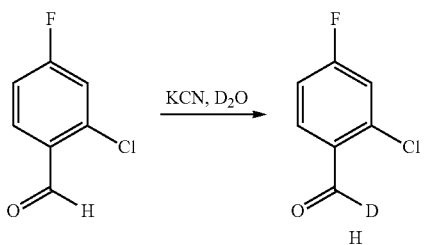

2-Chloro-4-fluorobenzaldehyde (1.6 g, 4.2 mL, 10 mmol) in diethyl ether (4 mL) was added to a stirred solution of KCN (0.70 g, 11 mmol) in D₂O (4.0 mL) at room temperature. After the reaction mixture was vigorously stirred for 3 days, it was extracted twice with diethyl ether (50 mL). The aqueous layer was back-extracted with diethyl ether (1×20 mL). The organic layers were dried over Na₂SO₄ and concentrated in vacuo to give 2-chloro-4-fluoro-[$^2$H1]-benzaldehyde as a yellow solid (1.7 g) which was used as is for the next step. Isotopical purity is determined as 90% by $^1$H NMR. $^1$H NMR (CDCl₃-d, 400 MHz): δ ppm 7.99 (dd, J=8.78, 6.27 Hz, 1H), 7.1-7.24 (m, 1H), 7.13 (td, J=8.16, 2.26 Hz, 1H).

Example 4

(R)-6-(S)-2-Carboxy-4,4-difluoro-pyrrolidin-1-ylmethyl)-4-(2-chloro-4-fluoro-phenyl)-2-(3,5-difluoro-pyridin-2-yl)-1,4-dihydro-pyrimidine-5-carboxylic acid methyl ester The title compound was prepared in analogy to Example 2 with Procedure A shown in Scheme 4 by using 3,5-difluoro-pyridine-2-carboxamidine (for its synthesis, please see: Stolting, J. et al. PCT Int. Appl. 2000, WO 2000058302 A1 20001005) instead of thiazole-2-carboxamidine. The stereochemistry of Example 4 was determined by comparing its $^1$H NMR data and HPLC retention time with Example 2.

Example 5

(S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid The title compound was prepared in analogy to Example 2 with Procedure B shown in Scheme 5 by using (S)-morpholine-3-carboxylic acid (Aldrich, CAS: 106825-79-0) instead of (S)-4,4-difluoro-pyrrolidine-2-carboxylic acid.

Example 6

(S)-4-[(R)-6-(2-Chloro-4-fluoro-phenyl)-2-(3,5-difluoro-pyridin-2-yl)-5-methoxycarbonyl-3,6-dihydro-pyrimidin-4-ylmethyl]-morpholine-3-carboxylic acid The title compound was prepared in analogy to Example 2 with Procedure A shown in Scheme 4 by using 3,5-difluoro-pyridine-2-carboxamidine and (S)-morpholine-3-carboxylic acid instead of thiazole-2-carboxamidine and (S)-4,4-difluoro-pyrrolidine-2-carboxylic acid. The stereochemistry of Example 6 was determined by comparing its $^1$H NMR data and HPLC retention time with Example 2.

Example 7

(R)-6-(2-Carboxy-5,5-difluoro-piperidin-1-ylmethyl)-4-(2-chloro-4-fluoro-phenyl)-2-thiazol-2-yl-1,4-dihydro-pyrimidine-5-carboxylic acid methyl ester The title compound was prepared in analogy to Example 2 with Procedure B shown in Scheme 5 by using 5,5-difluoro-piperidine-2-carboxylic acid (for its synthesis, please see: Golubev, A. et al. Tetrahedron Lett. 2004, 45, 1445-1447) instead of (S)-4,4-difluoro-pyrrolidine-2-carboxylic acid.

Example 8

(R)-6-(S)-2-Carboxy-4,4-difluoro-pyrrolidin-1-ylmethyl)-4-(2-chloro-4-fluoro-phenyl)-2-(4-methyl-pyridin-2-yl)-1,4-dihydro-pyrimidine-5-carboxylic acid methyl ester The title compound was prepared in analogy to Example 2 with Procedure A shown in Scheme 4 by using 4-methyl-pyridine-2-carboxamidine instead of thiazole-2-carboxamidine. The stereochemistry of Example 8 was determined by comparing its $^1$H NMR data and HPLC retention time with Example 2.

Preparation of 4-methyl-pyridine-2-carboxamidine (Compound A₂)

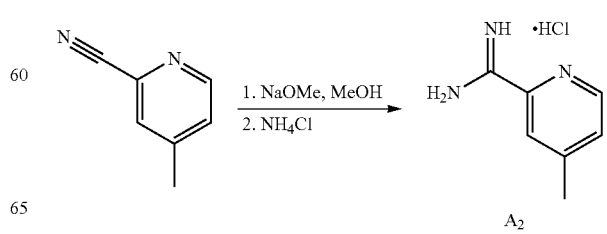

4-Methyl-pyridine-2-carboxamidine (Compound $A_2$) was prepared in analogy to compound thiazole-2-carboxamidine with the procedure shown in Scheme 5 by using 4-methyl-pyridine-2-carbonitrile instead of thiazole-2-carbonitrile. MS: calc'd (MH$^+$) 136, measured (MH$^+$) 136.

Example 9

(S)-4-[(R)-6-(2-Chloro-4-fluoro-phenyl)-5-methoxy-carbonyl-2-(4-methyl-pyridin-2-yl)-3,6-dihydro-pyrimidin-4-ylmethyl]-morpholine-3-carboxylic acid The title compound was prepared in analogy to Example 2 with Procedure A shown in Scheme 4 by using 4-methyl-pyridine-2-carboxamidine and (S)-morpholine-3-carboxylic acid instead of thiazole-2-carboxamidine and (S)-4,4-difluoro-pyrrolidine-2-carboxylic acid. The stereochemistry of Example 9 was determined by comparing its $^1$H NMR data and HPLC retention time with Example 2.

Example 10

(R)-6-(S)-2-Carboxy-4,4-difluoro-pyrrolidin-1-ylmethyl)-4-(2-chloro-4-fluoro-phenyl)-2-(4-cyclopropyl-thiazol-2-yl)-1,4-dihydro-pyrimidine-5-carboxylic acid methyl ester The title compound was prepared in analogy to Example 2 with Procedure A shown in Scheme 4 by using 4-cyclopropyl-thiazole-2-carboxamidine (Compound M) instead of thiazole-2-carboxamidine. The stereochemistry of Example 10 was determined by comparing its $^1$H NMR data and HPLC retention time with Example 2.

Preparation of 4-cyclopropyl-thiazole-2-carboxamidine (Compound M)

To a stirred solution of 2-bromo-1-cyclopropyl-ethanone (16 g, 100 mmol) in EtOH (150 mL) was added successively thiourea (8.0 g, 105 mmol) and Cu(OAc)$_2$ (0.90 g, 5.0 mmol) at room temperature. After the mixture was heated at 80° C. for 1 hour, the solvent was removed under reduced pressure. The residue was neutralized with saturated NaHCO$_3$ (100 mL) to pH=8-9, and then DCM (200 mL) was added. The organic layer was separated and the aqueous layer was further extracted with DCM (200 mL×2). The combined organic layers were washed with sat. NaHCO$_3$ (100 mL), brine (100 mL) and dried over anhydrous Na$_2$SO$_4$. After filtration and concentration, the residue was purified by column chromatography (eluent: EA:PE=1:4) to afford the desired product J (11 g) as a yellow solid. $^1$H NMR (CDCl$_3$-d, 400 MHz): δ ppm 6.06 (s, 1H), 4.86 (br s, 2H), 1.85-1.79 (m, 1H), 0.84-0.74 (m, 4H).

To a stirred solution of Compound J (5.6 g, 40 mmol) and CuBr (8.5 g, 60 mmol) in CH$_3$CN (100 mL) was added dropwise t-BuONO (6.2 g, 7.2 mL, 60 mmol) at 0° C. Then the reaction mixture was warmed to room temperature and further stirred for additional 30 mins. After that, the precipitate was filtered and the solvent was removed under reduced pressure. The residue was purified by column chromatography (eluent: 100% petroleum ether) to afford the desired product K (3.5 g, 43%) as a light yellow oil containing small amount of petroleum ether. $^1$H NMR (400 MHz, CDCl3): δ 6.77 (s, 1H), 2.00-1.95 (m, 1H), 0.94-0.85 (m, 4H).

A mixture of Compound K (3.3 g, 16 mmol) and CuCN (4.3 g, 49 mmol) in DMAc (15 mL) was heated to 135° C. for 3 hours. The reaction mixture was extracted with PE and dried over Na$_2$SO$_4$. The solvent was removed under reduced pressure to afford the crude product L (0.9 g, 38%) as a yellow oil, which was used as it in the next step.

Compound M was prepared in analogy to thiazole-2-carboxamidine (Compound $A_1$) with the procedure shown in Scheme 5 by using 4-cyclopropyl-thiazole-2-carbonitrile instead of thiazole-2-carbonitrile. $^1$H NMR (CDCl$_3$-d, 400 MHz): δ 9.68 (br, 1H), 9.56 (br, 1H), 2.23-2.19 (m, 1H), 1.01-0.92 (m, 4H).

Example 11

(R)-2-(4-tert-Butyl-thiazol-2-yl)-6-(S)-2-carboxy-4,4-difluoro-pyrrolidin-1-ylmethyl)-4-(2-chloro-4-fluoro-phenyl)-1,4-dihydro-pyrimidine-5-carboxylic acid methyl ester The title compound was prepared in analogy to Example 2 with Procedure A shown in Scheme 4 by using 4-tert-butyl-thiazole-2-carboxamidine instead of thiazole-2-carboxamidine. The stereochemistry of Example 11 was determined by comparing its $^1$H NMR data and HPLC retention time with Example 2.

Preparation of 4-tert-butyl-thiazole-2-carboxamidine (Compound N)

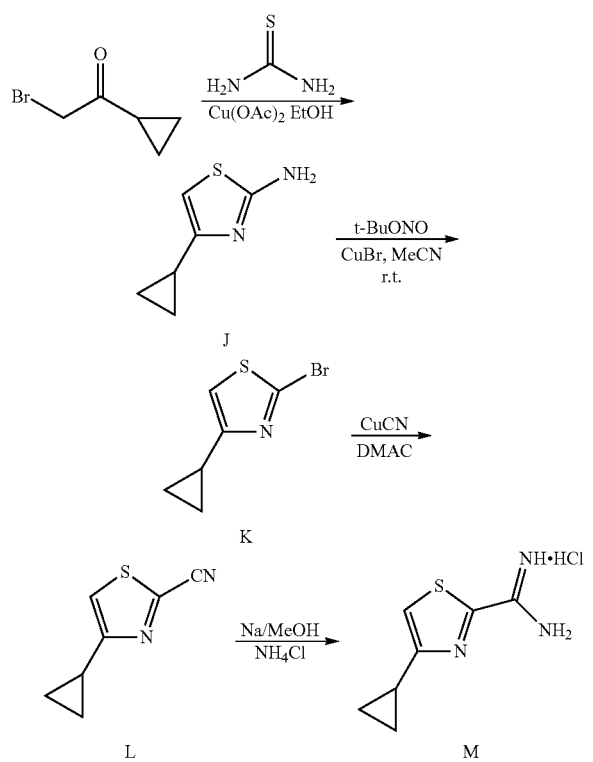

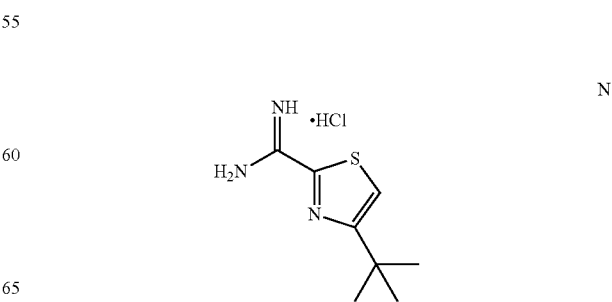

4-tert-Butyl-thiazole-2-carboxamidine (Compound N) was prepared in analogy to Compound M with procedure shown in Example 10 by using 1-bromo-3,3-dimethyl-butan-2-one instead of 2-bromo-1-cyclopropyl-ethanone. MS: calc'd (MH+) 184, measured (MH+) 184.

Example 12

(R)-6-((S)-2-Carboxy-4,4-difluoro-pyrrolidin-1-ylmethyl)-4-(2-chloro-4-fluoro-phenyl)-2-(4-fluoro-thiophen-2-yl)-1,4-dihydro-pyrimidine-5-carboxylic acid methyl ester The title compound was prepared in analogy to Example 2 with Procedure A shown in Scheme 4 by using 4-fluoro-thiophene-2-carbonitrile instead of thiazole-2-carbonitrile. The stereochemistry of Example 12 was determined by comparing its $^1$H NMR data and HPLC retention time with Example 2.

Example 13

(S)-4-[6-(2-Chloro-4-fluoro-phenyl)-5-methoxycarbonyl-2-(1-methyl-1H-imidazol-2-yl)-3,6-dihydro-pyrimidin-4-ylmethyl]-morpholine-3-carboxylic acid The title compound was prepared in analogy to Example 1 with Procedure A shown in Scheme 4 by using 1-methyl-1H-imidazole-2-carbonitrile and (S)-morpholine-3-carboxylic acid instead of thiazole-2-carbonitrile and (S)-4,4-difluoro-pyrrolidine-2-carboxylic acid.

Example 14

(R)-6-[((R)-5-Carboxy-3,3-difluoro-piperidin-1-ylmethyl)-4-(2-chloro-4-fluoro-phenyl)]-2-thiazol-2-yl-1,4-dihydro-pyrimidine-5-carboxylic acid methyl ester Scheme 6

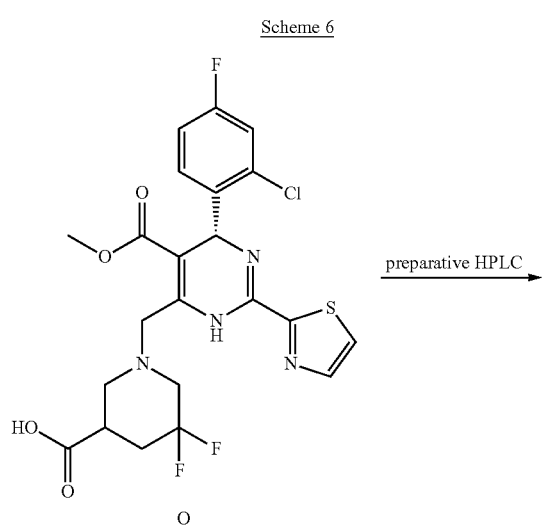

preparative HPLC

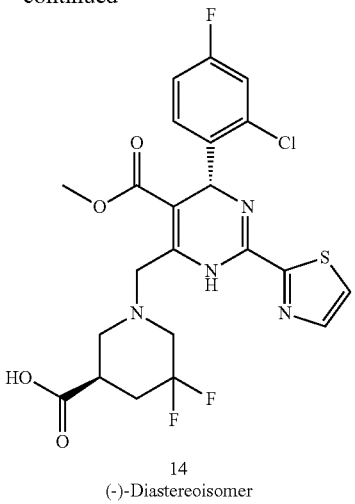

14
(−)-Diastereoisomer

The title compound was prepared from the diastereomeric mixture of (R)-6-(5-carboxy-3,3-difluoro-piperidin-1-ylmethyl)-4-(2-chloro-4-fluoro-phenyl)-2-thiazol-2-yl-1,4-dihydro-pyrimidine-5-carboxylic acid methyl ester (Compound O) through preparative HPLC separation. $[\alpha]_D^{20}$ −26.9 (c 0.110, MeOH).

Preparation of (R)-6-(5-carboxy-3,3-difluoro-piperidin-1-ylmethyl)-4-(2-chloro-4-fluoro-phenyl)-2-thiazol-2-yl-1,4-dihydro-pyrimidine-5-carboxylic acid methyl ester (Compound O)

Compound O was prepared in analogy to Example 2 with Procedure B shown in Scheme 5 by using 5,5-difluoro-piperidine-3-carboxylic acid (Shanghai AQ BioPharma Co. Ltd., CAS: 1255666-96-6) instead of (S)-4,4-difluoro-pyrrolidine-2-carboxylic acid.

Example 15

(R)-6-(S)-2-Carboxy-4,4-difluoro-pyrrolidin-1-ylmethyl)-4-(2-chloro-4-fluoro-phenyl)-2-(4-methyl-oxazol-2-yl)-1,4-dihydro-pyrimidine-5-carboxylic acid methyl ester The title compound was prepared in analogy to Example 2 with Procedure A shown in Scheme 4 by using 4-methyl-oxazole-2-carbonitrile and instead of thiazole-2-carbonitrile. The stereochemistry of Example 15 was determined by comparing its $^1$H NMR data and HPLC retention time with Example 2.

Example 16

(R)-6-(S)-2-Carboxy-4,4-difluoro-pyrrolidin-1-ylmethyl)-4-(2-chloro-4-fluoro-phenyl)-2-(4-methyl-thiazol-2-yl)-1,4-dihydro-pyrimidine-5-carboxylic acid methyl ester The title compound was prepared in analogy to Example 2 with Procedure A shown in Scheme 4 by using 4-methyl-thiazole-2-carbonitrile instead of thiazole-2-carbonitrile. The stereochemistry of Example 16 was determined by comparing its $^1$H NMR data and HPLC retention time with Example 2.

Example 17

(S)-4-[(R)-6-(2-Chloro-4-fluoro-phenyl)-5-methoxycarbonyl-2-(4-methyl-thiazol-2-yl)-3,6-dihydro-pyrimidin-4-ylmethyl]-morpholine-3-carboxylic acid The title compound was prepared in analogy to Example 2 with Procedure A shown in Scheme 4 by using 4-methyl-thiazole-2-carbonitrile and (S)-morpholine-3-carboxylic acid instead of thiazole-2-carbonitrile and (S)-4,4-difluoro-pyrrolidine-2-carboxylic acid. The stereochemistry of Example 17 was determined by comparing its $^1$H NMR data and HPLC retention time with Example 2.

Example 18

(R)-6-(S)-2-Carboxy-4,4-difluoro-pyrrolidin-1-ylmethyl)-4-(2-chloro-4,5-difluoro-phenyl)-2-thiazol-2-yl-1,4-dihydro-pyrimidine-5-carboxylic acid methyl ester The title compound was prepared in analogy to Example 2 with Procedure A shown in Scheme 4 by using 2-chloro-4,5-difluoro-benzaldehyde instead of 2-chloro-4-fluoro-benzaldehyde. The stereochemistry of Example 18 was determined by comparing its $^1$H NMR data and HPLC retention time with Example 2.

Example 19

(R)-6-(S)-2-Carboxy-[3,3-$^2$H2]-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester The title compound was prepared in analogy to Example 2 with Procedure B shown in Scheme 5 by using (R)-[3,3-$^2$H2]-4,4-difluoro-pyrrolidine-2-carboxylic acid hydrochloric acid salt instead of (S)-4,4-difluoro-pyrrolidine-2-carboxylic acid.

Preparation of (R)-3,3-$^2$H2'-4,4-difluoro-pyrrolidine-2-carboxylic acid hydrochloric acid salt (Compound R)

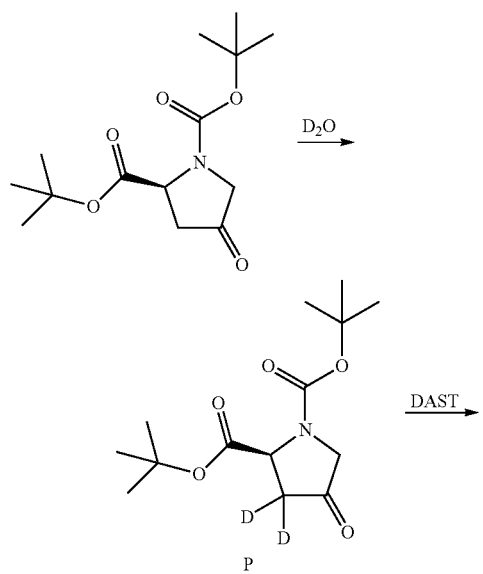

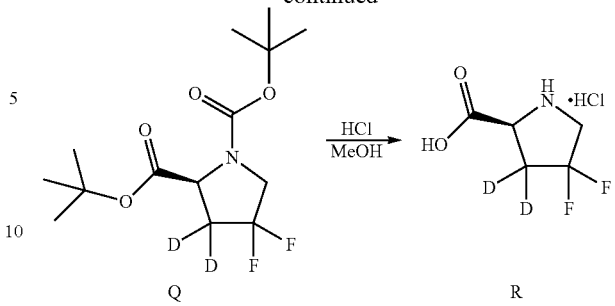

D$_2$O (10 mL) and prewashed (with D$_2$O) silica gel (4 g) were added to a solution of (S)-di-tert-butyl 4-oxopyrrolidine-1,2-dicarboxylate (4.0 g, 14 mmol) in dry THF (10 mL). After the reaction mixture was stirred at room temperature for 8 days, the silica gel was removed by filtration. The filtrate was extracted with ethyl acetate and the organic phase was concentrated to give (R)-[3,3-$^2$H2]-4-oxo-pyrrolidine-1,2-dicarboxylic acid di-tert-butyl ester (Compound P) as a light yellow oil (4.0 g). $^1$H NMR (CDCl$_3$-d, 400 MHz): δ ppm 4.55-4.70 (m, 1H), 3.82-3.92 (m, 2H), 1.49 (s, 9H), 1.48 (s, 9H).

Diethylaminosulfur trifluoride (DAST) (1.4 g, 1.2 mL, 8.7 mmol) was added to a solution of (R)-[3,3-$^2$H2]-4-oxo-pyrrolidine-1,2-dicarboxylic acid di-tert-butyl ester (1.0 g, 3.5 mmol) in anhydrous dichloromethane (15 mL) under ice cooling, and the resultant mixture was stirred 20 hrs at room temperature. Then the resulting mixture was poured onto ice and extracted with ethyl acetate. The organic layer was washed with saturated sodium bicarbonate aqueous solution followed by brine and dried over sodium sulfate. It was filtered and concentrated in vacuo to give (R)-[3,3-$^2$H2]-4,4-difluoro-pyrrolidine-1,2-dicarboxylic acid di-tert-butyl ester (Compound Q) as a yellow oil (0.94 g). $^1$H NMR (CDCl$_3$-d, 400 MHz): δ ppm 4.32-4.47 (m, 1H), 3.74-3.90 (m, 2H), 1.43-1.52 (m, 18H).

To a 5 mL microwave vial was added (R)-[3,3-$^2$H2]-4,4-difluoro-pyrrolidine-1,2-dicarboxylic acid di-tert-butyl ester (0.30 g) in 1,1,3,3-hexafluoroisopropanol (2 mL). The vial was capped and heated in the microwave at 135° C. for 40 mins. The light yellow reaction mixture turned red. The reaction mixture was concentrated. The residue was dissolved in methanol and treated with 10 N HCl solution (0.10 mL) and stirred overnight. The reaction mixture was concentrated to give (R)-[3,3-$^2$H2]-4,4-difluoro-pyrrolidine-2-carboxylic acid hydrochloric acid salt (Compound R) as a black amorphous solid (0.40 g) which was used as is without further purification for the next step.

Example 20

6-((S)-2-Carboxy-4,4-difluoro-pyrrolidin-1-ylmethyl)-4-(2-chloro-4-fluoro-phenyl)-2-(1,4-dimethyl-1H-imidazol-2-yl)-1,4-dihydro-pyrimidine-5-carboxylic acid methyl ester The title compound was prepared in analogy to Example 1 with Procedure A shown in Scheme 4 by using 1,4-dimethyl-1H-imidazole-2-carboxamidine instead of thiazole-2-carboxamidine.

Preparation of 1,4-dimethyl-1H-imidazole-2-carboxamidine (Compound T)

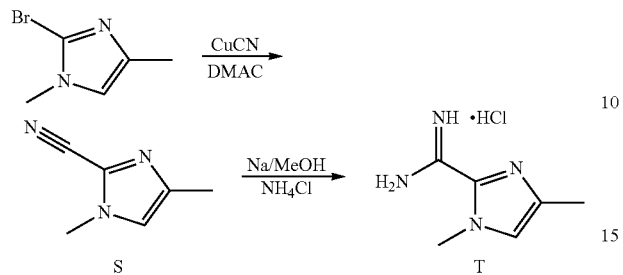

Compound T was prepared in analogy to Compound M with procedure shown in Example 10 by using 2-bromo-1,4-dimethyl-1H-imidazo directly instead of 2-bromo-1-cyclopropyl-ethanone. MS: calc'd (MH$^+$) 139, measured (MH$^+$) 139.

Example 21

(S)-4-[(R)-6-(2-Chloro-4,5-difluoro-phenyl)-5-methoxycarbonyl-2-thiazol-2-yl-3,6-dihydro-pyrimidin-4-ylmethyl]-morpholine-3-carboxylic acid The title compound was prepared in analogy to Example 2 with Procedure A shown in Scheme 4 by using 2-chloro-4,5-difluoro-benzaldehyde and (S)-morpholine-3-carboxylic acid instead of 2-chloro-4-fluoro-benzaldehyde and (S)-4,4-difluoro-pyrrolidine-2-carboxylic acid. The stereochemistry of Example 21 was determined by comparing its $^1$H NMR data and HPLC retention time with Example 2.

Example 22

(R)-6-((S)-2-Carboxy-4,4-difluoro-pyrrolidin-1-ylmethyl)-4-(2-chloro-4-fluoro-phenyl)-2-(3-fluoro-pyridin-2-yl)-1,4-dihydro-pyrimidine-5-carboxylic acid methyl ester The title compound was prepared in analogy to Example 2 with Procedure A shown in Scheme 4 by using 3-fluoro-pyridine-2-carbonitrile instead of thiazole-2-carbonitrile. The stereochemistry of Example 22 was determined by comparing its $^1$H NMR data and HPLC retention time with Example 2.

Example 23

(R)-6-((S)-2-Carboxy-4,4-difluoro-pyrrolidin-1-ylmethyl)-4-(2-chloro-4-fluoro-phenyl)-2-(4-chloro-thiophen-2-yl)-1,4-dihydro-pyrimidine-5-carboxylic acid methyl ester The title compound was prepared in analogy to Example 2 with Procedure A shown in Scheme 4 by using 4-chloro-thiophene-2-carbonitrile instead of thiazole-2-carbonitrile. The stereochemistry of Example 23 was determined by comparing its $^1$H NMR data and HPLC retention time with Example 2.

Example 24

(R)-6-((S)-2-Carboxy-4,4-difluoro-pyrrolidin-1-ylmethyl)-4-(2-chloro-4-fluoro-phenyl)-2-(3-methyl-pyridin-2-yl)-1,4-dihydro-pyrimidine-5-carboxylic acid methyl ester The title compound was prepared in analogy to Example 2 with Procedure A shown in Scheme 4 by using 3-methyl-pyridine-2-carbonitrile instead of thiazole-2-carbonitrile. The stereochemistry of Example 24 was determined by comparing its $^1$H NMR data and HPLC retention time with Example 2.

Example 25

(R)-6-(S)-2-Carboxy-4,4-difluoro-pyrrolidin-1-ylmethyl)-4-(2-chloro-4-fluoro-phenyl)-2-(4-trifluoromethyl-thiazol-2-yl)-1,4-dihydro-pyrimidine-5-carboxylic acid methyl ester The title compound was prepared in analogy to Example 2 with Procedure A shown in Scheme 4 by using 4-trifluoromethyl-thiazole-2-carboxamidine instead of thiazole-2-carboxamidine. The stereochemistry of Example 25 was determined by comparing its $^1$H NMR data and HPLC retention time with Example 2.

Preparation of 4-trifluoromethyl-thiazole-2-carboxamidine (Compound U)

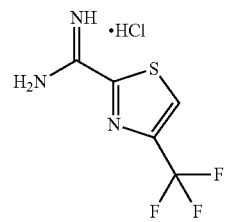

4-Trifluoromethyl-thiazole-2-carboxamidine (Compound U) was prepared in analogy to Compound M with procedure shown in Example 10 by using 2-bromo-4-trifluoromethyl-thiazole (CAS: 41731-39-9) instead of 2-bromo-4-cyclopropyl-thiazole which is made from 2-bromo-1-cyclopropyl-ethanone in Example 10. MS: calc'd (MH$^+$) 196, measured (MH$^+$) 196.

Example 26

6-((S)-2-Carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid ethyl ester The title compound was prepared in analogy to Example 1 with Procedure A shown in Scheme 4 by using ethyl acetoacetate instead of methyl acetoacetate.

Example 27

(R)-6-(S)-2-Carboxy-4,4-difluoro-pyrrolidin-1-ylmethyl)-4-(2-chloro-4-fluoro-phenyl)-2-(4-methyl-thiophen-2-yl)-1,4-dihydro-pyrimidine-5-carboxylic acid methyl ester The title compound was prepared in analogy to Example 2 with Procedure A shown in Scheme 4 by using 4-methylthiophene-2-carbonitrile instead of thiazole-2-carbonitrile. The stereochemistry of Example 27 was determined by comparing its ¹H NMR data and HPLC retention time with Example 2.

Example 28

(R)-6-(S)-2-Carboxy-4,4-difluoro-pyrrolidin-1-ylmethyl)-4-(2-chloro-4-fluoro-phenyl)-2-(4-isopropyl-thiazol-2-yl)-1,4-dihydro-pyrimidine-5-carboxylic acid methyl ester The title compound was prepared in analogy to Example 2 with Procedure A shown in Scheme 4 by using 4-isopropyl-thiazole-2-carboxamidine instead of thiazole-2-carboxamidine. The stereochemistry of Example 28 was determined by comparing its ¹H NMR data and HPLC retention time with Example 2.

Preparation of 4-isopropyl-thiazole-2-carboxamidine (Compound V)

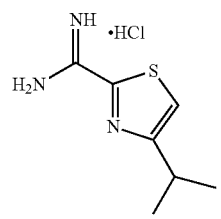

V

4-Isopropyl-thiazole-2-carboxamidine (Compound V) was prepared in analogy to Compound M with procedure shown in Example 10 by using 1-bromo-3-methyl-butan-2-one instead of 2-bromo-1-cyclopropyl-ethanone. MS: calc'd (MH⁺) 170, measured (MH⁺) 170.

Example 29

(R)-4-(4-Bromo-2-chloro-phenyl)-6-((S)-2-carboxy-4,4-difluoro-pyrrolidin-1-ylmethyl)-2-thiazol-2-yl-1,4-dihydro-pyrimidine-5-carboxylic acid methyl ester The title compound was prepared in analogy to Example 2 with Procedure A shown in Scheme 4 by using 4-bromo-2-chloro-benzaldehyde instead of 4-fluoro-2-chloro-benzaldehyde. The stereochemistry of Example 29 was determined by comparing its ¹H NMR data and HPLC retention time with Example 2.

Example 30

(R)-6-(S)-2-Carboxy-4,4-difluoro-pyrrolidin-1-ylmethyl)-4-(2-chloro-4-cyano-phenyl)-2-thiazol-2-yl-1,4-dihydro-pyrimidine-5-carboxylic acid methyl ester The title compound was prepared in analogy to Example 2 with Procedure A shown in Scheme 4 by using 4-cyano-2-chloro-benzaldehyde instead of 4-fluoro-2-chloro-benzaldehyde. The stereochemistry of Example 30 was determined by comparing its ¹H NMR data and HPLC retention time with Example 2.

Example 31

(S)-4-[(R)-6-(2-Chloro-4-fluoro-phenyl)-5-ethoxy-carbonyl-2-thiazol-2-yl-3,6-dihydro-pyrimidin-4-ylmethyl]-morpholine-3-carboxylic acid The title compound was prepared in analogy to Example 1 with Procedure A shown in Scheme 4 by using ethyl acetoacetate and (S)-morpholine-3-carboxylic acid instead of methyl acetoacetate and (S)-4,4-difluoro-pyrrolidine-2-carboxylic acid. The stereochemistry of Example 31 was determined by comparing its ¹H NMR data and HPLC retention time with Example 2.

Example 32

(R)-6-((S)-2-Carboxy-4,4-difluoro-pyrrolidin-1-ylmethyl)-4-(2-chloro-4-fluoro-phenyl)-2-(1-methyl-1H-imidazol-2-yl)-1,4-dihydro-pyrimidine-5-carboxylic acid methyl ester The title compound was prepared in analogy to Example 1 with Procedure A shown in Scheme 4 by using 1-methyl-1H-imidazole-2-carbonitrile instead of thiazole-2-carbonitrile. The stereochemistry of Example 32 was determined by comparing its ¹H NMR data and HPLC retention time with Example 2.

Example 33

(R)-6-(S)-2-Carboxy-4,4-difluoro-pyrrolidin-1-ylmethyl)-4-(2-chloro-4-fluoro-phenyl)-2-(2,4-difluoro-phenyl)-1,4-dihydro-pyrimidine-5-carboxylic acid methyl ester The title compound was prepared in analogy to Example 1 with Procedure A shown in Scheme 4 by using 2,4-difluoro-benzonitrile instead of thiazole-2-carbonitrile. The stereochemistry of Example 33 was determined by comparing its ¹H NMR data and HPLC retention time with Example 2.

Example 34

(R)-6-(S)-2-Carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid ethyl ester The title compound was prepared in analogy to Example 2 with Procedure A shown in Scheme 4 by using ethyl acetoacetate instead of methyl acetoacetate. The stereochemistry of Example 34 was determined by comparing its ¹H NMR data and HPLC retention time with Example 2.

Example 35

(S)-4-[(R)-6-(2-Chloro-4-fluoro-phenyl)-5-ethoxy-carbonyl-2-(1-methyl-1H-imidazol-2-yl)-3,6-dihydro-pyrimidin-4-ylmethyl]-morpholine-3-carboxylic acid The title compound was prepared in analogy to Example 2 with Procedure A shown in Scheme 4 by using ethyl acetoacetate, 1-methyl-1H-imidazole-2-carbonitrile and (S)-morpholine-3-carboxylic acid instead of methyl acetoacetate, thiazole-2-carbonitrile and (S)-4,4-difluoro-pyrrolidine-2-carboxylic acid. The stereochemistry of Example 35

Example 36

(R)-6-((S)-2-Carboxy-4,4-difluoro-pyrrolidin-1-ylmethyl)-4-(2-chloro-4-fluoro-phenyl)-2-(1-methyl-1H-imidazol-2-yl)-1,4-dihydro-pyrimidine-5-carboxylic acid ethyl ester

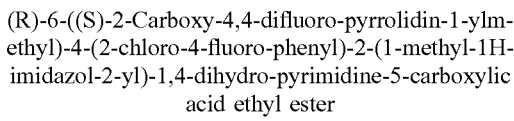

The title compound was prepared in analogy to Example 2 with Procedure A shown in Scheme 4 by using ethyl acetoacetate and 1-methyl-1H-imidazole-2-carbonitrile instead of methyl acetoacetate and thiazole-2-carbonitrile. The stereochemistry of Example 36 was determined by comparing its $^1$H NMR data and HPLC retention time with Example 2.

Example 37

(S)-4-[(R)-6-(2-Chloro-4-fluoro-phenyl)-5-ethoxycarbonyl-2-(6-methyl-pyridin-2-yl)-3,6-dihydro-pyrimidin-4-ylmethyl]-morpholine-3-carboxylic acid

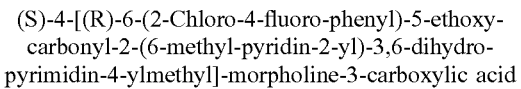

The title compound was prepared in analogy to Example 2 with Procedure A shown in Scheme 4 by using ethyl acetoacetate, 6-methyl-pyridine-2-carbonitrile and (S)-morpholine-3-carboxylic acid instead of methyl acetoacetate, thiazole-2-carbonitrile and (S)-4,4-difluoro-pyrrolidine-2-carboxylic acid. The stereochemistry of Example 37 was determined by comparing its $^1$H NMR data and HPLC retention time with Example 2.

Example 38

(R)-6-((S)-2-Carboxy-4,4-difluoro-pyrrolidin-1-ylmethyl)-4-(2,4-dichloro-phenyl)-2-thiazol-2-yl-1,4-dihydro-pyrimidine-5-carboxylic acid ethyl ester

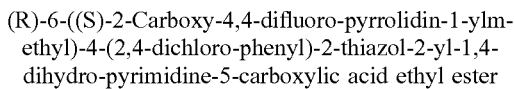

The title compound was prepared in analogy to Example 2 with Procedure A shown in Scheme 4 by using ethyl acetoacetate and 2,4-dichloro-benzaldehyde instead of methyl acetoacetate and 2-chloro-4-fluoro-benzaldehyde. The stereochemistry of Example 38 was determined by comparing its $^1$H NMR data and HPLC retention time with Example 2.

Example 39

(S)-4-[(R)-6-(2,4-Dichloro-phenyl)-5-ethoxycarbonyl-2-thiazol-2-yl-3,6-dihydro-pyrimidin-4-ylmethyl]-morpholine-3-carboxylic acid

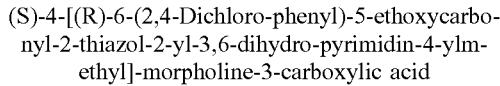

The title compound was prepared in analogy to Example 2 with Procedure A shown in Scheme 4 by using ethyl acetoacetate, 2,4-dichloro-benzaldehyde and (S)-morpholine-3-carboxylic acid instead of methyl acetoacetate, 2-chloro-4-fluoro-benzaldehyde and (S)-4,4-difluoro-pyrrolidine-2-carboxylic acid. The stereochemistry of Example 39 was determined by comparing its $^1$H NMR data and HPLC retention time with Example 2.

Example 40

(R)-6-((S)-2-Carboxy-4,4-difluoro-pyrrolidin-1-ylmethyl)-4-(2-chloro-4-fluoro-phenyl)-2-(1-methyl-4-trifluoromethyl-1H-imidazol-2-yl)-1,4-dihydro-pyrimidine-5-carboxylic acid ethyl ester

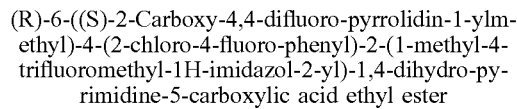

The title compound was prepared in analogy to Example 2 with Procedure A shown in Scheme 4 by using ethyl acetoacetate and 1-methyl-4-trifluoromethyl-1H-imidazole-2-carbonitrile instead of methyl acetoacetate and thiazole-2-carbonitrile. The stereochemistry of Example 40 was determined by comparing its $^1$H NMR data and HPLC retention time with Example 2.

Example 41

(S)-6-((S)-2-Carboxy-4,4-difluoro-pyrrolidin-1-ylmethyl)-4-(3,4-difluoro-phenyl)-2-thiazol-2-yl-1,4-dihydro-pyrimidine-5-carboxylic acid ethyl ester

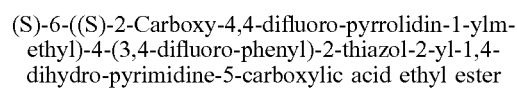

The title compound was prepared in analogy to Example 2 with Procedure A shown in Scheme 4 by using ethyl acetoacetate and 3,4-difluoro-benzaldehyde instead of methyl acetoacetate and 2-chloro-4-fluoro-benzaldehyde. The stereochemistry of Example 41 was determined by comparing its $^1$H NMR data and HPLC retention time with Example 2.

Example 42

(S)-4-[(S)-6-(3,4-Difluoro-phenyl)-5-ethoxycarbonyl-2-thiazol-2-yl-3,6-dihydro-pyrimidin-4-ylmethyl]-morpholine-3-carboxylic acid

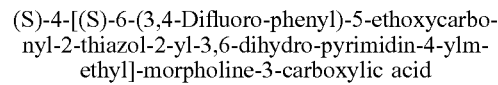

The title compound was prepared in analogy to Example 2 with Procedure A shown in Scheme 4 by using ethyl acetoacetate, 3,4-difluoro-benzaldehyde and (S)-morpholine-3-carboxylic acid instead of methyl acetoacetate, 2-chloro-4-fluoro-benzaldehyde and (S)-4,4-difluoro-pyrrolidine-2-carboxylic acid. The stereochemistry of Example 42 was determined by comparing its $^1$H NMR data and HPLC retention time with Example 2.

Example 43

(S)-4-[(S)-5-Ethoxycarbonyl-2-thiazol-2-yl-6-(3,4,5-trifluoro-phenyl)-3,6-dihydro-pyrimidin-4-ylmethyl]-morpholine-3-carboxylic acid

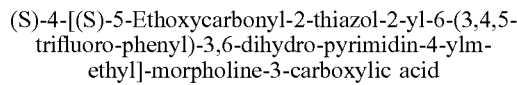

The title compound was prepared in analogy to Example 2 with Procedure A shown in Scheme 4 by using ethyl acetoacetate, 3,4,5-trifluoro-benzaldehyde and (S)-morpholine-3-carboxylic acid instead of methyl acetoacetate, 2-chloro-4-fluoro-benzaldehyde and (S)-4,4-difluoro-pyrrolidine-2-carboxylic acid. The stereochemistry of Example 43 was determined by comparing its $^1$H NMR data and HPLC retention time with Example 2.

Example 44

(S)-4-[(R)-5-Ethoxycarbonyl-2-thiazol-2-yl-6-(2,3,4-trifluoro-phenyl)-3,6-dihydro-pyrimidin-4-ylmethyl]-morpholine-3-carboxylic acid

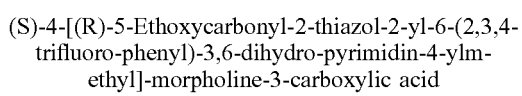

The title compound was prepared in analogy to Example 2 with Procedure A shown in Scheme 4 by using ethyl acetoacetate, 2,3,4-trifluoro-benzaldehyde and (S)-morpholine-3-carboxylic acid instead of methyl acetoacetate, 2-chloro-4-fluoro-benzaldehyde and (S)-4,4-difluoro-pyrrolidine-2-carboxylic acid. The stereochemistry of Example 44 was determined by comparing its $^1$H NMR data and HPLC retention time with Example 2.

Example 45

(S)-4-[(R)-6-(4-Bromo-2,3-difluoro-phenyl)-5-methoxycarbonyl-2-thiazol-2-yl-3,6-dihydro-pyrimidin-4-ylmethyl]-morpholine-3-carboxylic acid The title compound was prepared in analogy to Example 2 with Procedure A shown in Scheme 4 by using 4-bromo-2,3-difluoro-benzaldehyde and (S)-morpholine-3-carboxylic acid instead of 2-chloro-4-fluoro-benzaldehyde and (S)-4,4-difluoro-pyrrolidine-2-carboxylic acid. The stereochemistry of Example 45 was determined by comparing its $^1$H NMR data and HPLC retention time with Example 2.

Example 46

(S)-4-[(S)-6-(3,4-Dichloro-phenyl)-5-ethoxycarbonyl-2-thiazol-2-yl-3,6-dihydro-pyrimidin-4-ylmethyl]-morpholine-3-carboxylic acid The title compound was prepared in analogy to Example 2 with Procedure A shown in Scheme 4 by using ethyl acetoacetate, 3,4-dichloro-benzaldehyde and (S)-morpholine-3-carboxylic acid instead of methyl acetoacetate, 2-chloro-4-fluoro-benzaldehyde and (S)-4,4-difluoro-pyrrolidine-2-carboxylic acid. The stereochemistry of Example 46 was determined by comparing its $^1$H NMR data and HPLC retention time with Example 2.

Example 47

(S)-4-[(R)-6-(2-Chloro-3-fluoro-phenyl)-5-methoxycarbonyl-2-thiazol-2-yl-3,6-dihydro-pyrimidin-4-ylmethyl]-morpholine-3-carboxylic acid The title compound was prepared in analogy to Example 2 with Procedure A shown in Scheme 4 by using 2-chloro-3-fluoro-benzaldehyde and (S)-morpholine-3-carboxylic acid instead of 2-chloro-4-fluoro-benzaldehyde and (S)-4,4-difluoro-pyrrolidine-2-carboxylic acid. The stereochemistry of Example 47 was determined by comparing its $^1$H NMR data and HPLC retention time with Example 2.

Example 48

((S)-6-((S)-2-Carboxy-4,4-difluoro-pyrrolidin-1-ylmethyl)-4-(4-cyano-phenyl)-2-thiazol-2-yl-1,4-dihydro-pyrimidine-5-carboxylic acid ethyl ester The title compound was prepared in analogy to Example 2 with Procedure A shown in Scheme 4 by using ethyl acetoacetate and 4-formyl-benzonitrile instead of methyl acetoacetate and 2-chloro-4-fluoro-benzaldehyde. The stereochemistry of Example 48 was determined by comparing its $^1$H NMR data and HPLC retention time with Example 2.

Example 49

(S)-4-[(R)-6-(4-Chloro-2-fluoro-phenyl)-5-ethoxycarbonyl-2-thiazol-2-yl-3,6-dihydro-pyrimidin-4-ylmethyl]-morpholine-3-carboxylic acid The title compound was prepared in analogy to Example 2 with Procedure A shown in Scheme 4 by using ethyl acetoacetate, 4-chloro-2-fluoro-benzaldehyde and (S)-morpholine-3-carboxylic acid instead of methyl acetoacetate, 2-chloro-4-fluoro-benzaldehyde and (S)-4,4-difluoro-pyrrolidine-2-carboxylic acid. The stereochemistry of Example 49 was determined by comparing its $^1$H NMR data and HPLC retention time with Example 2.

Example 50

(R)-6-((S)-2-Carboxy-4,4-difluoro-pyrrolidin-1-ylmethyl)-4-(2,3-difluoro-phenyl)-2-thiazol-2-yl-1,4-dihydro-pyrimidine-5-carboxylic acid ethyl ester The title compound was prepared in analogy to Example 2 with Procedure A shown in Scheme 4 by using ethyl acetoacetate and 2,3-difluoro-benzaldehyde instead of methyl acetoacetate and 2-chloro-4-fluoro-benzaldehyde. The stereochemistry of Example 50 was determined by comparing its $^1$H NMR data and HPLC retention time with Example 2.

Example 51

(S)-4-[(R)-6-(2-Chloro-4-fluoro-phenyl)-2-thiazol-2-yl-5-(2,2,2-trifluoro-ethoxycarbonyl)-3,6-dihydro-pyrimidin-4-ylmethyl]-morpholine-3-carboxylic acid The title compound was prepared in analogy to Example 2 with Procedure A shown in Scheme 4 by using 3-oxo-butyric acid 2,2,2-trifluoro-ethyl ester and (S)-morpholine-3-carboxylic acid instead of methyl acetoacetate and (S)-4,4-difluoro-pyrrolidine-2-carboxylic acid. The stereochemistry of Example 51 was determined by comparing its $^1$H NMR data and HPLC retention time with Example 2.

Example 52

(S)-4-[(R)-5-Ethoxycarbonyl-2-thiazol-2-yl-6-(2,3,4-trifluoro-phenyl)-3,6-dihydro-pyrimidin-4-ylmethyl]-morpholine-3-carboxylic acid The title compound was prepared in analogy to Example 2 with Procedure A shown in Scheme 4 by using ethyl acetoacetate, 4-bromo-3-fluoro-benzaldehyde and (S)-morpholine-3-carboxylic acid instead of methyl acetoacetate, 2-chloro-4-fluoro-benzaldehyde and (S)-4,4-difluoro-pyrrolidine-2-carboxylic acid. The stereochemistry of Example 52 was determined by comparing its $^1$H NMR data and HPLC retention time with Example 2.

Example 53

(S)-4-[(S)-5-Ethoxycarbonyl-6-(3-fluoro-phenyl)-2-thiazol-2-yl-3,6-dihydro-pyrimidin-4-ylmethyl]-morpholine-3-carboxylic acid The title compound was prepared in analogy to Example 2 with Procedure A shown in Scheme 4 by using ethyl acetoacetate, 3-fluoro-benzaldehyde and (S)-morpholine-3-carboxylic acid instead of methyl acetoacetate, 2-chloro-4-fluoro-benzaldehyde and (S)-4,4-difluoro-pyrrolidine-2-carboxylic acid. The stereochemistry of Example 53 was determined by comparing its ¹H NMR data and HPLC retention time with Example 2.

Example 54

(S)-4-[(S)-5-Ethoxycarbonyl-6-(4-fluoro-phenyl)-2-thiazol-2-yl-3,6-dihydro-pyrimidin-4-ylmethyl]-morpholine-3-carboxylic acid The title compound was prepared in analogy to Example 2 with Procedure A shown in Scheme 4 by using ethyl acetoacetate, 4-fluoro-benzaldehyde and (S)-morpholine-3-carboxylic acid instead of methyl acetoacetate, 2-chloro-4-fluoro-benzaldehyde and (S)-4,4-difluoro-pyrrolidine-2-carboxylic acid. The stereochemistry of Example 54 was determined by comparing its ¹H NMR data and HPLC retention time with Example 2.

Example 55

(R)-6-((S)-2-Carboxy-4,4-difluoro-pyrrolidin-1-ylmethyl)-4-(2-chloro-3,4-difluoro-phenyl)-2-thiazol-2-yl-1,4-dihydro-pyrimidine-5-carboxylic acid ethyl ester The title compound was prepared in analogy to Example 2 with Procedure A shown in Scheme 4 by using ethyl acetoacetate and 2-chloro-3,4-difluoro-benzaldehyde instead of methyl acetoacetate and 2-chloro-4-fluoro-benzaldehyde. The stereochemistry of Example 55 was determined by comparing its ¹H NMR data and HPLC retention time with Example 2.

Example 56

(S)-6-((S)-2-Carboxy-4,4-difluoro-pyrrolidin-1-ylmethyl)-4-(3,4-difluoro-phenyl)-2-(1-methyl-1H-imidazol-2-yl)-1,4-dihydro-pyrimidine-5-carboxylic acid ethyl ester The title compound was prepared in analogy to Example 2 with Procedure A shown in Scheme 4 by using ethyl acetoacetate, 3,4-difluoro-benzaldehyde and 1-methyl-1H-imidazole-2-carbonitrile instead of methyl acetoacetate, 2-chloro-4-fluoro-benzaldehyde and thiazole-2-carbonitrile. The stereochemistry of Example 56 was determined by comparing its ¹H NMR data and HPLC retention time with Example 2.

Example 57

(S)-4-[(S)-6-(3,4-Difluoro-phenyl)-5-ethoxycarbonyl-2-(1-methyl-1H-imidazol-2-yl)-3,6-dihydro-pyrimidin-4-ylmethyl]-morpholine-3-carboxylic acid The title compound was prepared in analogy to Example 2 with Procedure A shown in Scheme 4 by using ethyl acetoacetate, 3,4-difluoro-benzaldehyde, 1-methyl-1H-imidazole-2-carbonitrile and (S)-morpholine-3-carboxylic acid instead of methyl acetoacetate, 2-chloro-4-fluoro-benzaldehyde, thiazole-2-carbonitrile and (S)-4,4-difluoro-pyrrolidine-2-carboxylic acid. The stereochemistry of Example 57 was determined by comparing its ¹H NMR data and HPLC retention time with Example 2.

Example 58

(S)-4-[(R)-6-(2,4-Difluoro-phenyl)-5-ethoxycarbonyl-2-thiazol-2-yl-3,6-dihydro-pyrimidin-4-ylmethyl]-morpholine-3-carboxylic acid The title compound was prepared in analogy to Example 2 with Procedure A shown in Scheme 4 by using ethyl acetoacetate, 2,4-difluoro-benzaldehyde and (S)-morpholine-3-carboxylic acid instead of methyl acetoacetate, 2-chloro-4-fluoro-benzaldehyde and (S)-4,4-difluoro-pyrrolidine-2-carboxylic acid. The stereochemistry of Example 58 was determined by comparing its ¹H NMR data and HPLC retention time with Example 2.

Example 59

(R)-6-((S)-2-Carboxy-4,4-difluoro-pyrrolidin-1-ylmethyl)-4-(2,4-difluoro-phenyl)-2-thiazol-2-yl-1,4-dihydro-pyrimidine-5-carboxylic acid ethyl ester The title compound was prepared in analogy to Example 2 with Procedure A shown in Scheme 4 by using ethyl acetoacetate and 2,4-difluoro-benzaldehyde instead of methyl acetoacetate and 2-chloro-4-fluoro-benzaldehyde. The stereochemistry of Example 59 was determined by comparing its ¹H NMR data and HPLC retention time with Example 2.

Example 60

(S)-4-[(R)-6-(2-Chloro-3,4-difluoro-phenyl)-5-ethoxycarbonyl-2-thiazol-2-yl-3,6-dihydro-pyrimidin-4-ylmethyl]-morpholine-3-carboxylic acid The title compound was prepared in analogy to Example 2 with Procedure A shown in Scheme 4 by using ethyl acetoacetate, 2-chloro-3,4-difluoro-benzaldehyde and (S)-morpholine-3-carboxylic acid instead of methyl acetoacetate, 2-chloro-4-fluoro-benzaldehyde and (S)-4,4-difluoro-pyrrolidine-2-carboxylic acid. The stereochemistry of Example 60 was determined by comparing its ¹H NMR data and HPLC retention time with Example 2.

Example 61

(2S)-1-[[(4R)-4-(2-chloro-4-fluorophenyl)-5-methoxycarbonyl-2-(4-methylsulfanyl-1,3-thiazol-2-yl)-1,4-dihydropyrimidin-6-yl]methyl]-4,4-difluoro-pyrrolidine-2-carboxylic acid The title compound was prepared in analogy to Example 2 with Procedure B shown in Scheme 5 by using 4-methylsulfanyl-thiazole-2-carbonitrile (Compound Y) instead of thiazole-2-carbonitrile. The stereochemistry of Example 61 was determined by comparing its ¹H NMR data and HPLC retention time with Example 2.

Preparation of 4-methylsulfanyl-thiazole-2-carbonitrile (Compound Y)

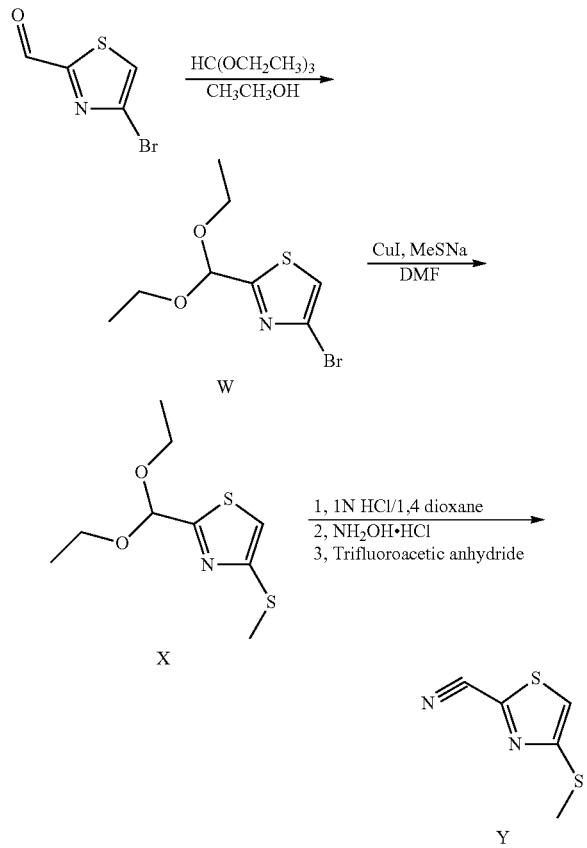

To a stirred solution of 4-bromo-thiazole-2-carbaldehyde (5.0 g, 26 mmol) in EtOH (50 mL) was added successively diethoxymethoxy-ethane (14 mL) at room temperature. After the mixture was heated at 80° C. for 24 hours, the solvent was removed under reduced pressure. The DCM (50 mL) was added. The organic layer was separated and the aqueous layer was further extracted with DCM (50 mL×2). The combined organic layers were washed with sat. NaHCO$_3$ (30 mL), brine (30 mL) and then dried over anhydrous Na$_2$SO$_4$. The solvent was removed under reduced pressure to afford the crude product W (7.0 g) as an oil, which was used in the next step.

To a stirred solution of Compound W (0.50 g, 1.9 mmol) and CuI (0.36 g, 1.9 mmol) in DMF (5 mL) was added MeSNa (0.53 g, 7.5 mmol) at room temperature. The reaction mixture was heated to 130° C. for 13 hours. The solvent was removed under reduced pressure. The DCM (50 mL) was added. The organic layer was separated and the aqueous layer was further extracted with DCM (50 mL×2). The combined organic layers were washed with sat. NaHCO$_3$ (30 mL), brine (30 mL) and dried over anhydrous Na$_2$SO$_4$. After filtration and concentration, the residue was purified by column chromatography (eluent: EA:PE=1:20) to afford the desired product X (250 mg) as an oil. MS: calc'd (MH$^+$) 234, measured (MH$^+$) 234.

The mixture of Compound X (2.0 g, 7.5 mmol) was added 1,4-dioxane (5 mL) and HCl (1N, 5 mL) at room temperature. After the mixture was stirred for 24 hour, The DCM (50 mL) was added. The organic layer was separated and the aqueous layer was further extracted with DCM (50 mL×2). The combined organic layers were washed with sat. NaHCO$_3$ (30 mL), brine (30 mL) and then dried over anhydrous Na$_2$SO$_4$. The solvent was removed under reduced pressure. The residue was dissolved in DCM (50 mL) with the addition of NH$_2$OH.HCl and pyridine at 0° C., and then the reaction mixture was stirred overnight at room temperature. After that, more DCM (100 mL) was added. The organic layer was separated and the aqueous layer was further extracted with DCM (50 mL×2). The combined organic layers were washed with sat. NaHCO$_3$ (100 mL), brine (100 mL) and then dried over anhydrous Na$_2$SO$_4$. The solvent was removed under reduced pressure to afford an oil. To this oil compound was added 1,4-dioxane, trifluoroacetic anhydride and triethyl amine at 0° C. After the reaction mixture was stirred overnight at room temperature, more DCM (100 mL) was added. The organic layer was separated and the aqueous layer was further extracted with DCM (50 mL×2). The combined organic layers were washed with sat. NaHCO$_3$ (100 mL), brine (100 mL) and then dried over anhydrous Na$_2$SO$_4$. After filtration and concentration, the residue was purified by column chromatography (eluent: EA:PE=1:20) to afford the desired product D (1.2 mg) as an oil. MS: calc'd (MH$^+$) 157, measured (MH$^+$) 157.

Example 62

(3S)-4-[[(4R)-4-(2-chloro-4-fluorophenyl)-5-methoxycarbonyl-2-(4-methylsulfanyl-1,3-thiazol-2-yl)-1,4-dihydropyrimidin-6-yl]methyl]morpholine-3-carboxylic acid The title compound was prepared in analogy to Example 2 with Procedure B shown in Scheme 5 by using 4-methylsulfanyl-thiazole-2-carbonitrile (Compound Y) and (S)-morpholine-3-carboxylic acid instead of thiazole-2-carbonitrile and (S)-4,4-difluoro-pyrrolidine-2-carboxylic acid. The stereochemistry of Example 62 was determined by comparing its $^1$H NMR data and HPLC retention time with Example 2.

Example 63

(S)-4-[(R)-6-(2-Chloro-3-fluoro-phenyl)-5-ethoxycarbonyl-2-thiazol-2-yl-3,6-dihydro-pyrimidin-4-ylmethyl]-morpholine-3-carboxylic acid The title compound was prepared in analogy to Example 2 with Procedure B shown in Scheme 5 by using 2-chloro-3-fluorobenzaldehyde, ethyl acetoacetate and (S)-morpholine-3-carboxylic acid instead of 2-chloro-4-fluorobenzaldehyde, methyl acetoacetate and (S)-4,4-difluoro-pyrrolidine-2-carboxylic acid. The stereochemistry of Example 63 was determined by comparing its $^1$H NMR data and HPLC retention time with Example 2.

Example 64

(R)-6-(S)-2-Carboxy-4,4-difluoro-pyrrolidin-1-ylmethyl)-4-(2-chloro-3-fluoro-phenyl)-2-thiazol-2-yl-1,4-dihydro-pyrimidine-5-carboxylic acid ethyl ester The title compound was prepared in analogy to Example 2 with Procedure B shown in Scheme 5 by using 2-chloro-3-fluorobenzaldehyde and ethyl acetoacetate instead of 2-chloro-4-fluorobenzaldehyde and methyl acetoacetate. The stereochemistry of Example 64 was determined by comparing its ¹H NMR data and HPLC retention time with Example 2.

Example 65

(S)-4-[(R)-6-(2-Bromo-4-fluoro-phenyl)-5-methoxy-carbonyl-2-(5-methyl-oxazol-4-yl)-3,6-dihydro-pyrimidin-4-ylmethyl]-morpholine-3-carboxylic acid The title compound was prepared in analogy to Example 2 with Procedure A shown in Scheme 4 by using 2-bromo-4-fluorobenzaldehyde, 5-methyl-oxazole-4-carboxamidine (Compound AB) and (S)-morpholine-3-carboxylic acid instead of 2-chloro-4-fluorobenzaldehyde, thiazole-2-carboxamidine and (S)-4,4-difluoro-pyrrolidine-2-carboxylic acid. The stereochemistry of Example 65 was determined by comparing its ¹H NMR data and HPLC retention time with Example 2.

Preparation of 5-methyloxazole-4-carboxamidine (Compound AB)

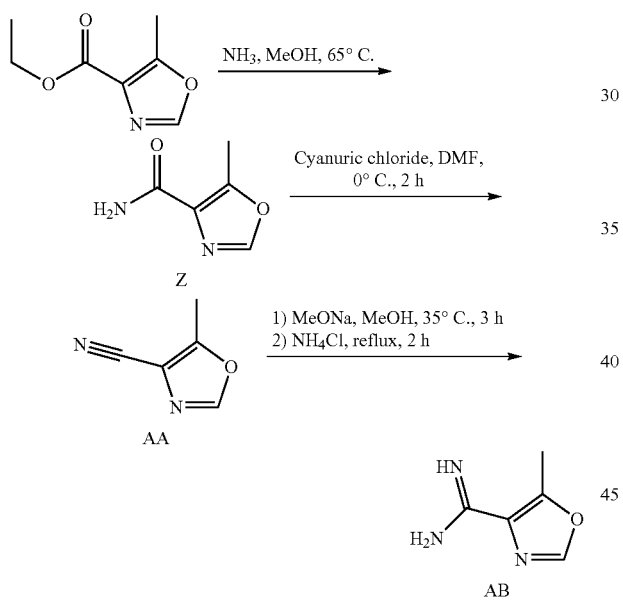

A mixture of ethyl 5-methyloxazole-4-carboxylate (CAS: 32968-44-8) (2.5 g, 16 mmol) and ammonia (100 mL, 7M in MeOH) was stirred at 65° C. for 48 hours. The solvent was removed under reduced pressure to give Compound Z (1.94 g, 98%). ¹H NMR (DMSO-d₆, 400 MHz) δ ppm: 8.29 (s, 1H), 7.47 (s, 2H), 2.55 (s, 3H). MS: calc'd (MH⁺) 127, measured (MH⁺) 127.

To a white suspension of 5-methyloxazole-4-carboxamide Z (1.3 g, 10 mmol) in dry DMF (10 mL) was added cyanuric chloride (3.8 g, 21 mmol) at 0° C., the reaction was stirred at 0° C. for 2 h. The reaction was quenched with ice water (20 mL) carefully, and then basified with 2N NaOH solution to pH 10. The mixture was extracted with EtOAc (50 mL×3), the combined organic layer was washed with water (30 mL×2), brine (30 mL×1), and then dried over Na₂SO₄, then filtered and concentrated under reduced pressure. The residue was purified by flash chromatography (Biotage, 40 g silica gel, EtOAc in PE 30%-100%) to afford colorless oil AA (0.89 g, 79%). ¹H NMR (DMSO-d₆, 400 MHz) δ ppm: 8.55 (s, 1H), 2.52 (s, 3H).

To a solution of 5-methyloxazole-4-carbonitrile AA (0.76 g, 7.0 mmol) in anhydrous MeOH (30 mL) was added MeONa (0.57 g, 10 mmol), after stirred at 35° C. under nitrogen for 3 h, NH₄Cl (0.75 g, 14 mmol) was added, refluxed for 2 h. The solvent was removed and the residue was purified by flash chromatography (Biotage, 40 g silica gel, MeOH in DCM 5%~35%) to afford brown solid AB (587 mg, 67%). ¹H NMR (DMSO-d₆, 400 MHz) δ ppm: 9.11-9.19 (m, 3H), 8.60 (s, 1H), 2.59 (s, 3H). MS: calc'd (MH⁺) 126, measured (MH⁺) 126.

Example 66

(S)-4-[(R)-6-(2-Bromo-3-fluoro-phenyl)-5-ethoxy-carbonyl-2-thiazol-2-yl-3,6-dihydro-pyrimidin-4-ylmethyl]-morpholine-3-carboxylic acid The title compound was prepared in analogy to Example 2 with Procedure B shown in Scheme 5 by using 2-bromo-3-fluorobenzaldehyde, ethyl acetoacetate and (S)-morpholine-3-carboxylic acid instead of 2-chloro-4-fluorobenzaldehyde, methyl acetoacetate and (S)-4,4-difluoro-pyrrolidine-2-carboxylic acid. The stereochemistry of Example 66 was determined by comparing its ¹H NMR data and HPLC retention time with Example 2.

Example 67

(R)-4-(2-Bromo-3-fluoro-phenyl)-6-((S)-2-carboxy-4,4-difluoro-pyrrolidin-1-ylmethyl)-2-thiazol-2-yl-1,4-dihydro-pyrimidine-5-carboxylic acid ethyl ester The title compound was prepared in analogy to Example 2 with Procedure B shown in Scheme 5 by using 2-bromo-3-fluorobenzaldehyde and ethyl acetoacetate instead of 2-chloro-4-fluorobenzaldehyde and methyl acetoacetate. The stereochemistry of Example 67 was determined by comparing its ¹H NMR data and HPLC retention time with Example 2.

Example 68

(S)-4-[(R)-6-(2-Chloro-4-fluoro-phenyl)-5-methoxy-carbonyl-2-(5-methyl-oxazol-4-yl)-3,6-dihydro-pyrimidin-4-ylmethyl]-morpholine-3-carboxylic acid The title compound was prepared in analogy to Example 1 with Procedure A shown in Scheme 4 by using 5-methyl-oxazole-4-carboxamidine (Compound AB) and (S)-morpholine-3-carboxylic acid instead of thiazole-2-carboxamidine and (S)-4,4-difluoro-pyrrolidine-2-carboxylic acid. The stereochemistry of Example 68 was determined by comparing its ¹H NMR data and HPLC retention time with Example 2.

Example 69

(S)-4-[(R)-6-(2-Bromo-4-fluoro-phenyl)-5-ethoxy-carbonyl-2-(5-methyl-oxazol-4-yl)-3,6-dihydro-pyrimidin-4-ylmethyl]-morpholine-3-carboxylic acid The title compound was prepared in analogy to Example 1 with Procedure A shown in Scheme 4 by using 2-bromo-4-fluorobenzaldehyde, 5-methyl-oxazole-4-carboxamidine (Compound AB), ethyl acetoacetate and (S)-morpholine-3- carboxylic acid instead of 2-chloro-4-fluorobenzaldehyde, thiazole-2-carboxamidine, methyl acetoacetate and (S)-4,4-difluoro-pyrrolidine-2-carboxylic acid. The stereochemistry of Example 69 was determined by comparing its $^1$H NMR data and HPLC retention time with Example 2.

Example 70

(S)-4-[(R)-6-(2,3-Difluoro-phenyl)-5-ethoxycarbonyl-2-thiazol-2-yl-3,6-dihydro-pyrimidin-4-ylmethyl]-morpholine-3-carboxylic acid The title compound was prepared in analogy to Example 2 with Procedure A shown in Scheme 4 by using (S)-morpholine-3-carboxylic acid instead of (S)-4,4-difluoropyrrolidine-2-carboxylic acid, ethyl acetoacetate instead of methyl acetoacetate, and 2,3-difluoro benzaldehyde instead of 2-chloro-4-fluoro-benzaldehyde. The stereochemistry of Example 70 was determined by comparing its $^1$H NMR data and HPLC retention time with Example 2.

Example 71

(S)-4-[(R)-6-(2-Bromo-phenyl)-5-methoxycarbonyl-2-thiazol-2-yl-3,6-dihydro-pyrimidin-4-ylmethyl]-morpholine-3-carboxylic acid The title compound was prepared in analogy to Example 2 with Procedure B shown in Scheme 5 by using (S)-morpholine-3-carboxylic acid instead of (S)-4,4-difluoropyrrolidine-2-carboxylic acid, 2-bromobenzaldehyde instead of 2-chloro-4-difluoro-benzaldehyde. The stereochemistry of Example 70 was determined by comparing its $^1$H NMR data and HPLC retention time with Example 2.

Example 73

(S)-4-[(R)-6-(2-Chloro-3,4-difluoro-phenyl)-5-methoxycarbonyl-2-thiazol-2-yl-3,6-dihydro-pyrimidin-4-ylmethyl]-morpholine-3-carboxylic acid The title compound was prepared in analogy to Example 2 with Procedure B shown in Scheme 5 by using (S)-morpholine-3-carboxylic acid instead of (S)-4,4-difluoropyrrolidine-2-carboxylic acid, and 2-chloro-3,4-difluorobenzaldehyde instead of 2-chloro-4-fluoro-benzaldehyde. The stereochemistry of Example 73 was determined by comparing its $^1$H NMR data and HPLC retention time with Example 2.

Example 74

(R)-6-(S)-2-Carboxy-4,4-difluoro-pyrrolidin-1-ylmethyl)-4-(2-chloro-3,4-difluoro-phenyl)-2-thiazol-2-yl-1,4-dihydro-pyrimidine-5-carboxylic acid methyl ester The title compound was prepared in analogy to Example 2 with Procedure B shown in Scheme 5 by using 2-chloro-3,4-difluorobenzaldehyde instead of 2-chloro-4-fluoro-benzaldehyde. The stereochemistry of Example 74 was determined by comparing its $^1$H NMR data and HPLC retention time with Example 2.

Example 75

(S)-4-[(R)-6-(4-Chloro-2-fluoro-phenyl)-5-methoxycarbonyl-2-thiazol-2-yl-3,6-dihydro-pyrimidin-4-ylmethyl]-morpholine-3-carboxylic acid The title compound was prepared in analogy to Example 2 with Procedure B shown in Scheme 5 by using (S)-morpholine-3-carboxylic acid instead of (S)-4,4-difluoropyrrolidine-2-carboxylic acid and 2-fluoro-4-chloro-benzaldehyde instead of 2-chloro-4-fluoro-benzaldehyde. The stereochemistry of Example 75 was determined by comparing its $^1$H NMR data and HPLC retention time with Example 2.

Example 77

(S)-4-[(S)-6-(4-Chloro-3-fluoro-phenyl)-5-methoxycarbonyl-2-thiazol-2-yl-3,6-dihydro-pyrimidin-4-ylmethyl]-morpholine-3-carboxylic acid The title compound was prepared in analogy to Example 2 with Procedure B shown in Scheme 5 by using (S)-morpholine-3-carboxylic acid instead of (S)-4,4-difluoropyrrolidine-2-carboxylic acid and 3-fluoro-4-chloro-benzaldehyde instead of 2-chloro-4-fluoro-benzaldehyde. The stereochemistry of Example 77 was determined by comparing its $^1$H NMR data and HPLC retention time with Example 2.

Example 78 and 79

(S)-4-[(R)-6-(4-Chloro-2-fluoro-phenyl)-5-methoxycarbonyl-2-thiazol-2-yl-3,6-dihydro-pyrimidin-4-ylmethyl]-3-methyl-morpholine-3-carboxylic acid (Example 78) and (R)-4-[(R)-6-(4-Chloro-2-fluoro-phenyl)-5-methoxycarbonyl-2-thiazol-2-yl-3,6-dihydro-pyrimidin-4-ylmethyl]-3-methyl-morpholine-3-carboxylic acid (Example 79)

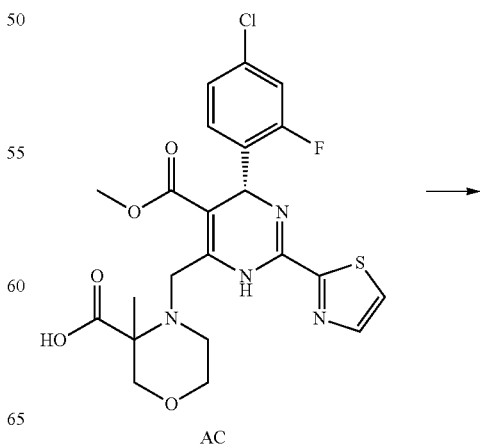

AC

-continued

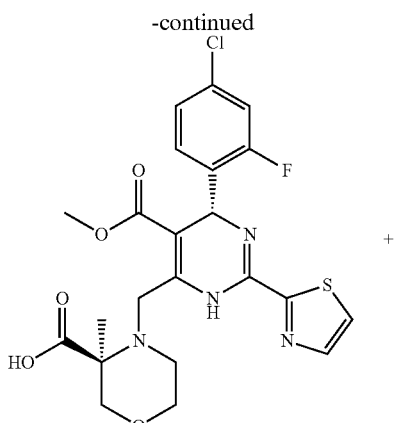

Example 78

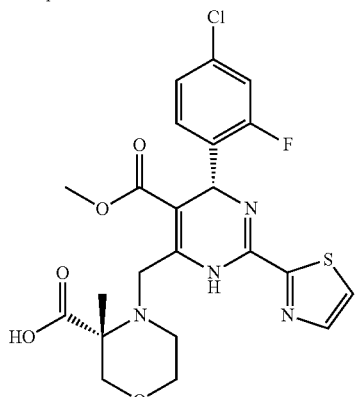

Example 79

The title compounds was prepared from the diastereomeric mixture of 4-[(R)-6-(4-chloro-2-fluoro-phenyl)-5-methoxycarbonyl-2-thiazol-2-yl-3,6-dihydro-pyrimidin-4-ylmethyl]-3-methyl-morpholine-3-carboxylic acid (Compound AC) through preparative HPLC separation. The absolute stereochemistry was tentatively assigned based on SAR knowledge.

Preparation of 4-[(R)-6-(4-Chloro-2-fluoro-phenyl)-5-methoxycarbonyl-2-thiazol-2-yl-3,6-dihydro-pyrimidin-4-ylmethyl]-3-methyl-morpholine-3-carboxylic acid (Compound AC)

Compound AC was prepared in analogy to Example 2 with Procedure B shown in Scheme 5 by using 3-methyl-morpholine-3-carboxylic acid (Compound AD) instead of (S)-4,4-difluoropyrrolidine-2-carboxylic acid, 2-fluoro-4-chloro-benzaldehyde instead of 2-chloro-4-fluoro-benzaldehyde.

Preparation of 3-methylmorpholine-3-carboxylic acid (Compound AD)

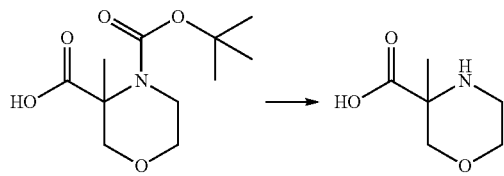

To a solution of 3-methyl-4-[(2-methylpropan-2-yl)oxycarbonyl]morpholine-3-carboxylic acid (Accela ChemBio Co., Ltd., CAS: 1052680-53-1, 50 mg, 0.2.0 mmol) in DCM (1 ml) was added trifluoroacetic acid (1 mL) dropwise at room temperature. The resulting mixture was stirred at room temperature for one hour and then concentrated under the vacuum. The residue was used directly in next step without further purification, Example 80

(R)-6-(R)-5-Carboxy-3,3-difluoro-piperidin-1-ylmethyl)-4-(2-chloro-4-fluoro-phenyl)-2-(4-methyl-thiazol-2-yl)-1,4-dihydro-pyrimidine-5-carboxylic acid methyl ester The title compound was prepared in analogy to Example 14 shown in Scheme 6 by using 4-methyl-thiazole-2-carboxamidine instead of thiazole-2-carboxamidine.

Example 81

(S)-4-[(R)-6-(2-Bromo-4-fluoro-phenyl)-5-methoxycarbonyl-2-thiazol-2-yl-3,6-dihydro-pyrimidin-4-ylmethyl]-morpholine-3-carboxylic acid The title compound was prepared in analogy to Example 2 with Procedure A shown in Scheme 4 by using 2-bromo-4-fluoro-benzaldehyde instead of 2-chloro-4-fluoro-benzaldehyde and using (S)-morpholine-3-carboxylic acid instead of(S)-4,4-difluoro-pyrrolidine-2-carboxylic acid. The stereochemistry of Example 81 was determined by comparing its $^1$H NMR data and HPLC retention time with Example 2.

Example 82

(S)-4-[(R)-6-(2-Chloro-phenyl)-5-ethoxycarbonyl-2-thiazol-2-yl-3,6-dihydro-pyrimidin-4-ylmethyl]-morpholine-3-carboxylic acid The title compound was prepared in analogy to Example 2 with Procedure A shown in Scheme 4 by using 2-chloro-benzaldehyde instead of 2-chloro-4-fluoro-benzaldehyde, using ethyl acetoacetate instead of methyl acetoacetate and (S)-morpholine-3-carboxylic acid instead of (S)-4,4-difluoro-pyrrolidine-2-carboxylic acid. The stereochemistry of Example 82 was determined by comparing its $^1$H NMR data and HPLC retention time with Example 2.

Example 83

(S)-4-[(S)-6-(4-Chloro-3-fluoro-phenyl)-5-ethoxycarbonyl-2-thiazol-2-yl-3,6-dihydro-pyrimidin-4-ylmethyl]-morpholine-3-carboxylic acid The title compound was prepared in analogy to Example 2 with Procedure A shown in Scheme 4 by using 4-chloro-3-fluoro-benzaldehyde instead of 2-chloro-4-fluoro-benzaldehyde, using ethyl acetoacetate instead of methyl acetoacetate and using (S)-morpholine-3-carboxylic acid instead of (S)-4,4-difluoro-pyrrolidine-2-carboxylic acid. The stereochemistry of Example 83 was determined by comparing its $^1$H NMR data and HPLC retention time with Example 2.

Example 84

(R)-4-(2-Bromo-4-fluoro-phenyl)-6-((S)-2-carboxy-4,4-difluoro-pyrrolidin-1-ylmethyl)-2-thiazol-2-yl-1,4-dihydro-pyrimidine-5-carboxylic acid methyl ester The title compound was prepared in analogy to Example 2 with Procedure A shown in Scheme 4 by using 2-bromo-4-fluoro-benzaldehyde instead of 2-chloro-4-fluoro-benzaldehyde. The stereochemistry of Example 84 was determined by comparing its $^1$H NMR data and HPLC retention time with Example 2.

Example 85

(R)-6-(S)-2-Carboxy-4,4-difluoro-pyrrolidin-1-ylmethyl)-4-(2,4-dichloro-phenyl)-2-thiazol-2-yl-1,4-dihydro-pyrimidine-5-carboxylic acid methyl ester The title compound was prepared in analogy to Example 2 with Procedure A shown in Scheme 4 by using 2,4-dichloro-benzaldehyde instead of 2-chloro-4-fluoro-benzaldehyde. The stereochemistry of Example 85 was determined by comparing its $^1$H NMR data and HPLC retention time with Example 2.

Example 86

3-[[(4R)-4-(2-chloro-4-fluoro-phenyl)-5-methoxycarbonyl-2-thiazol-2-yl-1,4-dihydropyrimidin-6-yl]methyl]-1,3-thiazinane-4-carboxylic acid The title compound was prepared in analogy to Example 2 with Procedure B shown in Scheme 5 by using 1,3-thiazinane-4-carboxylic acid (WuXi AppTec (Wuhan) Co., Ltd, CAS: 60175-95-3) instead of (S)-4,4-difluoro-pyrrolidine-2-carboxylic acid.

Example 87

(3S)-4-[[(4R)-4-(2-chloro-4-fluoro-phenyl)-2-(4-cyclopropylthiazol-2-yl)-5-methoxycarbonyl-1,4-dihydropyrimidin-6-yl]methyl]morpholine-3-carboxylic acid The title compound was prepared in analogy to Example 2 with Procedure A shown in Scheme 4 by using 4-cyclopropyl-thiazole-2-carboxamidine (Compound M) instead of thiazole-2-carboxamidine and (S)-morpholine-3-carboxylic acid instead of (S)-4,4-difluoro-pyrrolidine-2-carboxylic acid. The stereochemistry of Example 87 was determined by comparing its $^1$H NMR data and HPLC retention time with Example 2.

Example 88

(3S)-4-[[(4R)-4-(2-chloro-4-fluoro-phenyl)-2-[4-(difluoromethyl)thiazol-2-yl]-5-methoxycarbonyl-1,4-dihydropyrimidin-6-yl]methyl]morpholine-3-carboxylic acid The title compound was prepared in analogy to Example 2 with Procedure B shown in Scheme 5 by using (3S)-morpholine-3-carboxylic acid and 4-(difluoromethyl)thiazole-2-carboxamidine (Compound AL) instead of (S)-4,4-difluoro-pyrrolidine-2-carboxylic acid and thiazole-2-carboxamidine.

Preparation of 4-(difluoromethyl)thiazole-2-carboxamidine (Compound AL)

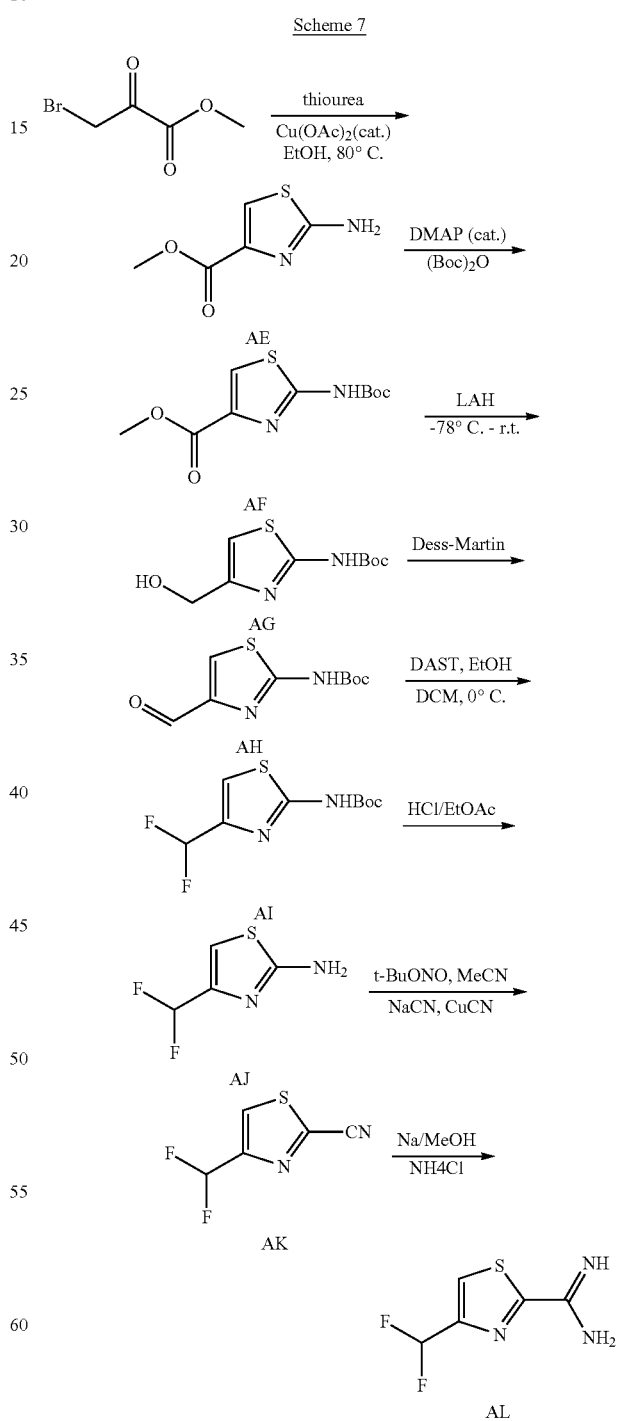

Scheme 7

A solution of methyl 3-bromo-2-oxo-propanoate (10 g, 51 mmol) and thiourea (4.0 g, 552 mmol) in EtOH (200 mL)

was added CuOAc (0.3 g, 2.62 mmol), then stirred at room temperature for 10 h. The mixture was concentrated to give the crude product (16 g). The crude product was basified with NaHCO$_3$ to pH=8, then extracted with EtOAc (200 mL×3). The organic layer was washed with H$_2$O (100 mL), brine (100 mL), and then dried over anhydrous Na$_2$SO$_4$, and then concentrated to give the product Compound AE (8.0 g) as a yellow solid.

To a mixture of Compound AE (15 g, 87 mmol) in DCM (200 mL) was added (Boc)$_2$O (28.48 g, 130.65 mmol) and DMAP (0.37 g). The mixture was stirred at room temperature overnight. After diluted with EA (200 mL), the mixture was washed with water, aq. NaHCO$_3$ (100 mL). The organic layer was dried and then concentrated to afford light yellow oil. The residue was purified by column chromatography in silica gel (PE:EA=10:1) to give Compound AF (20.0 g) as light yellow oil.

To a mixture of Compound AF (18 g, 66 mmol) in THF (300 mL) was added LAH (3.0 g, 79 mmol) at −78° C. The mixture was kept for 2 hrs. After the addition of aq. NaOH (3.0 mL 15% in water), the mixture was diluted with EA (100 mL), and then filtrated. The filtrate was concentrated to afford light yellow oil. The residue was purified by column chromatography in silica gel (PE:EA=30:1) to give Compound AG (14.0 g) as light yellow oil.

To a mixture of Compound AG (14 g, 60.79 mmol) in DCM (200 mL) was added Dess-Martin (30.9 g, 72.95 mmol) at rt. The mixture was kept for 2 hrs. Na$_2$O$_3$ was added then the mixture was washed with water, aq. NaHCO$_3$. The organic layer was dried and concentrated to afford light yellow oil. The residue was purified by column chromatography in silica gel (PE: EA=10:1) to give Compound AH (7.0 g) as light yellow oil.

To a solution of Compound AH (7.0 g, 31 mmol) in DCM (200 mL) and EtOH (100 mL) was added DAST (7.4 g, 46.05 mmol). The reaction mixture was stirred at room temperature overnight. The mixture was poured into water and diluted with DCM (200 mL), and then washed with water (100 mL), sat. NaHCO$_3$ (100 mL). The organic layer was dried and concentrated to afford light yellow oil. The residue was purified by column chromatography in silica gel (PE:EA=30:1) to give the Compound AI (5.8 g) as a light yellow solid.

A solution of Compound AI (6.0 g, 24 mmol) in HCl/EtOAc (60 mL) was stirred at room temperature overnight. After removal of solvent, aq. sat NaHCO$_3$ (100 mL) was added and the mixture was diluted with DCM (100 mL), then washed with water (50 mL), brine (50 mL). The organic layer was dried and concentrated to afford light yellow oil. The residue was purified by column chromatography in silica gel (PE: EA=30:1) to give Compound AJ (3.0 g) as light yellow oil.

To a mixture of CuCN (3.6 g, 40 mmol), NaCN (1.7 g, 35 mmol) and t-BuONO (4.1 g, 40 mmol) in MeCN (100 mL) was added Compound AJ (3.0 g, 20 mmol) at 0° C. The reaction mixture was stirred at room temperature overnight. After it was diluted with petroleum ether (100 mL), the mixture was washed with water, aq. NaHCO$_3$ (100 mL), and the organic layer was dried and concentrated to afford light yellow oil (1.0 g). The crude AK was used in next step directly without further purification.

To a flask charged with 60 mL MeOH was added Na (16 mg, 0.69 mmol, 0.11 eq) at rt. Then the above Compound AK (1.0 g, 6.3 mmol) was added into the resulting NaOMe solution. The reaction was stirred at rt for 24 hrs under N$_2$. Then NH$_4$Cl (230 mg, 4.3 mmol) was added. The reaction was stirred at 30° C. for 24 hrs. The reaction was concentrated and then 1.0 mL of isoproapnol and 10 mL of t-butylmethylether were added with stirring. The precipitate was collected and dried under vacuum to give the desired product AL (490 mg) as a white solid.

Example 89

(R)-6-((S)-2-Carboxy-4,4-difluoro-3,3-dimethyl-pyrrolidin-1-ylmethyl)-4-(2-chloro-4-fluoro-phenyl)-2-thiazol-2-yl-1,4-dihydro-pyrimidine-5-carboxylic acid methyl ester The title compound was prepared in analogy to Example 2 with Procedure B shown in Scheme 5 by using (2S)-4,4-difluoro-3,3-dimethyl-pyrrolidine-2-carboxylic acid (CAS: 1408278-20-5, for synthesis, see: Hu, Shanghui; Martinez, Carlos A.; Kline, Billie; Yazbeck, Daniel; Tao, Junhua; Kucera, David J. *Organic Process Research & Development*, 2006, 10, 650-654) instead of (S)-4,4-difluoro-pyrrolidine-2-carboxylic acid.

Example 90

(3R)-4-[[(4R)-4-(2-chloro-4-fluoro-phenyl)-5-methoxycarbonyl-2-thiazol-2-yl-1,4-dihydropyrimidin-6-yl]methyl]-2,2-dimethyl-thiomorpholine-3-carboxylic acid The title compound was prepared in analogy to Example 2 with Procedure B shown in Scheme 5 by using (3R)-2,2-dimethylthiomorpholine-3-carboxylic acid (WuXi AppTec (Wuhan) Co., Ltd, CAS:774243-35-5) instead of (S)-4,4-difluoro-pyrrolidine-2-carboxylic acid.

Example 91

(3S)-4-[[(4R)-4-(2-chloro-4-fluoro-phenyl)-5-methoxycarbonyl-2-thiazol-2-yl-1,4-dihydropyrimidin-6-yl]methyl]thiomorpholine-3-carboxylic acid The title compound was prepared in analogy to Example 14 shown in Scheme 6 by using thiomorpholine-3-carboxylic acid (PharmaBlock (Nanjing) R & D Co., Ltd. CAS: 20960-92-3) instead of 5,5-difluoro-piperidine-3-carboxylic acid.

Example 92

(S)-4-[(R)-6-(2-Chloro-4-fluoro-phenyl)-2-(1,4-dimethyl-1H-imidazol-2-yl)-5-methoxycarbonyl-3,6-dihydro-pyrimidin-4-ylmethyl]-morpholine-3-carboxylic acid The title compound was prepared in analogy to Example 2 with Procedure B shown in Scheme 5 by using 1,4-dimethyl-1H-imidazole-2-carbonitrile and (S)-morpholine-3-carboxylic acid instead of thiazole-2-carbonitrile and (S)-4,4-difluoro-pyrrolidine-2-carboxylic acid. The stereochemistry of Example 92 was determined by comparing its $^1$H NMR data and HPLC retention time with Example 2.

Example 93

(S)-4-[(R)-6-(4-Bromo-2-fluoro-phenyl)-5-ethoxycarbonyl-2-thiazol-2-yl-3,6-dihydro-pyrimidin-4-ylmethyl]-morpholine-3-carboxylic acid The title compound was prepared in analogy to Example 2 with Procedure B shown in Scheme 5 by using 4-bromo- 2-fluoro-benzaldehyde, ethyl acetoacetate and (S)-morpholine-3-carboxylic acid instead of 2-chloro-4-fluoro-benzaldehyde, methyl acetoacetate, and (S)-4,4-difluoro-pyrrolidine-2-carboxylic acid. The stereochemistry of Example 93 was determined by comparing its $^1$H NMR data and HPLC retention time with Example 2.

Example 94

(S)-4-[(R)-6-(4-Bromo-2-fluoro-phenyl)-5-methoxy-carbonyl-2-thiazol-2-yl-3,6-dihydro-pyrimidin-4-ylmethyl]-morpholine-3-carboxylic acid The title compound was prepared in analogy to Example 2 with Procedure B shown in Scheme 5 by using 4-bromo-2-fluoro-benzaldehyde and (S)-morpholine-3-carboxylic acid instead of 2-chloro-4-fluoro-benzaldehyde and (S)-4,4-difluoro-pyrrolidine-2-carboxylic acid. The stereochemistry of Example 94 was determined by comparing its $^1$H NMR data and HPLC retention time with Example 2.

Example 95

(S)-4-[(R)-6-(2-Chloro-4-fluoro-phenyl)-5-methoxy-carbonyl-2-(4-trifluoromethyl-thiazol-2-yl)-3,6-di-hydro-pyrimidin-4-ylmethyl]-morpholine-3-carboxylic acid The title compound was prepared in analogy to Example 2 with Procedure B shown in Scheme 5 by using 4-trifluoromethyl-thiazole-2-carboxamidine (Compound U) and (S)-morpholine-3-carboxylic acid instead of thiazole-2-carboxamidine and (S)-4,4-difluoro-pyrrolidine-2-carboxylic acid. The stereochemistry of Example 95 was determined by comparing its $^1$H NMR data and HPLC retention time with Example 2.

Example 96

(S)-4-[(S)-6-(3,4-Difluoro-2-methyl-phenyl)-5-ethoxycarbonyl-2-thiazol-2-yl-3,6-dihydro-pyrimi-din-4-ylmethyl]-morpholine-3-carboxylic acid The title compound was prepared in analogy to Example 2 with Procedure B shown in Scheme 5 by using 3,4-difluoro-2-methyl-benzaldehyde, ethyl acetoacetate and (S)-morpholine-3-carboxylic acid instead of 2-chloro-4-fluoro-benzaldehyde, methyl acetoacetate, and (S)-4,4-difluoro-pyrrolidine-2-carboxylic acid. The stereochemistry of Example 96 was determined by comparing its $^1$H NMR data and HPLC retention time with Example 2.

Example 97

(S)-4-[(R)-6-(2-Chloro-3-fluoro-phenyl)-5-ethoxy-carbonyl-2-(1-methyl-1H-imidazol-2-yl)-3,6-di-hydro-pyrimidin-4-ylmethyl]-morpholine-3-carboxylic acid The title compound was prepared in analogy to Example 2 with Procedure B shown in Scheme 5 by using 2-chloro-3-fluoro-benzaldehyde, ethyl acetoacetate, 1-methyl-1H-imidazole-2-carbonitrile and (S)-morpholine-3-carboxylic acid instead of 2-chloro-4-fluoro-benzaldehyde, methyl acetoacetate, thiazole-2-carbonitrile and (S)-4,4-difluoro-pyrrolidine-2-carboxylic acid. The stereochemistry of Example 97 was determined by comparing its $^1$H NMR data and HPLC retention time with Example 2.

Example 98

(S)-4-[(R)-6-(2-Chloro-4-fluoro-phenyl)-5-iso-propoxycarbonyl-2-thiazol-2-yl-3,6-dihydro-pyrimidin-4-ylmethyl]morpholine-3-carboxylic acid The title compound was prepared in analogy to Example 2 with Procedure A shown in Scheme 4 by using 3-oxo-butyric acid isopropyl ester instead of methyl acetoacetate and (S)-morpholine-3-carboxylic acid instead of (S)-4,4-difluoro-pyrrolidine-2-carboxylic acid. The stereochemistry of Example 98 was determined by comparing its $^1$H NMR data and HPLC retention time with Example 2.

Example 99

(S)-4-[6-(2-Chloro-4-fluoro-phenyl)-5-propoxycar-bonyl-2-thiazol-2-yl-3,6-dihyro-pyrimidin-4-ylm-ethyl]-morpholine-3-carboxylic acid The title compound was prepared in analogy to Example 1 with Procedure A shown in Scheme 4 by using 3-oxo-butyric acid propyl ester instead of methyl acetoacetate and (S)-morpholine-3-carboxylic acid instead of (S)-4,4-difluoro-pyrrolidine-2-carboxylic acid.

Example 100

(S)-4-[(S)-6-(3,4-Difluoro-phenyl)-5-isopropoxycar-bonyl-2-thiazol-2-yl-3,6-dihydro-pyrimidin-4-ylm-ethyl]-morpholine-3-carboxylic acid The title compound was prepared in analogy to Example 2 with Procedure A shown in Scheme 4 by using 3,4-difluoro-benzaldehyde instead of 2-chloro-4-fluoro-benzaldehyde, 3-oxo-butyric acid isopropyl ester instead of methyl acetoacetate and (S)-morpholine-3-carboxylic acid instead of (S)-4,4-difluoro-pyrrolidine-2-carboxylic acid. The stereochemistry of Example 100 was determined by comparing its $^1$H NMR data and HPLC retention time with Example 2.

Example 101

(S)-4-[(R)-6-(2-Chloro-3-fluoro-phenyl)-5-iso-propoxycarbonyl-2-thiazol-2-yl-3,6-dihydro-pyrimidin-4-ylmethyl]-morpholine-3-carboxylic acid The title compound was prepared in analogy to Example 2 with Procedure A shown in Scheme 4 by using 2-chloro-3-fluoro-benzaldehyde instead of 2-chloro-4-fluoro-benzaldehyde, 3-oxo-butyric acid isopropyl ester instead of methyl acetoacetate and (S)-morpholine-3-carboxylic acid instead of (S)-4,4-difluoro-pyrrolidine-2-carboxylic acid. The stereochemistry of Example 101 was determined by comparing its $^1$H NMR data and HPLC retention time with Example 2.

Example 102

(R)-6-((S)-2-Carboxy-4,4-difluoro-pyrrolidin-1-ylm-ethyl)-4-(2-chloro-4-fluoro-phenyl)-2-(5-methyl-oxazol-4-yl)-1,4-dihydro-pyrimidine-5-carboxylic acid methyl ester The title compound was prepared in analogy to Example 2 with Procedure A shown in Scheme 4 by using 5-methyloxazole-4-carboxamidine (Compound AB) instead of thiazole-2-carboxamidine. The stereochemistry of Example 102 was determined by comparing its $^1$H NMR data and HPLC retention time with Example 2.

Example 103

(S)-4-[(R)-6-(2-Chloro-3-fluoro-phenyl)-5-methoxycarbonyl-2-(5-methyl-oxazol-4-yl)-3,6-dihydro-pyrimidin-4-ylmethyl]-morpholine-3-carboxylic acid The title compound was prepared in analogy to Example 2 with Procedure A shown in Scheme 4 by using 5-methyloxazole-4-carboxamidine (Compound AB) instead of thiazole-2-carboxamidine, 2-chloro-3-fluorobenzaldehyde instead of 2-chloro-4-fluorobenzaldehyde and (3S)-morpholine-3-carboxylic acid instead of (2S)-4,4-difluoropyrrolidine-2-carboxylic acid. The stereochemistry of Example 103 was determined by comparing its $^1$H NMR data and HPLC retention time with Example 2.

Example 104

(2R,3S)-4-[(R)-6-(2-Chloro-4-fluoro-phenyl)-5-methoxycarbonyl-2-thiazol-2-yl-3,6-dihydro-pyrimidin-4-ylmethyl]-2-methyl-morpholine-3-carboxylic acid

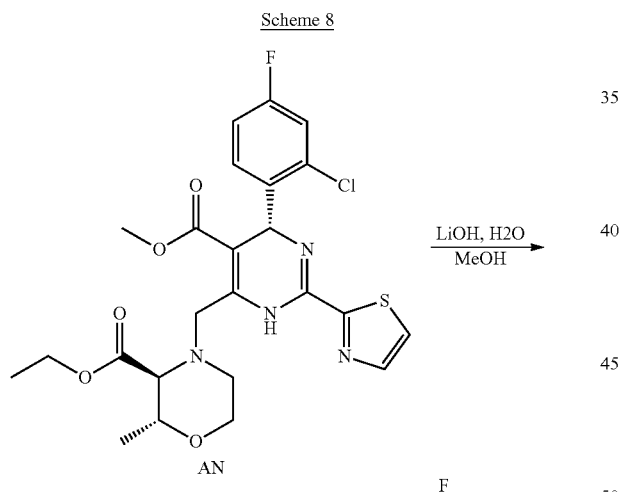

Scheme 8

Example 104

The title compounds was prepared from (2R,3S)-4-[(R)-6-(2-chloro-4-fluoro-phenyl)-5-methoxycarbonyl-2-thiazol-2-yl-3,6-dihydro-pyrimidin-4-ylmethyl]-2-methyl-morpholine-3-carboxylic acid ethyl ester (ester Compound AN) through saponification reaction and preparative HPLC separation.

A mixture of (2R,3S)-4-[(R)-6-(2-chloro-4-fluoro-phenyl)-5-methoxycarbonyl-2-thiazol-2-yl-3,6-dihydro-pyrimidin-4-ylmethyl]-2-methyl-morpholine-3-carboxylic acid ethyl ester (Compound AN) (100 mg, 0.19 mmol), lithium hydroxide monohydrate (78.4 mg, 1.9 mmol), water (0.5 mL) in methanol (2 mL) was stirred for 12 hours at room temperature. Then the mixture was treated with hydrochloric acid (10%) to adjust pH~4. After filtration, the filtrate was purified by preparative HPLC separation to afford Example 104 as yellow solid. Yield: 60%.

Preparation of (2R,3S)-4-[(R)-6-(2-Chloro-4-fluorophenyl)-5-methoxycarbonyl-2-thiazol-2-yl-3,6-dihydro-pyrimidin-4-ylmethyl]-2-methyl-morpholine-3-carboxylic acid ethyl ester (ester Compound AN)

Compound AN was prepared in analogy to Example 2 with Procedure B shown in Scheme 5 by using (2R,3S)-2-methyl-morpholine-3-carboxylic acid ethyl ester (for its synthesis, see: WO2011025889) instead of (2S)-4,4-difluoropyrrolidine-2-carboxylic acid.

Example 105

(S)-4-[5-tert-Butoxycarbonyl-6-(2-chloro-4-fluorophenyl)-2-thiazol-2-yl-3,6-dihydro-pyrimidin-4-ylmethyl]-morpholine-3-carboxylic acid The title compound was prepared in analogy to Example 1 with Procedure A shown in Scheme 4 by using 3-oxobutyric acid tert-butyl ester instead of methyl acetoacetate and (3S)-morpholine-3-carboxylic acid instead of (2S)-4,4-difluoropyrrolidine-2-carboxylic acid.

Example 106

(2R,3S)-4-[(R)-6-(2-Bromo-4-fluoro-phenyl)-5-methoxycarbonyl-2-thiazol-2-yl-3,6-dihydro-pyrimidin-4-ylmethyl]-2-methyl-morpholine-3-carboxylic acid The title compound was prepared in analogy to Example 104 with the same procedure shown in Scheme 8 by using 2-bromo-4-fluoro-benzaldehyde instead of 2-chloro-4-fluoro-benzaldehyde.

Example 107 and 108

(R)-4-(2-Bromo-4-fluoro-phenyl)-6-(S)-2-carboxy-5,5-difluoro-piperidin-1-ylmethyl)-2-thiazol-2-yl-1,4-dihydro-pyrimidine-5-carboxylic acid ethyl ester (Example 107) and (R)-4-(2-Bromo-4-fluoro-phenyl)-6-(R)-2-carboxy-5,5-difluoro-piperidin-1-ylmethyl)-2-thiazol-2-yl-1,4-dihydro-pyrimidine-5-carboxylic acid ethyl ester (Example 108)

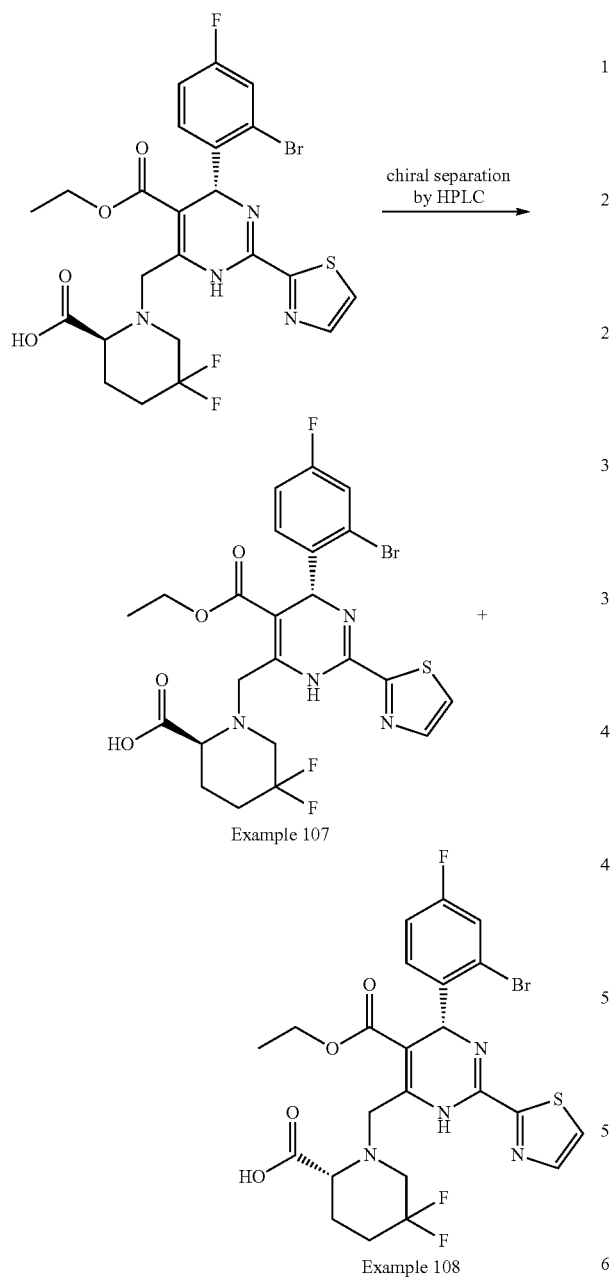

Example 107

Example 108

The title compounds was prepared in analogy to Example 14 with Procedure C shown in Scheme 6 by using 5,5-difluoro-piperidine-2-carboxylic acid (Nanjing Pharmablock Co. Ltd. CAS: 1255663-89-8), 2-bromo-4-fluoro-benzaldehyde and ethyl acetoacetate instead of 5,5-difluoro-piperidine-3-carboxylic acid, 2-chloro-4-fluoro-benzaldehyde and methyl acetoacetate.

Example 109 and 110

(R)-6-(S)-2-Carboxy-5,5-difluoro-piperidin-1-ylmethyl)-4-(2-chloro-3-fluoro-phenyl)-2-thiazol-2-yl-1,4-dihydro-pyrimidine-5-carboxylic acid methyl ester (Example 109) and (R)-6-(R)-2-Carboxy-5,5-difluoro-piperidin-1-ylmethyl)-4-(2-chloro-3-fluoro-phenyl)-2-thiazol-2-yl-1,4-dihydro-pyrimidine-5-carboxylic acid methyl ester (Example 110)

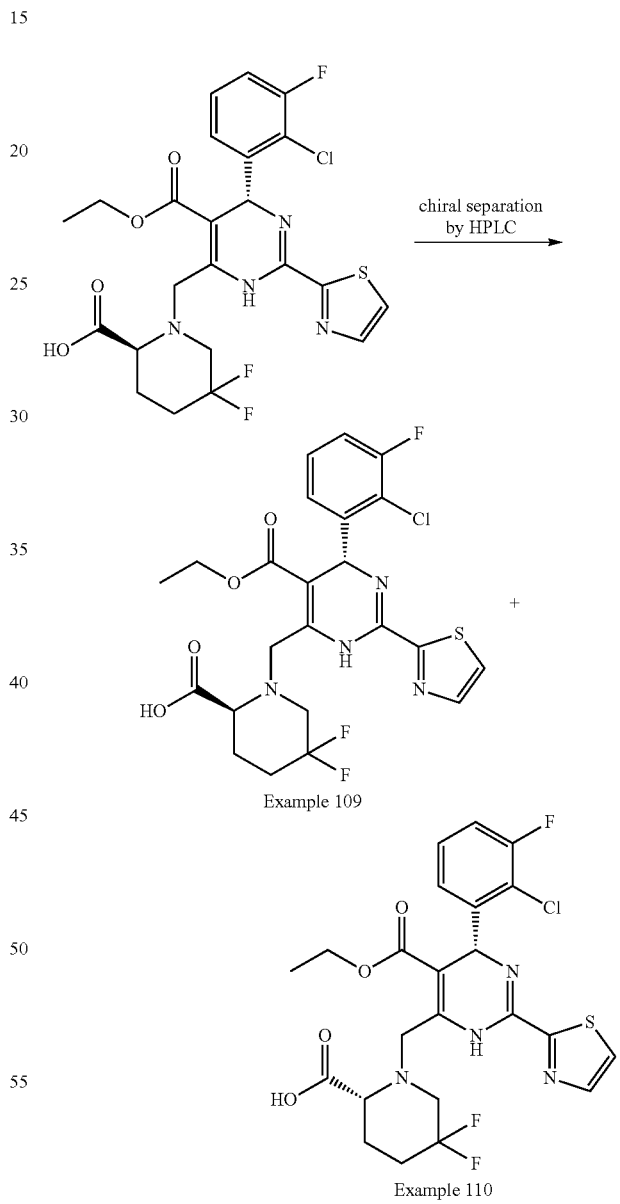

Example 109

Example 110

The title compounds was prepared in analogy to Example 14 with Procedure C shown in Scheme 6 by using 5,5-difluoro-piperidine-2-carboxylic acid (Nanjing Pharmablock Co. Ltd. CAS: 1255663-89-8) and 2-chloro-3-fluoro-benzaldehyde instead of 5,5-difluoro-piperidine-3-carboxylic acid and 2-chloro-4-fluoro-benzaldehyde.

Example 111

(R)-6-(S)-2-Carboxy-5,5-difluoro-piperidin-1-ylm-ethyl)-4-(2-chloro-phenyl)-2-thiazol-2-yl-1,4-di-hydro-pyrimidine-5-carboxylic acid ethyl ester The title compound was prepared in analogy to Example 14 with Procedure C shown in Scheme 6 by using 5,5-difluoro-piperidine-2-carboxylic acid (Nanjing Pharmablock Co. Ltd. CAS: 1255663-89-8), 2-chloro-benzaldehyde and ethyl acetoacetate instead of 5,5-difluoro-piperidine-3-carboxylic acid, 2-chloro-4-fluoro-benzaldehyde and methyl acetoacetate.

Example 112

(2R,3S)-4-[(S)-6-(3,4-Difluoro-phenyl)-5-ethoxycar-bonyl-2-thiazol-2-yl-3,6-dihydro-pyrimidin-4-ylm-ethyl]-2-methyl-morpholine-3-carboxylic acid The title compound was prepared in analogy to Example 104 with the procedure shown in Scheme 8 by using 3,4-difluoro-benzaldehyde and ethyl acetoacetate instead of 2-chloro-4-fluoro-benzaldehyde and methyl acetoacetate.

Example 113

(2R,3S)-4-[(S)-6-(3,4-Difluoro-phenyl)-5-methoxy-carbonyl-2-thiazol-2-yl-3,6-dihydro-pyrimidin-4-ylmethyl]-2-methyl-morpholine-3-carboxylic acid The title compound was prepared in analogy to Example 104 with the procedure shown in Scheme 8 by using 3,4-difluoro-benzaldehyde instead of 2-chloro-4-fluoro-benzaldehyde

Example 114

(2R,3S)-4-[(R)-5-Methoxycarbonyl-2-thiazol-2-yl-6-(2,3,4-trifluoro-phenyl)-3,6-dihydro-pyrimidin-4-ylmethyl]-2-methyl-morpholine-3-carboxylic acid The title compound was prepared in analogy to Example 104 with the procedure shown in Scheme 8 by using 2,3,4-trifluoro-benzaldehyde instead of 2-chloro-4-fluoro-benzaldehyde.

Example 115

(2R,3S)-4-[(R)-6-(2-Chloro-3-fluoro-phenyl)-5-methoxycarbonyl-2-thiazol-2-yl-3,6-dihydro-pyrimidin-4-ylmethyl]-2-methyl-morpholine-3-carboxylic acid The title compound was prepared in analogy to Example 104 with the procedure shown in Scheme 8 by using 2-chloro-3-fluoro-benzaldehyde instead of 2-chloro-4-fluoro-benzaldehyde.

Example 116

(2R,3S)-4-[(R)-6-(2-Bromo-4-fluoro-phenyl)-5-ethoxycarbonyl-2-thiazol-2-yl-3,6-dihydro-pyrimidin-4-ylmethyl]-2-methyl-morpholine-3-carboxylic acid The title compound was prepared in analogy to Example 104 with the procedure shown in Scheme 8 by using 2-bromo-4-fluoro-benzaldehyde and ethyl acetoacetate instead of 2-chloro-4-fluoro-benzaldehyde and methyl acetoacetate.

Example 117

(2R,3S)-4-[(R)-6-(2-Chloro-phenyl)-5-ethoxycarbo-nyl-2-thiazol-2-yl-3,6-dihydro-pyrimidin-4-ylm-ethyl]-2-methyl-morpholine-3-carboxylic acid The title compound was prepared in analogy to Example 104 with the procedure shown in Scheme 8 by using 2-chloro-benzaldehyde and ethyl acetoacetate instead of 2-chloro-4-fluoro-benzaldehyde and methyl acetoacetate.

Example 118

(2R,3S)-4-[(R)-6-(2-Chloro-3-fluoro-phenyl)-5-ethoxycarbonyl-2-thiazol-2-yl-3,6-dihydro-pyrimi-din-4-ylmethyl]-2-methyl-morpholine-3-carboxylic acid The title compound was prepared in analogy to Example 104 with the procedure shown in Scheme 8 by using 2-chloro-3-fluoro-benzaldehyde and ethyl acetoacetate instead of 2-chloro-4-fluoro-benzaldehyde and methyl acetoacetate.

Example 119

(2R,3S)-4-[(R)-6-(2-Bromo-phenyl)-5-methoxycar-bonyl-2-thiazol-2-yl-3,6-dihydro-pyrimidin-4-ylm-ethyl]-2-methyl-morpholine-3-carboxylic acid The title compound was prepared in analogy to Example 104 with the procedure shown in Scheme 8 by using 2-bromo-benzaldehyde instead of 2-chloro-4-fluoro-benzaldehyde.

Example 120

(2R,3S)-4-[(R)-6-(2-Chloro-4-fluoro-phenyl)-5-methoxycarbonyl-2-thiazol-2-yl-3,6-dihydro-pyrimi-din-4-ylmethyl]-2-isopropyl-morpholine-3-carbox-ylic acid The title compound was prepared in analogy to Example 104 with the procedure shown in Scheme 8 by using (2R,3S)-2-isopropyl-morpholine-3-carboxylic acid methyl ester (Compound AO) instead of (2R,3S)-2-methyl-morpholine-3-carboxylic acid ethyl ester.

Preparation of (2R,3S)-2-Isopropyl-morpholine-3-carboxylic acid methyl ester (Compound AQ)

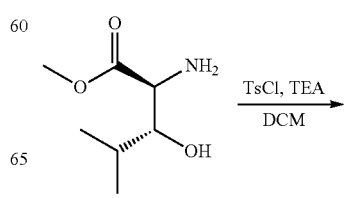

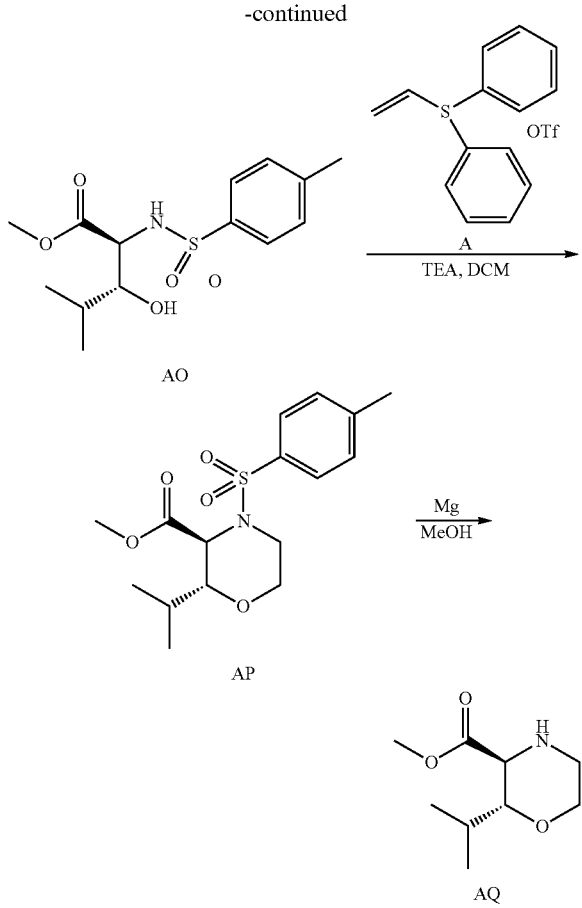

Preparation of (2S,3R)-3-hydroxy-4-methyl-2-(toluene-4-sulfonylamino)-pentanoic acid methyl ester (Compound AO)

A mixture of (2S,3R)-2-amino-3-hydroxy-4-methyl-pentanoic acid methyl ester (0.50 g, 3.4 mmol) and triethylamine (0.69 g, 6.8 mmol) in dichloromethane (10 mL) was added 4-methyl-benzenesulfonyl chloride (0.71 g, 3.7 mmol) at 0° C. After stirring for 2 hours at room temperature, the mixture was washed with water and the organic layer was separated and then dried over sodium sulfate. After removal of solvent, the residue was used in next step without purification. MS: calc'd (MH$^+$) 316, measured (MH$^+$) 316.

Preparation of (2R,3S)-2-isopropyl-4-(toluene-4-sulfonyl)-morpholine-3-carboxylic acid methyl ester (Compound AP)

A mixture of (2S,3R)-3-hydroxy-4-methyl-2-(toluene-4-sulfonylamino)-pentanoic acid methyl ester (0.4 g, 1.27 mmol) and diphenylvinylsulfonium triflate (0.5 g, 1.4 mmol) in dichloromethane (10 mL) was added triethylamine dropwise at 0° C. After stirring for 12 hours, the mixture was diluted with water, and then extracted with ethyl acetate, then dried over sodium sulfate. After removal of solvent, the residue was purified by flash chromatopraphy (eluented with ethyl acetate/hexane=1:4) to afford the product as a white solid. MS: calc'd (MH$^+$) 342, measured (MH$^+$) 342.

Preparation of (2R,3S)-2-isopropyl-morpholine-3-carboxylic acid methyl ester (Compound AQ)

A mixture of (2R,3S)-2-isopropyl-4-(toluene-4-sulfonyl)-morpholine-3-carboxylic acid methyl ester (0.20 g, 0.59 mmol) and magnesium powder (70 mg, 2.9 mmol) in anhydrous methanol (5 mL) was stirred for 3 hours at 60° C. The solid was removed by filtration, and the filtrate was concentrated under reduced pressure. The residue as crude product was used in next step without purification. MS: calc'd (MH$^+$) 188, measured (MH$^+$) 188.

Example 121

(S)-4-(((R)-6-(2-chloro-4-fluorophenyl)-5-(methoxycarbonyl)-2-(thiazol-2-yl)-3,6-dihydropyrimidin-4-yl)methyl)-3-methylmorpholine-3-carboxylic acid The title compound was prepared in analogy to Example 78 with the procedure by using 2-chloro-4-fluoro-benzaldehyde instead of 2-chloro,3,4-dofluoro-benzaldehyde.

Example 122

(S)-4-(((R)-6-(2-bromo-4-fluorophenyl)-5-(ethoxycarbonyl)-2-(thiazol-2-yl)-3,6-dihydropyrimidin-4-yl)methyl)morpholine-3-carboxylic acid The title compound was prepared in analogy to Example 2 with Procedure B shown in Scheme 5 by using 2-bromo-4-fluoro-benzaldehyde instead of 2-chloro-4-fluoro-benzaldehyde, using ethyl acetoacetate instead of methyl acetoacetate and using (S)-morpholine-3-carboxylic acid instead of (S)-4,4-difluoro-pyrrolidine-2-carboxylic acid. The stereochemistry of Example 122 was determined by comparing its $^1$H NMR data and HPLC retention time with Example 2.

Example 123

(3S)-4-[[(4S)-4-(4-Bromophenyl)-5-ethoxycarbonyl-2-(1,3-thiazol-2-yl)-1,4-dihydropyrimidin-6-yl]methyl]morpholine-3-carboxylic acid The title compound was prepared in analogy to Example 2 with Procedure A shown in Scheme 4 by using 4-bromo-benzaldehyde instead of 2-chloro-4-fluoro-benzaldehyde, using ethyl acetoacetate instead of methyl acetoacetate and using (S)-morpholine-3-carboxylic acid instead of (S)-4,4-difluoro-pyrrolidine-2-carboxylic acid. The stereochemistry of Example 123 was determined by comparing its $^1$H NMR data and HPLC retention time with Example 2.

Example 124

(3S)-4-[[(4S)-4-(3-Bromo-4-chlorophenyl)-5-ethoxycarbonyl-2-(1,3-thiazol-2-yl)-1,4-dihydropyrimidin-6-yl]methyl]morpholine-3-carboxylic acid The title compound was prepared in analogy to Example 2 with Procedure A shown in Scheme 4 by using 3-bromo-4-chloro-benzaldehyde instead of 2-chloro-4-fluoro-benzaldehyde, using ethyl acetoacetate instead of methyl acetoacetate and using (S)-morpholine-3-carboxylic acid instead of (S)-4,4-difluoro-pyrrolidine-2-carboxylic acid. The stereochemistry of Example 124 was determined by comparing its ¹H NMR data and HPLC retention time with Example 2.

Example 125

(3S)-4-[[(4S)-4-(3-Chloro-5-fluorophenyl)-5-ethoxy-carbonyl-2-(1,3-thiazol-2-yl)-1,4-dihydropyrimidin-6-yl]methyl]morpholine-3-carboxylic acid The title compound was prepared in analogy to Example 2 with Procedure A shown in Scheme 4 by using 3-chloro-5-fluoro-benzaldehyde instead of 2-chloro-4-fluoro-benzaldehyde, using ethyl acetoacetate instead of methyl acetoacetate and using (S)-morpholine-3-carboxylic acid instead of (S)-4,4-difluoro-pyrrolidine-2-carboxylic acid. The stereochemistry of Example 125 was determined by comparing its ¹H NMR data and HPLC retention time with Example 2.

Example 126

(3S)-4-[[(4S)-4-(4-chlorophenyl)-5-ethoxycarbonyl-2-(1,3-thiazol-2-yl)-1,4-dihydropyrimidin-6-yl]methyl]morpholine-3-carboxylic acid The title compound was prepared in analogy to Example 2 with Procedure A shown in Scheme 4 by using 4-chloro-benzaldehyde instead of 2-chloro-4-fluoro-benzaldehyde, using ethyl acetoacetate instead of methyl acetoacetate and using (S)-morpholine-3-carboxylic acid instead of (S)-4,4-difluoro-pyrrolidine-2-carboxylic acid. The stereochemistry of Example 126 was determined by comparing its ¹H NMR data and HPLC retention time with Example 2.

Example 127

(S)-4-(((R)-6-(2-bromophenyl)-5-(ethoxycarbonyl)-2-(thiazol-2-yl)-3,6-dihydropyrimidin-4-yl)methyl)morpholine-3-carboxylic acid The title compound was prepared in analogy to Example 2 with Procedure B shown in Scheme 5 by using 2-promo-benzaldehyde instead of 2-chloro-4-fluoro-benzaldehyde, using ethyl acetoacetate instead of methyl acetoacetate and using (S)-morpholine-3-carboxylic acid instead of (S)-4,4-difluoro-pyrrolidine-2-carboxylic acid. The stereochemistry of Example 127 was determined by comparing its ¹H NMR data and HPLC retention time with Example 2.

Example 128

(3S)-4-[[(4R)-4-(2-bromo-3,4-difluorophenyl)-5-ethoxycarbonyl-2-(1,3-thiazol-2-yl)-1,4-dihydropyrimidin-6-yl]methyl]morpholine-3-carboxylic acid The title compound was prepared in analogy to Example 2 with Procedure B shown in Scheme 5 by using 2-promo-3,4-difluoro-benzaldehyde (Compound AR) instead of 2-chloro-4-fluoro-benzaldehyde, using ethyl acetoacetate instead of methyl acetoacetate and using (S)-morpholine-3-carboxylic acid instead of (S)-4,4-difluoro-pyrrolidine-2-carboxylic acid. The stereochemistry of Example 128 was determined by comparing its ¹H NMR data and HPLC retention time with Example 2.

Preparation of 2-bromo-3,4-difluoro-benzaldehyde (Compound AS)

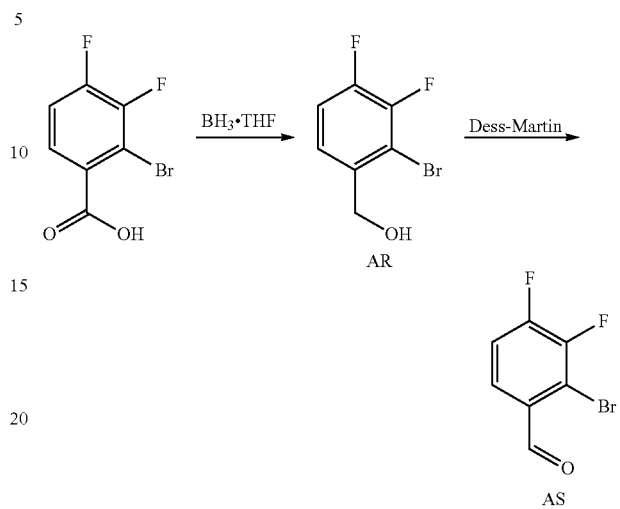

2-Bromo-3,4-difluorobenzoic acid (3.7 g, 16 mmol, Eq: 1.00) was dissolved in anhydrous THF (20 ml) and the solution was cooled to 0° C. BH₃.THF (62.6 ml, 62.6 mmol, Eq: 4) was added dropwise. The resulting solution was allowed to warm up to room temperature and stirred overnight. The solution was cooled with an ice bath, and then 10% aqueous Na₂CO₃ (30 mL) was added slowly. The suspension was concentrated in vacuo to give a white solid. The residue was acidified with 3M aqueous HCl solution (100 mL), diluted with dichloromethane (50 mL), and the mixture was filtered through Celite. The organic layers was separated and dried over sodium sulfate, and then followed by a filtration. Resulting filtrate was concentrated in vacuum to give an off-white solid AR (2.5 g). ¹H NMR (DMSO) δ 7.46-7.53 (m, 1H), 7.35-7.41 (m, 1H), 4.51 (s, 2H), 4.44-4.58 (m, 2H)

(2-Bromo-3,4-difluorophenyl)methanol (Compound AR) (2.55 g, 11.4 mmol, Eq: 1.00) was dissolved in dichloromethane (15 ml). Dess-Martin periodinane (4.85 g, 11.4 mmol, Eq: 1.00) was added. The reaction mixture was stirred for 2 hrs at room temperature. The reaction mixture was filtered over a plug of celite and washed with DCM (30 ml). Filtrate was concentrated to give a semi solid. Crude product was dissolved in EtOAc/DCM and loaded into a silica gel column (4 g). Silica gel column was flushed with EtOAc to give a light yellow solid (3 g). ¹H NMR (DMSO) δ 10.13 (s, 1H), 7.74-7.82 (m, 1H), 7.70 (ddd, J=9.5, 7.3, 0.8 Hz, 1H).

Example 129

(3S)-4-[[(4R)-5-ethoxycarbonyl-4-(2-iodophenyl)-2-(1,3-thiazol-2-yl)-1,4-dihydropyrimidin-6-yl]methyl]morpholine-3-carboxylic acid The title compound was prepared in analogy to Example 2 with Procedure A shown in Scheme 4 by using 2-iodo-benzaldehyde instead of 2-chloro-4-fluoro-benzaldehyde, using ethyl acetoacetate instead of methyl acetoacetate and using (5)-morpholine-3-carboxylic acid instead of (S)-4,4-difluoro-pyrrolidine-2-carboxylic acid. The stereochemistry of Example 129 was determined by comparing its $^1$H NMR data and HPLC retention time with Example 2.

Example 130

(2S)-1-[[(4S)-4-(4-bromophenyl)-5-ethoxycarbonyl-2-(1,3-thiazol-2-yl)-1,4-dihydropyrimidin-6-yl]methyl]-4,4-difluoropyrrolidine-2-carboxylic acid The title compound was prepared in analogy to Example 2 with Procedure A shown in Scheme 4 by using 4-bromobenzaldehyde instead of 2-chloro-4-fluoro-benzaldehyde, using ethyl acetoacetate instead of methyl acetoacetate. The stereochemistry of Example 130 was determined by comparing its $^1$H NMR data and HPLC retention time with Example 2.

Example 131

HBV Inhibition Assays

Cells and Culture Conditions

HepG2.2.15 and HepDE19 are stably-transfected cell lines containing the HBV genome. Both cell lines are derived from the hepatoblastoma cell line Hep G2 (American Type Culture Collection, ATCC® HB-8065™) by the published procedures described in references: MA Selles et al. Proc. Natl. Acad. Sci. USA 1987, 84, 1005-1009 and H Guo et al. Journal of Virology 2007, 81, 12472-12484, respectively. Both cell lines were maintained in Dulbecco's modified Eagle's medium (DMEM)-F12 medium supplemented with 10% fetal bovine serum, 100 U/mL penicillin, 100 µg/mL streptomycin, and 0.5 mg/mL of G418.

While HepG2.2.15 cells constitutively support HBV replication and production of virus particles, HepDE19 cells are inducible by tetracycline. Addition of 1 µg/mL tetracycline in culture medium suppresses HBV replication in HepDE19 cells, whereas switching to tetracycline-free medium resumes this process.

Anti-HBV Activity In Vitro:

HepG2.2.15 cells were seeded into 96-well plates ($3 \times 10^4$ cells in 100 µl media per well) and incubated overnight at 37° C. The test compounds were serially half-log diluted in DMSO, then diluted 100 times in culture media. 100 µL diluted compounds were added into the plates to reach 0.5% final concentration of DMSO in every well. Five days after compound treatment, culture supernatant was collected for further analysis.

For quantitative PCR detection of extracellular HBV DNA, 100 µL culture supernatant was collected and processed in MagNA Pure 96 Nucleic Acid Purification System (Roche Applied Science) for viral DNA extraction. The extracted samples were subjected to HBV DNA quantification by qPCR. The effective compound concentration at which HBV replication is inhibited by 50% ($EC_{50}$) was determined.

The compounds of the present invention were tested for their capacity to inhibit a HBV activity and activation as described herein. The Examples were tested in the above assays as described herein and found to have $EC_{50}$<0.10 µM in HepG2.2.15 assay. Particular compounds of formula I were found to have $EC_{50}$<0.02 µM in HepG2.2.15 assay (See Table 3).

Cytotoxicity and Selectivity Index:

In a cell culture model, apparent antiviral activity of a compound can be the result of host cell death after exposure to the compound. To determine whether the anti-HBV effect of a test compound is due to cytotoxicity, HepDE19 cells were seeded into 96-well plates ($5 \times 10^3$ cells per well) and treated with compounds as described above for $EC_{50}$ determination. Five days after treatment, cell viability was measured by addition of 20 µL of CCK-8 reagent. Two hours after incubation at 37° C., the absorbance at wavelengths of 450 nm and 630 nm ($OD_{450}$ and $OD_{630}$) was recorded by a plate reader. The concentration results in the death of 50% of the host cells ($CC_{50}$) of each compound was determined (See Table 6).

The relative effectiveness of the compound in inhibiting viral replication compared to inducing cell death is defined as the selectivity index ($CC_{50}$ value/$EC_{50}$ value). It is desirable to have a high selectivity index giving maximum antiviral activity with minimal cell toxicity. Based on $CC_{50}$ and $EC_{50}$ data, selectivity indexes were determined as shown in Table 7. Based on $CC_{50}$ and $EC_{50}$ data, selectivity indexes were determined as shown in Table 7.

Example 132

Mouse SDPK Description

The single dose PK in male ICR mouse was performed to assess their pharmacokinetic properties. Two groups of animals were dosed via either bolus intravenous (IV) or oral gavage (PO) of the respective compound. The animals for oral administration were fasted overnight prior to dosing and food was resumed 4 hours postdose. Blood samples (approximately 400 µL) were collected via cardiac puncture after euthanasia by carbon dioxide inhalation at 2 mins, 5 mins, 15 mins, 30 mins, 1 h, 2 hrs, 4 hrs, 6 hrs, 8 hrs, and 24 hrs postdose for IV group, and at 5 mins, 15 mins, 30 mins, 1 h, 2 hrs, 4 hrs, 6 hrs, 8 hrs, and 24 hrs postdose for PO group. Blood samples were placed into tubes containing sodium heparin and centrifuged at 8000 rpm for 6 minutes at 4° C. to separate plasma from the samples.

Following centrifugation, the resulting plasma was transferred to clean tubes for bioanalysis on LC/MS/MS. The pharmacokinetic parameters were calculated using non-compartmental module of WinNonlin® Professional 5.2.

Results of SDPK are given in Table 4.

Example 133

Description of Metabolic Stability Study

Human Microsomes were preincubated with test compound for 10 min at 37° C. in 100 mM phosphate buffer, pH 7.4. The reactions were initiated by adding NADPH or NADPH regenerating system to give a final incubation volume of 400 µL. For NADPH system, the final incubations contained 1 µM test compound, 0.5 mg/mL liver microsomal protein, 1 mM NADPH in 100 mM phosphate buffer, pH 7.4. For the NADPH regenerating system, the final incubations contained 1 µM test compound, 0.5 mg/mL liver microsomal protein, 3 mM glucose 6-phosphate, 1 mM NADP, 3 mM MgCl$_2$ and 0.05 mg/mL glucose 6-phosphate dehydrogenase in 100 mM phosphate buffer, pH 7.4. After incubation times of 0, 3, 6, 9, 15 and 30 minutes at 37° C., 50 µL samples was removed and transferred to 150 µL methanol solution which was maintained at 4° C. containing 2 µM tolbutamide (internal standard) to terminating the reaction. Following precipitation and centrifugation, the amount of compound remaining in the samples were determined by LC-MS/MS. Controls of no NADPH or NADPH regenerating system at zero and 30 min were also prepared and analyzed.

Results of metabolic stability study in human microsome are given in Table 5.

Example 134

LYSA Description

Samples are prepared in duplicate from 10 mM DMSO stock solutions. After evaporation of DMSO with a centrifugal vacuum evaporator, the residue is solved in 0.05 M phosphate buffer (pH 6.5), stirred for one hour and shaken for two hours. After one night, the solutions is filtered using a microtiter filter plate and the filtrate and its 1/10 dilution are then analyzed by direct UV measurement or by HPLC-UV. In addition a four-point calibration curve is prepared from the 10 mM stock solutions and used for the solubility determination of the compounds. The results are in µg/mL. In case the percentage of sample measured in solution after evaporation divided by the calculated maximum of sample amount is bigger than 80% the solubility is reported as bigger than this value.

Results of Lysa are given in Table 6.

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound selected from

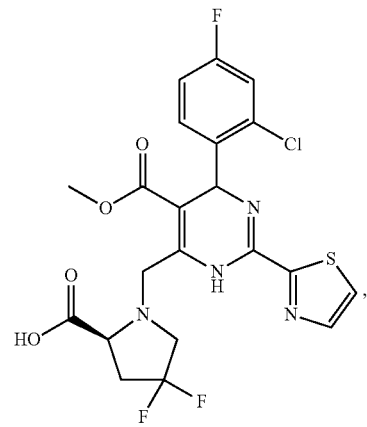

1

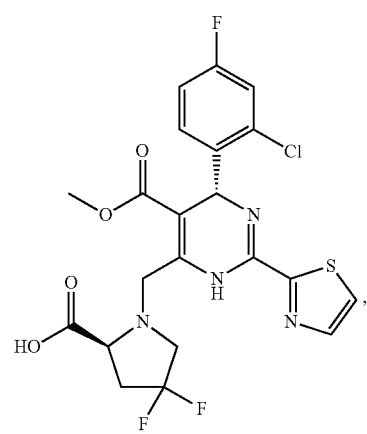

2

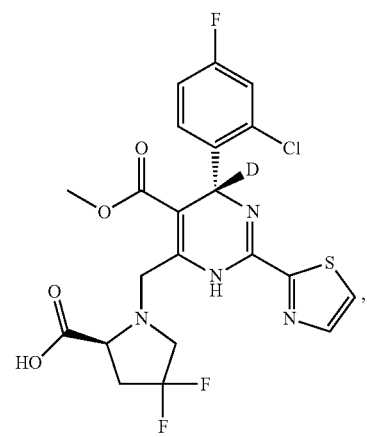

3

4
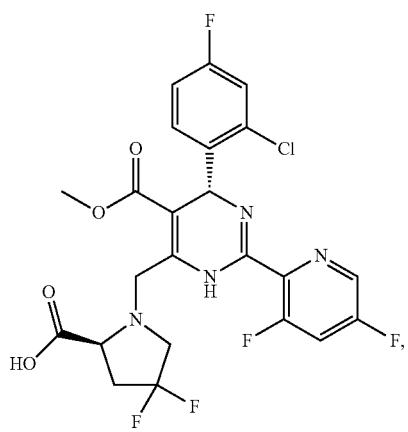
6
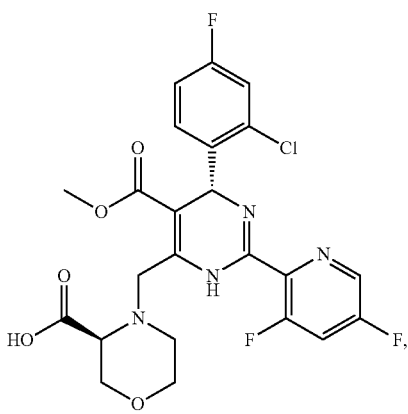
7
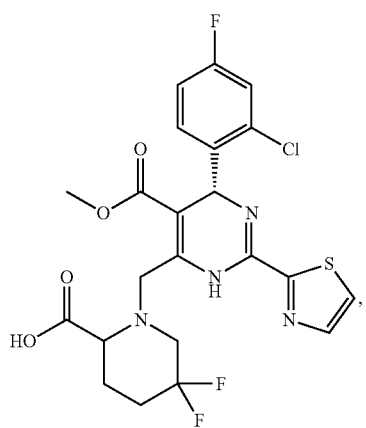
8
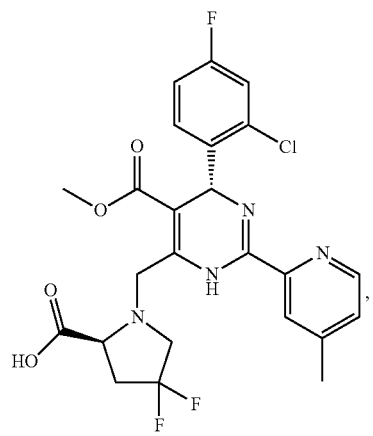
9
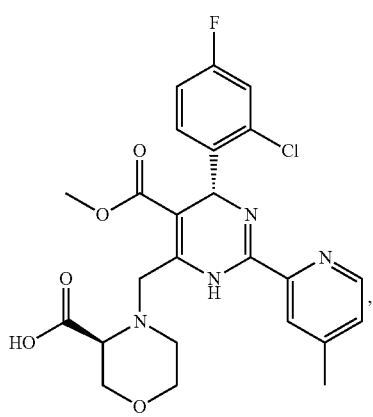
10
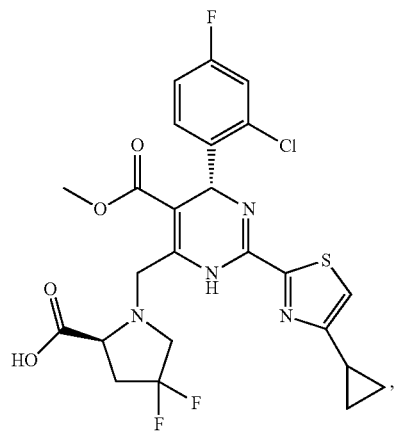

191
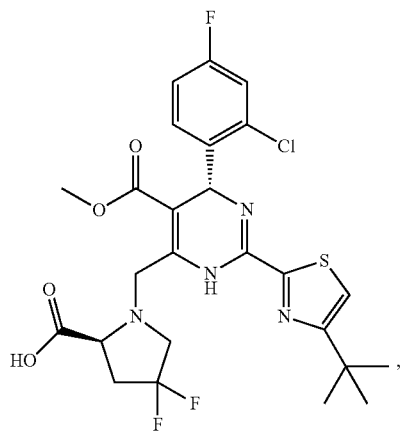
11
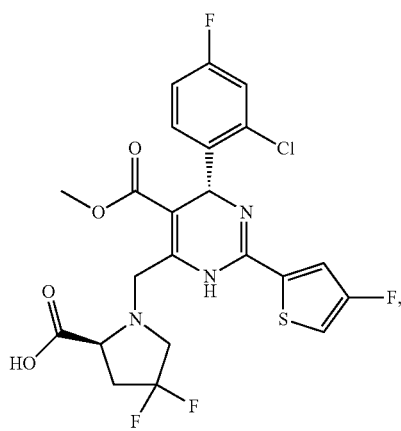
12
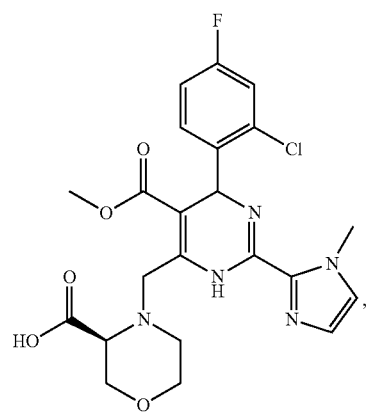
13
192
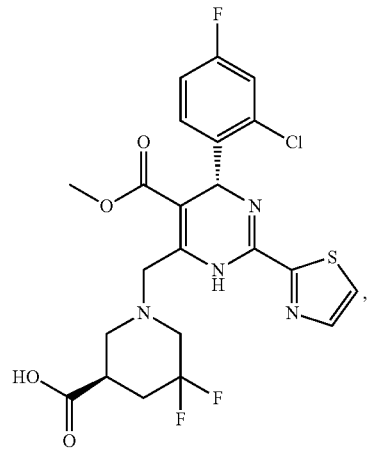
14
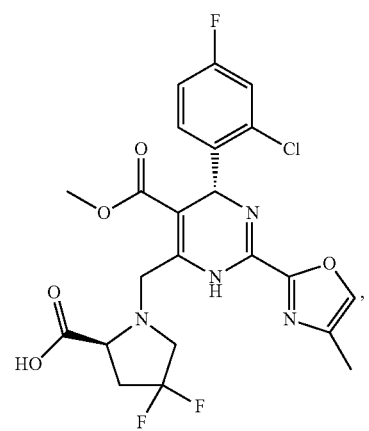
15
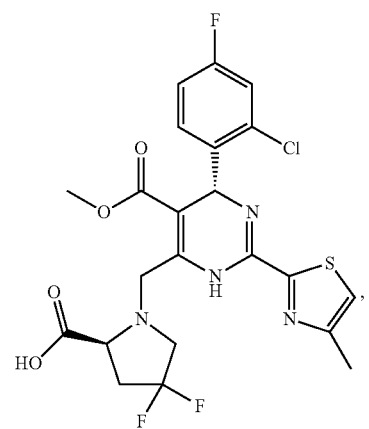
16

17
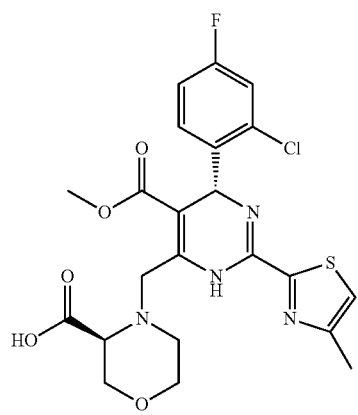
18
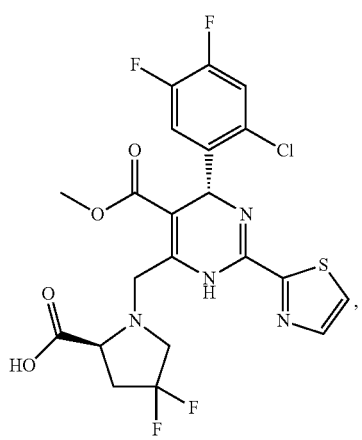
19
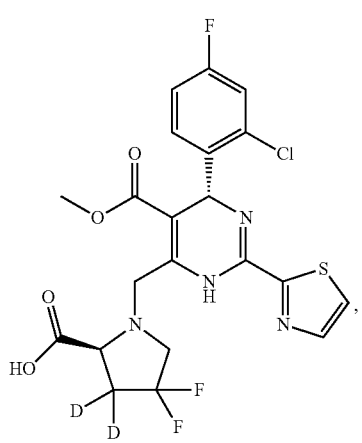
20
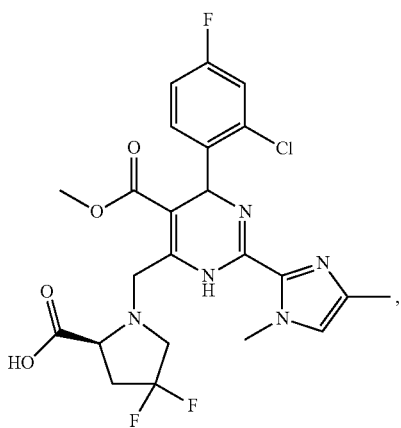
21
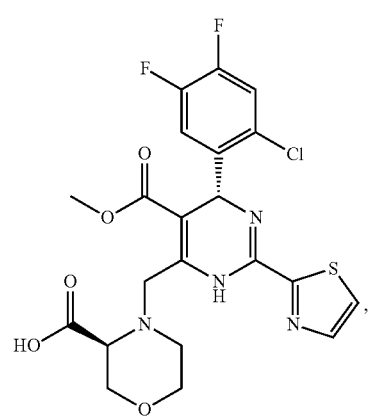
22
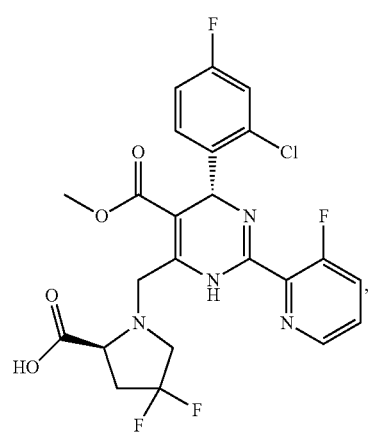

23
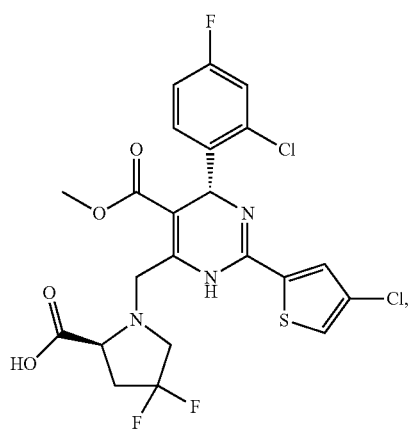
24
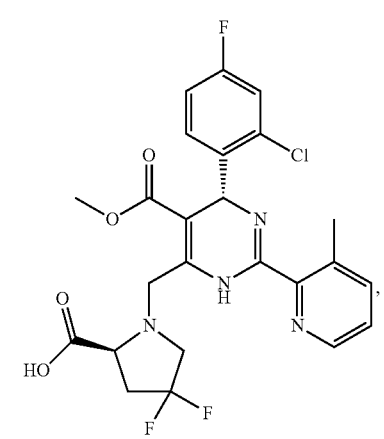
25
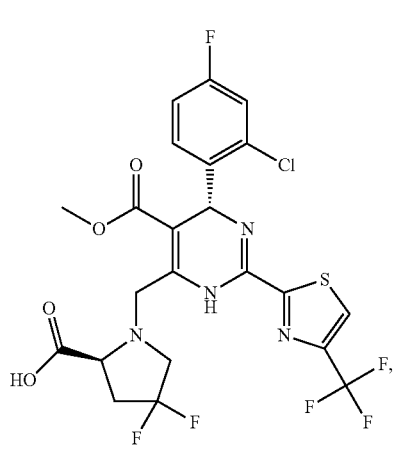
27
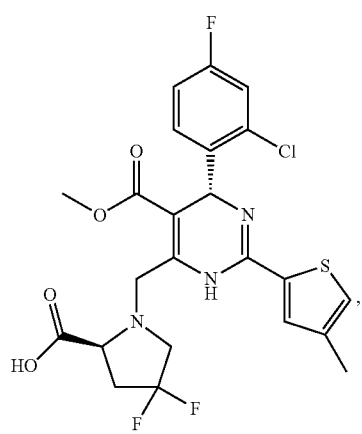
28
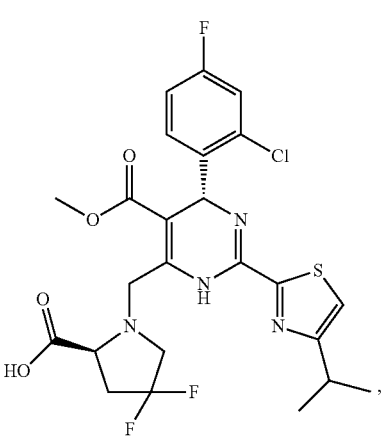
29
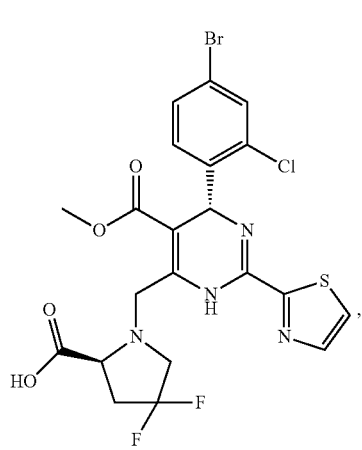

197
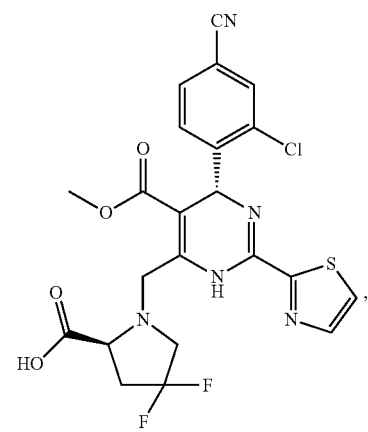
32
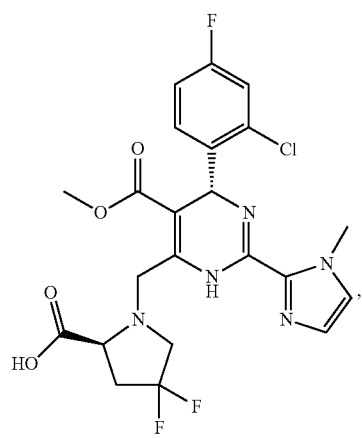
33
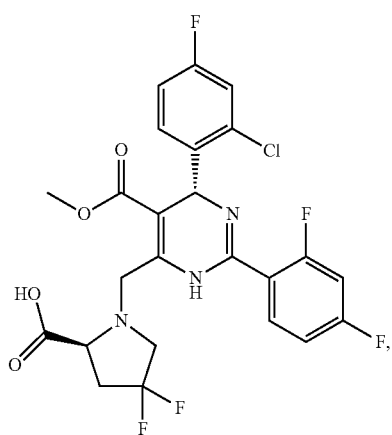
198
45
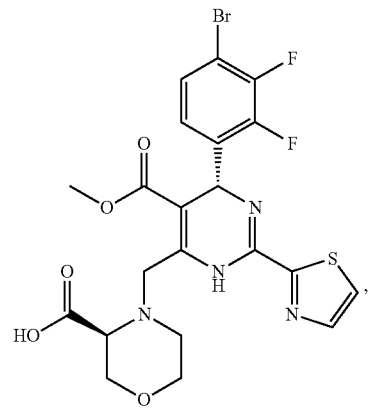
47
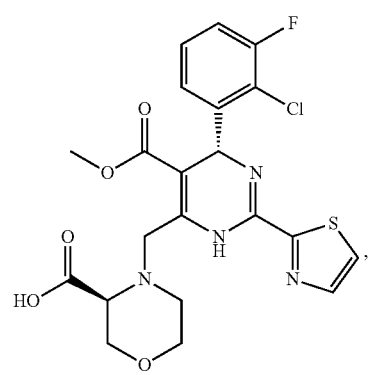
61
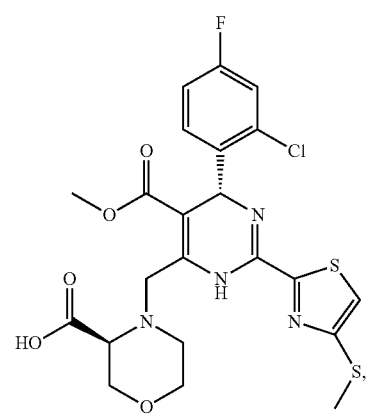
62
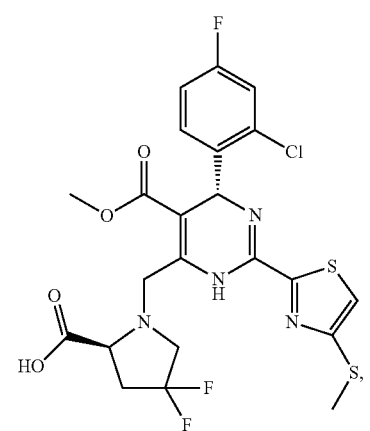

65
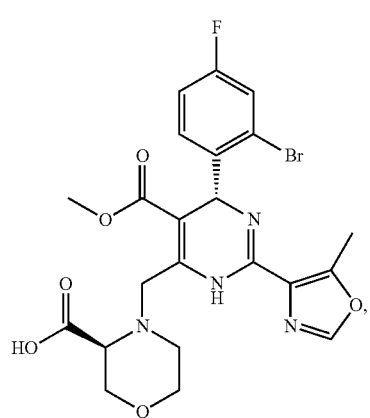
68
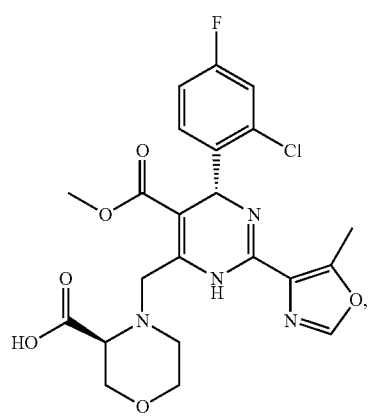
71
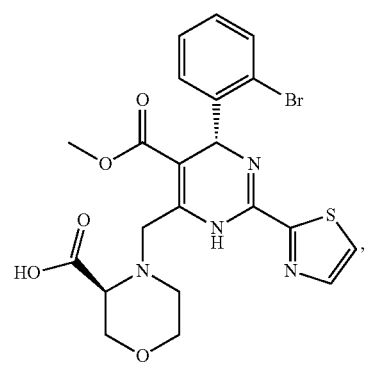
72
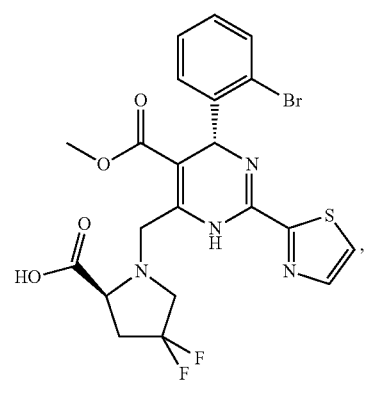
73
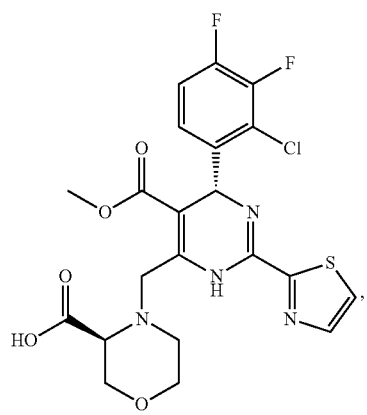
74
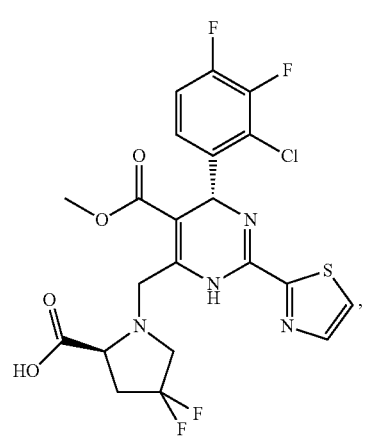
75
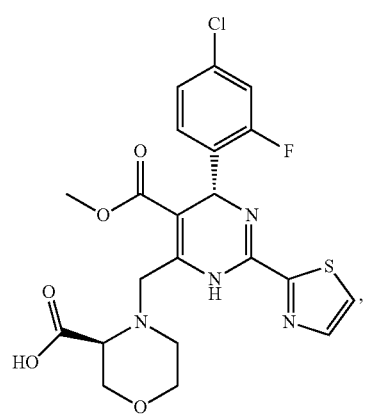

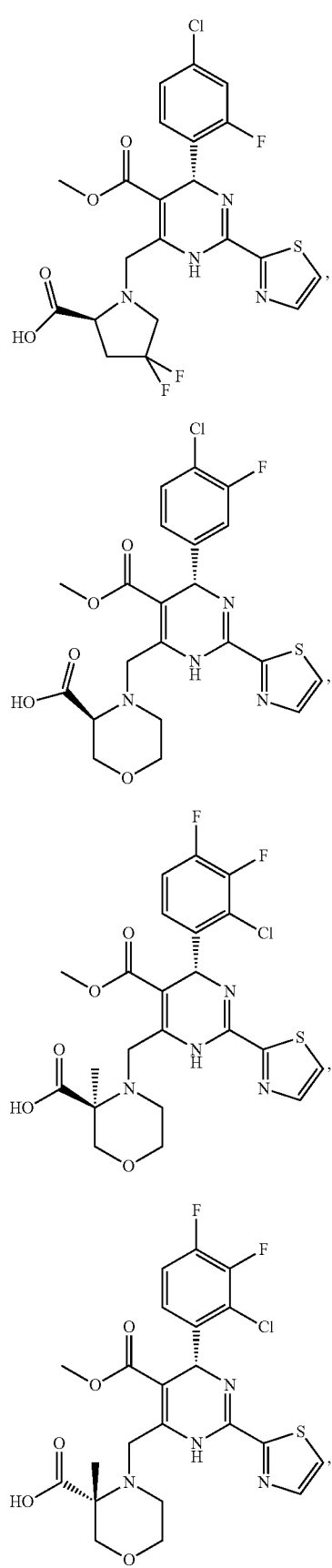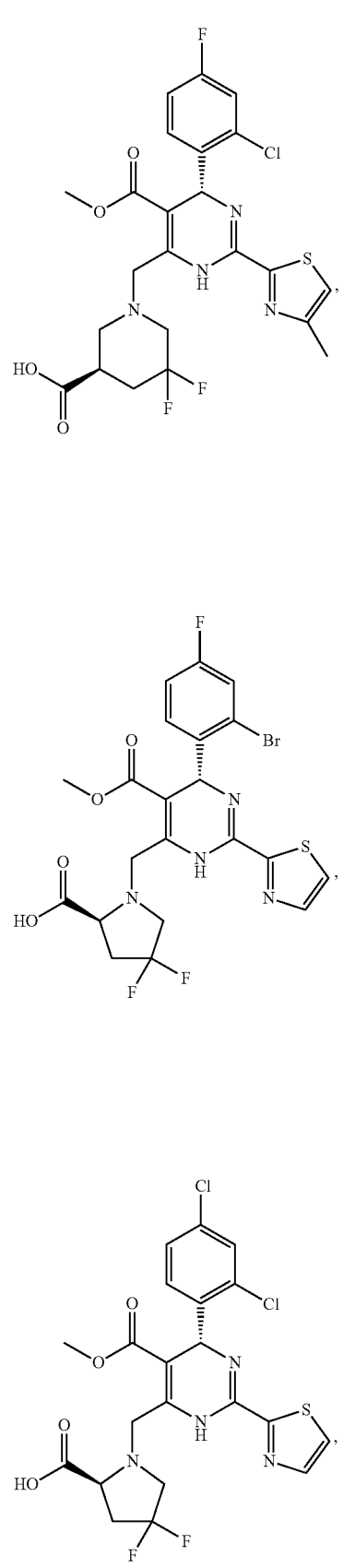

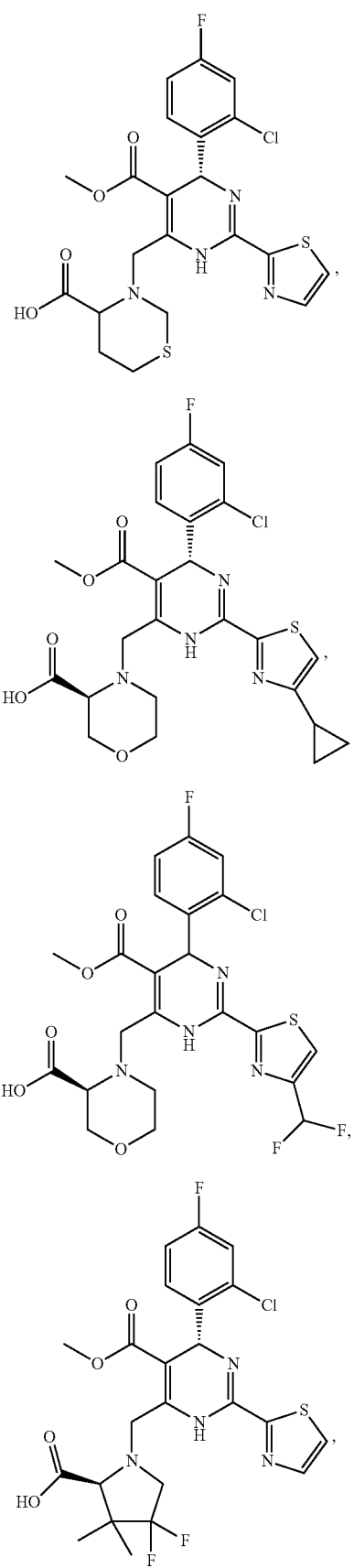
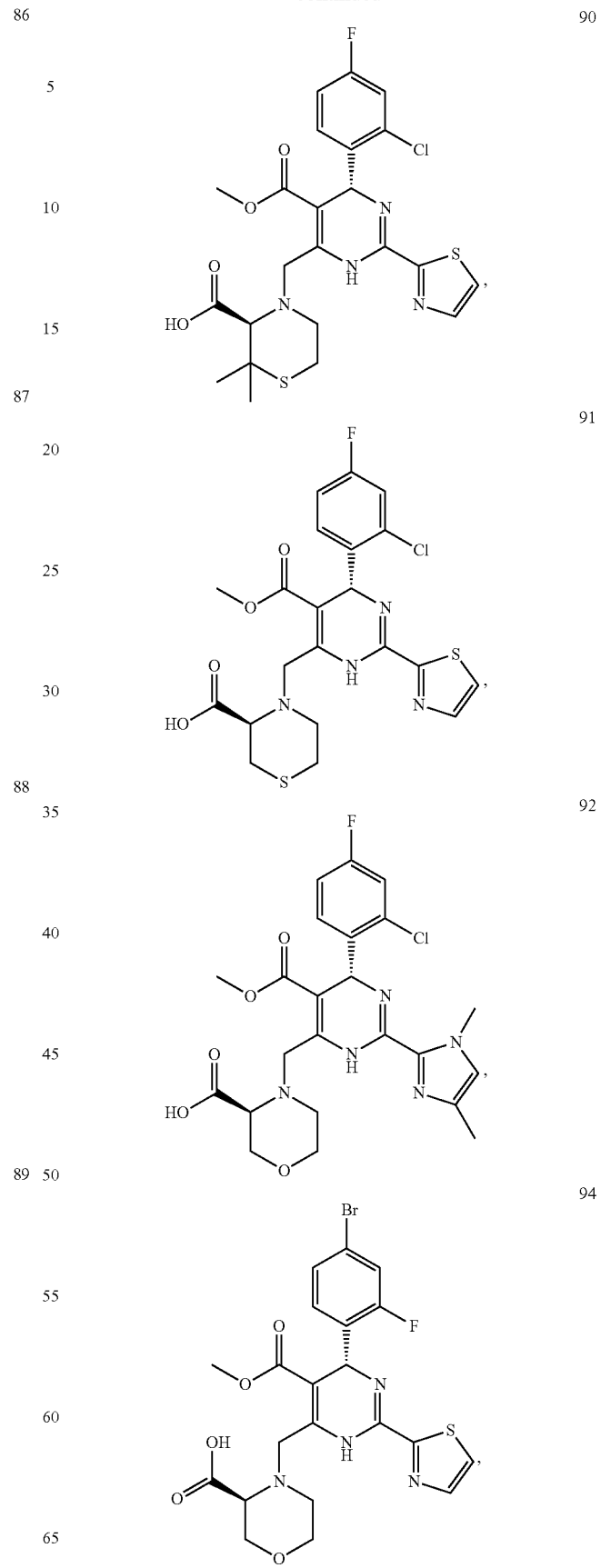

-continued
95
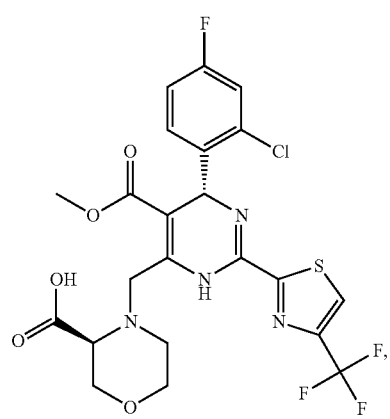
102
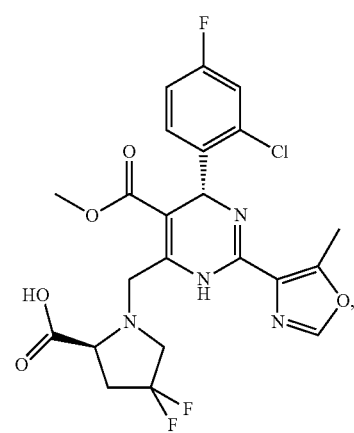
103
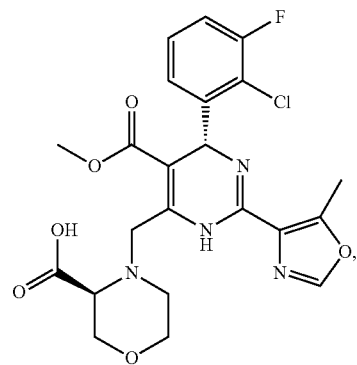
109
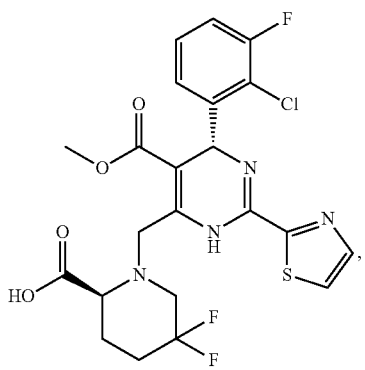
-continued
110
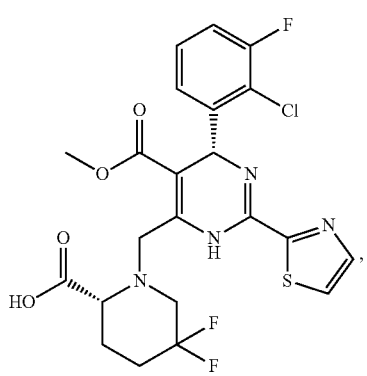
113
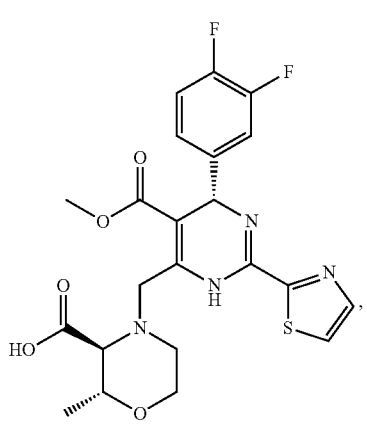
114
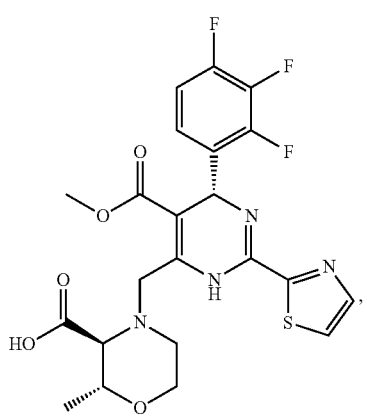
115
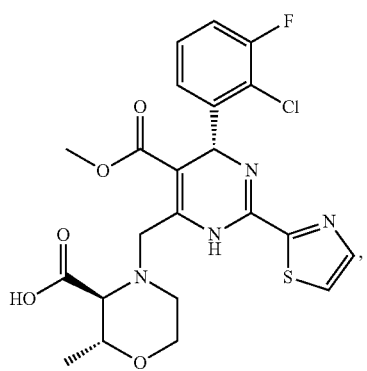

-continued

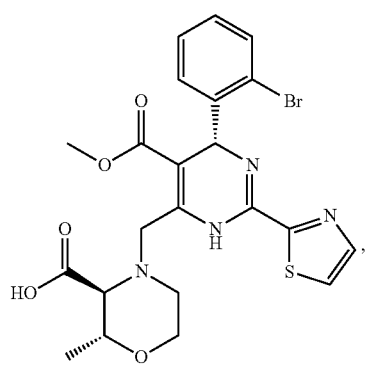

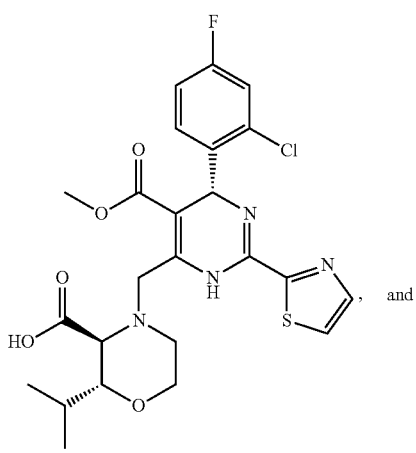
, and

-continued

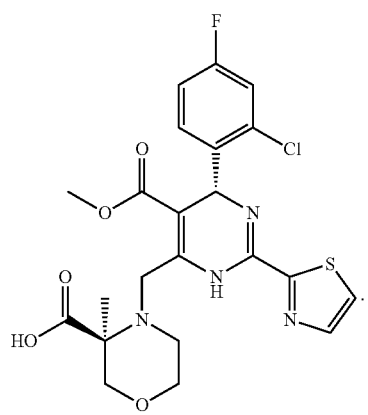
.

2. A pharmaceutical composition comprising a compound in accordance with claim 1 and a therapeutically inert carrier.

3. A method of inhibiting hepatitis B virus in a human, which method comprises administering an effective amount to said human of a compound as defined in claim 1.

4. A method for the treatment of hepatitis B virus infection in a human, which method comprises administering an effective amount to said human of a compound as defined in claim 1.

5. A method for the treatment of hepatitis B virus infection in a human, which method comprises administering an effective amount to said human of a compound as defined in claim 1 together with an agent selected from the group consisting of interferon, pegylated interferons, Lamivudine, Adefovir dipivoxil, Entecavir, Telbivudine, and Tenofovir disoproxil.

* * * * *